US008143050B2

(12) United States Patent
Yang et al.

(10) Patent No.: US 8,143,050 B2
(45) Date of Patent: Mar. 27, 2012

(54) RECOMBINANT β-GLUCOSIDASE VARIANTS FOR PRODUCTION OF SOLUBLE SUGARS FROM CELLULOSIC BIOMASS

(75) Inventors: Jie Yang, Foster City, CA (US); Xiyun Zhang, Fremont, CA (US); Attila Andor, Budapest (HU)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 12/954,447

(22) Filed: Nov. 24, 2010

(65) Prior Publication Data

US 2011/0129881 A1     Jun. 2, 2011

Related U.S. Application Data

(60) Provisional application No. 61/264,608, filed on Nov. 25, 2009, provisional application No. 61/355,511, filed on Jun. 16, 2010.

(51) Int. Cl.
*C12N 9/42* (2006.01)
*C12P 19/02* (2006.01)
*C12P 19/00* (2006.01)
*C07H 21/04* (2006.01)

(52) U.S. Cl. .......... 435/209; 435/105; 435/72; 536/23.2

(58) Field of Classification Search ........................ None
See application file for complete search history.

(56) References Cited

U.S. PATENT DOCUMENTS

| | | |
|---|---|---|
| 6,117,679 A | 9/2000 | Stemmer |
| 6,376,246 B1 | 4/2002 | Crameri et al. |
| 6,586,182 B1 | 7/2003 | Patten et al. |
| 7,923,236 B2 | 4/2011 | Gusakov et al. |
| 2004/0253702 A1 | 12/2004 | Fidantsef et al. |
| 2006/0041961 A1 | 2/2006 | Abad et al. |
| 2007/0238155 A1 | 10/2007 | Gusakov et al. |
| 2008/0220990 A1 | 9/2008 | Fox |
| 2008/0233613 A1 | 9/2008 | Harris et al. |
| 2009/0042266 A1 | 2/2009 | Vehmaanpera et al. |
| 2009/0312196 A1 | 12/2009 | Colbeck et al. |

FOREIGN PATENT DOCUMENTS

| | | |
|---|---|---|
| WO | WO 2009/018537 A2 | 2/2009 |
| WO | WO 2011/041594 A1 | 4/2011 |
| WO | WO 2011/063308 A2 | 5/2011 |

OTHER PUBLICATIONS

Breves, Roland et al.; "Genes Encoding Two Different β-Glucosidases of *Thermoanaerobacter brockii* are Clustered in a Common Operon"; 1997, *Applied and Environmental Microbiology*, vol. 63, No. 10, pp. 3902-3910.
Choi, Jung-Youn et al.; "Purification and Characterization of an Extracellular β-Glucosidases produced by *Phoma* sp. KCTC11825BP Isolated from Rotten Mandarin Peal"; 2011, *J. Microbiol. Biotechnol.*, vol. 21, No. 5, pp. 503-508.
Fang, Zemin et al.; "Cloning and Characterization of a β-Glucosidase from Marine Microbial Metagenome with Excellent Glucose Tolerance"; 2010, *J. Microbiol. Biotechnol.*, vol. 20, No. 9, pp. 1351-1358.
Hrmova, Maria et al.; "Structural Rationale for Low-Nanomolar Binding of Transition State Mimics to a family GH3 β-d-Glucan Glucohydrolase from Barley"; 2005, *Biochemistry*, vol. 44, No. 50, pp. 16529-16539.
Hrmova, Maria et al.; "Dissecting the catalytic mechanism of a plant β-d-Glucan Glucohydrolase through structural biology using inhibitors and substrate analogues"; 2007, *Carbohydrate Research*, vol. 342, pp. 1613-1623.
Igarashi, Kiyohiko et al.; "Family 3 β-Glucosidase from Cellulose-Degrading Culture of the White-Rot Fungus *Phanerochaete chrysosporium* is a Glucan 1,3-Glucosidase"; 2003, *Journal of Bioscience and Bioengineering*, vol. 95, No. 6, pp. 572-576.
Kawai, Rie et al.; "Production and Characterization of Recombinant Phanerochaete chrysosporium β-Glucosidase in the Methylotrophic Yeast *Pichia pastoris*"; 2003, *Biosci. Biotechnol. Biochem.*, vol. 67, No. 1, pp. 1-7.
Kim, Han-Woo et al.; "Complete Saccharification of Cellulose at High Temperature Using Endocellulase and β-Glucosidase from *Pyrococcus* sp."; 2010, *J. Microbiol. Biotechnol.*, vol. 20, No. 5, pp. 889-892.
Pozzo, Tania et al.; "Structural and Functional Analysis of β-Glucosidase 3B from *Thermotoga neapolitana*: A Thermostable Three-Domain Representative of Glycoside Hydrolase 3"; 2010, *J. Mol. Biol.*, pp. 1-16.
Saloheimo, Markku et al.; "Enzymatic Properties and Intracellular Localization of the Novel *Trichoderma reesei* β-Glucosidase BGLII (Cel1A)"; 2002, *Applied and Environmental Microbiology*, vol. 68, No. 9, pp. 4546-4553.
Yun, Soo-In et al.; "Purification and Some Properties of a β-Glucosidase from *Trichoderma hatzianum* Type C-4"; 2008, *Biosci. Biotechnol. Biochem.*, vol. 65, No. 9, pp. 2028-2032.
Xiong, Ai-Sheng et al.; "Directed evolution of a beta-glucosidase from Pyrococcus woesei resulting in increased thermostable beta-glucosidase activity"; 2007, *Appl. Microbio. Biotechno.*, vol. 77, pp. 569-578.

*Primary Examiner* — Anand Desai
*Assistant Examiner* — Iqbal H Chowdhury
(74) *Attorney, Agent, or Firm* — Kilpatrick Townsend & Stockton LLP

(57) ABSTRACT

The invention relates to recombinant expression of a variant form of a fungal C1 strain β-glucosidase. The invention also relates to the generation of fermentable sugars from biomass and the production of biofuels by fermentation of the sugars using genetically modified organisms expressing the β-glucosidase variant. The invention provides methods for producing a fermentable sugar, such as glucose, from cellobiose by contacting cellobiose with a recombinant β-glucosidase variant protein, such as a variant protein secreted by a recombinant host cell into culture medium. Methods of the invention may be used for conversion of a biomass substrate to a fermentable sugar, and ultimately to ethanol or other biofuel.

20 Claims, 9 Drawing Sheets

```
Variant885   (1)   MKAAALSCLFGSTLAVAGAIESRKVHQRPLARSEPFYPSPWMNPMAIGMA
Variant871   (1)   MKAAALSCLFGSTLAVAGAIESRKVHQRPLARSEPFYPSPWMNPMAIGRA
Variant269   (1)   MKAAALSCLFGSTLAVAGAIESRKVHQRPLARSEPFYPSPWMNPMAIGRA
Variant3     (1)   MKAAALSCLFGSTLAVAGAIESRKVHQRPLARSEPFYPSPWMNPMAIGMA
WT           (1)   MKAAALSCLFGSTLAVAGAIESRKVHQRPLARSEPFYPSPWMNPMADGMA
Variant481   (1)   MKAAALSCLFGSTLAVAGAIESRKVHQRPLARSEPFYPSPWMNPMADGMA
Variant647   (1)   MKAAALSCLFGSTLAVAGAIESRKVHQRPLARSEPFYPSPWMNPMADGRA
Variant664   (1)   MKAAALSCLFGSTLAVAGAIESRKVHQRPLARSEPFYPSPWMNPMADGMA
Variant916   (1)   MKAAALSCLFGSTLAVAGAIESRKVHQRPLARSEPFYPSPWMNPMAIGRA Variant885  (51)   EAYAQAKSFVSQMTLLEKVNLTTGYWGWABQCVGNVGAIPRLGLRSLCMB
Variant871  (51)   EAYAQAKSFVSQMTLLEKVNLTTGYWGWABQCVGNVGAIPRLGLRSLCMB
Variant269  (51)   EAYAQAKSFVSQMTLLEKVNLTTGYWGWABQCVGQVGAIPRLGLRSLCMB
Variant3    (51)   EAYAQAKSFVSQMTLLEKVNLTTGYWGWABQCVGQVGAIPRLGLRSLCMB
WT          (51)   EAYAQAKSFVSQMTLLEKVNLTTGYWGWABQCVGQVGAIPRLGLRSLCMB
Variant481  (51)   EAYAQAKSFVSQMTLLEKVNLTTGYWGWABQCVGQVGAIPRLGLRSLCMB
Variant647  (51)   EAYAQAKSFVSQMTLLEKVNLTTGYWGWABQCVGQVGAIPRLGLRSLCMB
Variant664  (51)   EAYAQAKSFVSQMTLLEKVNLTTGYWGWABQCVGQVGAIPRLGLRSLCMB
Variant916  (51)   EAYAQAKSFVSQMTLLEKVNLTTGYWGWGMEQCVGQVGAIPRLGLRSLCMB Variant885 (101)   DSPLGVRGSDYNSAPFSGQTVAATWDRGLMYRGYAMGQEAKGKGINVLL
Variant871 (101)   DSPLSYRGSDYNSAPFSGQTVAATWDRGLMYRGYAMGQEAKGKGINVLL
Variant269 (101)   DSPLGTRGADYNSAPFSGQTVAATWDRGLMYRGYAMGQEAKGKGINVLL
Variant3   (101)   DSPLGTRGADYNSAPFSGQTVAATWDRGLMYRGYAMGQEAKGKGINVLL
WT         (101)   DSPLGTRGADYNSAPFSGQTVAATWDRGLMYRGYAMGQEAKGKGINVLL
Variant481 (101)   DSPLGTRGADYNSAPFSGQTVAATWDRGLMYRGYAMGQEAKGKGINVLL
Variant647 (101)   DSPLGTRGADYNSAPFSGQTVAATWDRGLMYRGYAMGQEAKGKGINVLL
Variant664 (101)   DSPLGTRGADYNSAPFSGQTVAATWDRGLMYRGYAMGQEAKGKGINVLL
Variant916 (101)   DSPLGVRGADYNSAPFSGQTVAATWDRGLMYRGYAMGQEAKGKGINVLL
```

```
                                    301                                                        350
Variant885    (301) VAGLDMSMPGDTMNTGVSFWGANLTLAVLNGTVFAYRLIGMCKRIMAAL
Variant871    (301) VAGLDMSMPGDTMNTGVSFWGANLTLAVLNGTVFAYRLIGMCKRIMAAL
Variant269    (301) VAGLDMSMPRDMFNTGVSFWGANLTLAVLNGTVFAYRLIDNGAKRIMAAL
         WT   (301) VAGLDMSMPGDTQNTGVSFWGANLTLAVLNGTVFAYRLIDMAMRIMAAL
Variant3      (301) VAGLDMSMPGDTQNTGVSFWGANLTLAVLNGTVFAYRLIDMAMRIMAAL
Variant481    (301) VAGLDMSMPGDTMNTGVSFWGANLTLAVLNGTVFAYRLIDMAMRIMAAL
Variant647    (301) VAGLDMSMPGDTMNTGVSFWGANLTLAVLNGTVFAYRLIDMCMRIMAAL
Variant664    (301) VAGLDMSMPGDTMLNTGVSFWGANLTLAVLNGTVFAYRLIDMAMRIMAAL
Variant916    (301) VAGLDMSMPGDTMLNTGVSFWGANLTLAVLNGTVFAYRLIDMAKRIMAAL 351                                                        400
Variant885    (351) FKVTKTTDLEPINFSFWTRDTYGPIMWAAKQGYQEINSHVDVRADHGNLI
Variant871    (351) FKVTKTTDLEPINFSFWTRDTYGPIMWAAKQGYQEINSHVDVRADHGNLI
Variant269    (351) FKVTKTTDLEPINFSFWTRDTYGPIMWAAKQGYQEIKSHVDVRADHGNLI
         WT   (351) FKVTKTTDLEPINFSFWTLDTFGPIMWAAKQGYQEIKSHVDVRADHGNLI
Variant3      (351) FKVTKTTDLEPINFSFWTDPTYGPIMWAAKQGYQEIKSHVDVRADHGRLI
Variant481    (351) FKVTKTTDLEPINFSFWTDPTYGPIMWAAKQGYQEINSHVDVRADHGRLI
Variant647    (351) FKVTKTTDLEPINFSFWTDRTYGPIMWAAKQGYQEINSHVVPRADHGNLI
Variant664    (351) FKVTKTTDLEPINFSFWTDRTYGPIMWAAKQGYQEINSHVVPRADHGNLI
Variant916    (351) FKVTKTTDLEPINFSFWTDRTYGPIMWAAKQGYQEINSHVVPRADHGNLI 401                                                        450
Variant885    (401) RNIAAKGTVLIKNTGSLPLAKPKFYAVIGEDAGPSPNGPNGCSDRGCNEG
Variant871    (401) RNIAAKGTVLIKNTGSLPLAKPKFYAVIGEDAGPSPNGPNGCSDRGCNEG
Variant269    (401) RNIAAKGTVLIKNTGSLFLNRFEFYAVIGEDAGPSPNGPNGCSDRGCNEG
         WT   (401) RNIAAKGTVLIKNTGSLPLAKPKFYAVIGEDAGPSPNGPNGCSDRGCNEG
Variant3      (401) RNIAAKGTVLIKNTGSLPLAKPKFYAVIGEDAGGSPNGPNGCSDRGCNEG
Variant481    (401) RNIAAKGTVLIKNTGSLPLAKPKFYAVIGEDAGGSPNGPKPGPNGCSDRGCNEG
Variant647    (401) RNIAAKGTVLIKNTGSLPLAKPKFYAVIGEDAGPSPNGPNGCSDRGCNEG
Variant664    (401) RNIAAKGTVLIKNTGSLPFILNKPKFYAVIGEDAGPSPNGPNGCSDRGCNEG
Variant916    (401) RNIAAKGTVLIKNTGSLPTLNKPKFYAVIGEDAGPSPNGPNGCSDRGCNEG
```

RECOMBINANT β-GLUCOSIDASE VARIANTS FOR PRODUCTION OF SOLUBLE SUGARS FROM CELLULOSIC BIOMASS

CROSS-REFERENCE TO RELATED APPLICATIONS

This applications claims benefit of U.S. provisional application 61/264,608, filed Nov. 25, 2009 and U.S. provisional application No. 61/355,511, filed Jun. 16, 2010, each of which is herein incorporated by reference in its entirety for all purposes.

FIELD OF THE INVENTION

The invention relates to expression of recombinant β-glucosidase variants and their use in the production of soluble sugars from cellulosic biomass.

BACKGROUND OF THE INVENTION

Cellulosic biomass is a significant renewable resource for the generation of soluble sugars. These sugars can be used as reactants in various metabolic processes, including fermentation, to produce biofuels, chemical compounds, and other commercially valuable products. While the fermentation of simple sugars such as glucose to ethanol is relatively straightforward, the efficient conversion of cellulosic biomass to soluble sugars is challenging (see, e.g., Ladisch et al., 1983, Enzyme Microb. Technol. 5:82). Cellulose may be pretreated chemically, mechanically, enzymatically or in other ways to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down the β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "BGL"). Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetraose. β-Glucosidases split cellobiose into glucose monomers.

Cellulases with improved properties for use in processing cellulosic biomass would reduce costs and increase the efficiency of production of biofuels and other commercially valuable compounds.

SUMMARY OF THE INVENTION

In one aspect, the invention provides an isolated or recombinant β-glucosidase variant comprising an amino acid sequence that is at least about 60% identical, sometimes at least about 65% identical and often at least about 70% identical to residues 20-870 of SEQ ID NO:2 (wild-type C1 β-glucosidase), or which is encoded by a nucleic acid that hybridizes under stringent conditions to SEQ ID NO:1 or the exact complement of SEQ ID NO:1, and which has at least one substitution, relative to SEQ ID NO:2, of an amino acid residue described herein, where the variant has greater β-glucosidase activity than the wild-type protein and/or is more thermostable than the wild-type protein. Also provided are polynucleotides encoding the β-glucosidase variants, expression vectors comprising said polynucleotides, and host cells transformed with the expression vectors.

The invention also provides a method of producing a β-glucosidase variant by culturing a host cell transformed with a polynucleotide encoding a β-glucosidase variant under conditions suitable for the expression of the β-glucosidase. In some embodiments. the β-glucosidase polypeptide is recovered from the culture medium or from the transformed and cultured cells.

The invention also provides an enzyme composition comprising an isolated or recombinant C1 β-glucosidase variant. Optionally the enzyme composition also includes at least one additional cellulase enzyme.

In a related and/or other aspect, the invention provides a method of converting a biomass substrate, such as cellobiose, to a fermentable sugar by contacting a β-glucosidase variant with the biomass substrate under conditions suitable for the production of the fermentable sugar. In one embodiment the biomass substrate is maintained in a medium containing cells expressing a β-glucosidase variant. In one embodiment the recombinant host cell expressing a β-glucosidase variant also expresses at least one other recombinant cellulase and/or other enzyme. Optionally the biomass substrate is pretreated before contacting the substrate with a β-glucosidase polypeptide variant.

BRIEF DESCRIPTION OF THE FIGURES

FIG. 5. FIG. 5 shows an alignment of native (wildtype), C1 Bgl1 amino acid sequence (SEQ ID NO:2) with the amino acid sequences of Variants 3 (SEQ ID NO:5), 269 (SEQ ID NO:7), 481 (SEQ ID NO:9), 647 (SEQ ID NO:15), 664 (SEQ ID NO:13), 871 (SEQ ID NO:17), 885 (SEQ ID NO:19), and 916 (SEQ ID NO:21).

DETAILED DESCRIPTION OF THE INVENTION

I. Definitions

Figure 1A:
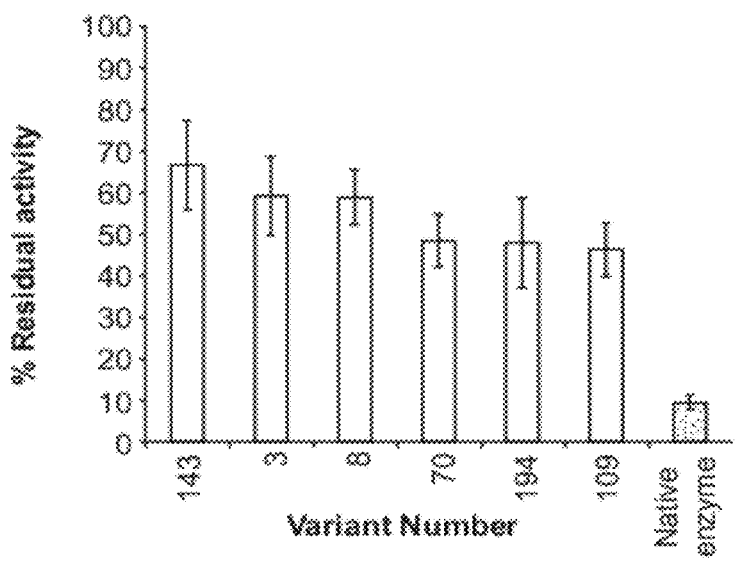
FIG. 1. (A) Thermostabilities of improved C1 Bgl1 variants produced in the C1 strain; Residual enzyme activity after 6 hr incubation at pH 5, 65° C. was determined by pNPG assay at pH 5, 50° C. for 20 mins. N=6-8; Error bars represent ±1 standard deviation. (B) Thermostabilities of improved C1 Bgl1 variants produced in the C1 strain; Residual enzyme activity after 24 hr incubation at pH 5, 65° C. was determined by pNPG assay at pH 5, 50° C. for 20 mins. N=6-30; Error bars represent ±1 standard deviation. (C) C1 Bgl1 thermostability correlation between yeast and C1 hosts.

The following definitions are provided to assist the reader. Unless otherwise defined, all terms of art are intended to have the meanings commonly understood by those of skill in the molecular biology and microbiology arts. In some cases, terms with commonly understood meanings are defined herein for clarity and/or for ready reference, and the inclusion of such definitions herein should not necessarily be construed to represent a substantial difference over the definition of the term as generally understood in the art.

The term "cellulase" refers to a category of enzymes capable of hydrolyzing cellulose (β-1,4-glucan or β-D-glucosidic linkages) to shorter oligosaccharides, cellobiose and/or glucose.

The terms "β-glucosidase" and "cellobiase" are used interchangeably and refer to a β-D-glucoside glucohydrolase which catalyzes the hydrolysis of a sugar dimer, including but not limited to cellobiose, with the release of a corresponding sugar monomer. In one embodiment, a β-glucosidase is a β-glucosidase glucohydrolase of the classification E.C. 3.2.1.21 which catalyzes the hydrolysis of cellobiose to glucose. Some of the β-glucosidases have the ability to also hydrolyze β-D-galactosides, β-L-arabinosides and/or β-D-fucosides and further some β-glucosidases can act on α-1,4-substrates such as starch. β-glucosidase activity may be measured by methods well known in the art, including the assays described hereinbelow.

The term "β-glucosidase polypeptide" refers to a polypeptide having β-glucosidase activity.

The term "β-glucosidase polynucleotide" refers to a polynucleotide encoding a polypeptide having β-glucosidase activity.

"Cellulolytic activity" encompasses exoglucanase activity (CBH), endoglucanase (EG) activity and/or β-glucosidase activity.

The terms "exoglucanase", "exo-cellobiohydrolase" or "CBH" refer to a group of cellulase enzymes classified as E.C. 3.2.1.91. These enzymes hydrolyze cellobiose from the reducing or non-reducing end of cellulose.

The terms "endoglucanase" or "EG" refer to a group of cellulase enzymes classified as E.C. 3.2.1.4. These enzymes hydrolyze internal β-1,4 glucosidic bonds of cellulose.

As used herein, the term "isolated" refers to a nucleic acid, polynucleotide, polypeptide, protein, or other component that is partially or completely separated from components with which it is normally associated (other proteins, nucleic acids, cells, etc.).

The term "wildtype" as applied to a polypeptide (protein) means a polypeptide (protein) expressed by a naturally occurring microorganism such as bacteria or filamentous fungus. As applied to a microorganism, the term "wildtype" refers to the native, non-recombinant micro-organism. With reference to C1 β-glucosidase, wild-type Bgl1 refers to the mature (secreted) form of the protein having the sequence of residues 20-870 of SEQ ID NO:2.

A "variant" as used herein means a β-glucosidase polypeptide or polynucleotide encoding a β-glucosidase comprising one or more modifications relative to wildtype C1 β-glucosidase (Bgl1) or the wildtype polynucleotide such as substitutions, insertions, deletions and/or truncations of one or more specific amino acid residues or of one or more specific nucleotides or codons in the polypeptide or polynucleotide.

A "reference β-glucosidase sequence" refers to a defined sequence used as a basis for a sequence comparison, such as SEQ ID NO:2. A reference β-glucosidase sequence may be a subset of a larger sequence. Generally a reference sequence is at least 25 amino acid residues in length, at least 50 residues in length, at least 100 residues in length, at least 150 residues in length at least 200 residues in length, at least 300 residues in length, at least 350 residues in length, at least 500 residues in length, at least 600 residues in length, at least 700 residues in length, or the full length of the polypeptide.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An "improved property" refers to a β-glucosidase polypeptide that exhibits an improvement in any property as compared to the wildtype C1 β-glucosidase (Bgl1) (residues 20-870 of SEQ ID NO:2). Improved properties may include increased protein expression, thermoactivity, thermostability, pH activity, pH stability, product specificity, increased specific activity, substrate specificity, increased resistance to substrate or end-product inhibition, altered pH/temperature profile, and chemical stability.

A variant with "improved β-glucosidase activity," as the term is used herein, means a variant displaying an increase, relative to a reference sequence, in the amount of substrate hydrolysis that occurs in a specified time under specified reaction conditions. β-glucosidase activity can be measured using a variety of methods known in the art, such as the cellobiose assays described hereinbelow. To compare β-glucosidase activity of two recombinantly expressed proteins, the specific activity (activity per mole enzyme or activity per gram enzyme) can be compared. Alternatively, cells expressing and secreting the recombinant proteins can be cultured under the same conditions and the β-glucosidase activity per volume culture medium can be compared.

The term "improved thermostability" as used herein means a variant enzyme displays an increase in "residual activity" relative to the wildtype enzyme. Residual activity is determined by exposing the enzyme (variant or reference, e.g., wild-type) to stress conditions of elevated temperature for a period of time and then determining β-glucosidase activity under conditions in which the reference (e.g., wild-type) enzyme normally has activity. The β-glucosidase activity of the enzyme exposed to stress conditions ("a") is compared to that of a control in which the enzyme is not exposed to the stress conditions ("b"), and residual activity is equal to the ratio a/b. A variant with increased thermostability will have greater residual activity than the reference (e.g., wild-type) enzyme. Exemplary conditions for determining thermostability are provided in the Examples, infra. In one embodiment the enzymes are exposed to stress conditions of 65° C. at pH 5 for 6 hrs, and assayed at 50° C., pH 5, for 1.5 hrs.

The terms "percent identity," "% identity," "percent identical," and "% identical" are used interchangeably herein to refer to the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art. See e.g., Dayhoff et al. (1978), "A model of evolutionary change in proteins"; "Atlas of Protein Sequence and Structure," Vol. 5, Suppl. 3 (Ed. M. O. Dayhoff), pp. 345-352, Natl. Biomed. Res. Round., Washington, D.C.; And Henikoff et al. (1992) Proc. Natl. Acad. Sci. USA, 89:10915-10919, both of which are incorporated herein by reference. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul, et al. (1997) *Nucleic Acids Res.*, 25:3389-3402 (incorporated herein by reference), and made available to the public at the National Center for Biotechnology Information Website. Optimal alignments and multiple alignments can be prepared using readily available programs such as PSI-BLAST, which is described by Altschul, et al. (1997), supra. One useful alignment tool is "T-Coffee" (Notredame et al., 2000, *J. Mol. Bio.* 302:205-17). T-Coffee alignments may be carried out using default parameters (T-Coffee Technical Documentation, Version 8.01, July 2009, WorldWideWeb.tcoffee.org).

"Corresponding to," "reference to, or "relative to," when used in the context of the numbering of a given amino acid or polynucleotide sequence, refers to the numbering of the residues of a specified reference sequence when the given amino acid or polynucleotide sequence is compared to the reference sequence.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

Nucleic acids "hybridize" when they associate to form double-stranded structures, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, N.Y.), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "culturing" or "cultivation" refer to growing a population of microbial cells under suitable conditions in a liquid or solid medium.

The term "contacting" refers to the placing of a respective enzyme in sufficiently close proximity to a respective substrate to enable the enzyme to convert the substrate to a product. For example, combining a solution containing the enzyme with the respective substrate will effect contacting. Such contacting also includes incubating a cell secreting an enzyme in a medium containing an enzyme substrate.

As used herein, reference to a cell "metabolizing" a soluble sugar or other substrate to produce an end product means the sugar serves as a carbon source and/or energy source for a metabolic reaction in the cell. Typically the cell is a microbial cell such as a fungal cell or bacterial cell.

As used herein the term "transformed" or "transformation" used in reference to a cell means a cell has a non-native nucleic acid sequence integrated into its genome or as an episomal plasmid that is maintained through multiple generations.

The term "introduced" in the context of inserting a nucleic acid sequence into a cell means transfected, transduced or transformed (collectively "transformed") or otherwise incorporated into the genome of, or maintained as an episome in, the cell.

The term "operably linked" refers herein to a configuration in which a control sequence is appropriately placed at a position relative to the coding sequence of the DNA sequence such that the control sequence influences the expression of a polypeptide.

When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

A promoter sequence, signal peptide, or other sequence is "heterologous", when it is operably linked to a nucleic acid or protein sequence with which the promoter, signal peptide or other sequence is not associated in nature.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

A β-glucosidase variant polypeptide is "enzymatically active" when it has β-glucosidase activity.

The term "pre-protein" refers to a protein including an amino-terminal signal peptide (or leader sequence) region attached. The signal peptide is cleaved from the pre-protein by a signal peptidase prior to secretion to result in the "mature" or "secreted" protein.

As used herein, a "start codon" is the ATG codon that encodes the first amino acid residue (methionine) of a protein.

In the context of sequence identity, a reference to "at least x % sequence identity" in this specification is intended, unless otherwise specified, to refer to "x % sequence identity" as well as to alternative embodiments in which % sequence identity is defined by each integer from (x+1) % to 99% identity, just as if each alternative embodiment was explicitly listed. For example, reference to "at least 70% sequence identity to SEQ ID NO:2", or "amino acid residues 20-870 of SEQ ID NO:2", refers to alternative embodiments with at least 71% sequence identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to amino acid SEQ ID NO:2, or residues 20-870 of SEQ ID NO:2. For an alignment that extends for the entire 851 amino acid length of residues 20-870 of SEQ ID NO:2, there may be at least 596 identities between a variant sequence and SEQ ID NO:2, sometimes at least 604, at least 613, at least 622, at least 630, at least 638, at least 647, at least 655, at least 664, at least 672, at least 681, at least 723, at least 766, or at least 808 identities.

As used herein, "C1" refers to a fungal strain described by Garg, A., 1966, "An addition to the genus *Chrysosporium Corda*" *Mycopathologia* 30: 3-4. "*Chrysosporium lucknowense*" includes the strains described in U.S. Pat. Nos. 6,015, 707, 5,811,381 and 6,573,086; US Pat. Pub. Nos. 2007/ 0238155, US 2008/0194005, US 2009/0099079; International Pat. Pub. Nos., WO 2008/073914 and WO 98/15633, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophilia*. Exemplary C1 derivatives include modified organisms in which one or more endogenous genes or sequences has been deleted or modified and/or one or more heterologous genes or sequences has been introduced. Derivatives include UV18#100fΔalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp 1 Δpep4 Δalp2. as described in WO2008073914, incorporated herein by reference.

The following nomenclature may by used to describe substitutions in a polypeptide or polynucleotide sequence relative to a reference sequence: "R-#-V," where # refers to the position in the reference sequence, R refers to the amino acid (or base) at that position in the reference sequence, and V refers to the amino acid (or base) at the corresponding position in the variant sequence. For example, for a variant polypeptide described with reference to SEQ ID NO: 2, "D369L" indicates that in the variant polypeptide, the aspartic acid at position 369 of the reference sequence is replaced by leucine, with amino acid position being determined by optimal alignment of the variant sequence with SEQ ID NO:2. Similarly, "S182L/W" describes two variants: a variant in which the serine at position 182 is replaced by leucine, and a variant in which the serine at position 182 is replaced by tryptophan.

The following conventions are used to describe amino acid positions in Bgl1 variants. Amino acid positions are numbered in relation the reference sequence SEQ ID NO: 2, which is the sequence of the wild-type C1 Bgl1 pre-protein (including the signal peptide). Alignments to determine a degree of sequence identity (e.g., "at least 70% identity") or to describe deletions (e.g., deletions of residues at the c-terminus of the protein) are in relation to the secreted form of the wild-type Bgl1 protein, residues 20-870 of SEQ ID NO:2. Nucleotide base substitutions are numbered relative to SEQ ID NO:1. Substitutions in the signal peptide (residues 1-19 of SEQ ID NO: 2) refer to the sequence of the Bgl1 pre-protein.

II. Introduction

The fungus C1 produces a variety of cellulases and other enzymes that act in concert to catalyze decrystallization and hydrolysis of cellulose to yield soluble sugars. C1 was described by Garg, 1966, "An addition to the genus *Chrysosporium corda*" *Mycopathologia* 30: 3-4. Also see U.S. Pat. Nos. 6,015,707 and 6,573,086, which are incorporated herein by reference for all purposes.

The C1 genome has been at least partially sequenced, as indicated in U.S. patent publications US 2007/0238155, US 2008/0194005, and US 2009/0099079, incorporated herein by reference for all purposes. The sequence of the C1 β-glucosidase 1 (bgl1) gene and the encoded protein (Bgl1) are set forth herein as SEQ ID NOs:1 and 2 (also see copending application Nos. 61/247,379 and PCT/US10/50982, incorporated herein by reference). Note that these sequences differs from the Bgl1 sequences of patent publication US 2007/ 0238155.

The C1 β-glucosidase variants described herein are particularly useful for production of soluble sugars from cellulosic biomass. In one aspect the invention relates to a method of producing glucose by contacting a composition comprising cellobiose with a recombinantly expressed C1 β-glucosidase variant under conditions in which the cellobiose is enzymatically converted to glucose. In one aspect, recombinant host cells expressing a β-glucosidase variant may be combined with cellobiose under conditions in which the β-glucosidase is expressed (and in some embodiments, secreted) by the cells. Alternatively, purified or partially purified recombinant β-glucosidase protein may be contacted with cellobiose. In one aspect of the present invention, contacting comprises culturing a recombinant host cell in a medium that contains cellobiose produced from a cellulosic feedstock. For example, the C1 β-glucosidase variants described herein demonstrate benefit in saccharification reactions in conjunction with other cellulases, such as *T. reesei* cellulases (e.g., *T. reesei* CBH1, CBH2, and/or EG1 or variants thereof, and/or *T. reesei* broth) and C1 cellulases (see U.S. Pat. Nos. 6,015,707, 5,811,381 and 6,573,086; US Pat. Pub. Nos. 2007/0238155, US 2008/0194005, US 2009/0099079; International Pat. Pub. Nos. WO 2008/073914 and WO 98/15633, all incorporated herein by reference).

Various aspects of the invention are described in the following sections.

III. Properties of β-Glucosidase Proteins for Use in Methods of the Invention In one aspect, the invention provides a method for expressing a β-glucosidase protein by culturing a host cell comprising a vector or episomal plasmid comprising a nucleic acid sequence encoding a C1 Bgl1 variant, or which has a nucleic acid sequence encoding a C1 Bgl1 variant integrated into its genome, under conditions in which the β-glucosidase protein or an enzymatically active fragment thereof is expressed. Generally the expressed protein comprises a signal peptide which is removed by the cell as the enzyme is secreted. In one embodiment, transcription of the sequence encoding the C1 Bgl1 variant is controlled by an operably linked heterologous promoter.

β-Glucosidase Polypeptide Variants

The present invention provides novel enzymes that are C1 β-glucosidase (Bgl1) variants. β-glucosidase polypeptide variants of the present invention are variants of Bgl1 that exhibit β-glucosidase activity, typically greater β-glucosidase activity than the wild-type C1 β-glucosidase (residues 20-870 of SEQ ID NO:2) especially under conditions relevant to commercial saccharification processes. Also included are β-glucosidase polypeptide variants that exhibit greater stability under conditions relevant to commercial saccharification processes (e.g., increased thermostability relative to wild-type β-glucosidase).

The present invention provides Bgl1 variants having greater activity and/or thermostability than the wild-type (WT) C1 Bgl1 protein and having at least one of the substitutions found in an increased-activity and/or increased—thermostability variant described herein. As is discussed in more detail below, a polynucleotide encoding the wild-type (WT) C1 Bgl1 protein (SEQ ID NO: 2) was prepared. The polynucleotide was inserted into an expression vector as described in Example 1, infra, libraries of polynucleotides encoding variant Bgl1 proteins were prepared by mutagenesis and directed evolution, and the properties (e.g., β-glucosidase activity and thermostability) of individual Bgl1 variants were assessed (See Tables 2-7 and Examples 2-9, infra). A number of amino acid substitutions and combinations of substitutions were identified in variants with greater than wild-type activity and/or greater than wild-type thermostability. See Table 2. A variant with elevated activity and thermostability was selected and subjected to further mutagenesis and screening. See Table 3. A variant from this round of mutagenesis and screening was selected and subjected to further mutagenesis and screening. See Table 4. A variant from this further round of screening was selected and subjected to additional mutagenesis and screening. See Table 5. Two variants from this round of screening were selected and subjected to further mutagenesis and screening. See Tables 6 and 7.

More specifically, the present invention provides an isolated and/or recombinant β-glucosidase polypeptide variant having greater activity and/or thermostability than the wild-type C1 protein, and which comprises an amino acid sequence that is at least about 70% identical to wild-type C1 β-glucosidase (Bgl1) (residues 20-870 of SEQ ID NO:2) and has at least one substitution of an amino acid residue at a position selected from the group consisting of K57; A88; I106; N112; Q119; T120; A123; R132; Y135; A136; A141; K142; L149; G158; P161; P172; T177; I179; G180; M181; S182; E183; K186; A197; G202; Y219; N220; S222; T224; I229; M234; F242; A243; V246; Q258; D274; V286; Q291; Q313; V318; A343; T354; T357; D358; E360; D369; P374; I375; A378; Q381; E385; S388; V390; A394; N398; E402; K406; I428; S434; N437; E449; Q474; A475; T482; S489; Y491; K530; N536; T540; T565; V674; R682; I867; E868; P870 (wherein amino acid position is determined by optimal alignment with SEQ ID NO:2). "Substitution," in this context, means that the residue in the variant protein is other then the residue shown. For example, "A88" denotes a variant comprising an amino acid other than alanine at position 88 (i.e., one of the other 19 naturally occurring amino acids). In some embodiments, the amino acid in the variant protein is neither the wild-type residue nor a residue that is a conservative substitute for the wild-type residue. As discussed below, in this context, a conservative substitute for a residue is another residue in the same group identified in Table 1.

The present invention additionally provides an isolated and/or recombinant β-glucosidase polypeptide variant having greater activity and/or thermostability than the (WT) C1 Bgl1 protein, wherein the variant comprises an amino acid sequence that is at least about 70% identical to wildtype C1 (Bgl1) (residues 20-870 of SEQ ID NO:2); has a substitution at each of positions Q291, D369 and E402; and has at least one substitution of an amino acid residue at a position selected from the group consisting of I106, A109, Q119, T120, R132, Y135, M181, Q215, A243, V246, Q258, A265, D274, N278, Q313, F314, G332, T357, D358, P374, E385, S434, N437, A475, S489, Y491, E493, K495, K497, S501. A503E N504, A505, N521, K530, N536. T540, D566, T591, A601, K610, T611, R612, S614, L620, G628, T635, V638, V648, D650, S652, N670, R672, V674, S676, T685, T687, A689, Q690, T699, D703, K708, Y715, A732, E742, L757, V775, T777, and D781; (wherein amino acid position is determined by optimal alignment with SEQ ID NO:2). In some embodiments, the amino acid in the variant protein is neither the wild-type residue nor a residue that is a conservative substitute for the wild-type residue. As discussed below, in this context, a conservative substitute for a residue is another residue in the same group identified in Table 1.

The present invention additionally provides an isolated and/or recombinant β-glucosidase polypeptide variant having greater activity and/or thermostability than the wild-type C1 Bgl1 protein, wherein the variant comprises an amino acid sequence that is at least about 70% identical to wild-type C1 β-glucosidase (Bgl1) (residues 20-870 of SEQ ID NO:2); has a substitution at each of positions Q258, Q291, Q313, D369, E402, S434, A475, K495, and G628; and has at least one substitution of an amino acid residue at a position selected from the group consisting of A4, A15, E21, S22, K24, V25, H26, Q27, P29, L30, N45, D47, Q55, S58, A79, Q85, I106, A109, Q119, Y135, A136, P161, V175, G180, G202, G216, I221, L237, D244, V253, V260, L275, D311, F314, A343, D358, E360, Q381, E385, A394, A404, A405, K421, I428, P436, N437, M454, D470, R476, A477, Q479, T482, Y491, E493, E494, T496, S501, A505, N536, V559, V562, N588, S604, R612, G616, A617, G626, N627, F634, D646, D650, S652, R672, V673, T685, T687, A689, Q690, K708, Y715, Q716, A732, A748, D751, L757K, S764, R769, V775, T777, T783, T785, S787, S799, P806, K807, R817, E819, E822, T823, V840, V846, I847, S848, Y850, K866, and P870, (wherein amino acid position is determined by optimal alignment with SEQ ID NO:2). In some embodiments, the amino acid in the variant protein is neither the wild-type residue nor a residue that is a conservative substitute for the wild-type residue. As discussed below, in this context, a conservative substitute for a residue is another residue in the same group identified in Table 1.

The present invention additionally provides an isolated and/or recombinant β-glucosidase polypeptide variant having greater activity and/or thermostability than the wild-type C1 Bgl1 protein, wherein the variant comprises an amino acid sequence that is at least about 70% identical to wild-type C1 β-glucosidase (Bgl1) (residues 20-870 of SEQ ID NO:2); has a substitution at each of positions Q258, Q291, Q313, D369, E402, S434, A475, K495, G628, A689, and Y715; and has at least one substitution of an amino acid residue at a position selected from the group consisting of C8, L9, K24, V25, D47, S58, A79, Q85, I106, A109, A136, V175, L237, A243, V253, V260, D274, L275, F314, A343, Q381, E385, P436, N437, Q474, R476, A505, S550, N588, S604, G616, G626, D650, D651, S652, V674, T687, Q690, D709, E710, A732, D733, Y736N, L757, S764, T777, T783, T785, K807, M816, D844, V846, L869, and P870 (wherein amino acid position is determined by optimal alignment with SEQ ID NO:2). In some embodiments, the amino acid in the variant protein is neither the wild-type residue nor a residue that is a conservative substitute for the wild-type residue. As discussed below, in this context, a conservative substitute for a residue is another residue in the same group identified in Table 1.

The present invention additionally provides an isolated and/or recombinant β-glucosidase polypeptide variant having greater activity and/or thermostability than the wild-type C1 Bgl1 protein, wherein the variant comprises an amino acid sequence that is at least about 70% identical to wild-type C1 β-glucosidase (Bgl1) (residues 20-870 of SEQ ID NO:2); has a substitution at each of positions D47, Q258, Q291, Q313, A343, D369, E402, S434, A475, K495, G628, T687, A689, and Y715; and has at least one substitution of an amino acid residue at a position selected from the group consisting of A79, Q85, V260, L275, F314, D395, P439, A505, D646, T693, N723, A730, A732, S764, R769, T827, and Y855, (wherein amino acid position is determined by optimal alignment with SEQ ID NO:2). In some embodiments, the amino acid in the variant protein is neither the wild-type residue nor a residue that is a conservative substitute for the wild-type residue. As discussed below, in this context, a conservative substitute for a residue is another residue in the same group identified in Table 1.

The present invention additionally provides an isolated and/or recombinant β-glucosidase polypeptide variant having greater activity and/or thermostability than the wild-type C1 Bgl1 protein, wherein the variant comprises an amino acid sequence that is at least about 70% identical to wild-type C1 β-glucosidase (Bgl1) (residues 20-870 of SEQ ID NO:2); has a substitution at each of positions I106, Q258, V260, Q291W, Q313, F314, D369, E402, S434, K495, G628, A689, Y715, and A732; and has at least one substitution of an amino acid residue at a position selected from the group consisting of A109, A343, A475, A505, A689, A79, C8, D47, L275, N315, Q85, T591, and T687, (wherein amino acid position is determined by optimal alignment with SEQ ID NO:2). In some embodiments, the amino acid in the variant protein is neither the wild-type residue nor a residue that is a conservative substitute for the wild-type residue. As discussed below, in this context, a conservative substitute for a residue is another residue in the same group identified in Table 1.

TABLE 1

| basic amino acids | arginine, lysine, histidine |
| acidic amino acids | glutamic acid, aspartic acid |
| polar amino acids | glutamine, asparagine |
| hydrophobic amino acids | leucine, isoleucine, valine |
| aromatic amino acids | phenylalanine, tryptophan, tyrosine |
| small amino acids | glycine, alanine, serine, threonine, proline, cysteine, methionine |

In some embodiments, the amino acid in the variant protein is neither the wild-type residue nor a residue that is a residue commonly exchanged with the wild-type residue as defined by the following pairs: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

As summarized in Table 2, in certain embodiments, the present invention provides an isolated and/or recombinant β-glucosidase polypeptide variant comprising an amino acid sequence that has greater activity and/or thermostability than the wild-type wild-type C1 Bgl1 protein, is at least about 70% identical to wild-type C1 β-glucosidase (Bgl1) (residues 20-870 of SEQ ID NO:2), and which has at least one substitution of an amino acid residue selected from the group consisting of K57R; A88S; I106V; N112V; Q119E/L; T120M/Y/V/H; A123N; R132K/G/W; Y135I/Q/M; A136E; A141F; K142R; L149Q/M; G158D; P161S; P172A; T177I; I179M; G180E; M181Y; S182L/W; E183G/M/Q/K; K186R; A197V; G202M/V; Y219V; N220Y/S/L; S222Q/E; T224N; I229M; M234E/I; F242L; A243V; V246L; Q258N; D274Y/N; V286I; Q291W/A/F; Q313M; V318E; A343V/T; T354Q; T357L/P; D358K/N; E360R/A/D; P374Y; I375V; A378K/T; Q381V/D/I/L; D369Q/L/Y/C/A/I/P/E/K/R/F/M/H/V; E385L; S388W/C; V390I; A394G/V/L/P/Q; N398G; E402N; K406D; I428V; S434P; N437F/Y/D/L/W; E449Q; Q474I; A475F/Y/H/W/C; T482A; S489L; Y491H/F; K530M/G; N536K; T540; T565A/G/P; V674I; R682W; I867M; E868R; P870S (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 25, 30, 35, 40, 45, 50, 55, 60, 65, 70, 75, or more of the above-identified positions.

As summarized in Table 3, in certain embodiments, the present invention provides an isolated and/or recombinant β-glucosidase polypeptide variant comprising an amino acid sequence that has greater activity and/or thermostability than the wild-type C1 Bgl1 protein, wherein the variant is at least about 70% identical to wild-type C1 (Bgl1) (residues 20-870 of SEQ ID NO:2); has the substitutions Q291W, D369H/L/R/Y, and E402N; and has at least one substitution of an amino acid residue at a position selected from the group consisting of A109S, A243V, A265S, A475C/F/L/W, A503E, A505C, A601T, A689I, A732G/M, D274Y, D358E/K/N, D566G, D650F/V, D703K, D781N, E385L, E493A/V/Y, E742G, F314L/V, G332D, G628L/V/W, I106V, K495F/H/I/N/Q/V, K497R, K530C/D/E/I/M/N/V, K610S, K708F, L620M, L757K, M181Y, N278Y, N437D/F/I/K/L/V/W/Y, N504Y, N521C, N536K, N670D, P374Y, Q119E, Q215E/M, Q258H/N, Q313M, Q690A/K/R, R132H, R612H/P, R672A/D/F/G/

I/S/T/V, S434P, S489I/L/N/T, S501H/N/R, S614A/C/D/H/L/ R/V/Y, S652D, S676C, S764F, T120H/Y, T357A, T540K, T591A/C/R, T611A/H/Q, T635A/I/V, T685V. T687C/F/K/L/ M/W/Y, T699L, T777T, T779S, V2461, V638E/R/S, V648W, V674M, V775C, Y135Q, Y491F/H/L, and Y715P; (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 25, 30, 35, 40, 45, 50, 55, 60, 65, or 70, or more of the above-identified positions.

As summarized in Table 4, in certain embodiments, the present invention provides an isolated and/or recombinant β-glucosidase polypeptide variant comprising an amino acid sequence that has greater activity and/or thermostability than the wild-type C1 Bgl1 protein, is at least about 70% identical to wild-type C1 β-glucosidase (Bgl1) (residues 20-870 of SEQ ID NO:2), has the substitutions Q258N, Q291W, Q313M, D369R, E402N, S434P, A475L, K495N, and G628W; and has at least one substitution selected from the group consisting of: A4V, A15V, A109S/T, A136L, A343C, A394G, A404S, A405T, A477G, A505C, A617V, A689I, A732G/M/S, A748T, A79E/G/M, D244H, D311N, D358K, D470N, D47I, D646N, D650F/N/Y, D751N, E21Q/R, E360D, E385L, E493A/V/Y, E494K, E819A/L/V, E822A/G/ K/M, F314L/V, F634A, G180E, G202M, G216L, G616D, G626D, H26R, I106V, I221V, I428V, I847T, K24G/L/T, K421R, K708F, K807R, K866I/Q, L237Y, L275Y, L30K, L757K, M454E, N437W, N45H, N536K, N588F, N627H, P161S, P29M/Q/R, P436E/Q, P806L, P870S, Q119E, Q27H/ R, Q381V, Q479R, Q55R, Q690A/H/K, Q716R, Q85N, R476Q, R612H, R672G, R769H, R817P, S22L/R, S501C/R, S58G, S604I, S652D, S764F, S787G, S799N, S848N, T482A, T496A, T685V, T687C/K/M, T777N, T783H/Q, T785L, T823K, V175A, V253F, V25A/G/R, V260G/L, V559T, V562C/L, V673A, V775C, V840I, V846F, Y135M/ Q, Y491F, Y715P, and Y850H/Q, (wherein amino acid position is determined by optimal alignment with SEQ ID NO:2). In some embodiments, the Bgl1 polypeptide does not have a substitution at position A475. Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 25, 30, 35, 40, 45, 50, 55, 60, 65, 70, 75, 80, or more of the above-identified positions.

As summarized in Table 5, in certain embodiments, the present invention provides an isolated and/or recombinant β-glucosidase polypeptide variant comprising an amino acid sequence that has greater activity and/or thermostability than the wild-type C1 Bgl1 protein, is at least about 70% identical to wild-type C1 β-glucosidase (Bgl1) (residues 20-870 of SEQ ID NO:2), has the substitutions Q258N, Q291W, Q313M, D369R, E402N, S434P, A475L, K495N, G628W, A689I, and Y715P; and has at least one substitution selected from the group consisting of: C8A, L9F, K24G/T, V25A, D47I/N, S58G, A79E/G/M, Q85H/N, I106V, A109S/T, A136L, V175A, L237Y, A243G, V253F, V260G, D274Y, L275F/Y, F314L/V, A343C/G, Q381V, E385L, P436Q, N437D/K, Q474I/L, R476G, A505C, S550C, N588F, S604A/ C/I/V, G616D, G626D, D650N/Y, D651E, S652D, V674I, T687C/K/W, Q690H/K, D709E, E710G, A732G/M/V, D733G, Y736N, L757I/K, S764F, T777N, T783A, T785L, K807R, M816L, D844G, V846F/L/Q, L869R, and P870S (wherein amino acid position is determined by optimal alignment with SEQ ID NO:2). In some embodiments, the Bgl1 polypeptide variant does not have a substitution at position A475. Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 25, 30, 35, 40, 45, 50, or more of the above-identified positions.

As summarized in Table 6, in certain embodiments, the present invention provides an isolated and/or recombinant β-glucosidase polypeptide variant comprising an amino acid sequence that has greater activity and/or thermostability than the wild-type C1 Bgl1 protein, is at least about 70% identical to wild-type C1 β-glucosidase (Bgl1) (residues 20-870 of SEQ ID NO:2), has the substitutions D47I, Q258N, Q291W, Q313M, A343C, D369R, E402N, S434P, A475L, K495N, G628W, T687K, A689I, Y715P; and has at least one substitution selected from the group consisting of: A79E/G/M, Q85N, V260G, L275Y, F314L/V, D395N, P439S, A505C, D646N, T693A/E, N723G, A730S, A732G/M/V, S764Y, R769H, T8271, and Y855, (wherein amino acid position is determined by optimal alignment with SEQ ID NO:2). In some embodiments, the Bgl1 variant polypeptide has the substitution T687K or T687W in place of T687K. In some embodiments, the Bgl variant polypeptide does not have a substitution at position A475. Beneficial combinations of the above-listed substitutions include any combination of substitutions at any 2, 3, 4, 5, 6, 7, 8, 9, 10, 11, 12, 13, 14, or 15, or more of the above-identified positions.

As summarized in Table 7, in certain embodiments, the present invention provides an isolated and/or recombinant β-glucosidase polypeptide variant comprising an amino acid sequence that has greater activity and/or thermostability than the wild-type C1 Bgl1 protein, is at least about 70% identical to wild-type C1 β-glucosidase (Bgl1) (residues 20-870 of SEQ ID NO:2), has the substitutions I106V, Q258N, V260G, Q291W, Q313M, F314L/V, D369R, E402N, S434P, K495N, G628W, A689I, Y715P, and A732G; and has at least one substitution selected from the group consisting of: A109S/T, A343C/G, A475L, A505C, A79E/G/M, C8G, D47I, L275F/ Y, N315D, Q85H/N, and T5911, T687C/K/W, (wherein amino acid position is determined by optimal alignment with SEQ ID NO:2). In some embodiments, the Bgl1 protein additionally has the substitution F314V. Beneficial combinations of the above-listed substitutions include any combination of substitutions at any 2, 3, 4, 5, 6, 7, 8, 9, 10, 11, or 12 or more of the above-identified positions.

The present invention further provides an isolated and/or recombinant β-glucosidase polypeptide variant having greater activity and/or thermostability than the wild-type C1 Bgl1 protein and having an amino acid sequence encoded by a nucleic acid that hybridizes under stringent conditions to the complement of SEQ ID NO:1 (e.g., over substantially the entire length of a nucleic acid exactly complementary to SEQ ID NO:1) wherein the encoded polypeptide has at least one substitution of an amino acid residue selected from the group consisting of K57; A88; I106; N112; Q119; T120; A123; R132; Y135; A136; A141; K142; L149; G158; P161; P172; T177; I179; G180; M181; S182; E183; K186; A197; G202; Y219; N220; S222; T224; I229; M234; F242; A243; V246; Q258; D274; V286I; Q291; Q313; V318; A343; T354; T357; D358; E360; P374; I375; A378; Q381; D369; E385L; S388; V390I; A394; N398; E402; K406; I428; S434; N437; E449Q; Q474I; A475; T482; S489; Y491; K530; N536; T540; T565; V674; R682; I867; E868; P870 (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 24, 25 or more of the above-identified positions.

The present invention further provides an isolated and/or recombinant β-glucosidase polypeptide variant having greater activity and/or thermostability than the wild-type C1 Bgl1 protein and having an amino acid sequence encoded by a nucleic acid that hybridizes under stringent conditions to the complement of SEQ ID NO:1 (e.g., over substantially the entire length of a nucleic acid exactly complementary to SEQ ID NO:1); wherein the encoded polypeptide has a substitution at each of positions Q291, D369 and E402; and has at least one substitution of an amino acid residue at a position selected from the group consisting of I106, A109, Q119, T120, R132, Y135, M181, Q215, A243, V246, Q258, A265, D274, N278, Q313, F314, G332, T357, D358, P374, E385, S434, N437, A475, S489, Y491, E493, K495, K497, S501. A503E N504, A505, N521, K530, N536. T540, D566, T591, A601, K610, T611, R612, S614, L620, G628, T635, V638, V648, D650, S652, N670, R672, V674, S676, T685, T687, A689, Q690, T699, D703, K708, Y715, A732, E742, L757, V775, T777, and D781; (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 24, or more of the above-identified positions.

The present invention further provides an isolated and/or recombinant β-glucosidase polypeptide variant having greater activity and/or thermostability than the WT C1 Bgl1 protein and having an amino acid sequence encoded by a nucleic acid that hybridizes under stringent conditions to the complement of SEQ ID NO:1 (e.g., over substantially the entire length of a nucleic acid exactly complementary to SEQ ID NO:1); wherein the encoded polypeptide has substitutions at each of positions Q258, Q291, Q313, D369, E402, S434, A475, K495, and G628; and has at least one substitution of an amino acid residue at a position selected from the group consisting of A4, A15, E21, S22, K24, V25, H26, Q27, P29, L30, N45, D47, Q55, S58, A79, Q85, I106, A109, Q119, Y135, A136, P161, V175, G180, G202, G216, I221, L237, D244, V253, V260, L275, D311, F314, A343, D358, E360, Q381, E385, A394, A404, A405, K421, I428, P436, N437, M454, D470, R476, A477, Q479, T482, Y491, E493, E494, T496, S501, A505, N536, V559, V562, N588, S604, R612, G616, A617, G626, N627, F634, D646, D650, S652, R672, V673, T685, T687, A689, Q690, K708, Y715, Q716, A732, A748, D751, L757K, S764, R769, V775, T777, T783, T785, S787, S799, P806, K807, R817, E819, E822, T823, V840, V846, I847, S848, Y850, K866, and P870; (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 24, 25, or more of the above-identified positions.

The present invention further provides an isolated and/or recombinant β-glucosidase polypeptide variant having greater activity and/or thermostability than the wild-type C1 Bgl1 protein and having an amino acid sequence encoded by a nucleic acid that hybridizes under stringent conditions to the complement of SEQ ID NO:1 (e.g., over substantially the entire length of a nucleic acid exactly complementary to SEQ ID NO:1) wherein the encoded polypeptide has at least one substitution of an amino acid residue selected from the group consisting of K57R; A88S; I106V; N112V; Q119E/L; T120M/Y/V/H; A123N; R132K/G/W; Y135I/Q/M; A136E; A141F; K142R; L149Q/M; G158D; P161S; P172A; T177I; I179M; G180E; M181Y; S182L/W; E183G/M/Q/K; K186R; A197V; G202M/V; Y219V; N220Y/S/L; S222Q/E; T224N; I229M; M234E/I; F242L; A243V; V246L; Q258N; D274Y/ N; V286I; Q291W/A/F; Q313M; V318E; A343V/T; T354Q; T357L/P; D358K/N; E360R/A/D; P374Y; I375V; A378K/T; Q381V/D/I/L; D369Q/L/Y/C/A/I/P/E/K/R/F/M/H/V; E385L; S388W/C; V390I; A394G/V/L/P/Q; N398G; E402N; K406D; I428V; S434P; N437F/Y/D/L/W; E449Q; Q474I; A475F/Y/H/W/C; T482A; S489L; Y491H/F; K530M/G; N536K; T540K; T565A/G/P; V674I; R682W; I867M; E868R; P870S (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 24, 25 or more of the above-identified positions.

The present invention further provides an isolated and/or recombinant β-glucosidase polypeptide variant having greater activity and/or thermostability than the wild-type C1 Bgl1 protein and having an amino acid sequence encoded by a nucleic acid that hybridizes under stringent conditions to the complement of SEQ ID NO:1 (e.g., over substantially the entire length of a nucleic acid exactly complementary to SEQ ID NO:1) wherein the encoded polypeptide has a substitution Q291W, D369H/L/R/Y, and E402N; and has at least one substitution of an amino acid residue selected from the group consisting of A109S, A243V, A265S, A475C/F/L/W, A503E, A505C, A601T, A689I, A732G/M, D274Y, D358E/K/N, D369H/L/R/Y, D566G D650F/V, D703K, D781N, E385L, E402N, E493A/V/Y, E742G, F314V, G332D, G628L/V/W, I106V, K495F/H/I/N/Q/V, K497R, K530C/D/E/I/M/N/V, K610S, K708F, L620M, L757K, M181Y, N278Y, N437D/F/ I/K/L/V/W/Y, N504Y, N521C, N536K, N670D, P374Y, Q119E, Q215E/M, Q258H/N, Q291W, Q313M, Q690A/K/ R, R132H, R612H/P, R672A/D/F/G/I/S/T/V, S434P, S489I/ L/N/T, S501H/N/R, S614A/C/D/H/L/R/V/Y, S652D, S676C S764F, T120H/Y, T357A, T540K, T591A/C/R, T611A/H/Q, T635A/I/V, T685V. T687C/F/K/L/M/W/Y, T699L, T777N, T779S, V246I, V638E/R/S, V648W, V674M, V775C, Y135Q, Y491F/H/L, and Y715P (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 24, 25 or more of the above-identified positions.

The present invention further provides an isolated and/or recombinant β-glucosidase polypeptide variant having greater activity and/or thermostability than the wild-type C1 Bgl1 protein and having an amino acid sequence encoded by a nucleic acid that hybridizes under stringent conditions to the complement of SEQ ID NO:1 (e.g., over substantially the entire length of a nucleic acid exactly complementary to SEQ ID NO:1) wherein the encoded polypeptide has a substitution at position Q258N, Q291W, Q313M, D369R, E402N, S434P, A475L, K495N, and G628W; and has at least one substitution selected from the group consisting of A4V, A15V, A109S/T, A136L, A343C, A394G, A404S, A405T, A477G, A505C, A617V, A689I, A732G/M/S, A748T, A79E/G/M, D244H, D311N, D358K, D470N, D47I, D646N, D650F/N/Y, D751N, E21Q/R, E360D, E385L, E493A/V/Y, E494K, E819A/L/V, E822A/G/K/M, F314L/V, F634A, G180E, G202M, G216L, G616D, G626D, H26R, I106V, I221V, I428V, I847T, K24G/L/T, K421R, K708F, K807R, K866I/Q, L237Y, L275Y, L30K, L757K, M454E, N437W, N45H, N536K, N588F, N627H, P161S, P29M/Q/R, P436E/Q, P806L, P870S, Q119E, Q27H/R, Q381V, Q479R, Q55R, Q690A/H/K, Q716R, Q85N, R476Q, R612H, R672G, R769H, R817P, S22L/R, S501C/R, S58G, S604I, S652D, S764F, S787G, S799N, S848N, T482A, T496A, T685V, T687C/K/M, T777N, T783H/Q, T785L, T823V, V175A, V253F, V25A/G/R, V260G/L, V559T, V562C/L, V673A, V775C, V840I, V846F, Y135M/Q, Y491F, Y715P, Y850H/Q, (wherein amino acid position is determined by optimal alignment with SEQ ID NO:2). Beneficial combinations of the above-listed substitutions include any combination of substitutions at any 2, 3, 4, 5, 6, 7, 8, 9, 10, 11, 12, 13, 14, 15, 16, 17, 18, 19, 20, 21, 22, 23, 24, 25 or more of the above-identified positions. In certain embodiments, the C1 Bgl1 protein has the substitutions Q258N, Q291W, Q313M, D369L, E402N, S434P, A475L, K495N, and G628W.

It will be appreciated that Bgl1 variants of the invention may encompass additional amino acid substitutions beyond those listed above (such as additional conservative substitutions) and may be less-than-full length compared to wild-type C1 Bgl1 protein. Thus, Bgl1 variants of the invention may comprise insertions or deletions (e.g., truncation at the amino- and/or carboxy-termini) relative to residues 20-870 of SEQ ID NO:2. The wild-type secreted form of C1 Bgl1 protein is about 851 amino acids in length; variants of the present invention may be longer or shorter than wild-type. For illustration and not limitation, in some embodiments the variant may be longer or shorter by up to 10% of the wild-type length, sometimes up to 5%, sometimes up to 4%, sometimes up to 3%, sometimes up to 2%, sometimes up to 1%.

Sequence-activity analysis of variants was performed in accordance with the methods described in WO 03/075129, U.S. Ser. No. 10/379,378 filed Mar. 3, 2003; R. Fox et al., 2003, "Optimizing the search algorithm for protein engineering by directed evolution," *Protein Eng.* 16(8):589-597, and R. Fox et al., 2005, "Directed molecular evolution by machine learning and the influence of nonlinear interactions," *J. Theor. Biol.* 234(2):187-199, all of which are incorporated herein by reference, to identify substitutions with likely the most significant effects on activity.

Certain β-glucosidase variants of the present invention have an amino acid sequence that includes at least one substitution of an amino acid residue selected from the group consisting of Q119E; R132H; Y135Q; G180E; G202M/V; Q258N; D274Y; Q291W/A/F; D358K/N; D369L/Y/V/A/H/R/F/E/M/I/K/C/P/Q; P374Y; E385L; A394L; E402N; S434P; N437F/D/L/W/Y; Q474I; A475F/Y/H/C/W; T482A; S489L; K530M; N536K; T540K, which are predicted to be highly beneficial substitutions for increasing β-glucosidase activity.

Certain β-glucosidase variants of the present invention have an amino acid sequence that includes the substitutions Q291W+D369L+E402N (as found in Variant 3), or the substitutions Q291W+D369H/L/R/Y+E402N. In some embodiments, the sequence includes at least one substitution of an amino acid residue selected from the group consisting of Q258N/H, D358K/N, I106V, E385L, D274Y, K495H/I/N/Q, Q119E, Y135Q, G628W, R132H, N437I, S501R, P374Y, N437V, S614A, Q313M, L369H, S434P, N437W/D, and Y491F. In some embodiments, the at least one substituted amino acid residue is Q258N. In some embodiments, the at least one substituted amino acid residue is D358K or Q258H. In some embodiments, the at least one substituted amino acid residue is I106V, E385L, D274Y, or K495H. In some embodiments, the at least one substituted amino acid residue is K495I/N, Q119E, Y135Q, or D358N. In some embodiments, the at least one substituted amino acid residue is G628W, R132H, K495Q, N437I, S501R, or P374Y. In some embodiments, the at least one substituted amino acid residue is N437V, S614A, Q313M, L369H, S434P, N437W/D, or Y491F. These substitutions are predicted to be highly beneficial substitutions for increasing β-glucosidase activity.

Certain β-glucosidase variants of the present invention have an amino acid sequence that includes the substitutions Q258N, Q291W, Q313M, D369R, E402N, S434P, A475L, K495N, and G628W (as found in Variant 269). and least one substitution of an amino acid residue selected from the group consisting of Y715P, S764F, E385D/L, A732G/M, A689I, A109T, T687M/C/K, L757K, Q381V/D, A109S, T777N, I106V, T823K, Q716R, V846F, T685V, T687K, D650Y, F314V/L, S652D, and I428V. In some embodiments, the at least one substituted amino acid residue is Y715P. In some embodiments, the at least one substituted amino acid residue is S764F, E385L, A732G, A689I, or A109T, or E285D. In some embodiments, the at least one substituted amino acid residue is T687M, A732M, or L757K. In some embodiments, the at least one substituted amino acid residue is Q381V, A109S, T777N, I106V, T823K, T687C, or Q716R. In some embodiments, the at least one substituted amino acid residue is V846F, T685V, T687K, D650Y, F314V/L, S652D, Q381D, or I428V. These substitutions, are predicted to be highly beneficial substitutions for increasing β-glucosidase activity.

Certain β-glucosidase variants of the present invention have an amino acid sequence that includes the substitutions Q258N, Q291W, Q313M, D369R, E402N, S434P, A475L, K495N, G628W, A689I, and Y715P (as found in Variant 481); or the substitutions 258N, Q291W, Q313M, D369R, E402N, S434P, K495N, G628W, A689I, and Y715P; and least one substitution of an amino acid residue selected from the group consisting of A79E/M/G, Q85N, I106V, A109S/T, V260G, F314L/V, A343C/G, A505C, T687K/W/C, and A732G/M/V. In some embodiments, the at least one substituted amino acid residue is T687W. In some embodiments, the at least one substituted amino acid residue is T687C or T687W, V260G, A343C, A732G, or A109T. In some embodiments, the at least one substituted amino acid residue is F314V/L, A732M/V, A109S, or A343G. In some embodiments, the at least one substituted amino acid residue is A79E, A505C, I106V, or A79M/G. In some embodiments, the variant These substitutions, are predicted to be highly beneficial substitutions for increasing β-glucosidase activity.

Certain β-glucosidase variants of the present invention have an amino acid sequence that includes the substitutions D47I, Q258N, Q291W, Q313M, A343C, D369R, E402N, A475L, S434P, K495N, G628W, T687K, A689I, and Y715P (as found in Variant 647) or the substitutions D47I, Q258N, Q291W, Q313M, A343C, D369R, E402N, S434P, A475L, K495N, G628W, T687W, A689I, and Y715P; or the substitutions D47I, Q258N, Q291W, Q313M, A343C, D369R, E402N, S434P, K495N, G628W, T687K/W/C, A689I, and Y715P; and least one substitution of an amino acid residue selected from the group consisting of A79G/E/M, Q85N, V260G, L275Y, and F314L/V, and A732G/M. In some embodiments, the at least one substituted amino acid residue is A79E, A79M, A79G, A732G, V260G, or F314L. In some embodiments, the at least one substituted amino acid residue is Q85N, F314V, or A732M. These substitutions, are predicted to be highly beneficial substitutions for increasing β-glucosidase activity.

Certain β-glucosidase variants of the present invention have an amino acid sequence that includes the substitutions I106V, Q258N, V260G, Q291W, Q313M, F314L/V, D369R, E402N, S434P, K495N, G628W, A689I, Y715P, and A732G (as found in Variant 664) and least one substitution of an amino acid residue selected from the group consisting of D47I, A79G/E/M, A109T, A505C, A343C/G, T687W/C/K, N315D, and L275F. In some embodiments, the at least one substituted amino acid residue is A79E or A79G. In some embodiments, the at least one substituted amino acid is A109T, A79M, A505C, or A343C. In some embodiments, the at least one substituted amino acid is T687W, T687C, D47I, T687K N315D, or A343G. These substitutions, are predicted to be highly beneficial substitutions for increasing β-glucosidase activity.

Certain β-glucosidase variants of the present invention have an amino acid sequence that includes at least one substitution of an amino acid residue selected from the group consisting of I106V; A123N; G180E; M181Y; M234E; Q258N; Q291W/F/A; T357L/P; D358K; E360D; D369L/V/C/Y/R/K/M/A/H/E/F/Q/P/I; P374Y; E385L; A394G; N437D/L; T482A; S489L; K530M; N536K; T540K, which are predicted to be highly beneficial substitutions for increasing thermostability.

Certain β-glucosidase variants of the present invention have an amino acid sequence that includes the substitutions Q291W, D369H/L/R/Y, and E402N; and at least one substitution of an amino acid residue selected from the group consisting of Q313M, Q258N/H, N536K, Q119E, S489I/N/L/T, T120Y, K495N/V/I/H/Q, I106V, T120H, N437I/D/W/F/K/L/V/Y, E385L, M181Y, D274Y, S434P, S501R, T591C, Y135Q, Y491H/F, T540K, N521C, T591R, G628W, and A475L. In some embodiments, the at least one substituted amino acid residue is Q313M or Q258N. In some embodiments, the at least one substituted amino acid residue is N4371, K495N, Q258H, or N536K. In some embodiments, the at least one substituted amino acid residue is Q119E, S489I, T120Y, K495V, S489L, I106V, T120H, or N437D. In some embodiments, the at least one substituted amino acid residue is N437W, K4951, N437F, E385L, K495H, N437K, N437L, S489T, M181Y, D274YS434P, or N437V. In some embodiments, the at least one substituted amino acid residue is S501R, T591C, Y135q, Y491H, R491F, T540K, N521C, T591R, K495K, G628W, N437Y, S489N, or A475L. These substitutions are predicted to be highly beneficial substitutions for increasing thermostability.

Certain β-glucosidase variants of the present invention have an amino acid sequence that includes the substitutions Q258N, Q291W, Q313M, D369R, Q381V, E385L, E402N, S434P, A475L, K495N, and G628W; and least one substitution of an amino acid residue selected from the group consisting of S764F, Y715P, E385L/D, A732G/M, A109T/S, T687M/C/K, T777N, I106V, L475A, F314V, D650Y, L757K. Q716R, T685V, or F314L. In some embodiments, the at least one substituted amino acid residue is S764F or Y715P. In some embodiments, the at least one substituted amino acid residue is E385L or A732G. In some embodiments, the at least one substituted amino acid residue is A109T or T687M. In some embodiments, the at least one substituted amino acid residue is T777N, I106V, I732M, T687C, T687K, E385D, L475A or A109S. In some embodiments, the at least one substituted amino acid residue is P720P, F314V, D650Y, L757K, Q716R, T685V, or F314L. These substitutions are predicted to be highly beneficial substitutions for increasing thermostability.

Certain β-glucosidase variants of the present invention have an amino acid sequence that includes the substitutions Q258N, Q291W, Q313M, D369R, E402N, S434P, A475L, K495N, G628W, A689I and 715P (as found in Variant 481); and least one substitution of an amino acid residue selected from the group consisting of D47I, A79E, Q85N, I106V, A109S/T, V260G, L275Y, F314L/V, A505C, T687W/C/K, and A732G/M/V. In some embodiments, the at least one substituted amino acid residue is T687K/W/C. In some embodiments, the at least one substituted amino acid is I106V, V260G, F314V, A732G, A109T, F314L, A732M, Q85N, or A109S. In some embodiments, the at least one substituted amino acid is F314, A732V, A505C, D47I, L275Y, or A79E. These substitutions are predicted to be highly beneficial substitutions for increasing thermostability.

Certain β-glucosidase variants of the present invention have an amino acid sequence that includes the substitutions D47I, Q258N, Q291W, Q313M, A343C, D369R, E402N, S434P, A475L, K495N, G628W, T687K/W, A689I, and Y715P (as found in Variant 647); or the substitutions D47I, Q258N, Q291W, Q313M, A343C, D369R, E402N, S434P, K495N, G628W, T687K/W, A689I, and Y715P; and least one substitution of an amino acid residue selected from the group consisting of A79E/G/M, Q85N, V260G, L275Y, F314V/L, D395N, and A732G, which are predicted to be highly beneficial substitutions for increasing thermostability. In some embodiments, the at least one substituted amino acid residue is A79M, F314V, or A79G. In some embodiments, the at least one substituted amino acid residue is A79E, F314L, V260G, A85N, D395N, or A732G.

Certain β-glucosidase variants of the present invention have an amino acid sequence that includes the substitutions I106V, Q258N, V260G, Q291W, Q313M, F314L/V, D369R, E402N, S434P, K495N, G628W, A689I, Y715P, and A732G (as found in Variant 664) and least one substitution of an amino acid residue selected from the group consisting of A109S/T, A79G/E/M, D47I, Q85N/H, L314V, and T5911. In some embodiments, the at least one substituted amino acid residue is A109S, A79G, A109T, or A79E. In some embodiments, the at least one substituted amino acid residue is D47I, A79M, A85N, or A85H. These substitutions, are predicted to be highly beneficial substitutions for increasing thermostability.

Certain β-glucosidase variants of the present invention have an amino acid sequence that includes at least one substitution of an amino acid residue at a position selected from the group consisting of G180E; Q258N; Q291W/A/F; D358K; D369L/Y/V/A/H/R/F/E/M/I/K/C/P/Q; P374Y; E385L; N437D/L; T482A; S489L; K530M; N536K; and T540K, which are predicted to be highly beneficial substitutions for increasing both thermostability and β-glucosidase activity.

Certain β-glucosidase variants of the present invention have an amino acid sequence that includes Q291W, D369H/L/R/Y, and E402N; and least one substitution of an amino acid residue selected from the group consisting of Q258N/H, I106V, E385L, D274Y, K495H/I/N/Q, Q119E, Y135Q, G628W, N437I/V/W/D, S501R, Q313M, S434P, and Y491F, which are predicted to be highly beneficial substitutions for increasing both thermostability and β-glucosidase activity.

Certain β-glucosidase variants of the present invention have an amino acid sequence that includes Q258N, Q291W, Q313M, D369R, E402N, S434P, A475L, K495N, and G628W; or Q258N, Q291W, Q313M, D369R, E402N, S434P, K495N, and G628W; and least one substitution of an amino acid residue selected from the group consisting of S764F, Y715P, E385L/D, A732G/M, A109T/S, T687M/C/K, T777N, I106V, F314V, D650Y, L757K. Q716R, T685V, and F314L. the substitutions are predicted be highly beneficial substitutions for increasing both thermostability and β-glucosidase activity.

Certain β-glucosidase variants of the present invention have an amino acid sequence that includes Q258N, Q291W, Q313M, D369R, E402N, S434P, A475L, K495N, G628W, A689I and 715P (as found in Variant 481); and least one substitution of an amino acid residue selected from the group consisting of A79E, Q85N, T687K/W/C, I106V, A109T/S, V260G, F314V/L, A505C, and A732G/M/V. The substitutions are predicted be highly beneficial substitutions for increasing both thermostability and β-glucosidase activity.

Certain β-glucosidase variants of the present invention have an amino acid sequence that includes D47I, Q258N, Q291W, Q313M, A343C, D369R, E402N, S434P, A475L, K495N, G628W, T687K/W, A689I, and Y715P (as found in Variant 647); or the D47I, Q258N, Q291W, Q313M, A343C, D369R, E402N, S434P, K495N, G628W, T687K/W, A689I, and Y715P; and least one substitution of an amino acid residue selected from the group consisting of A79E/G/M, Q85N, V260G, F314V/L, A732G, and L275Y. In some embodiments, the substituted amino acid residue is A79E, A79M, A79G, Q85N, V260G, F314V, F314L, or A732G. The substitutions are predicted be highly beneficial substitutions for increasing both thermostability and β-glucosidase activity.

Certain β-glucosidase variants of the present invention have an amino acid sequence that includes the substitutions I106V, Q258N, V260G, Q291W, Q313M, F314L/V, D369R, E402N, S434P, K495N, G628W, A689I, Y715P, and A732G (as found in Variant 664) and least one substitution of an amino acid residue selected from the group consisting of D47I, A79E/M/G, and A109T, which are predicted be highly beneficial substitutions for increasing both thermostability and β-glucosidase activity.

Notably, a number of variants with superior activity and/or thermostability comprise substitutions at position 369, with 14 different alternative (i.e., non-aspartic acid) residues appearing in beneficial variants. Substitutions at position 369 are predicted to increase activity and/or thermostability. Thus, in one aspect the invention provides an isolated and/or recombinant β-glucosidase polypeptide variant comprising an amino acid sequence that is at least about 70% identical to wild-type C1 β-glucosidase (Bgl1) (residues 20-870 of SEQ ID NO:2) wherein the amino acid at position 369 is not aspartic acid. In some embodiments the amino acid at position 369 is selected from the group consisting of Q, L, Y, C, A, I, P, E, K, R, F, M, H, and V. In some embodiments the amino acid at position 369 is L (leucine), which appears particularly beneficial for β-glucosidase and thermostability.

A number of variants with superior activity and/or thermostability comprise substitutions at position 291. Substitutions at position 291 are predicted to increase activity and/or thermostability. Thus, in one aspect the invention provides an isolated and/or recombinant β-glucosidase polypeptide variant comprising an amino acid sequence that is at least about 70% identical to wild-type C1 β-glucosidase (Bgl1) (residues 20-870 of SEQ ID NO:2) wherein the amino acid at position 291 is not glutamine. In some embodiments the amino acid at position 291 is W, A, or F. In some embodiments the amino acid at position 369 is W (tryptophan), which appears particularly beneficial for β-glucosidase and thermostability.

A number of variants with superior activity and/or thermostability comprise substitutions at position 402. Substitutions at position 402 are predicted to increase activity and/or thermostability. Thus, in one aspect the invention provides an isolated and/or recombinant β-glucosidase polypeptide variant comprising an amino acid sequence that is at least about 70% identical to wild-type C1 β-glucosidase (Bgl1) (residues 20-870 of SEQ ID NO:2) wherein the amino acid at position 402 is not glutamic acid. In some embodiments, the amino acid is neither glutamic acid nor aspartic acid. In some embodiments, the amino acid is not glutamic acid, aspartic acid, or proline. In some embodiments, the amino acid at position 402 is asparagine, glutamine, histidine, lysine, or arginine. In some embodiments, the amino acid at position 402 is asparagine or glutamine. In some embodiments the amino acid at position 402 is N (asparagine), which appears particularly beneficial for β-glucosidase and thermostability.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of:
M181Y+Q291W+E402N+S434P; R132K+L149M+Q313M+D369L+E385L+N437D; Q291W+D369L+E402N; Y135I+Q258N+Q474I; M181Y+Q291W+E360D+D369V+P374Y+T482A; Q258N+N437F+S489L+Y491H; Q119E+Q258N+T357L+Q474I+S489L; Q258N+D369R+S489L+Y491H; N220Y+Q258N+T357L+D369R+Q474I+Y491F; M234E+V246L+D358K+D369L+N398G+K530M; Y135Q+I229M+F242L+D369L+K530M; D369Q+P374Y+E402N+T540K; Y135Q+P172A+I179M+I229M+Q291A+D358K+D369L+N398G; R132K+D369L+E385L; Y135M+I179M+Q291A+D358K+D369L; Q291W+P374Y+E402N+S434P; Q119E+N220Y+Q258N+T357L+S489L; I179M+Q291A+D358K+D369L+I375V+S388W; Q291W+D369C; R132K+T354Q+D369L+N437L; Q291A+D369L+N398G+K530M; Q119E+Q258N+D274Y+S489L; Q119E+N220Y+Q258N+Q474I+S489L; M181Y+D369L; T120M+S222E+Q313M+T354Q+D369L+E385L; A4G+Q258N+D274Y+T357L+N437W+Q474I+Y491H; R132G+D369L+N437D; S182L+Q313M+D369L+E385L; R132G+D369L+E385L; N112V+D358K+D369L+S388W+K530M; I106V+G180E+D369L+Q381V; I179M+Q291A+D369L; I179M+D358K+D369L+S388W; M234E+Q291A+D369L+N398G; I179M+Q291A+D358K+D369L+Q381I; Y135Q+N220L+Q291A+D369L+N398G; Y135I+D369L; S182L+D369L+E385L+N437L; T120Y+R132K+D369L+N437D; M234E+D369L+S388W+N398G+K530M; Y135M+I179M+D369L+V390I+K530M; L149Q+A197V+Q313M+D369L; T120M+R132K+D369L+N437L; T120M+R132W+L149M+Q313M+T354Q+D369L+E385L+N437D; A4G+Y135I+N220Y+Q258N+T357P+N437Y; D358K+D369L+S388W; Q258N+D274Y+N437F; D369L+S434P+T540K; G158D+I179M+Q291A+D358K+D369L+I375V+N398G+K530M; Y135I+D274Y+D369R; Q258N+D369L+Q474I+S489L+Y491F; R132W+S182W+D369L+E385L; S182L+T354Q+D369L+E385L; S222Q+T354Q+D369L+E385L+N437D+T565G; Y135M+P161S+Q291A+A343T+D369L+I375V+K406D; Q291W+D369C+T540K; D369L+P374Y+E402N; Y135I+A343V+D369F+S489L; M234E+D358K+D369L+S388W; T120M+L149Q+D369L+E385L; Q313M+D369L+E385L; T120Y+D369L+E385L; D369L+N437D+T565A; N112V+Q291A+D369L+I375V; R132W+L149Q+Q313M+T354Q+D369L; Y135M+D369L+I375V+N398G; D369L+E385L; T120M+S182L+Q313M+T354Q+D369L+E385L; T177I+Q291W+P374Y+T482A; Q258N+N437F; T120V+R132W+D369L+T565G; N112V+Q291A+D358N+D369E+S388C+K406D; Q291A+D358K+D369L+S388W+K406D; I106V+E360R+D369L+Q381V; M234E+Q291A+D369L+S388W+N398G; L149M+Q313M+D369L; M234I+Q291W+E360D+D369V+T482A; T120V+T354Q+D369L+E385L+T565P; M234I+Q291W+E360D+S434P; D369Y+I867M+E868R; R132W+S182L+Q313M+D369L; M234I+Q291W+P374Y+T482A; Y219V+M234I+D369C+P374Y+S434P; S182L+Q313M+D369L+E385L+N437L; M234E+D358K+D369L+S388W+K530M; R132G+5222E+D369L+E385L; R132K+L149M+S182L+D369L+N437L; T120H+Q313M+D369L; R132W+D369L; D369L+P374Y; N112V+N220L+Q291A+D369L+S388W+N398G; Q291A+D369L+I375V+K530G; R132K+L149M+S182L+T354Q+D369L+N437D+T565G; T120H+5222E+Q313M+D369L+N437D+T565G; A123N+Q291W+T482A+T540K; S222E+Q313M+T354Q+D369L+E385L; R132W+D369L+T565G; G202M+E360A+D369I+A394L; R132G+S222Q+

Q313M+D369L; R132W+L149M+D369L; L149M+Q313M+T354Q+D369L; Q119L+G202M+D369L; M181Y+M234I+D369C; I179M+N220L+Q291A+D369L+I375V; S222E+Q313M+D369L+E385L+N437L; I179M+M234E+D358K+D369L+S388W+N398G; A123N+Y219V+Q291W+E360D+P374Y+S434P; D369L+E402N; D369L; Y219V+M234I+Q291W+T482A; Q291W+E360D+S434P; D369L+S434P; G180E+E360R+D369L; A123N+M181Y+Q291W+D369K+S434P+T540K; Q119E+T357L+D369M+S489L; Q119E+D369F+Y491H; Q119L+D369L; Q119E+N220Y+V286I+S489L; Q291A+D369L+Q381I; A475F; D369L+N536K; Q119E+Y135I+D369H; Q258N+S489L; Q119E+Y135I+N437Y; Q119E+Y135I+N437F+Y491F; Q119L+D369L+A394V; E183G+E360A+D369L+I428V; D369L+E449Q+N536K; Q119L+G202M+E360A+A475F; I106V+D369L; Y135I+D369M; M234I+D369C+S434P; D369L+A475Y; Q119E+Y135I+S489L; D369Y+N536K; E360R+D369L; G202V+A475H; D369L+Q381V+N536K; N220Y+Q258N+S489L+Y491F; Q258N+T357L+D369M; I179M+Q291A+D369L+Q381L+S388W+N398G; D369Y+A394G+N536K; Q291W+E360D+D369V+P374Y; T120M+L149Q+T354Q+D369L+E385L; S489L+Y491H; N220S+Q291F+D369L; D369C+S434P+T540K; V318E+D369L+I428V; E183M+G202M+E360A+D369L+A378K+A394V; A394G+N536K; Q291W+T540K; N220L+Q291A+D369L+Q381L+S388W+K530M; T120V+R132W+E385L+N437D; Q119L+E360A+D369L+A378K; D369A+N536K; G202V+D369L+A475H; Q381V+A475Y+N536K; S434P; I106V+G180E+D369Y+A394G; G180E+Q381V+A475H; Q119E+N220Y+Q474I; I106V+D369Q; A475Y+N536K; K142R+Y219V+Q291W+S434P+V674I; L149Q+S182L+Q313M+D369L+N437L; N112V+I179M+M234E+D369L+N398G; E360A+D369L+A378K; E360R+D369Y+N536K; E360R+D369A+Q381V+N536K; D369L+Q381D; N437F+S489L; E183M+G202M+V318E+D369I+A394L+I428V; E360D+D369L+E402N+S434P; Q119L+A141F+G202M+A394L+I428V+A475F; T357L+D369R+S489L+Y491H; Y135I+Q258N+T357L; K142R+Q291W+E360D+D369C+E402N; E183M+A243V+D369L+A378K+A475F; R132K+L149M+E385L; D369Y; M234I+E402N+S434P; N437Y; Q119E+N437F; N536K; Q119L+E183Q+G202M+D369P; N112V+I179M+Q291A+D358K+K406D; A123N+Q291W+T540K; D369I+A394L+I428V; A88S+N536K; Q119E+Y135I+N437F; A141F+G202M+E360A+D369P+A378K; A123N+T482A; Q313M+N437D; E360R+D369Y; E183M+G202M+A475F; Q119L+E360A+A394V+A475F; D369L+A378K; E360R+D369L+A394G; M181Y+D369E+S434P; D369I; N112V+Y135Q+I375V+K406D+K530M+P870S; Q119E+Y135I+N220Y+Q258N; D369P+A394V+I428V; V318E+D369L; K186R+N536K; Q119L+D369L+A378K; M234I+D369K+S434P; N112V+I179M+N220L+Q291A+Q381I+S388W+N398G; E402N+S434P; Q119L+A141F+G202M+A394Q; Q313M+T354Q+N437D; N112V+M234E+D369L+I375V+K406D; Q119E+A136E+N220Y; Q381D+A394G+N536K; Q119L+E183G+D369Q+A378T+V390I; Y135I+T357L+Q474I+S489L+Y491F; D369E+A394P+I428V; N112V+Q291A+Q381I+N398G; E360R+N536K; E360D+D369C; R132W+S182L+E385L; I179M+Q291A+D358K+N398G+K530G; N220Y+Q258N+T357L; T224N+D274Y+T357L+N437F; N437D; M234I+E360D+T482A; A141F+G202M+D274N+V318E+E360A+I428V; D369Q; N112V+N220L+D358K+D369L+I375V+Q381I+N398G; Y135I+D369F; A243V+V318E+E360A+A475W; N220L+D369L+Q381L+S388W+N398G+K530G; S489L; K142R+Y219V; Y135I+N220Y+Y491F; S182W+T354Q+E385L; I179M+D358K+S388W; L149M+Q313M+T565P; R132G+E385L; V318E; Q119L+E183K; R132W+E385L; E183G+V318E+E360A+A394Q+A475C; E183M+G202M+E360A; A394G; D369P; Y135M+Q291A+S388W+N398G; Y219V+D369C; A394V+I428V; Q119L; Y135I; E360R+D369Q+Q381D+N536K; N220L+M234E+Q291A+I375V+K530M; Q119L+G202M+E360A; N220Y+Q258N+D369R; M181Y+M234I+Q291W+E402N; A394V; T120M+L149Q+Q313M; Q119L+V318E+I428V; E360R+Q381V; K57R+G202M+E360A+A394V; I179M+D358K+I375V+Q381L; E360A; I179M+R682W; E360A+I428V; and D369K+P374Y (where amino acid position is determined by optimal alignment with SEQ ID NO:2).

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of: I106V+Q258N+Q291W+D369L+E402N+S434P; I106V+Y135Q+Q258N+Q291W+Q313M+D369H+E402N+K495N+G628W; Q258N+Q291W+Q313M+D369R+E402N+S434P+A475L+K495N+G628W; I106V+Q258N+Q291W+Q313M+D369H+E402N+S434P+A475C+K495I+T540K+G628W; I106V+Q258N+Q291W+D369R+E402N+S434P+K495H+G628L; D274Y+Q291W+D358K+D369L+E385L+E402N+N437I+S489N; Q258N+Q291W+Q313M+D369H+E402N+S434P+T540K; I106V+Q258N+Q291W+D369L+E402N+S434P+A475F+K495H+G628V; Q258N+Q291W+Q313M+D369L+E402N+S434P+A475C+K495I+G628W; I106V+Y135Q+M181Y+Q258N+Q291W+Q313M+D369L+E402N+S434P+K495N; Y135Q+Q258N+Q291W+D369L+E402N+K495N; Q119E+D274Y+Q291W+D358K+D369L+E385L+E402N+N437V+S489N+S614A; Y135Q+Q258N+Q291W+Q313M+D369L+E402N+S434P+A475F+K495N+G628V; R132H+Q258N+Q291W+D369Y+E402N+K495Q; Y135Q+Q258N+Q291W+D369L+E402N+S434P+A475F+K495H; Y135Q+Q258N+Q291W+D369R+E402N+S434P+K495I+G628V; I106V+M181Y+Q258N+Q291W+D369L+E402N; I106V+Q258N+Q291W+D369H+E402N+S434P+A475F+K495F+G628V; Q258N+Q291W+Q313M+D369L+E402N+S434P+G628V; Q258N+Q291W+D369L+E402N+A475F+K495I; Q119E+D274Y+Q291W+D369L+E385L+E402N+N437I; Q258N+Q291W+Q313M+D369R+E402N+S434P+A475L; Q258N+Q291W+D369Y+E402N+S434P+K495H+G628W; D274Y+Q291W+D369L+E385L+E402N+N437I+S489N+K530C; I106V+Y135Q+Q258N+Q291W+Q313M+D369Y+E402N+S434P+A475F+K495H+T540K; Q119E+Q291W+D358K+D369L+E385L+E402N; I106V+M181Y+Q258N+Q291W+Q313M+D369H+E402N+S434P+A475L+K495Q+G628V; Q119E+D274Y+Q291W+D358N+D369L+E385L+E402N+N437D; Q258N+Q291W+D369R+E402N+S434P+G628V; Q258N+Q291W+Q313M+D369H+E402N+S434P+G628L; Q258N+Q291W+D369L+E402N; D274Y+Q291W+D358K+D369L+E385L+E402N+N437F+S614D; Q119E+D274Y+Q291W+D358N+D369L+E385L+E402N+N437L+K530V; Q119E+D274Y+Q291W+D358N+D369L+E385L+E402N+N437V+S489L+K530N; Q258N+Q291W+D369L+E402N+S434P+A475F+K495F+T540K; M181Y+Q291W+Q313M+D369Y+E402N; A243V+D274Y+Q291W+D358K+D369L+E402N+N437I+K530C; Q119E+D274Y+Q291W+D358E+D369L+E385L+E402N+N437V+K530V+S614A; Q291W+D358K+D369L+E385L+E402N+N437W+K530C+S614A; Q119E+D274Y+Q291W+D369L+E385L+E402N+N437W; D274Y+Q291W+D358N+D369L+E385L+E402N+N437I+

K530N+S614V; M181Y+Q258N+Q291W+Q313M+D369L+E402N+S434P; A109T+Q291W+D369L+E402N; Q119E+Q291W+D369L+E385L+E402N+N437Y+S489I+K530N; Q119E+Q274Y+Q291W+D358N+D369L+E402N+N437D; D274Y+Q291W+D358K+D369L+E385L+E402N+N437W+K530V+S614D; Q258N+Q291W+D369R+E402N+A475W+K495H+G628V; A109S+Q291W+D369L+E402N; Q119E+D274Y+Q291W+D358E+D369L+E385L+E402N+N437L+S614A; Q291W+D369L+E402N+E493Y+N504Y+T611A; Q119E+D274Y+Q291W+D358K+D369L+E402N+S614V; D274Y+Q291W+D358E+D369L+E385L+E402N+N437L+K530N+S614A; Q258H+Q291W+Q313M+D369R+E402N+A475F+K495N+G628L; Q258N+Q291W+Q313M+D369Y+E402N+A475W+K495V+T540K+G628W; D274Y+Q291W+D358N+D369L+E385L+E402N+N437W+S614V; I106V+Y135Q+Q291W+Q313M+D369L+E402N+A475L+K495Q; Q258N+Q291W+D369R+E402N+S434P+A475F+G628V; Q119E+D274Y+Q291W+D369L+E385L+E402N+N437V; D274Y+Q291W+D358K+D369L+E385L+E402N+N437Y+S489L+K530V; Q119E+D274Y+Q291W+D358N+D369L+E402N; Q291W+D369L+E402N+K495V+S501R+A503E+K530N+T611H; Q119E+D274Y+Q291W+D358N+D369L+E385L+E402N+N437V+S489I+K530C; Q119E+Q291W+D358K+D369L+E402N+N437L+S489N; D274Y+Q291W+D369L+E385L+E402N+N437W+K530C+S614D; Q258N+Q291W+D369R+E402N+A475F+K495N+T540K+G628V; Q291W+D369L+E402N+E493V+N504Y; Q291W+D358E+D369L+E385*+E402N+S489T; Q258N+Q291W+Q313M+D369R+E402N+A475L+K495V+A601T+G628W; D274Y+Q291W+D358N+D369L+E385L+E402N+S489N+S614C; D274Y+Q291W+D358K+D369L+E402N+N437V+S489L+K530C+S614A; Q119E+D274Y+Q291W+D358E+D369L+E402N+N437D; Q119E+D274Y+Q291W+D358N+D369L+E402N+N437L+5614R; D274Y+Q291W+D358N+D369L+E402N+N437Y+K530V; D274Y+Q291W+D358E+D369L+E402N+N437Y+S489N+K530N+S614V+D781N; Q258H+Q291W+D369*+E402N+S434P+T540K+G628L; Q119E+Q291W+D358E+D369L+E385L+E402N+N437L+S489N+K530V; Q258N+Q291W+D369L+E402N+G628V; Q291W+D358K+D369L+E385L+E402N+S489I+K530N; Q119E+Q291W+D369L+E385L+E402N+S489N+K530V+S614A; I106V+Y135Q+Q291W+D369L+E402N+S434P+A475F+K495H+G628L; Q119E+Q291W+D358K+D369L+E402N+N437V+K497R+S614A; Q119E+D274Y+Q291W+D358E+D369L+E385L+E402N+N437L; D274Y+Q291W+D358K+D369L+E402N+N437L+S489I+K530V+S614A; I106V+Q291W+Q313M+D369L+E402N+S434P+A475W+K495N+G628W; Q291W+D369L+E402N+A505C+L620M+T635I; Q291W+D369L+E402N+E493A+N504Y+A505C+L620M+T635A; D274Y+Q291W+D358N+D369L+E402N+S489N+K530C+S614A; D274Y+Q291W+D358K+D369L+E385L+E402N+N437W+K530D; Q291W+D369L+E402N+S489N+K495H+S501R+K530N; D274Y+Q291W+D358E+D369L+E385L+E402N+N437D+K530C+S614H; Q119E+Q291W+D358E+D369L+E385L+E402N+N437W+S489N+K530E+S614A; Q291W+D369L+E402N+E493Y+N504Y+N521C+T591A+R612P+L620M+T635I; Q291W+D358K+D369L+E385L+E402N+N437I+K530M+S614L; Q291W+D369L+E402N+R6721; D274Y+Q291W+D358E+D369L+E385L+E402N+N437L+S489L; A265S+Q291W+D369L+E402N; Q215M+Q291W+D369L+E402N; Q291W+D369L+E402N+E493V+N504Y+N521C+T591A+L620M+T635I; Q119E+D274Y+Q291W+D369L+E385L+E402N+N437L+S489N+K530M+S614D; Q119E+Q291W+D369L+E385L+E402N; Q291W+D369L+E402N+E493A+N504Y+D566G+R612P+L620M+T635A; Q119E+D274Y+Q291W+D369L+E385L+E402N+S614Y; I106V+Y135Q+M181Y+Q258N+Q291W+D369L+E402N; Q119E+Q291W+D358E+D369L+E385L+E402N+N437W+K530V; Q215E+Q291W+D369L+E402N; Q291W+D369L+E402N+N504Y+N521C+T591A+R612H+L620M+T635I; Q119E+D274Y+Q291W+D358K+D369L+E402N+N437Y+K5301; Q258H+Q291W+D369L+E402N+K495N; Q291W+D358N+D369L+E385L+E402N+N437D+S489N+K530I; Q291W+D369L+P374Y+E402N+Y491L+S501R; Q258N+Q291W+Q313M+G332D+D369H+E402N+S434P; Q291W+D358N+D369L+E385L+E402N+N437F+S489L+K530V; Q291W+D369L+E402N+R672S; Q291W+D369L+E402N+T687M; Q291W+F314V+D369L+E402N; Q258N+Q291W+T357A+D369H+E402N+S434P+K495F; Q291W+D369L+P374Y+E402N+Y491F+S501R+N521C; Q291W+D369L+E402N+Q690K; Q291W+D358E+D369L+E385L+E402N+N437F+K530V+S614A; Q291W+D369L+E402N+R672A; Q291W+D369L+E402N+R672T; Q291W+D369L+E402N+D703K; D274Y+Q291W+D369L+E402N; Q291W+D369L+E402N+R672F; Q291W+D369L+E402N+R672D; Q291W+D369L+E402N+Y491F+S501R+N536K+D566G; Q291W+D369L+E402N+A732G; Q291W+D369L+E402N+E493Y+N504Y+N521C+T591C+R612P+L620M; I106V+Y135Q+Q291W+D369L+E402N+A475F+G628W; Q291W+D369L+E402N+R672G; Q291W+D369L+E402N+T777N; Q291W+Q313M+D369L+E402N+T540K; Q291W+D369L+E402N+K708F; Q291W+D369L+P374Y+E402N+S501H; Q291W+D369L+E402N+Y715P; Q291W+D369L+E402N+A732M; Q291W+D369L+E402N+E493A+N504Y+N521C+D566G+R612P+L620M; Q291W+D369L+E402N+Q690R; D274Y+Q291W+D369L+E385L+E402N+N437V+K530I+S614D; Q291W+D369L+E402N+L757K; Q291W+D369L+E402N+T687Y; Q291W+D369L+E402N+Y491H+S501R+N521C+T591A; Q291W+D369L+E402N+V775C; Q291W+D369L+E402N+R672V; Q291W+D369L+E402N+N670D; Q291W+D369L+E402N+T779S; Q291W+D369L+E402N+V638R; Q291W+D369L+E402N+T687F; Q291W+D369L+E402N+T687L; Q291W+D369L+E402N+K610S; Q291W+D369L+E402N+Y491L+S501R+N521C; D274Y+Q291W+D358E+D369L+E402N+K530V+S614V; I106V+M181Y+Q258N+Q291W+D369R+E402N+S434P+A475W+K495V+T540K+G628V; Q291W+D369L+E402N+N536K; Q291W+D369L+E402N+E493V+N504Y+R612P+L620M; Q291W+D369L+E402N+S676C; Q291W+D369L+E402N+T540K+G628W; Q291W+D369L+E385L+E402N+N437D+S489L+K530C+S614D; Q119E+D274Y+Q291W+D358N+D369L+E402N+N437F+S489N+S614L; Q291W+D369L+E402N+S434P+A475W+K495V; Q291W+D369L+E402N+A689I; Q291W+D369L+E402N+E493A+N504Y+N521C+D566G+R612H+L620M; Q291W+D369L+E402N+V638S; Q291W+D369L+E402N+V648W; Q291W+D369L+E402N+D650V; Q291W+D369L+E402N+V674M; Q291W+D369L+E402N+V638E; I106V+Q291W+D369L+E402N; Y135Q+Q291W+D369L+E402N; Q291W+D369L+E402N+S764F; Q291W+D369L+E402N+E493A+N504Y+A505C+N521C+T591A+R612P; Q291W+D369L+E402N+S489N+K495Q+S501R+K530N+T611Q; Q291W+D369L+E402N+T685V; I106V+Q291W+D369L+E402N+S434P+A475C+K495N+T540K; Q119E+Q291W+D358N+D369L+E402N+N437D+K530N+S614V; Q291W+D369L+E402N+T687K; Q291W+D369L+

E402N+S652D; Q291W+D369R+E402N+A475F+K495Q+ T540K+G628L; Y135Q+Q291W+D369L+E402N+G628V; Q291W+D369L+E402N+E493Y+A505C+N521C+ T591A+L620M; Q291W+D369L+E402N+T687W; Q291W+D369L+E402N+D650F; Q291W+D369L+ E402N+T687C; Q291W+D369L+E402N+S434P+K495N+ G628V; Q291W+D369L+E402N+S501N; D274Y+ Q291W+D369L+E402N+N437K+S489I+K530V+S614L

E21Q+Q258N+Q291W+Q313M+D369R+Q381V+ E402N+S434P+A475L+K495N+G628W; Q258N+L275Y+ Q291W+Q313M+D369R+E402N+S434P+A475L+ K495N+G628W; Q258N+Q291W+Q313M+D369R+ E402N+S434P+A475L+K495N+A505C+G628W; E21R+ Q258N+Q291W+Q313M+D369R+E402N+S434P+ A475L+K495N+G628W; V25A+Q258N+Q291W+ Q313M+D369R+E402N+S434P+A475L+K495N+G628W; H26R+Q258N+Q291W+Q313M+D369R+E402N+S434P+ A475L+K495N+G628W; L30K+Q258N+Q291W+ Q313M+D369R+E402N+S434P+A475L+K495N+G628W; N45H+Q258N+Q291W+Q313M+D369R+E402N+S434P+ A475L+K495N+G628W; Q258N+Q291W+Q313M+D369R+E402N+S434P+A475L+E493V+K495N+G628W; P29R+Q258N+Q291W+Q313M+D369R+E402N+S434P+A475L+K495N+G628W; P29M+Q258N+Q291W+Q313M+D369R+E402N+S434P+A475L+K495N+G628W+A732S+A748T+V840I; Q55R+Q258N+Q291W+Q313M+D369R+E402N+S434P+A475L+K495N+G628W; K24G+Q258N+Q291W+Q313M+D369R+E402N+S434P+A475L+K495N+G628W; G180E+Q258N+Q291W+Q313M+D369R+E402N+S434P+A475L+K495N+G628W; Q258N+Q291W+Q313M+D369R+E402N+S434P+K495N+G628W; Q258N+Q291W+Q313M+D369R+E402N+S434P+A475L+Q479R+K495N+S501R+G628W+Y715P+E819L; A79E+Q258N+Q291W+Q313M+D369R+E402N+S434P+A475L+K495N+G628W; Q258N+Q291W+Q313M+D369R+E402N+S434P+A475L+K495N+G628W+R672G; Q258N+Q291W+Q313M+F314V+D369R+E402N+S434P+A475L+K495N+A505C+G628W; Q258N+Q291W+Q313M+D369R+E402N+S434P+A475L+K495N+G628W+T687K; Q27R+Q258N+Q291W+Q313M+D369R+E402N+S434P+A475L+K495N+G628W; V253F+Q258N+Q291W+Q313M+D369R+E402N+S434P+A475L+K495N+G628W; S22L+Q258N+Q291W+Q313M+D369R+E402N+S434P+A475L+K495N+G628W; Q258N+Q291W+Q313M+D369R+E402N+S434P+A475L+K495N+G628W+Q690H; Q258N+Q291W+Q313M+D369R+E402N+S434P+A475L+K495N+G628W+S799N; Q258N+Q291W+Q313M+F314V+E360D+D369R+E402N+S434P+A475L+K495N+G628W; Q258N+Q291W+Q313M+D369R+E402N+S434P+A475L+K495N+G628W+E822M; K24T+Q258N+Q291W+Q313M+D369R+E402N+S434P+A475L+K495N+G628W; Q258N+Q291W+Q313M+D369R+E402N+S434P+A475L+K495N+G628W+S787G; Q258N+Q291W+Q313M+D369R+E402N+S434P+A475L+K495N+R612H+G628W+L757K+S787G; S22L+Q258N+Q291W+Q313M+D369R+E402N+S434P+A475L+Q479R+K495N+G628W; Q258N+Q291W+Q313M+D369R+E402N+S434P+A475L+K495N+G628W+T687K+E822M; Q258N+Q291W+Q313M+D369R+E402N+S434P+M454E+A475L+K495N+G628W; Q258N+Q291W+Q313M+D369R+E402N+S434P+A475L+K495N+V562C+G628W; S22R+Q258N+Q291W+Q313M+D369R+E402N+S434P+A475L+K495N+G628W; V25G+Q258N+Q291W+Q313M+D369R+E402N+S434P+A475L+K495N+G628W; Q258N+Q291W+Q313M+D369R+E402N+S434P+A475L+K495N+G628W+T685V; Q258N+Q291W+Q313M+D369R+E402N+A404S+S434P+A475L+K495N+G628W; G216L+Q258N+Q291W+Q313M+D369R+E402N+S434P+A475L+K495N+G628W; V25R+Q258N+Q291W+Q313M+D369R+E402N+S434P+A475L+K495N+G628W; V25G+Q258N+Q291W+Q313M+D369R+E402N+S434P+A475L+K495N+G628W; Q27H+Q258N+Q291W+Q313M+D369R+E402N+S434P+A475L+K495N+G628W; K24L+Q258N+Q291W+Q313M+D369R+E402N+S434P+A475L+K495N+G628W; Q258N+Q291W+Q313M+D369R+E402N+S434P+A475L+K495N+G628W+D650F+L757K; Q258N+Q291W+Q313M+D369R+E402N+S434P+A475L+T482A+K495N+G628W; Q258N+Q291W+Q313M+D369R+E402N+S434P+A475L+K495N+A617V+G628W; Q258N+Q291W+Q313M+D369R+E402N+S434P+A475L+K495N+S501C+G628W; Q258N+Q291W+Q313M+D369R+E402N+S434P+K495N+N536K+G628W+R817P; G180E+Q258N+Q291W+Q313M+D369R+E402N+S434P+A475L+R476Q+K495N+G628W; Q258N+Q291W+Q313M+D369R+E402N+S434P+A475L+K495N+G628W+T777N; Q119E+Q258N+Q291W+Q313M+D369R+E402N+S434P+A475L+K495N+G628W; A109S+Q258N+Q291W+Q313M+D369R+E402N+S434P+K495N+G628W+S848N; Q258N+Q291W+Q313M+D369R+E402N+S434P+A475L+K495N+G628W+Y850H; Q258N+Q291W+Q313M+D369R+E402N+S434P+P436E+A475L+K495N+G628W; Q258N+Q291W+Q313M+D369R+E402N+S434P+A475L+K495N+G628W+R769H+E819A; Q258N+Q291W+Q313M+D369R+E402N+S434P+A475L+K495N+T496A+G628W; Q258N+V260L+Q291W+Q313M+D369R+E402N+S434P+A475L+K495N+G628W; D244H+Q258N+Q291W+Q313M+D369R+E402N+S434P+A475L+K495N+G628W; Q258N+Q291W+Q313M+D369R+E402N+S434P+A475L+K495N+G628W+E819V; Q258N+Q291W+Q313M+D369R+E402N+S434P+A475L+K495N+G628W+S652D; Q258N+Q291W+D311N+Q313M+D369R+E402N+S434P+A475L+K495N+R612H+G628W+A689I+K866I; Q258N+Q291W+Q313M+D369R+E402N+S434P+A475L+K495N+G628W+T783H; Q258N+Q291W+Q313M+D369R+E402N+S434P+A475L+K495N+G628W+T823K; Q258N+Q291W+Q313M+D369R+E402N+S434P+A475L+K495N+G628W+D650N+S787G; Q258N+Q291W+Q313M+D369R+E402N+S434P+A475L+K495N+G628W+K708F; Q258N+Q291W+Q313M+E360D+D369R+E402N+S434P+A475L+K495N+G628W+S652D; Q258N+Q291W+Q313M+D369R+E402N+S434P+A475L+K495N+G628W+E822G; L237Y+Q258N+Q291W+Q313M+D369R+E402N+S434P+A475L+K495N+G628W; Q258N+Q291W+Q313M+D369R+E402N+S434P+A475L+E494K+K495N+G628W; Q258N+Q291W+Q313M+E360D+D369R+E402N+S434P+D470N+A475L+K495N+G628W+L757K; Q258N+Q291W+Q313M+D369R+E402N+S434P+A475L+K495N+G628W+S764F; Q258N+Q291W+Q313M+D369R+E402N+S434P+A475L+K495N+G628W+D650F; Q258N+Q291W+Q313M+D369R+E402N+S434P+A475L+K495N+G628W+S848N; Q258N+Q291W+Q313M+D369R+E402N+S434P+A475L+K495N+T496A+N536K+G628W; Q258N+Q291W+Q313M+D369R+E402N+K421R+S434P+A475L+K495N+G628W+T777N; Q258N+Q291W+Q313M+D369R+E402N+S434P+A475L+K495N+N627H+G628W+E822M; Q258N+Q291W+Q313M+D369R+E402N+S434P+A475L+K495N+G628W+F634A; A4V+Q258N+Q291W+Q313M+D369R+E402N+S434P+A475L+K495N+G628W; Q258N+Q291W+Q313M+D369R+E402N+S434P+N437W+A475L+K495N+G628W; Y135Q+Q258N+Q291W+Q313M+D369R+E402N+S434P+A475L+K495N+G628W; Y135Q+Q258N+Q291W+Q313M+D369R+E402N+S434P+A475L+K495N+G628W+V673A+T685V; Q258N+Q291W+Q313M+D369R+E402N+S434P+A475L+K495N+G628W+L757K+P806L; Q258N+Q291W+Q313M+D369R+E402N+S434P+A475L+K495N+V559T+

G628W; Y135M+Q258N+Q291W+Q313M+D369R+ E402N+S434P+A475L+K495N+G628W; Q258N+ Q291W+Q313M+D369R+E402N+S434P+A475L+ K495N+G628W+V775C; Q258N+Q291W+Q313M+ D369R+E402N+S434P+A475L+K495N+N627H+G628W; Q258N+Q291W+Q313M+D369R+E402N+A405T+ S434P+A475L+K495N+G628W; I221V+Q258N+Q291W+ Q313M+D369R+E402N+S434P+A475L+K495N+G628W; Q258N+Q291W+Q313M+D369R+E402N+S434P+ A475L+K495N+S501R+G628W+T685V; Q258N+ Q291W+Q313M+D369R+A394G+E402N+S434P+ A475L+K495N+G628W+L757K; P161S+Q258N+Q291W+Q313M+D358K+D369R+E402N+S434P+A475L+K495N+G628W; Q258N+Q291W+Q313M+D369R+E402N+S434P+A475L+K495N+G616D+G628W; Q258N+Q291W+Q313M+D369R+E402N+S434P+A475L+K495N+G628W+K807R; Q258N+Q291W+Q313M+D369R+E402N+S434P+A475L+K495N+G628W+A732M; Q258N+Q291W+Q313M+D369R+E402N+S434P+A475L+K495N+A505C+G628W+E822G; Q258N+Q291W+Q313M+D369R+E402N+S434P+A475L+E493V+K495N+G628W+S652D; A15V+Q258N+Q291W+Q313M+D369R+E402N+S434P+A475L+K495N+G628W; Q258N+Q291W+Q313M+D369R+E402N+S434P+A475L+K495N+G628W+K866Q; Q258N+Q291W+Q313M+D369R+E402N+S434P+A475L+E493A+K495N+G628W+S652D+Q690A; Q258N+Q291W+Q313M+D369R+E402N+S434P+A475L+K495N+G628W+E819L; Q258N+Q291W+Q313M+D369R+E402N+S434P+A475L+K495N+G628W+E819V; G180E+Q258N+Q291W+Q313M+D369R+E385L+E402N+S434P+A475L+K495N+G628W; Q258N+Q291W+Q313M+D369R+E402N+S434P+A475L+K495N+G628W+D751N; G202M+Q258N+Q291W+Q313M+D369R+E402N+S434P+A475L+K495N+N627H+G628W+T687K+E822A; Q258N+Q291W+Q313M+D369R+E402N+S434P+A475L+K495N+G628W+K866I; Q258N+Q291W+Q313M+D369R+E402N+S434P+A475L+K495N+G628W+T783Q; Q258N+Q291W+Q313M+D369L+E402N+S434P+A475L+K495N+G628W; Q258N+Q291W+Q313M+D369R+E402N+S434P+A475L+E493Y+K495N+A505C+G628W; Q258N+Q291W+Q313M+D369R+E402N+S434P+A475L+T482A+K495N+G628W+D646N; Q258N+Q291W+Q313M+D369R+E402N+S434P+A475L+A477G+K495N+G628W+S764F+S848N; Q258N+Q291W+Q313M+D369R+E402N+S434P+A475L+K495N+G628W+I847T; Q258N+Q291W+Q313M+D369R+E402N+S434P+A475L+K495N+G628W+T685V+Y850Q; Y135M+Q258N+Q291W+Q313M+D369R+E402N+S434P+A475L+K495N+S501R+G628W+T685V+T777N; and Q258N+Q291W+Q313M+D369R+E402N+S434P+A475L+K495N+G628W+Y850Q; (where amino acid position is determined by optimal alignment with SEQ ID NO:2).

In some embodiments, the isolated and/or recombinant β-glucosidase polypeptide variant of the present invention is at least about 70% identical to WT C1 Bgl1 (residues 20-870 of SEQ ID NO:2) and comprises a substitution set selected from the group consisting of:

Q258N+Q291W+Q313M+D369R+E402N+S434P+A475L+K495N+G628W+A689I+Y715P; D47I+Q258N+Q291W+Q313M+A343C+D369R+E402N+S434P+A475L+K495N+G628W+T687K+A689I+Y715P; A109S+Q258N+V260G+Q291W+Q313M+A343C+D369R+E402N+S434P+A475L+K495N+G628W+A689I+Y715P; A109T+Q258N+V260G+Q291W+Q313M+A343C+D369R+E402N+S434P+A475L+K495N+G628W+T687W+A689I+Y715P+S764F; D47I+Q258N+V260G+Q291W+Q313M+A343C+D369R+E402N+S434P+A475L+K495N+G628W+T687C+A689I+Y715P+S764F; Q258N+V260G+Q291W+Q313M+A343C+D369R+E402N+S434P+A475L+K495N+G628W+A689I+Y715P; D47I+Q258N+V260G+Q291W+Q313M+D369R+E402N+S434P+A475L+K495N+G628W+T687C+A689I+Y715P; D47I+A109T+Q258N+V260G+Q291W+Q313M+A343C+D369R+E402N+S434P+A475L+K495N+G628W+A689I+Y715P; Q258N+V260G+Q291W+Q313M+D369R+E402N+S434P+A475L+K495N+G628W+T687W+A689I+Y715P; Q258N+V260G+Q291W+Q313M+A343C+D369R+E402N+S434P+A475L+K495N+G628W+A689I+Y715P+S764F; Q258N+V260G+Q291W+Q313M+D369R+E402N+S434P+A475L+K495N+G628W+A689I+Y715P+A732G; D47I+A109T+Q258N+V260G+Q291W+Q313M+A343C+D369R+E402N+S434P+A475L+K495N+G628W+A689I+Y715P+S764F; Q258N+V260G+Q291W+Q313M+A343C+D369R+E402N+S434P+A475L+K495N+G628W+A689I+Y715P+S764F; D47I+A109T+Q258N+V260G+Q291W+Q313M+A343C+D369R+E402N+S434P+A475L+K495N+G628W+A689I+Y715P+S764F; D47I+A109T+Q258N+V260G+Q291W+Q313M+A343C+D369R+E402N+S434P+A475L+K495N+G628W+A689I+Y715P; A109T+Q258N+V260G+Q291W+Q313M+A343C+D369R+E402N+S434P+A475L+K495N+G628W+T687C+A689I+Y715P; D47I+I106V+Q258N+V260G+Q291W+Q313M+F314L+D369R+E402N+S434P+A475L+K495N+G628W+A689I+Y715P+A732G; Q258N+Q291W+Q313M+A343C+D369R+E402N+S434P+A475L+K495N+G628W+T687W+A689I+Y715P; I106V+Q258N+V260G+Q291W+Q313M+F314L+D369R+E402N+S434P+K495N+G628W+A689I+Y715P+A732G; Q258N+V260G+Q291W+Q313M+F314L+D369R+E402N+S434P+A475L+K495N+G628W+A689I+Y715P; D47I+A109S+Q258N+V260G+Q291W+Q313M+A343C+D369R+E402N+S434P+A475L+K495N+G628W+T687W+A689I+Y715P; Q258N+V260G+Q291W+Q313M+F314V+D369R+E402N+S434P+A475L+K495N+G628W+S652D+A689I+Y715P+A732G; Q258N+V260G+Q291W+Q313M+A343C+D369R+E402N+S434P+A475L+K495N+G628W+A689I+Y715P; I106V+Q258N+V260G+Q291W+Q313M+F314V+D369R+E402N+S434P+A475L+K495N+G628W+S652D+A689I+Y715P+A732G; Q258N+V260G+Q291W+Q313M+A343C+D369R+E402N+S434P+A475L+K495N+G628W+A689I+Y715P+S764F; D47I+Q258N+V260G+Q291W+Q313M+A343C+D369R+E402N+S434P+A475L+K495N+G628W+A689I+Y715P; I106V+Q258N+V260G+Q291W+Q313M+F314L+D369R+E402N+S434P+A475L+K495N+G628W+S652D+A689I+Y715P+A732M; A109T+Q258N+V260G+Q291W+Q313M+D369R+E402N+S434P+A475L+K495N+G628W+A689I+Y715P+S764F; Q258N+V260G+Q291W+Q313M+A343C+D369R+E402N+S434P+A475L+K495N+G628W+A689I+Y715P; Q258N+V260G+Q291W+Q313M+A343G+D369R+E402N+S434P+Q474L+A475L+K495N+G628W+A689I+Y715P; D47I+Q258N+V260G+Q291W+Q313M+A343C+D369R+E402N+S434P+A475L+K495N+G628W+A689I+Y715P+S764F; D47I+A109T+Q258N+V260G+Q291W+Q313M+D369R+E402N+S434P+A475L+K495N+G628W+A689I+Y715P+S764F; Q258N+V260G+Q291W+Q313M+A343C+D369R+E402N+S434P+A475L+K495N+G628W+A689I+Y715P+S764F; D47I+A109T+Q258N+V260G+Q291W+Q313M+A343C+D369R+E402N+S434P+A475L+K495N+

G628W+A689I+Y715P; Q258N+V260G+Q291W+ Q313M+A343C+D369R+E402N+S434P+A475L+K495N+ G628W+A689I+Y715P+S764F; Q258N+V260G+Q291W+ Q313M+D369R+E402N+S434P+A475L+K495N+ G628W+A689I+Y715P; D47I+Q258N+V260G+Q291W+ Q313M+A343C+D369R+E402N+S434P+A475L+K495N+ G628W+A689I+Y715P; Q258N+V260G+Q291W+ Q313M+D369R+E402N+S434P+A475L+K495N+ G628W+A689I+Y715P; A109T+Q258N+V260G+ Q291W+Q313M+A343C+D369R+E402N+S434P+ A475L+K495N+G628W+A689I+Y715P; I106V+Q258N+ V260G+Q291W+Q313M+D369R+E402N+S434P+ A475L+K495N+G628W+A689I+Y715P+A732G+P870S; Q258N+V260G+Q291W+Q313M+D369R+E402N+ S434P+A475L+K495N+G628W+A689I+Y715P; I106V+ Q258N+V260G+Q291W+Q313M+F314V+D369R+ E402N+S434P+A475L+K495N+G628W+A689I+Y715P+ A732M; Q258N+Q291W+Q313M+F314V+D369R+ E402N+S434P+A475L+K495N+G628W+A689I+Y715P+A732G; I106V+Q258N+V260G+Q291W+Q313M+D369R+E402N+S434P+A475L+K495N+G628W+A689I+Y715P+A732V; Q258N+V260G+Q291W+Q313M+A343C+D369R+E402N+S434P+A475L+K495N+G628W+A689I+Y715P; Q258N+V260G+Q291W+Q313M+A343C+D369R+E402N+S434P+A475L+K495N+G628W+A689I+Y715P; D47I+I106V+Q258N+Q291W+Q313M+F314L+D369R+E402N+S434P+A475L+K495N+G628W+A689I+Y715P+A732G; Q258N+V260G+Q291W+Q313M+D369R+E402N+S434P+A475L+K495N+G628W+A689I+Y715P; Q258N+V260G+Q291W+Q313M+D369R+E402N+S434P+A475L+K495N+G628W+A689I+Y715P; Q258N+V260G+Q291W+Q313M+D369R+E402N+S434P+K495N+G628W+S652D+A689I+Y715P+A732G; D47I+I106V+Q258N+V260G+Q291W+Q313M+D369R+E402N+S434P+K495N+G628W+S652D+A689I+Y715P+A732G; D47I+I106V+Q258N+V260G+Q291W+Q313M+D369R+E402N+S434P+K495N+G628W+S652D+A689I+Y715P; Q258N+V260G+Q291W+Q313M+A343C+D369R+E402N+S434P+A475L+K495N+G628W+A689I+Y715P; C8A+L9F+D47I+Q258N+V260G+Q291W+Q313M+D369R+E402N+S434P+K495N+G628W+A689I+Y715P+A732G; D47I+Q258N+V260G+Q291W+Q313M+F314V+D369R+E402N+S434P+A475L+K495N+G628W+A689I+Y715P+A732G+D844G; Q258N+V260G+Q291W+Q313M+D369R+E402N+S434P+A475L+K495N+G628W+A689I+Y715P; I106V+Q258N+V260G+Q291W+Q313M+D369R+E402N+S434P+A475L+K495N+G628W+A689I+Y715P+A732G; D47N+Q258N+V260G+Q291W+Q313M+F314V+D369R+E402N+S434P+A475L+K495N+G628W+A689I+Y715P+A732G; Q258N+V260G+Q291W+Q313M+D369R+E402N+S434P+A475L+K495N+G628W+A689I+Y715P; D47I+I106V+Q258N+Q291W+Q313M+D369R+E402N+S434P+A475L+K495N+G628W+S652D+A689I+Y715P+A732M; A109T+Q258N+Q291W+Q313M+D369R+E402N+S434P+A475L+K495N+G628W+T687W+A689I+Y715P; Q258N+V260G+Q291W+Q313M+A343C+D369R+E402N+S434P+A475L+K495N+G628W+A689I+Y715P; V25A+Q258N+Q291W+Q313M+D369R+E402N+S434P+A475L+K495N+G628W+A689I+Y715P; D47I+Q258N+V260G+Q291W+Q313M+D369R+E402N+S434P+A475L+K495N+G628W+A689I+Y715P+A732M; Q258N+Q291W+Q313M+D369R+E402N+S434P+A475L+K495N+G628W+T687W+A689I+Y715P; D47I+I106V+Q258N+V260G+Q291W+Q313M+F314V+D369R+E402N+S434P+A475L+K495N+G628W+S652D+A689I+Y715P; D47I+A109T+Q258N+Q291W+Q313M+A343C+D369R+E402N+S434P+A475L+K495N+G628W+A689I+Y715P; D47I+Q258N+Q291W+Q313M+A343C+D369R+E402N+S434P+A475L+K495N+G628W+A689I+Y715P+S764F; Q258N+V260G+Q291W+Q313M+D369R+E402N+S434P+A475L+K495N+G628W+T687K+A689I+Y715P; A109T+Q258N+Q291W+Q313M+A343C+D369R+E402N+S434P+A475L+K495N+G628W+A689I+Y715P+S764F; Q258N+V260G+Q291W+Q313M+D369R+E402N+S434P+A475L+K495N+G628W+A689I+Y715P; D47I+I106V+Q258N+V260G+Q291W+Q313M+D369R+E402N+S434P+A475L+K495N+G628W+A689I+Y715P; Q258N+V260G+Q291W+Q313M+D369R+E402N+S434P+A475L+K495N+G628W+A689I+Y715P+S764F; Q258N+V260G+Q291W+Q313M+F314L+D369R+E402N+S434P+K495N+G628W+S652D+A689I+Y715P; Q258N+V260G+Q291W+Q313M+D369R+E402N+S434P+A475L+K495N+G628W+A689I+Y715P; Q258N+V260G+Q291W+Q313M+A343C+D369R+E402N+S434P+A475L+K495N+G628W+A689I+Y715P; Q258N+Q291W+Q313M+D369R+E402N+S434P+A475L+K495N+G628W+A689I+Y715P+S764F; Q258N+V260G+Q291W+Q313M+F314V+D369R+E402N+S434P+K495N+G628W+A689I+Y715P; L237Y+Q258N+V260G+Q291W+Q313M+A343C+D369R+E402N+S434P+A475L+K495N+G628W+A689I+Y715P; Q258N+V260G+Q291W+Q313M+D369R+E402N+S434P+A475L+K495N+G628W+A689I+Y715P; Q258N+V260G+Q291W+Q313M+D369R+E402N+S434P+A475L+K495N+G628W+A689I+Y715P; Q258N+V260G+Q291W+Q313M+D369R+E402N+S434P+A475L+K495N+G628W+A689I+Y715P; Q85N+Q258N+Q291W+Q313M+D369R+E402N+S434P+A475L+K495N+G628W+A689I+Y715P+L757K; Q258N+V260G+Q291W+Q313M+D369R+E402N+S434P+A475L+K495N+G628W+A689I+Y715P; Q258N+V260G+Q291W+Q313M+D369R+E402N+S434P+A475L+K495N+G628W+A689I+Y715P; Q258N+V260G+Q291W+Q313M+D369R+E402N+S434P+A475L+K495N+S604C+G628W+A689I+Y715P; D47I+Q258N+V260G+Q291W+Q313M+D369R+E402N+S434P+A475L+R476G+K495N+N588F+G628W+D651E+A689I+Y715P; Q85N+Q258N+Q291W+Q313M+D369R+E402N+S434P+P436Q+A475L+K495N+G628W+A689I+Y715P+L757K; I106V+Q258N+Q291W+Q313M+D369R+E402N+S434P+A475L+K495N+G628W+A689I+Y715P+A732M; Q258N+V260G+Q291W+Q313M+D369R+E402N+S434P+A475L+K495N+G628W+A689I+Y715P; Q258N+V260G+Q291W+Q313M+F314L+D369R+E402N+S434P+A475L+K495N+G628W+A689I+Y715P; Q258N+Q291W+Q313M+D369R+E402N+S434P+K495N+G628W+S652D+A689I+Y715P+A732G; A109T+Q258N+Q291W+Q313M+A343C+D369R+E402N+S434P+A475L+K495N+G628W+A689I+Y715P; D47I+Q258N+Q291W+Q313M+F314L+D369R+E402N+S434P+A475L+K495N+G628W+A689I+Y715P+Y736N; Q258N+Q291W+Q313M+F314L+D369R+E402N+S434P+A475L+K495N+G628W+S652D+A689I+Y715P+A732G; V25A+Q85N+Q258N+Q291W+Q313M+D369R+E402N+S434P+P436Q+A475L+K495N+G616D+G628W+D650Y+A689I+Y715P+L757K; Q258N+Q291W+Q313M+D369R+E402N+S434P+A475L+K495N+G628W+A689I+Y715P+S764F; V253F+Q258N+Q291W+Q313M+D369R+E402N+S434P+A475L+K495N+G628W+A689I+Q690K+D709E+E710G+Y715P; Q85N+V175A+Q258N+L275Y+Q291W+Q313M+D369R+

E402N+S434P+A475L+K495N+G628W+A689I+Y715P; Q258N+Q291W+Q313M+D369R+E402N+S434P+ A475L+K495N+G628W+A689I+Q690K+Y715P; V25A+ Q85N+Q258N+Q291W+Q313M+D369R+E402N+S434P+ A475L+K495N+G616D+G628W+A689I+Y715P+L757K; Q85N+Q258N+Q291W+Q313M+D369R+E402N+S434P+A475L+K495N+G628W+A689I+Y715P; V25A+Q85N+Q258N+Q291W+Q313M+D369R+E402N+S434P+A475L+K495N+G628W+A689I+Y715P; Q258N+Q291W+Q313M+D369R+E402N+S434P+A475L+K495N+G628W+T687C+A689I+Y715P; Q258N+Q291W+Q313M+D369R+E402N+S434P+A475L+K495N+G628W+A689I+Q690H+Y715P+M816L; V25A+Q85N+Q258N+L275Y+Q291W+Q313M+D369R+E402N+S434P+A475L+K495N+G616D+G628W+A689I+Y715P+V846F; Q258N+Q291W+Q313M+D369R+E402N+S434P+A475L+K495N+G628W+A689I+Y715P+V846Q; A79E+Q258N+Q291W+Q313M+D369R+E402N+S434P+A475L+K495N+G626D+G628W+A689I+Y715P; Q258N+Q291W+Q313M+A343C+D369R+E402N+S434P+A475L+K495N+G628W+A689I+Y715P; A79E+Q258N+Q291W+Q313M+D369R+E402N+S434P+A475L+K495N+A505C+G628W+A689I+Y715P; Q258N+Q291W+Q313M+F314L+D369R+Q381V+E402N+S434P+A475L+K495N+G628W+A689I+Y715P; D47I+I106V+Q258N+V260G+Q291W+Q313M+D369R+E402N+S434P+A475L+K495N+G628W+A689I+Y715P; Q85N+Q258N+Q291W+Q313M+D369R+E402N+S434P+A475L+K495N+G628W+A689I+Y715P; V25A+Q85N+Q258N+Q291W+Q313M+D369R+E402N+S434P+P436Q+A475L+K495N+G628W+A689I+Y715P+L757K+V846Q; V25A+Q85N+Q258N+Q291W+Q313M+D369R+E402N+S434P+P436Q+A475L+K495N+G628W+D650N+A689I+Y715P; D47I+I106V+Q258N+V260G+Q291W+Q313M+D369R+E402N+S434P+A475L+K495N+S550C+G628W+S652D+A689I+Y715P+A732G; A109S+Q258N+V260G+Q291W+Q313M+D369R+E402N+S434P+A475L+K495N+S604A+G628W+A689I+Y715P; V25A+Q85N+Q258N+Q291W+Q313M+D369R+E402N+S434P+A475L+K495N+G628W+A689I+Y715P+V846Q; D47I+Q258N+V260G+Q291W+Q313M+D369R+E402N+S434P+A475L+K495N+G628W+A689I+Y715P; A109T+Q258N+Q291W+Q313M+D369R+E402N+S434P+A475L+K495N+G628W+A689I+Y715P; Q258N+V260G+Q291W+Q313M+F314L+D369R+E402N+S434P+K495N+N588F+G628W+A689I+Y715P+A732M; Q85N+Q258N+Q291W+Q313M+D369R+E402N+S434P+A475L+K495N+G616D+G628W+A689I+Y715P; V25A+Q85N+Q258N+Q291W+Q313M+D369R+E402N+S434P+P436Q+A475L+K495N+G616D+G628W+D650N+A689I+Y715P; A79E+Q258N+Q291W+Q313M+D369R+E402N+S434P+A475L+K495N+A505C+G628W+V674I+A689I+Y715P; V25A+Q258N+Q291W+Q313M+D369R+E402N+S434P+A475L+K495N+G628W+A689I+Y715P+L757K; V25A+Q85H+Q258N+L275F+Q291W+Q313M+D369R+E402N+S434P+A475L+K495N+G628W+D650N+A689I+Y715P+L7571; K24T+A79E+A136L+Q258N+D274Y+Q291W+Q313M+D369R+E402N+S434P+A475L+K495N+A505C+G628W+A689I+Y715P; V25A+Q85N+Q258N+Q291W+Q313M+D369R+E402N+S434P+A475L+K495N+G628W+A689I+Y715P; Q258N+Q291W+Q313M+D369R+E402N+S434P+A475L+K495N+G628W+A689I+Y715P; Q258N+Q291W+Q313M+D369R+E402N+S434P+A475L+K495N+G628W+A689I+Y715P; K24G+A79E+Q258N+D274Y+Q291W+Q313M+D369R+E402N+S434P+A475L+K495N+A505C+G628W+A689I+Y715P; Q85N+V175A+Q258N+Q291W+Q313M+D369R+E402N+S434P+A475L+K495N+G628W+A689I+Y715P; V25A+Q85N+Q258N+Q291W+Q313M+D369R+E402N+S434P+A475L+K495N+G628W+D650N+A689I+Y715P; V25A+Q85N+Q258N+L275Y+Q291W+Q313M+D369R+E402N+S434P+A475L+K495N+G628W+A689I+Y715P+L757K; A79M+Q258N+Q291W+Q313M+D369R+E402N+S434P+A475L+K495N+A505C+G628W+A689I+Y715P; Q85N+Q258N+Q291W+Q313M+D369R+E402N+S434P+P436Q+A475L+K495N+G628W+A689I+Y715P+; Q85N+Q258N+Q291W+Q313M+D369R+E402N+S434P+A475L+K495N+G628W+A689I+Y715P; Q85N+Q258N+Q291W+Q313M+D369R+E402N+S434P+A475L+K495N+G628W+A689I+Y715P; Q258N+Q291W+Q313M+D369R+E402N+S434P+A475L+K495N+G628W+A689I+Y715P; Q258N+Q291W+Q313M+A343C+D369R+E402N+S434P+A475L+K495N+G628W+A689I+Y715P; Q258N+Q291W+Q313M+D369R+E402N+S434P+A475L+K495N+G628W+A689I+Y715P; Q258N+Q291W+Q313M+D369R+E402N+S434P+A475L+K495N+G628W+A689I+Y715P; Q258N+Q291W+Q313M+D369R+E402N+S434P+A475L+K495N+G628W+A689I+Y715P; Q85N+Q258N+Q291W+Q313M+D369R+E402N+S434P+A475L+K495N+G628W+A689I+Y715P; I106V+Q258N+Q291W+Q313M+D369R+E402N+S434P+A475L+K495N+G628W+A689I+Y715P; D47I+Q258N+V260G+Q291W+Q313M+D369R+E402N+S434P+A475L+K495N+S604A+G628W+A689I+Y715P; Q258N+Q291W+Q313M+D369R+E402N+S434P+A475L+K495N+G628W+A689I+Y715P; Q258N+Q291W+Q313M+D369R+E402N+S434P+A475L+K495N+G628W+A689I+Y715P; V25A+Q258N+Q291W+Q313M+D369R+E402N+S434P+A475L+K495N+G628W+A689I+Y715P; Q258N+V260G+Q291W+Q313M+A343C+D369R+E402N+S434P+Q474I+A475L+K495N+G628W+A689I+Y715P+S764F; Q258N+Q291W+Q313M+A343C+D369R+E402N+S434P+A475L+K495N+G628W+A689I+Y715P; D47I+Q258N+Q291W+Q313M+D369R+E402N+S434P+A475L+K495N+N588F+G628W+A689I+Y715P; S58G+Q258N+Q291W+Q313M+D369R+Q381V+E402N+S434P+A475L+K495N+G628W+A689I+Y715P; V253F+Q258N+Q291W+Q313M+D369R+E402N+S434P+A475L+K495N+G628W+A689I+Y715P+T785L+M816L; A243G+Q258N+V260G+Q291W+Q313M+D369R+E402N+S434P+A475L+K495N+G628W+A689I+Y715P+S764F; I106V+Q258N+V260G+Q291W+Q313M+D369R+E402N+S434P+A475L+K495N+N588F+G628W+S652D+A689I+Y715P+D733G; Q258N+Q291W+Q313M+D369R+E402N+S434P+A475L+K495N+G628W+A689I+Y715P+V846L; Q258N+Q291W+Q313M+D369R+E402N+S434P+A475L+K495N+S604A+G628W+A689I+Y715P; A79G+Q258N+Q291W+Q313M+D369R+E402N+S434P+A475L+K495N+G628W+A689I+Y715P+T777N; Q258N+Q291W+Q313M+D369R+E402N+S434P+A475L+K495N+G628W+A689I+Y715P; V25A+Q258N+Q291W+Q313M+D369R+E402N+S434P+A475L+K495N+G628W+A689I+Y715P; K24T+A79E+Q258N+D274Y+Q291W+Q313M+D369R+E402N+S434P+A475L+K495N+A505C+G628W+A689I+Y715P+T777N; D47I+Q258N+Q291W+Q313M+A343C+D369R+E402N+S434P+A475L+K495N+S604V+G628W+T687C+A689I+Y715P+S764F+L869R; Q258N+D274Y+Q291W+Q313M+D369R+E385L+E402N+S434P+A475L+K495N+G626D+G628W+A689I+Y715P+T777N; S58G+Q258N+Q291W+Q313M+D369R+Q381V+E402N+S434P+N437D+A475L+K495N+G628W+A689I+Q690H+

D709E+E710G+Y715P; D47I+Q258N+V260G+Q291W+ Q313M+A343C+D369R+E402N+S434P+Q474I+A475L+ K495N+G628W+A689I+Y715P; Q258N+Q291W+ Q313M+D369R+E402N+S434P+N437G+A475L+ K495N+G628W+A689I+Y715P+T785L; A109S+Q258N+ Q291W+Q313M+D369R+E402N+S434P+A475L+ K495N+S604I+G628W+A689I+Y715P; Q258N+V260G+ Q291W+Q313M+D369R+E402N+S434P+A475L+ K495N+S604V+G628W+A689I+Y715P+K807R; Q258N+ Q291W+Q313M+A343C+D369R+E402N+S434P+ A475L+K495N+S604V+G628W+A689I+Y715P; Q258N+ Q291W+Q313M+D369R+E402N+S434P+A475L+ K495N+G628W+A689I+Y715P+L757K; D47I+Q258N+ Q291W+Q313M+D369R+E402N+S434P+K495N+ N588F+G628W+S652D+A689I+Y715P; A79M+A136L+ Q258N+D274Y+Q291W+Q313M+D369R+E402N+ S434P+A475L+K495N+A505C+G628W+A689I+Y715P+ T783A; D47I+A109T+Q258N+V260G+Q291W+Q313M+ D369R+E402N+S434P+A475L+K495N+S604V+G628W+ A689I+Y715P+S764F; S58G+Q258N+Q291W+Q313M+ D369R+E402N+S434P+A475L+K495N+G628W+A689I+ Y715P+T785L; K24G+A136L+Q258N+D274Y+Q291W+ Q313M+D369R+E402N+S434P+A475L+K495N+A505C+ G628W+A689I+Y715P+T777N; S58G+Q258N+Q291W+ Q313M+D369R+Q381V+E402N+S434P+A475L+ K495N+G628W+A689I+Y715P+T785L; and S58G+ Q258N+Q291W+Q313M+D369R+E402N+S434P+ A475L+K495N+G628W+A689I+Y715P+T785L+M816L; (where amino acid position is determined by optimal alignment with SEQ ID NO:2).

In some embodiments, the isolated and/or recombinant β-glucosidase polypeptide variant of the present invention is at least about 70% identical to WT C1 Bgl1 (residues 20-870 of SEQ ID NO:2) and comprises a substitution set selected from the group consisting of: D47I+Q258N+Q291W+ Q313M+A343C+D369R+E402N+S434P+A475L+K495N+ G628W+T687K+A689I+Y715P; D47I+A79G+Q85N+ Q258N+V260G+Q291W+Q313M+A343C+D369R+ E402N+S434P+A475L+K495N+G628W+T687K+A689I+ Y715P+A732M; D47I+Q258N+V260G+Q291W+Q313M+ F314L+A343C+D369R+E402N+S434P+A475L+K495N+ G628W+T687C+A689I+Y715P+A732G; D47I+A79E+ Q85N+Q258N+Q291W+Q313M+A343C+D369R+ E402N+S434P+A475L+K495N+A505C+G628W+ T687W+A689I+Y715P; D47I+A79E+Q85N+Q258N+ V260G+Q291W+Q313M+F314L+A343C+D369R+ E402N+S434P+A475L+K495N+G628W+T687K+A689I+ Y715P; D47I+A79G+Q85N+Q258N+V260G+L275Y+ Q291W+Q313M+F314V+A343C+D369R+E402N+ S434P+A475L+K495N+A505C+G628W+T687C+A689I+ Y715P+S764Y+R769H; D47I+A79G+Q85N+Q258N+ V260G+Q291W+Q313M+F314V+A343C+D369R+ E402N+S434P+A475L+K495N+G628W+T687K+A689I+ Y715P; D47I+A79M+Q85N+Q258N+V260G+L275Y+ Q291W+Q313M+F314L+A343C+D369R+E402N+ S434P+A475L+K495N+A505C+G628W+T687K+A689I+ Y715P; D47I+A79M+Q85N+Q258N+Q291W+Q313M+ A343C+D369R+E402N+S434P+A475L+K495N+A505C+ G628W+T687C+A689I+Y715P+A732G; D47I+Q258N+ V260G+Q291W+Q313M+F314V+A343C+D369R+ E402N+S434P+K495N+A505C+G628W+T687C+A689I+ Y715P+A732G; D47I+A79M+Q258N+V260G+Q291W+ Q313M+F314V+A343C+D369R+E402N+S434P+K495N+ G628W+T687R+A689I+Y715P+A732G; D47I+Q258N+ L275Y+Q291W+Q313M+F314V+A343C+D369R+ E402N+S434P+K495N+G628W+T687K+A689I+Y715P+ A732G; D47I+A79E+Q85N+Q258N+V260G+Q291W+ Q313M+F314V+A343C+D369R+E402N+S434P+K495N+ A505C+G628W+T687W+A689I+Y715P+A732V; D47I+ A79M+Q258N+V260G+Q291W+Q313M+A343C+ D369R+E402N+S434P+K495N+A505C+G628W+ T687K+A689I+Y715P+A732M; D47I+Q85N+Q258N+ V260G+Q291W+Q313M+F314V+A343C+D369R+ E402N+S434P+A475L+K495N+G628W+T687C+A689I+ Y715P; D47I+A79G+Q258N+V260G+L275Y+Q291W+ Q313M+A343C+D369R+E402N+S434P+A475L+K495N+ G628W+T687K+A689I+Y715P+A732G; D47I+Q258N+ V260G+Q291W+Q313M+F314V+A343C+D369R+ E402N+S434P+A475L+K495N+G628W+T687W+A689I+ Y715P+A732G; D47I+Q258N+V260G+Q291W+Q313M+ F314V+A343C+D369R+E402N+S434P+A475L+K495N+ G628W+T687K+A689I+Y715P+A732M; D47I+A79G+ Q85N+Q258N+V260G+Q291W+Q313M+A343C+ D369R+E402N+S434P+A475L+K495N+G628W+T687K+ A689I+Y715P; D47I+A79G+Q85N+Q258N+V260G+ L275Y+Q291W+Q313M+F314V+A343C+D369R+ E402N+S434P+A475L+K495N+G628W+T687C+A689I+ Y715P+A732G; D47I+A79G+Q258N+V260G+Q291W+ Q313M+A343C+D369R+E402N+S434P+A475L+K495N+ G628W+T687K+A689I+Y715P+A732M; D47I+Q85N+ Q258N+V260G+Q291W+Q313M+A343C+D369R+ E402N+S434P+K495N+G628W+T687K+A689I+Y715P; D47I+Q85N+Q258N+V260G+L275Y+Q291W+Q313M+ A343C+D369R+E402N+S434P+K495N+G628W+ T687K+A689I+Y715P+A732G; D47I+A79M+Q85N+ Q258N+V260G+L275Y+Q291W+Q313M+A343C+ D369R+E402N+S434P+K495N+G628W+T687W+A689I+ Y715P; D47I+A79G+Q85N+Q258N+V260G+Q291W+ Q313M+A343C+D369R+E402N+S434P+A475L+K495N+ A505C+G628W+T687K+A689I+Y715P; D47I+Q258N+ V260G+Q291W+Q313M+F314V+A343C+D369R+ E402N+S434P+A475L+K495N+G628W+T687C+A689I+ Y715P+A732G; D47I+A79G+Q85N+Q258N+V260G+ L275Y+Q291W+Q313M+F314V+A343C+D369R+ E402N+S434P+A475L+K495N+G628W+T687K+A689I+ Y715P; D47I+Q85N+Q258N+Q291W+Q313M+A343C+ D369R+E402N+S434P+A475L+K495N+G628W+ T687W+A689I+Y715P+A732G; D47I+A79G+Q85N+ Q258N+V260G+L275Y+Q291W+Q313M+F314V+ A343C+D369R+E402N+S434P+A475L+K495N+A505C+ G628W+T687C+A689I+Y715P; D47I+Q258N+V260G+ Q291W+Q313M+A343C+D369R+E402N+S434P+ A475L+K495N+A505C+G628W+T687K+A689I+Y715P+ A732G; D47I+Q258N+Q291W+Q313M+F314V+A343C+ D369R+E402N+S434P+A475L+K495N+G628W+ T687W+A689I+Y715P+A732G; D47I+A79G+Q85N+ Q258N+Q291W+Q313M+F314V+A343C+D369R+ E402N+S434P+K495N+G628W+T687K+A689I+Y715P; D47I+A79M+Q85N+Q258N+Q291W+Q313M+A343C+ D369R+E402N+S434P+A475L+K495N+G628W+T687K+ A689I+Y715P+A732G; D47I+Q85N+Q258N+V260G+ Q291W+Q313M+F314V+A343C+D369R+E402N+ S434P+A475L+K495N+G628W+T687K+A689I+Y715P; D47I+Q85N+Q258N+L275Y+Q291W+Q313M+F314V+ A343C+D369R+E402N+S434P+K495N+G628W+T687C+ A689I+Y715P; D47I+A79G+Q85N+Q258N+V260G+ L275Y+Q291W+Q313M+F314V+A343C+D369R+ E402N+S434P+A475L+K495N+G628W+T687K+A689I+ Y715P+A732G; D47I+Q258N+V260G+Q291W+Q313M+ A343C+D369R+E402N+S434P+A475L+K495N+ G628W+T687K+A689I+Y715P; D47I+Q85N+Q258N+ V260G+L275Y+Q291W+Q313M+A343C+D369R+ E402N+S434P+A475L+K495N+G628W+T687K+A689I+ Y715P; D47I+A79G+Q258N+Q291W+Q313M+F314L+

A343C+D369R+E402N+S434P+A475L+K495N+
G628W+T687K+A689I+Y715P; D47I+Q258N+Q291W+
Q313M+F314V+A343C+D369R+E402N+S434P+K495N+
G628W+T687K+A689I+Y715P; D47I+Q258N+V260G+
L275Y+Q291W+Q313M+A343C+D369R+E402N+
S434P+A475L+K495N+A505C+G628W+D646N+
T687K+A689I+Y715P+A732G; D47I+Q258N+V260G+
Q291W+Q313M+A343C+D369R+E402N+S434P+
A475L+K495N+G628W+T687K+A689I+Y715P; D47I+
Q258N+V260G+Q291W+Q313M+F314V+A343C+
D369R+E402N+S434P+K495N+G628W+T687K+A689I+
Y715P+A732V; D47I+A79G+Q85N+Q258N+Q291W+
Q313M+A343C+D369R+E402N+S434P+P439S+A475

I106V+A109T+Q258N+V260G+Q291W+Q313M+
F314V+A343G+D369R+E402N+S434P+K495N+
G628W+A689I+Y715P+A732G; D47I+Q85N+I106V+
A109T+Q258N+V260G+Q291W+Q313M+F314L+
A343C+D369R+E402N+S434P+K495N+G628W+A689I+
Y715P+A732G; D47I+Q85N+I106V+A109S+Q258N+
V260G+L275Y+Q291W+Q313M+F314L+A343C+
D369R+E402N+S434P+K495N+G628W+A689I+Y715P+
A732G; D47I+I106V+Q258N+V260G+Q291W+Q313M+
F314V+A343C+D369R+E402N+S434P+K495N+G628W+
A689I+Y715P+A732G; I106V+Q258N+V260G+Q291W+
Q313M+F314V+D369R+E402N+S434P+K495N+
G628W+A689I+Y715P+A732G; D47I+I106V+Q258N+
V260G+Q291W+Q313M+F314L+A343C+D369R+
E402N+S434P+K495N+G628W+A689I+Y715P+A732G;
D47I+Q85N+I106V+A109S+Q258N+V260G+L275Y+
Q291W+Q313M+F314V+A343C+D369R+E402N+
S434P+A475L+K495N+G628W+T687C+A689I+Y715P+
A732G; D47I+A79M+I106V+Q258N+V260G+Q291W+
Q313M+F314L+D369R+E402N+S434P+K495N+
G628W+A689I+Y715P+A732G; A79G+Q85N+I106V+
A109S+Q258N+V260G+Q291W+Q313M+F314V+
D369R+E402N+S434P+K495N+A505C+G628W+A689I+
Y715P+A732G; D47I+A79E+Q85N+I106V+Q258N+
V260G+Q291W+Q313M+F314L+D369R+E402N+
S434P+K495N+G628W+A689I+Y715P+A732G; Q85N+
I106V+Q258N+V260G+L275Y+Q291W+Q313M+
F314V+A343C+D369R+E402N+S434P+K495N+G628W+
T687W+A689I+Y715P+A732G; I106V+Q258N+V260G+
L275Y+Q291W+Q313M+F314L+A343C+D369R+
E402N+S434P+K495N+G628W+A689I+Y715P+A732G;
D47I+Q85N+I106V+A109T+Q258N+V260G+Q291W+
Q313M+F314V+D369R+E402N+S434P+K495N+
G628W+A689I+Y715P+A732G; Q85N+I106V+A109S+
Q258N+V260G+L275Y+Q291W+Q313M+F314V+
A343C+D369R+E402N+S434P+K495N+G628W+A689I+
Y715P+A732G; D47I+A79M+I106V+A109S+Q258N+
V260G+Q291W+Q313M+F314L+A343C+D369R+
E402N+S434P+K495N+G628W+A689I+Y715P+A732G;
A79M+Q85N+I106V+Q258N+V260G+Q291W+Q313M+
F314L+A343C+D369R+E402N+S434P+K495N+G628W+
A689I+Y715P+A732G; and A79M+Q85N+I106V+
Q258N+V260G+L275Y+Q291W+Q313M+F314L+
A343C+D369R+E402N+S434P+K495N+A505C+
G628W+A689I+Y715P+A732G (where amino acid position is determined by optimal alignment with SEQ ID NO:2).

In some embodiments, the variant comprises a substitution set selected from those exemplified above (Table 2, 3, 4, 5, 6, 7) and comprises further substitutions that (a) do not diminish the activity or thermostability of the variant and (b) do not include substitutions at any additional residues in the group consisting of: K57; A88; I106; N112; Q119; T120; A123; R132; Y135; A136; A141; K142; L149; G158; P161; P172; T177; I179; G180; M181; S182; E183; K186; A197; G202; Y219; N220; S222; T224; I229; M234; F242; A243; V246; Q258; D274; V286; Q291; Q313; V318; A343; T354; T357; D358; E360; D369; P374; I375; A378; Q381; E385; S388; V390; A394; N398; E402; K406; I428; S434; N437; E449; Q474; A475; T482; S489; Y491; K530; N536; T540; T565; V674; R682; I867; E868; and P870.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 6.0 to 6.9 fold improvement in activity over the native C1 Bgl1, as identified in Table 2. In some embodiments, the variant comprises a substitution set selected from the group consisting of substitution sets showing at least 5.0 to 5.9 fold improvement in activity over the native C1 Bgl1, as identified in Table 2. In some embodiments, the variant comprises a substitution set selected from the group consisting of substitution sets showing at least 4.0 to 4.9 fold improvement in activity over the native C1 Bgl1, as identified in Table 2. In some embodiments, the variant comprises a substitution set selected from the group consisting of substitution sets showing at least 3.0 to 3.9 fold improvement in activity over the native C1 Bgl1, as identified in Table 2. In some embodiments, the variant comprises a substitution set selected from the group consisting of substitution sets showing at least 2.0 to 2.9 fold improvement in thermostability over the native C1 Bgl1, as identified in Table 2. In some embodiments, the variant comprises a substitution set selected from the group consisting of substitution sets showing at least 1.1 to 1.9 fold improvement in thermostability over the native C1 Bgl1, as identified in Table 2.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 6.0 to 6.9 fold improvement in activity over the Variant 3, as identified in Table 3. In some embodiments, the variant comprises a substitution set selected from the group consisting of substitution sets showing at least 5.0 to 5.9 fold improvement in activity over the Variant 3, as identified in Table 3. In some embodiments, the variant comprises a substitution set selected from the group consisting of substitution sets showing at least 4.0 to 4.9 fold improvement in activity over the Variant 3, as identified in Table 3. In some embodiments, the variant comprises a substitution set selected from the group consisting of substitution sets showing at least 3.0 to 3.9 fold improvement in activity over the Variant 3, as identified in Table 3. In some embodiments, the variant a substitution set selected from the group consisting of substitution sets showing at least 2.0 to 2.9 fold improvement in activity over the Variant 3, as identified in Table 3. In some embodiments, the variant comprises a substitution set selected from the group consisting of substitution sets showing at least 1.1 to 1.9 fold improvement in activity over the Variant 3, as identified in Table 3.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 4.0 to 4.9 fold improvement in activity over the Variant 269, as identified in Table 4. In some embodiments, the variant comprises a substitution set selected from the group consisting of substitution sets showing at least 3.0 to 3.9 fold improvement in activity over the Variant 269, as identified in Table 4. In some embodiments, the variant comprises a substitution set selected from the group consisting of substitution sets showing at least 2.0 to 2.9 fold improvement in activity over the Variant 269, as identified in Table 4. In some embodiments, the variant comprises a substitution set selected from the group consisting of substitution sets showing at least 1.1 to 1.9 fold improvement in activity over the Variant 269 as identified in Table 4.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 4.0 to 4.9 fold improvement in activity over Variant 481, as identified in Table 5. In some embodiments, the variant comprises a substitution set selected from the group consisting of substitution sets showing at least 3.0 to 3.9 fold improvement in activity over the Variant 481, as identified in Table 5. In some embodiments, the variant comprises a substitution set selected from the group consisting of substitution sets showing at least 2.0 to 2.9 fold improvement in activity over the Variant 481, as identified in Table 5. In some embodiments, the variant comprises a substitution set selected from the group consisting of substitution sets showing at least 1.1 to 1.9 fold improvement in activity over the Variant 481, as identified in Table 5.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 4.0 to 4.9 fold improvement in activity over Variant 647, as identified in Table 6. In some embodiments, the variant comprises a substitution set selected from the group consisting of substitution sets showing at least 3.0 to 3.9 fold improvement in activity over the Variant 647, as identified in Table 6. In some embodiments, the variant comprises a substitution set selected from the group consisting of substitution sets showing at least 2.0 to 2.9 fold improvement in activity over the Variant 647, as identified in Table 6. In some embodiments, the variant comprises a substitution set selected from the group consisting of substitution sets showing at least 1.1 to 1.9 fold improvement in activity over the Variant 647, as identified in Table 6. In some embodiments, the variant comprises a substitution set selected from the group consisting of substitution sets showing at least 0.6 to 1.0 fold improvement in activity over the Variant 647, as identified in Table 6.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 3.0 to 3.9 fold improvement in activity over Variant 664, as identified in Table 7. In some embodiments, the variant comprises a substitution set selected from the group consisting of substitution sets showing at least 2.0 to 2.9 fold improvement in activity over the Variant 664, as identified in Table 7.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 4.0 to 4.9 fold improvement in thermostability over the native C1 Bgl1, as identified in Table 2. In some embodiments, the variant comprises a substitution set selected from the group consisting of substitution sets showing at least 3.0 to 3.9 fold improvement in thermostability over the native C1 Bgl1, as identified in Table 2. In some embodiments, the variant comprises a substitution set selected from the group consisting of substitution sets showing at least 2.0 to 2.9 fold improvement in thermostability over the native C1 Bgl1, as identified in Table 2. In some embodiments, the variant comprises a substitution set selected from the group consisting of substitution sets showing at least 1.1 to 1.9 fold improvement in thermostability over the native C1 Bgl1, as identified in Table 2.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 3.0 to 3.9 fold improvement in thermostability over the Variant 3, as identified in Table 3. In some embodiments, the variant comprises a substitution set selected from the group consisting of substitution sets showing at least 2.0 to 2.9 fold improvement in thermostability over the Variant 3, as identified in Table 3. In some embodiments, the variant comprises a substitution set selected from the group consisting of substitution sets showing at least 1.1 to 1.9 fold improvement in thermostability over the Variant 3, as identified in Table 3.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 2.0 to 2.0 fold improvement in thermostability over the Variant 269, as identified in Table 4. In some embodiments, the variant comprises a substitution set selected from the group consisting of substitution sets showing at least 1.1 to 1.9 fold improvement in thermostability over the Variant 269, as identified in Table 4.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 4.0 to 4.9 fold improvement in thermostability over Variant 481, as identified in Table 5. In some embodiments, the variant comprises a substitution set selected from the group consisting of substitution sets showing at least 2.0 to 2.9 fold improvement in thermostability over the Variant 481, as identified in Table 5. In some embodiments, the variant comprises a substitution set selected from the group consisting of substitution sets showing at least 1.1 to 1.9 fold improvement in thermostability over the Variant 481, as identified in Table 5. In some embodiments, the variant comprises a substitution set selected from the group consisting of substitution sets showing at least 0.6 to 1.0 fold improvement in thermostability over the Variant 481, as identified in Table 5.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 2.0 to 2.9 fold improvement in thermostability over Variant 647, as identified in Table 6. In some embodiments, the variant comprises a substitution set selected from the group consisting of substitution sets showing at least 1.1 to 1.9 fold improvement in thermostability over the Variant 647, as identified in Table 6. In some embodiments, the variant comprises a substitution set selected from the group consisting of substitution sets showing at least 0.6 to 1.0 fold improvement in thermostability over the Variant 647, as identified in Table 6. In some embodiments, the variant comprises a substitution set selected from the group consisting of substitution sets showing at least 0.2 to 0.5 fold improvement in thermostability over the Variant 647, as identified in Table 6.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing at least 1.1 to 1.9 fold improvement in thermostability over Variant 664, as identified in Table 7. In some embodiments, the variant comprises a substitution set selected from the group consisting of substitution sets showing at least 0.6 to 1.0 fold improvement in thermostability over the Variant 664, as identified in Table 7.

In some embodiments, the isolated and/or recombinant β-glucosidase polypeptide variant of the present invention is at least about 70% identical to wild-type C1 Bgl1 (residues 20-870 of SEQ ID NO:2) and comprises a substitution set selected from the group consisting of substitution sets showing any improvement in activity and/or thermostability over the native C1 Bgl1, as identified in Table 2. In some embodiments, the variant comprises a substitution set selected from the group consisting of substitution sets showing any improvement in activity and/or thermostability over the Variant 3 as identified in Table 3. In some embodiments, the variant comprises a substitution set selected from the group consisting of substitution sets showing any improvement in activity and/or thermostability over the Variant 269 as identified in Table 4. In some embodiments, the variant comprises a substitution set selected from the group consisting of substitution sets showing any improvement in activity and/or thermostability over the Variant 481 as identified in Table 5. In some embodiments, the variant comprises a substitution set selected from the group consisting of substitution sets showing any improvement in activity and/or thermostability over the Variant 647 as identified in Table 6. In some embodiments, the variant comprises a substitution set selected from the group consisting of substitution sets showing any improvement in activity and/or thermostability over the Variant 664 as identified in Table 7.

As noted above, β-glucosidase polypeptides encompassed by the invention have at least about 70% sequence identity to residues 20-870 of SEQ ID NO:2. In some embodiments, β-glucosidase polypeptides encompassed by the invention include those having an amino acid sequence at least about 71% identical, at least about 72% identical, at least about 73% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical or at least about 99% identical to residues 20-870 of SEQ ID NO:2. Each recitation herein of "70%" should be understood to also include, in the alternative, any of the higher values above.

As noted above, Bgl1 variants of the invention may encompass additional amino acid substitutions beyond those listed above including, for example, variants with one or more additional conservative substitutions made in their amino acid sequences. Examples of conservative substitutions are within the group of basic amino acids (arginine, lysine and histidine), acidic amino acids (glutamic acid and aspartic acid), polar amino acids (glutamine and asparagines), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are known in the art and are described, for example, by H. Neurath and R. L. Hill, 1979, in "The Proteins," Academic Press, New York, which is incorporated herein by reference. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse.

Conservatively substituted variations of the β-glucosidase polypeptide variants of the present invention include substitutions of a small percentage, typically less than 5%, more typically less than 2%, and often less than 1% of the amino acids of the polypeptide sequence, with a conservatively selected amino acid of the same conservative substitution group. The addition of sequences which do not alter the encoded activity of a β-glucosidase, such as the addition of a non-functional or non-coding sequence, is considered a conservative variation of the β-glucosidase polynucleotide.

The present invention also provides enzymatically active fragments of the β-glucosidase polypeptide variants described herein having β-glucosidase activity and at least one substitution described herein. It is believed based on prior studies that C1 Bgl1 tolerates truncation (i.e., retains activity). It has been observed that a variant of C1 Bgl1 having a sequence that differed from wild-type at each of the N-terminal 25 amino acid positions retained β-glucosidase activity (not shown). Similarly, truncation at the carboxy termini of 16 amino acid residues is tolerated in *Azospirillum irakense* β-glucosidase (CelA). See U.S. Ser. No. 61/218,020, which is incorporated herein by reference. Accordingly, the present invention further provides an isolated or recombinant β-glucosidase polypeptide variant having an amino acid sequence having a deletion of from 1 to 50 amino acid residues from the carboxy (C-) terminus, the amino (N-) terminus, or both (i.e., a deletion of 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues from either or both the N- or C-terminus) with respect to SEQ ID NO:2. In certain embodiments, the deletion will be from 1 to 15 amino acid residues from the N-terminus and/or from 1 to 40 amino acid residues from the C-terminus. These β-glucosidase fragments are also referred to herein as N-terminally truncated and C-terminally truncated β-glucosidase polypeptide variants, respectively. In some embodiments, the deletion may be from 1 to 30, or 1 to 20, or 1 to 10 residues, or 1 to 5 residues from the C-terminus, the N-terminus, or both.

TABLE 2

| Variant Number | Amino Acid Changes[1] | Silent Nucleotide Changes[2] | Activity Fold improvement over WT (SEQ ID NO: 2)[3] | Stability Fold improvement over WT (SEQ ID NO: 2)[3] |
|---|---|---|---|---|
| 1 | M181Y + Q291W + E402N + S434P | | ++++++ | ++ |
| 2 | R132K + L149M + Q313M + D369L + E385L + N437D | | ++++++ | ++ |
| 3 | Q291W + D369L + E402N | | +++++ | +++ |
| 4 | Y135I + Q258N + Q474I | | +++++ | + |

TABLE 2-continued

| Variant Number | Amino Acid Changes[1] | Silent Nucleotide Changes[2] | Activity Fold improvement over WT (SEQ ID NO: 2)[3] | Stability Fold improvement over WT (SEQ ID NO: 2)[3] |
|---|---|---|---|---|
| 5 | M181Y + Q291W + E360D + D369V + P374Y + T482A | | +++++ | +++ |
| 6 | Q258N + N437F + S489L + Y491H | | +++++ | ++ |
| 7 | Q119E + Q258N + T357L + Q474I + S489L | | +++++ | ++ |
| 8 | Q258N + D369R + S489L + Y491H | | +++++ | ++ |
| 9 | N220Y + Q258N + T357L + D369R + Q474I + Y491F | g1428a | +++++ | ++ |
| 10 | M234E + V246L + D358K + D369L + N398G + K530M | | +++++ | ++ |
| 11 | Y135Q + I229M + F242L + D369L + K530M | | ++++ | ++ |
| 12 | D369Q + P374Y + E402N + T540K | | ++++ | ++ |
| 13 | Y135Q + P172A + I179M + I229M + Q291A + D358K + D369L + N398G | | ++++ | ++ |
| 14 | R132K + D369L + E385L | | ++++ | ++ |
| 15 | Y135M + I179M + Q291A + D358K + D369L | t573g | ++++ | ++ |
| 16 | Q291W + P374Y + E402N + S434P | | ++++ | ++ |
| 17 | Q119E + N220Y + Q258N + T357L + S489L | | ++++ | + |
| 18 | I179M + Q291A + D358K + D369L + I375V + S388W | c1068a + c1461t | ++++ | ++ |
| 19 | Q291W + D369C | c2580t | ++++ | ++ |
| 20 | R132K + T354Q + D369L + N437L | | ++++ | + |
| 21 | Q291A + D369L + N398G + K530M | | ++++ | ++ |
| 22 | Q119E + Q258N + D274Y + S489L | | ++++ | ++ |
| 23 | Q119E + N220Y + Q258N + Q474I + S489L | | ++++ | ++ |
| 24 | M181Y + D369L | | ++++ | + |
| 25 | T120M + S222E + Q313M + T354Q + D369L + E385L | | ++++ | ++ |
| 26 | A4G + Q258N + D274Y + T357L + N437W + Q474I + Y491H | c27t | ++++ | ++ |
| 27 | R132G + D369L + N437D | | ++++ | ++ |
| 28 | S182L + Q313M + D369L + E385L | | ++++ | ++ |
| 29 | R132G + D369L + E385L | | ++++ | ++ |
| 30 | N112V + D358K + D369L + S388W + K530M | | ++++ | ++ |
| 31 | I106V + G180E + D369L + Q381V | | ++++ | ++ |
| 32 | I179M + Q291A + D369L | c489t + c1284t | ++++ | ++ |
| 33 | I179M + D358K + D369L + S388W | | ++++ | ++ |
| 34 | M234E + Q291A + D369L + N398G | | ++++ | ++ |
| 35 | I179M + D358K + D369L + S388W + Q381I | | ++++ | ++ |
| 36 | Y135Q + N220L + Q291A + D369L + N398G | | ++++ | ++ |
| 37 | Y135I + D369L | | ++++ | + |
| 38 | S182L + D369L + E385L + N437L | | ++++ | ++ |
| 39 | T120Y + R132K + D369L + N437D | | ++++ | ++ |
| 40 | M234E + D369L + S388W + N398G + K530M | c1098t | ++++ | ++ |
| 41 | Y135M + I179M + D369L + V390I + K530M | t573g | ++++ | ++ |
| 42 | L149Q + A197V + Q313M + D369L | c852t + c1308t | ++++ | + |
| 43 | T120M + R132K + D369L + N437L | | ++++ | ++ |
| 44 | T120M + R132W + L149M + Q313M + T354Q + D369L + E385L + N437D | c540t | ++++ | ++ |
| 45 | A4G + Y135I + N220Y + Q258N + T357P + N437Y | | ++++ | + |
| 46 | D358K + D369L + S388W | t573g + c657t | ++++ | ++ |
| 47 | Q258N + D274Y + N437F | | ++++ | + |
| 48 | D369L + S434P + T540K | c285t | ++++ | ++ |
| 49 | G158D + I179M + Q291A + D358K + D369L + I375V + N398G + K530M | | ++++ | ++ |
| 50 | Y135I + D274Y + D369R | | ++++ | + |
| 51 | Q258N + D369L + Q474I + S489L + Y491F | | ++++ | ++ |
| 52 | R132W + S182W + D369L + E385L | | ++++ | ++ |
| 53 | S182L + T354Q + D369L + E385L | | ++++ | ++ |
| 54 | S222Q + T354Q + D369L + E385L + N437D + T565G | | ++++ | ++ |
| 55 | Y135M + P161S + Q291A + A343T + D369L + I375V + K406D | c1200a | ++++ | ++ |
| 56 | Q291W + D369C + T540K | c855t | ++++ | ++ |
| 57 | D369L + P374Y + E402N | | ++++ | + |
| 58 | Y135I + A343V + D369F + S489L | | ++++ | + |
| 59 | M234E + D358K + D369L + S388W | | ++++ | ++ |
| 60 | T120M + L149Q + D369L + E385L | | ++++ | ++ |
| 61 | Q313M + D369L + E385L | | ++++ | ++ |
| 62 | T120Y + D369L + E385L | c750g | +++ | ++ |
| 63 | D369L + N437D + T565A | | +++ | + |
| 64 | N112V + Q291A + D369L + I375V | c1128t | +++ | ++ |
| 65 | R132W + L149Q + Q313M + T354Q + D369L | c1305t | +++ | + |
| 66 | Y135M + D369L + I375V + N398G | | +++ | ++ |
| 67 | D369L + E385L | | +++ | ++ |
| 68 | T120M + S182L + Q313M + T354Q + D369L + E385L | | +++ | ++ |
| 69 | T177I + Q291W + P374Y + T482A | | +++ | + |
| 70 | Q258N + N437F | | +++ | + |
| 71 | T120V + R132W + D369L + T565G | | +++ | + |
| 72 | N112V + Q291A + D358N + D369E + S388C + K406D | | +++ | + |
| 73 | Q291A + D358K + D369L + S388W + K406D | t573g | +++ | ++ |
| 74 | I106V + E360R + D369L + Q381V | | +++ | + |

TABLE 2-continued

| Variant Number | Amino Acid Changes[1] | Silent Nucleotide Changes[2] | Activity Fold improvement over WT (SEQ ID NO: 2)[3] | Stability Fold improvement over WT (SEQ ID NO: 2)[3] |
|---|---|---|---|---|
| 75 | M234E + Q291A + D369L + S388W + N398G | | +++ | ++ |
| 76 | L149M + Q313M + D369L | | +++ | ++ |
| 77 | M234I + Q291W + E360D + D369V + T482A | | +++ | +++ |
| 78 | T120V + T354Q + D369L + E385L + T565P | | +++ | ++ |
| 79 | M234I + Q291W + E360D + S434P | t42n | +++ | ++ |
| 80 | D369Y + I867M + E868R | | +++ | + |
| 81 | R132W + S182L + Q313M + D369L | c285t + c1092t + c1095t | +++ | + |
| 82 | M234I + Q291W + P374Y + T482A | | +++ | ++ |
| 83 | Y219V + M234I + D369C + P374Y + S434P | | +++ | ++ |
| 84 | S182L + Q313M + D369L + E385L + N437L | c1044t | +++ | ++ |
| 85 | M234E + D358K + D369L + S388W + K530M | | +++ | ++ |
| 86 | R132G + S222E + D369L + E385L | a51g | +++ | ++ |
| 87 | R132K + L149M + S182L + D369L + N437L | | +++ | + |
| 88 | T120H + Q313M + D369L | | +++ | ++ |
| 89 | R132W + D369L | c1047t | +++ | + |
| 90 | D369L + P374Y | | +++ | ++ |
| 91 | N112V + N220L + Q291A + D369L + S388W + N398G | | +++ | ++ |
| 92 | Q291A + D369L + I375V + K530G | | +++ | ++ |
| 93 | R132K + L149M + S182L + T354Q + D369L + N437D + T565G | | +++ | + |
| 94 | T120H + S222E + Q313M + D369L + N437D + T565G | | +++ | ++ |
| 95 | A123N + Q291W + T482A + T540K | | +++ | ++ |
| 96 | S222E + Q313M + T354Q + D369L + E385L | | +++ | ++ |
| 97 | R132W + D369L + T565G | | +++ | + |
| 98 | G202M + E360A + D369I + A394L | | +++ | * |
| 99 | R132G + S222Q + Q313M + D369L | | +++ | ++ |
| 100 | R132W + L149M + D369L | | +++ | + |
| 101 | L149M + Q313M + T354Q + D369L | | +++ | + |
| 102 | Q119L + G202M + D369L | | +++ | + |
| 103 | M181Y + M234I + D369C | | +++ | + |
| 104 | I179M + N220L + Q291A + D369L + I375V | | +++ | ++ |
| 105 | S222E + Q313M + D369L + E385L + N437L | | +++ | ++ |
| 106 | I179M + M234E + D358K + D369L + S388W + N398G | | +++ | ++ |
| 107 | A123N + Y219V + Q291W + E360D + P374Y + S434P | | +++ | ++ |
| 108 | D369L + E402N | c1092t | +++ | + |
| 109 | D369L | | +++ | ++ |
| 110 | Y219V + M234I + Q291W + T482A | | +++ | + |
| 111 | Q291W + E360D + S434P | | +++ | ++ |
| 112 | D369L + S434P | | +++ | ++ |
| 113 | G180E + E360R + D369L | | +++ | ++ |
| 114 | A123N + M181Y + Q291W + D369K + S434P + T540K | | +++ | ++++ |
| 115 | Q119E + T357L + D369M + S489L | | +++ | + |
| 116 | Q119E + D369F + Y491H | | +++ | + |
| 117 | Q119L + D369L | | +++ | + |
| 118 | Q119E + N220Y + V286I + S489L | c1749t + g2280t | +++ | + |
| 119 | Q291A + D369L + Q381I | | +++ | ++ |
| 120 | A475F | | +++ | ** |
| 121 | D369L + N536K | | +++ | ++ |
| 122 | Q119E + Y135I + D369H | | +++ | + |
| 123 | Q258N + S489L | | +++ | + |
| 124 | Q119E + Y135I + N437Y | | +++ | ** |
| 125 | Q119E + Y135I + N437F + Y491F | | +++ | + |
| 126 | Q119L + D369L + A394V | | +++ | + |
| 127 | E183G + E360A + D369L + I428V | | +++ | + |
| 128 | D369L + E449Q + N536K | | +++ | + |
| 129 | Q119L + G202M + E360A + A475F | | +++ | ** |
| 130 | I106V + D369L | | +++ | ++ |
| 131 | Y135I + D369M | | +++ | + |
| 132 | M234I + D369C + S434P | | +++ | + |
| 133 | D369L + A475Y | | +++ | ++ |
| 134 | Q119E + Y135I + S489L | | +++ | + |
| 135 | D369Y + N536K | | +++ | + |
| 136 | E360R + D369L | | +++ | + |
| 137 | G202V + A475H | | +++ | + |
| 138 | D369L + Q381V + N536K | | +++ | ++ |
| 139 | N220Y + Q258N + S489L + Y491F | | +++ | + |
| 140 | Q258N + T357L + D369M | | +++ | ++ |
| 141 | I179M + Q291A + D369L + Q381L + S388W + N398G | a69g | +++ | + |
| 142 | D369Y + A394G + N536K | | +++ | ++ |
| 143 | Q291W + E360D + D369V + P374Y | | ++ | +++ |
| 144 | T120M + L149Q + T354Q + D369L + E385L | | ++ | ++ |
| 145 | S489L + Y491H | | ++ | + |
| 146 | N220S + Q291F + D369L | | ++ | ++ |
| 147 | D369C + S434P + T540K | | ++ | + |

TABLE 2-continued

| Variant Number | Amino Acid Changes[1] | Silent Nucleotide Changes[2] | Activity Fold improvement over WT (SEQ ID NO: 2)[3] | Stability Fold improvement over WT (SEQ ID NO: 2)[3] |
|---|---|---|---|---|
| 148 | V318E + D369L + I428V | | ++ | + |
| 149 | E183M + G202M + E360A + D369L + A378K + A394V | | ++ | ** |
| 150 | A394G + N536K | | ++ | + |
| 151 | Q291W + T540K | | ++ | + |
| 152 | N220L + Q291A + D369L + Q381L + S388W + K530M | | ++ | + |
| 153 | T120V + R132W + E385L + N437D | | ++ | + |
| 154 | Q119L + E360A + D369L + A378K | | ++ | + |
| 155 | D369A + N536K | t726c | ++ | + |
| 156 | G202V + D369L + A475H | | ++ | + |
| 157 | Q381V + A475Y + N536K | | ++ | + |
| 158 | S434P | | ++ | + |
| 159 | I106V + G180E + D369Y + A394G | | ++ | ++ |
| 160 | G180E + Q381V + A475H | | ++ | + |
| 161 | Q119E + N220Y + Q474I | | ++ | + |
| 162 | I106V + D369Q | | ++ | + |
| 163 | A475Y + N536K | | ++ | + |
| 164 | K142R + Y219V + Q291W + S434P + V674I | c1398t | ++ | ++ |
| 165 | L149Q + S182L + Q313M + D369L + N437L | | ++ | + |
| 166 | N112V + I179M + M234E + D369L + N398G | c1188t | ++ | ++ |
| 167 | E360A + D369L + A378K | | ++ | + |
| 168 | E360R + D369Y + N536K | | ++ | + |
| 169 | E360R + D369A + Q381V + N536K | | ++ | + |
| 170 | D369L + Q381D | c858t | ++ | + |
| 171 | N437F + S489L | | ++ | + |
| 172 | E183M + G202M + V318E + D369I + A394L + I428V | | ++ | ** |
| 173 | E360D + D369L + E402N + S434P | | ++ | + |
| 174 | Q119L + A141F + G202M + A394L + I428V + A475F | c2488t | ++ | * |
| 175 | T357L + D369R + S489L + Y491H | | ++ | + |
| 176 | Y135I + Q258N + T357L | | ++ | + |
| 177 | K142R + Q291W + E360D + D369C + E402N | | ++ | ++ |
| 178 | E183M + A243V + D369L + A378K + A475F | | ++ | + |
| 179 | R132K + L149M + E385L | | ++ | + |
| 180 | D369Y | a1266t | ++ | + |
| 181 | M234I + E402N + S434P | | ++ | ** |
| 182 | N437Y | c1641t | ++ | ** |
| 183 | Q119E + N437F | | ++ | + |
| 184 | N536K | | ++ | + |
| 185 | Q119L + E183Q + G202M + D369P | | ++ | + |
| 186 | N112V + I179M + Q291A + D358K + K406D | g1122a | ++ | + |
| 187 | A123N + Q291W + T540K | | ++ | + |
| 188 | D369I + A394L + I428V | t2364n | ++ | * |
| 189 | A88S + N536K | | ++ | + |
| 190 | Q119E + Y135I + N437F | c1473t | ++ | * |
| 191 | A141F + G202M + E360A + D369P + A378K | | ++ | * |
| 192 | A123N + T482A | | ++ | ** |
| 193 | Q313M + N437D | | ++ | + |
| 194 | E360R + D369Y | | ++ | + |
| 195 | E183M + G202M + A475F | | ++ | ** |
| 196 | Q119L + E360A + A394V + A475F | t2364g | ++ | ** |
| 197 | D369L + A378K | | ++ | + |
| 198 | E360R + D369L + A394G | c90a | ++ | + |
| 199 | M181Y + D369E + S434P | | ++ | + |
| 200 | D369I | t2364n | ++ | + |
| 201 | N112V + Y135I + I375V + K406D + K530M + P870S | | ++ | + |
| 202 | Q119E + Y135I + N220Y + Q258N | | ++ | + |
| 203 | D369P + A394V + I428V | | ++ | + |
| 204 | V318E + D369L | | ++ | + |
| 205 | K186R + N536K | | ++ | + |
| 206 | Q119L + D369L + A378K | | ++ | + |
| 207 | M234I + D369K + S434P | | + | + |
| 208 | N112V + I179M + N220L + Q291A + Q381I + S388W + N398G | | + | + |
| 209 | E402N + S434P | | + | + |
| 210 | Q119L + A141F + G202M + A394Q | c993t | + | * |
| 211 | Q313M + T354Q + N437D | | + | + |
| 212 | N112V + M234E + D369L + I375V + K406D | g1437a | + | ++ |
| 213 | Q119E + A136E + N220Y | | + | ** |
| 214 | Q381D + A394G + N536K | | + | ** |
| 215 | Q119L + E183G + D369Q + A378T + V390I | | + | ** |
| 216 | Y135I + T357L + Q474I + S489L + Y491F | | + | + |
| 217 | D369E + A394P + I428V | | + | + |
| 218 | N112V + Q291A + Q381I + N398G | | + | + |
| 219 | E360R + N536K | | + | + |
| 220 | E360D + D369C | | + | + |
| 221 | R132W + S182L + E385L | | + | ** |

TABLE 2-continued

| Variant Number | Amino Acid Changes[1] | Silent Nucleotide Changes[2] | Activity Fold improvement over WT (SEQ ID NO: 2)[3] | Stability Fold improvement over WT (SEQ ID NO: 2)[3] |
|---|---|---|---|---|
| 222 | I179M + Q291A + D358K + N398G + K530G | | + | + |
| 223 | N220Y + Q258N + T357L | | + | + |
| 224 | T224N + D274Y + T357L + N437F | | + | + |
| 225 | N437D | | + | + |
| 226 | M234I + E360D + T482A | | + | + |
| 227 | A141F + G202M + D274N + V318E + E360A + I428V | | + | * |
| 228 | D369Q | | + | + |
| 229 | N112V + N220L + D358K + D369L + I375V + Q381I + N398G | | + | + |
| 230 | Y135I + D369F | | + | + |
| 231 | A243V + V318E + E360A + A475W | | + | ** |
| 232 | N220L + D369L + Q381L + S388W + N398G + K530G | | + | + |
| 233 | S489L | | + | + |
| 234 | K142R + Y219V | | + | * |
| 235 | Y135I + N220Y + Y491F | | + | * |
| 236 | S182W + T354Q + E385L | | + | + |
| 237 | I179M + D358K + S388W | | + | ** |
| 238 | L149M + Q313M + T565P | | + | ** |
| 239 | R132G + E385L | | + | ** |
| 240 | V318E | | + | + |
| 241 | Q119L + E183K | | + | ** |
| 242 | R132G + E385L | | + | ** |
| 243 | E183G + V318E + E360A + A394Q + A475C | | + | ** |
| 244 | E183M + G202M + E360A | | + | ** |
| 245 | A394G | | + | + |
| 246 | D369P | | + | + |
| 247 | Y135M + Q291A + S388W + N398G | | + | * |
| 248 | Y219V + D369C | | + | ++ |
| 249 | A394V + I428V | g1428a | + | ** |
| 250 | Q119L | | + | + |
| 251 | Y135I | | + | ** |
| 252 | E360R + D369Q + Q381D + N536K | | + | ** |
| 253 | N220L + M234E + Q291A + I375V + K530M | | + | + |
| 254 | Q119L + G202M + E360A | | + | ** |
| 255 | N220Y + Q258N + D369R | | + | +++ |
| 256 | M181Y + M234I + Q291W + E402N | | + | + |
| 257 | A394V | g2382a | + | ** |
| 258 | T120M + L149Q + Q313M | c1686t | + | + |
| 259 | Q119L + V318E + I428V | | + | + |
| 260 | E360R + Q381V | | + | + |
| 261 | K57R + G202M + E360A + A394V | | + | ** |
| 262 | I179M + D358K + I375V + Q381L | | + | + |
| 263 | E360A | | + | + |
| 264 | I179M + R682W | | + | + |
| 265 | E360A + I428V | | + | + |
| 266 | D369K + P374Y | | + | + |

Table 2, Thermoactivity conditions: pH 5, 65° C. for 21 hrs. Thermostability conditions: enzyme residual activity was determined after incubated at pH 5, 65° C. for 6 hrs.
[1]Amino acid changes are indicated with respect to SEQ ID NO: 2.
[2]Nucleotide changes are indicated with respect to SEQ ID NO: 1.
[3]Fold improvement is represented as follows:
* = 0.3 to 0.5 fold improvement over the native C1 Bgl1 (SEQ ID NO: 2)
** = 0.6 to 1 fold improvement over the native C1 Bgl1 (SEQ ID NO: 2)
+ = 1.1 to 1.9 fold improvement over the native C1 Bgl1 (SEQ ID NO: 2)
++ = 2.0 to 2.9 fold improvement over the native C1 Bgl1 (SEQ ID NO: 2)
+++ = 3.0 to 3.9 fold improvement over the native C1 Bgl1 (SEQ ID NO: 2)
++++ = 4.0 to 4.9 fold improvement over the native C1 Bgl1 (SEQ ID NO: 2)
+++++ = 5.0 to 5.9 fold improvement over the native C1 Bgl1 (SEQ ID NO: 2)
++++++ = 6.0 to 6.9 fold improvement over the native C1 Bgl1 (SEQ ID NO: 2)

TABLE 3

| Variant Number | Amino Acid Changes[1] | Silent Nucleotide Changes[2] | Activity Fold improvement over Var. 3[3] | Stability Fold improvement over Var. 3[3] |
|---|---|---|---|---|
| 3 | Q291W + D369L + E402N | | | |
| 267 | I106V + Q258N + Q291W + D369L + E402N + S434P | | +++++ | ++ |
| 268 | I106V + Y135Q + Q258N + Q291W + Q313M + D369H + E402N + K495N + G628W | t1620a | +++++ | +++ |
| 269 | Q258N + Q291W + Q313M + D369R + E402N + S434P + A475L + K495N + G628W | | +++++ | ++ |
| 270 | I106V + Q258N + Q291W + Q313M + D369H + E402N + S434P + A475C + K495I + T540K + G628W | | +++++ | +++ |
| 271 | I106V + Q258N + Q291W + D369R + E402N + S434P + K495H + G628L | | +++++ | ++ |

TABLE 3-continued

| Variant Number | Amino Acid Changes[1] | Silent Nucleotide Changes[2] | Activity Fold improvement over Var. 3[3] | Stability Fold improvement over Var. 3[3] |
|---|---|---|---|---|
| 272 | D274Y + Q291W + D358K + D369L + E385L + E402N + N437I + S489N | g357a | ++++ | + |
| 273 | Q258N + Q291W + Q313M + D369H + E402N + S434P + T540K | c405t + t1884g | ++++ | ++ |
| 274 | I106V + Q258N + Q291W + D369L + E402N + S434P + A475F + K495N + G628V | t1620a | ++++ | ++ |
| 275 | Q258N + Q291W + Q313M + D369L + E402N + S434P + A475C + K495I + G628W | t60c + c246t + c318t + c405t + t1620a | ++++ | +++ |
| 276 | I106V + Y135Q + M181Y + Q258N + Q291W + Q313M + D369L + E402N + S434P + K495N | t1620a + t1884g | ++++ | +++ |
| 277 | Y135Q + Q258N + Q291W + D369L + E402N + K495N | t1620a + t1884g | ++++ | ++ |
| 278 | Q119E + D274Y + Q291W + D358K + D369L + E385L + E402N + N437V + S489N + S614A | t846c | ++++ | + |
| 279 | Y135Q + Q258N + Q291W + Q313M + D369L + E402N + S434P + A475F + K495N + G628V | c318t + c984a + t1620a | ++++ | ++ |
| 280 | R132H + Q258N + Q291W + D369Y + E402N + K495Q | c318t + c405t + t1620a | ++++ | + |
| 281 | Y135Q + Q258N + Q291W + D369L + E402N + S434P + A475F + K495H | | ++++ | ++ |
| 282 | Y135Q + Q258N + Q291W + D369R + E402N + S434P + A475F + K495I + G628V | t1620a | ++++ | + |
| 283 | I106V + M181Y + Q258N + Q291W + D369L + E402N | | ++++ | + |
| 284 | I106V + Q258N + Q291W + D369H + E402N + S434P + A475F + K495F + G628V | c405t + t1620a | ++++ | + |
| 285 | Q258N + Q291W + Q313M + D369L + E402N + S434P + G628V | | ++++ | ++ |
| 286 | Q258N + Q291W + D369L + E402N + A475F + K495I | t1620a + t1884g + c2463t | +++ | + |
| 287 | Q119E + D274Y + Q291W + D369L + E385L + E402N + N437I | | +++ | + |
| 288 | Q258N + Q291W + Q313M + D369R + E402N + S434P + A475L | c318t + c405t | +++ | ++ |
| 289 | Q258N + Q291W + D369R + E402N + S434P + K495H + G628W | t1620a | +++ | + |
| 290 | D274Y + Q291W + D369L + E385L + E402N + N437I + S489N + K530C | g357a + a1840t | +++ | + |
| 291 | I106V + Y135Q + Q258N + Q291W + Q313M + D369Y + E402N + S434P + A475F + K495H + T540K | t1884g | +++ | +++ |
| 292 | Q119E + Q291W + D358K + D369L + E385L + E402N | c822t | +++ | + |
| 293 | I106V + M181Y + Q258N + Q291W + Q313M + D369H + E402N + S434P + A475L + K495Q + G628V | c405t + c1581t + t1620a | +++ | ++ |
| 294 | Q119E + D274Y + Q291W + D358N + D369L + E385L + E402N + N437D | | +++ | + |
| 295 | Q258N + Q291W + D369R + E402N + S434P + G628V | | +++ | + |
| 296 | Q258N + Q291W + Q313M + D369H + E402N + S434P + G628L | t1620a | +++ | ++ |
| 297 | Q258N + Q291W + D369L + E402N | c318t | +++ | + |
| 298 | D274Y + Q291W + D358K + D369L + E385L + E402N + N437F + S614D | g357a + t1465a | +++ | + |
| 299 | Q119E + D274Y + Q291W + D358N + D369L + E385L + E402N + N437L + K530V | a1840t | +++ | + |
| 300 | Q119E + D274Y + Q291W + D358N + D369L + E385L + E402N + N437V + S489L + K530N | a1840t | +++ | ++ |
| 301 | Q258N + Q291W + D369L + E402N + S434P + A475F + K495F + T540K | c318t + c405t + t1884g | +++ | + |
| 302 | M181Y + Q291W + Q313M + D369Y + E402N | c318t + c405t | +++ | + |
| 303 | A243V + D274Y + Q291W + D369L + E402N + N437I + K530C | g357a + t1465a + a1840t | +++ | + |
| 304 | Q119E + D274Y + Q291W + D358E + D369L + E385L + E402N + N437V + K530V + S614A | t1465a | ++ | ** |
| 305 | Q291W + D358K + D369L + E385L + E402N + N437W + K530C + S614A | g357a + c822t | ++ | + |
| 306 | Q119E + D274Y + Q291W + D369L + E385L + E402N + N437W | | ++ | ++ |
| 307 | D274Y + Q291W + D358N + D369L + E385L + E402N + N437I + K530N + S614V | g357a + t1465a | ++ | + |
| 308 | M181Y + Q258N + Q291W + Q313M + D369L + E402N + S434P | c318t + c405t | ++ | +++ |
| 309 | A109T + Q291W + D369L + E402N | | ++ | + |
| 310 | Q119E + Q291W + D369L + E385L + E402N + N437Y + S489I + K530N | c822t + a1840t | ++ | ++ |
| 311 | Q119E + D274Y + Q291W + D358N + D369L + E402N + N437D | a1840t | ++ | + |
| 312 | D274Y + Q291W + D358K + D369L + E385L + E402N + N437W + K530V + S614D | g357a + t1465a | ++ | + |
| 313 | Q258N + Q291W + D369R + E402N + A475W + K495H + G628V | t1620a | ++ | + |
| 314 | A109S + Q291W + D369L + E402N | c1119t | ++ | + |
| 315 | Q119E + D274Y + Q291W + D358E + D369L + E385L + E402N + N437L + S614A | c1329t + t1465a | ++ | + |
| 316 | Q291W + D369L + E402N + E493Y + N504Y + T611A | c1563t + g1590a | ++ | + |
| 317 | Q119E + D274Y + Q291W + D358N + D369L + E402N + S614V | | ++ | + |
| 318 | D274Y + Q291W + D358E + D369L + E385L + E402N + N437L + K530N + S614A | g357a + t1465a | ++ | + |
| 319 | Q258H + Q291W + Q313M + D369R + E402N + A475F + K495N + G628L | t1620a | ++ | + |
| 320 | Q258N + Q291W + Q313M + D369Y + E402N + A475W + K495V + T540K + G628W | | ++ | ++ |
| 321 | D274Y + Q291W + D358N + D369L + E385L + E402N + S614V | g357a + c936a | ++ | + |
| 322 | I106V + Y135Q + Q291W + Q313M + D369L + E402N + A475L + K495Q | t1620a + t1884g | ++ | ++ |
| 323 | Q258N + Q291W + D369R + E402N + S434P + A475F + G628V | | ++ | + |
| 324 | Q119E + D274Y + Q291W + D369L + E385L + E402N + N437V | t1465a | ++ | + |
| 325 | D274Y + Q291W + D358K + D369L + E385L + E402N + N437Y + S489L + K530V | g357a | ++ | + |
| 326 | Q119E + D274Y + Q291W + D358N + D369L + E402N | a1840t | ++ | + |
| 327 | Q291W + D369L + E402N + K495V + S501R + A503E + K530N + T611H | t1465a | ++ | + |
| 328 | Q119E + D274Y + Q291W + D358N + D369L + E385L + E402N + N437V + S489I + K530C | | ++ | + |
| 329 | Q119E + Q291W + D358K + D369L + E402N + N437L + S489N | c822t | ++ | + |
| 330 | D274Y + Q291W + D369L + E385L + E402N + N437W + K530C + S614D | g357a | ++ | + |
| 331 | Q258N + Q291W + D369R + E402N + A475F + K495N + T540K + G628V | c318t + c405t | ++ | + |

TABLE 3-continued

| Variant Number | Amino Acid Changes[1] | Silent Nucleotide Changes[2] | Activity Fold improvement over Var. 3[3] | Stability Fold improvement over Var. 3[3] |
|---|---|---|---|---|
| 332 | Q291W + D369L + E402N + E493V + N504Y | c1563t + t1698c + c1773t + t1872c + c1905t | ++ | + |
| 333 | Q291W + D358E + D369L + E385* + E402N + S489T | g357a + c822t | ++ | + |
| 334 | Q258N + Q291W + Q313M + D369R + E402N + A475L + K495V + A601T + G628W | | ++ | ++ |
| 335 | D274Y + Q291W + D358N + D369L + E385L + E402N + S489N + S614C | g357a | ++ | + |
| 336 | D274Y + Q291W + D358N + D369L + E402N + N437V + S489L + K530C + S614A | g357a + g1140a | ++ | + |
| 337 | Q119E + D274Y + Q291W + D358E + D369L + E402N + N437D | a1840t | ++ | + |
| 338 | Q119E + D274Y + Q291W + D358N + D369L + E402N + N437L + S614R | t1465a | ++ | + |
| 339 | D274Y + Q291W + D358N + D369L + E402N + N437Y + K530V | g357a + t1465a + a1840t | ++ | ** |
| 340 | D274Y + Q291W + D358E + D369L + E402N + N437Y + S489N + K530N + S614V + D781N | g357a | ++ | + |
| 341 | Q258H + Q291W + D369* + E402N + S434P + T540K + G628L | c318t + c405t | ++ | + |
| 342 | Q119E + Q291W + D358E + D369L + E385L + E402N + N437L + S489N + K530V | c822t | ++ | + |
| 343 | Q258N + Q291W + D369L + E402N + G628V | c405t + c1179t | ++ | + |
| 344 | Q291W + D358K + D369L + E385L + E402N + S489I + K530N | g357a + c822t + a1840t | ++ | + |
| 345 | Q119E + Q291W + D369L + E385L + E402N + S489N + K530V + S614A | g6a + c822t | ++ | + |
| 346 | I106V + Y135Q + Q291W + D369L + E402N + S434P + A475F + K495V + G628L | t1620a | ++ | + |
| 347 | Q119E + Q291W + D358N + D369L + E402N + N437V + K497R + S614A | c822t + t1465a | ++ | + |
| 348 | Q119E + D274Y + Q291W + D358E + D369L + E385L + E402N + N437L | t1465a | ++ | + |
| 349 | D274Y + Q291W + D358K + D369L + E402N + N437L + S489I + K530V + S614A | g357a | ++ | + |
| 350 | I106V + Q291W + Q313M + D369L + E402N + S434P + A475W + K495N + G628W | c405t + t1620a | ++ | ++ |
| 351 | Q291W + D369L + E402N + A505C + L620M + T635I | g1479a + t1512c + c1563t + t1698c + c1773t + t1872c | ++ | + |
| 352 | Q291W + D369L + E402N + E493A + N504Y + A505C + L620M + T635A | c1563t + t1698c + c1773t + t1872c | ++ | + |
| 353 | D274Y + Q291W + D358N + D369L + E402N + S489N + K530C + S614A | g357a + c981t | ++ | + |
| 354 | D274Y + Q291W + D358K + D369L + E385L + E402N + N437W + K530D | g357a + t1465a + a1840t | ++ | + |
| 355 | Q291W + D369L + E402N + S489N + K495H + S501R + K530N | c1509g + c1833g | ++ | + |
| 356 | D274Y + Q291W + D358E + D369L + E385L + E402N + N437D + K530C + S614H | g357a | ++ | + |
| 357 | Q119E + Q291W + D358E + D369L + E385L + E402N + N437W + S489N + K530E + S614A | c822t | ++ | + |
| 358 | Q291W + D369L + E402N + E493Y + N504Y + N521C + T591A + R612P + L620M + T635I | t1698c + t1872c | ++ | + |
| 359 | Q291W + D358K + D369L + E385L + E402N + N437I + K530M + S614L | g357a + c822t + t1465a | + | ** |
| 360 | Q291W + D369L + E402N + R672I | | + | ** |
| 361 | D274Y + Q291W + D358E + D369L + E385L + E402N + N437L + S489L | g357a + a1840t | + | + |
| 362 | A265S + Q291W + D369L + E402N | | + | ** |
| 363 | Q215M + Q291W + D369L + E402N | | + | + |
| 364 | Q291W + D369L + E402N + E493V + N504Y + N521C + T591A + L620M + T635I | t1872c | + | + |
| 365 | Q119E + D274Y + Q291W + D358E + D369L + E385L + E402N + N437L + S489N + K530M + S614D | | + | + |
| 366 | Q119E + Q291W + D369L + E385L + E402N | c822t | + | + |
| 367 | Q291W + D369L + E402N + E493A + N504Y + D566G + R612P + L620M + T635A | c1563t + c1773t + c1863t + t1872c + c2403a | + | + |
| 368 | Q119E + D274Y + Q291W + D369L + E385L + E402N + S614Y | | + | + |
| 369 | I106V + Y135Q + M181Y + Q258N + Q291W + D369L + E402N | | + | ++ |
| 370 | Q119E + Q291W + D358E + D369L + E385L + E402N + N437W + K530V | c822t | + | + |
| 371 | Q215E + Q291W + D369L + E402N | | + | ** |
| 372 | Q291W + D369L + E402N + N504Y + N521C + T591A + R612H + L620M + T635I | g1479a + t1698c + t1872c | + | + |
| 373 | Q119E + D274Y + Q291W + D358K + D369L + E402N + N437Y + K530I | t1465a + a1840t | + | ** |
| 374 | Q258H + Q291W + D369L + E402N + K495N | c318t + t1620a + t1884g | + | + |
| 375 | Q291W + D358N + D369L + E385L + E402N + N437D + S489N + K530I | g357a + c822t + a1840t | + | + |
| 376 | Q291W + D369L + P374Y + E402N + Y491L + S501R | c360t + c1773g | + | + |
| 377 | Q258N + Q291W + Q313M + G332D + D369H + E402N + S434P | | + | ++ |
| 378 | Q291W + D358N + D369L + E385L + E402N + N437F + S489L + K530V | c822t + a1840t | + | + |
| 379 | Q291W + D369L + E402N + R672S | | + | ** |
| 380 | Q291W + D369L + E402N + T687M | | + | + |
| 381 | Q291W + F314V + D369L + E402N | | + | + |
| 382 | Q258N + Q291W + T357A + D369H + E402N + S434P + K495F | t1620a + t1884g | + | + |
| 383 | Q291W + D369L + P374Y + E402N + Y491F + S501R + N521C | c360t + c540a | + | + |
| 384 | Q291W + D369L + E402N + Q690K | | + | + |

TABLE 3-continued

| Variant Number | Amino Acid Changes[1] | Silent Nucleotide Changes[2] | Activity Fold improvement over Var. 3[3] | Stability Fold improvement over Var. 3[3] |
|---|---|---|---|---|
| 385 | Q291W + D358E + D369L + E385L + E402N + N437F + K530V + S614A | g357a + c822t + t1465a | + | + |
| 386 | Q291W + D369L + E402N + R672A | | + | ** |
| 387 | Q291W + D369L + E402N + R672T | | + | ** |
| 388 | Q291W + D369L + E402N + D703K | c1947t | + | ** |
| 389 | D274Y + Q291W + D369L + E402N | c1305t + t1465a + a1840t | + | + |
| 390 | Q291W + D369L + E402N + R672F | | + | ** |
| 391 | Q291W + D369L + E402N + R672D | | + | ** |
| 392 | Q291W + D369L + E402N + Y491F + S501R + N536K + D566G | c1773g | + | + |
| 393 | Q291W + D369L + E402N + A732G | | + | + |
| 394 | Q291W + D369L + E402N + E493Y + N504Y + N521C + T591C + R612P + L620M | t1698c + t1872c + c1905t | + | + |
| 395 | I106V + Y135Q + Q291W + D369L + E402N + A475F + G628W | | + | + |
| 396 | Q291W + D369L + E402N + R672G | | + | ** |
| 397 | Q291W + D369L + E402N + T777N | c2328t | + | + |
| 398 | Q291W + Q313M + D369L + E402N + T540K | c318t + c405t | + | + |
| 399 | Q291W + D369L + E402N + K708F | | + | + |
| 400 | Q291W + D369L + P374Y + E402N + S501H | | + | ** |
| 401 | Q291W + D369L + E402N + Y715P | c2241t | + | + |
| 402 | Q291W + D369L + E402N + A732M | | + | + |
| 403 | Q291W + D369L + E402N + E493A + N504Y + N521C + D566G + R612P + L620M | c1773t + t1872c + c1905t | + | + |
| 404 | Q291W + D369L + E402N + Q690R | | + | + |
| 405 | D274Y + Q291W + D369L + E385L + E402N + N437V + K530I + S614D | t1465a | + | ** |
| 406 | Q291W + D369L + E402N + L757K | c2454t | + | + |
| 407 | Q291W + D369L + E402N + T687Y | | + | + |
| 408 | Q291W + D369L + E402N + Y491H + S501R + N521C + T591A | | + | + |
| 409 | Q291W + D369L + E402N + V775C | | + | + |
| 410 | Q291W + D369L + E402N + R672V | | + | ** |
| 411 | Q291W + D369L + E402N + N670D | | + | ** |
| 412 | Q291W + D369L + E402N + T779S | | + | ** |
| 413 | Q291W + D369L + E402N + V638R | | + | ** |
| 414 | Q291W + D369L + E402N + T687F | | + | + |
| 415 | Q291W + D369L + E402N + T687L | | + | ** |
| 416 | Q291W + D369L + E402N + K610S | | + | ** |
| 417 | Q291W + D369L + E402N + Y491L + S501R + N521C | c1773g | + | + |
| 418 | D274Y + Q291W + D358E + D369L + E402N + K530V + S614V | g357a | + | ** |
| 419 | I106V + M181Y + Q258N + Q291W + D369R + E402N + S434P + A475W + K495V + T540K + G628V | c405t | + | ++ |
| 420 | Q291W + D369L + E402N + N536K | t1501a + c1773g | + | + |
| 421 | Q291W + D369L + E402N + E493V + N504Y + R612P + L620M | c1563t + t1698c + c1773t + t1872c + c1905t | + | + |
| 422 | Q291W + D369L + E402N + S676C | | + | ** |
| 423 | Q291W + D369L + E402N + T540K + G628W | c318t | + | ** |
| 424 | Q291W + D369L + E385L + E402N + N437D + S489L + K530C + S614D | g357a + c822t | + | + |
| 425 | Q119E + D274Y + Q291W + D358N + D369L + E402N + N437F + S489N + S614L | | + | + |
| 426 | Q291W + D369L + E402N + S434P + A475W + K495V | t1620a | + | + |
| 427 | Q291W + D369L + E402N + A689I | | + | + |
| 428 | Q291W + D369L + E402N + E493A + N504Y + N521C + D566G + R612H + L620M | c1773t + t1872c + c1905t | + | + |
| 429 | Q291W + D369L + E402N + V638S | | + | ** |
| 430 | Q291W + D369L + E402N + V648W | | + | ** |
| 431 | Q291W + D369L + E402N + D650V | | + | ** |
| 432 | Q291W + D369L + E402N + V674M | | + | ** |
| 433 | Q291W + D369L + E402N + V638E | | + | ** |
| 434 | I106V + Q291W + D369L + E402N | t1884g | + | + |
| 435 | Y135Q + Q291W + D369L + E402N | t1884g | + | ** |
| 436 | Q291W + D369L + E402N + S764F | | + | + |
| 437 | Q291W + D369L + E402N + E493A + N504Y + A505C + N521C + T591A + R612P | t1698c + t1872c + c1905t | + | + |
| 438 | Q291W + D369L + E402N + S489N + K495Q + S501R + K530N + T611Q | c1509g | + | + |
| 439 | Q291W + D369L + E402N + T685V | | + | + |
| 440 | I106V + Q291W + D369L + E402N + S434P + A475C + K495N + T540K | | + | + |
| 441 | Q119E + Q291W + D358N + D369L + E402N + N437D + K530N + S614V | c822t | + | + |
| 442 | Q291W + D369L + E402N + T687K | | + | + |
| 443 | Q291W + D369L + E402N + S652D | | + | + |
| 444 | Q291W + D369R + E402N + A475F + K495Q + T540K + G628L | | + | + |
| 445 | Y135Q + Q291W + D369L + E402N + G628V | c318t | + | ** |
| 446 | Q291W + D369L + E402N + E493Y + A505C + N521C + T591A + L620M | t1512c + t1698c + t1872c + c1905t | + | + |
| 447 | Q291W + D369L + E402N + T687W | | + | + |
| 448 | Q291W + D369L + E402N + D650F | | + | ** |

TABLE 3-continued

| Variant Number | Amino Acid Changes[1] | Silent Nucleotide Changes[2] | Activity Fold improvement over Var. 3[3] | Stability Fold improvement over Var. 3[3] |
|---|---|---|---|---|
| 449 | Q291W + D369L + E402N + T687C | | + | + |
| 450 | Q291W + D369L + E402N + S434P + K495N + G628V | | + | ** |
| 451 | Q291W + D369L + E402N + S501N | c540a + c1773g | + | * |
| 452 | D274Y + Q291W + D369L + E402N + N437K + S489I + K530V + S614L | g357a | + | + |
| 453 | Q291W + D369L + E402N + T699L | | + | + |
| 454 | Q119E + V246I + Q291W + D358E + D369L + E402N + S614L | c267t | + | ** |
| 455 | Q291W + D369L + E402N + N504Y + N521C + D566G + L620M + T635A | g1479a + c1773t + t1872c | ** | + |
| 456 | Q291W + D369L + E402N + E493Y + N504Y + D566G + T591A + R612P + L620M | c1563t + t1872c + c1905t | ** | + |
| 457 | Q291W + D369L + E402N + N536K + T591A | | ** | + |
| 458 | Q291W + D369L + E402N + Q690A | | ** | + |
| 459 | Q291W + D358K + D369L + E402N + N437L + S489I + K530D | g357a + c822t + c1458t + a1840t | ** | ** |
| 460 | Q119E + D274Y + Q291W + D358E + D369L + E385L + E402N + N437V + S489N + K530M + S614H | | ** | + |
| 461 | Q291W + D369L + P374Y + E402N + Y491L | | ** | ** |
| 462 | Q291W + D369L + E402N + S501R | c1773g+ | ** | + |
| 463 | Q291W + D369L + E402N + Y491L + N521C + N536K | c360t + c540a + t1501a + c1773g | ** | + |
| 464 | Q291W + D369L + E402N + E493Y + N504Y + N521C + T591C + R612P + L620M + T635V | t1698c + t1872c | ** | + |
| 465 | Q119E + Q291W + D358N + D369L + E385L + E402N + N437I + S489I + S614L | c822t | ** | ++ |
| 466 | T120Y + Q291W + D369L + E402N + S501R + N521C + D566G | c1773g | ** | + |
| 467 | Q291W + D369L + E402N + Y491L + N521C | t1501a | ** | ** |
| 468 | Q291W + D369L + E402N + Y491L + S501N + D566G + T591A | | ** | ** |
| 469 | D274Y + N278Y + Q291W + D358E + D369L + E402N + N437L + S489L + K530E | g357a | ** | + |
| 470 | I106V + Q291W + D369L + E402N + S434P + A475W + K495F + T540K + G628V | c405t + a636g | ** | + |
| 471 | Q119E + Q291W + D358N + D369L + E402N + N437Y + E742G | c822t | ** | ** |
| 472 | Y135Q + Q291W + D369Y + E402N + A475F + K495F | t1620a + t1884g | ** | ** |
| 473 | T120H + Q291W + D369L + E402N + Y491H + S501H + T591C | | * | + |
| 474 | Q119E + Q291W + D358N + D369L + E402N + N437F + S489N + K530E + S614L | c822t | * | + |
| 475 | Q119E + D274Y + Q291W + D358E + D369L + E402N + N437I + S489N + K530V + S614Y | | * | + |
| 476 | T120Y + Q291W + D369L + E402N + N521C + N536K | c540a + c1773g | * | ++ |
| 477 | Q291W + D369L + E402N + Y491F + S501N + N536K + T591R | c360t | * | + |
| 478 | Q291W + D369L + E402N + S501N + N521C + D566G + T591R | c1473t | * | ** |
| 479 | Q291W + D369L + E402N + Y491L + S501R + N536K + D566G + T591R | | * | + |
| 480 | D274Y + Q291W + D358E + D369L + E402N + N437Y + S489N + K530I + S614L | g357a | * | ** |

Table 3: Thermoactivity conditions: pH 5, 70° C. for 21 hrs. Thermostability conditions: enzyme residual activity was determined after incubated at pH 5, 65° C. for 16-48 hrs.
[1]Amino acid changes are indicated with respect to SEQ ID NO: 2; the backbone sequence contains substitutions Q291W + D369L + E402N.
[2]Nucleotide changes are indicated relative to SEQ ID NO: 1.
[3]Fold improvement is represented as follows:
* = 0.3 to 0.5 fold improvement over Variant 3 (SEQ ID NO: 5)
** = 0.6 to 1 fold improvement over Variant 3 (SEQ ID NO: 5)
+ = 1.1 to 1.9 fold improvement over Variant 3 (SEQ ID NO: 5)
++ = 2.0 to 2.9 fold improvement over Variant 3 (SEQ ID NO: 5)
+++ = 3.0 to 3.9 fold improvement over Variant 3 (SEQ ID NO: 5)
++++ = 4.0 to 4.9 fold improvement over Variant 3 (SEQ ID NO: 5)
+++++ = 5.0 to 5.9 fold improvement over Variant 3 (SEQ ID NO: 5)
++++++ = 6.0 to 6.9 fold improvement over Variant 3 (SEQ ID NO: 5)

TABLE 4

| Variant Number | Amino Acid Changes[1] | Silent Nucleotide Changes[2] | Activity Fold improvement over Var. 269[3] | Stability Fold improvement over Var. 269[3] |
|---|---|---|---|---|
| 269 | Q258N + Q291W + Q313M + D369R + E402N + S434P + A475L + K495N + G628W | | | |
| 481 | Q258N + Q291W + Q313M + D369R + E402N + S434P + A475L + K495N + G628W + A689I + Y715P | | ++++ | ++ |
| 482 | Q258N + Q291W + Q313M + D369R + E402N + S434P + A475L + K495N + G628W + Y715P + T823K | g1290a + g2160a | +++ | + |
| 483 | Q258N + Q291W + Q313M + D369R + E402N + S434P + A475L + K495N + G628W + T685V + Y715P + | | ++ | + |
| 484 | I106V + Q258N + Q291W + Q313M + D369R + E402N + S434P + A475L + K495N + G628W + S764P | | ++ | + |
| 485 | A109T + Q258N + Q291W + Q313M + D369R + E402N + I428V + S434P + A475L + K495N + G628W | | ++ | + |
| 486 | Q258N + Q291W + Q313M + D369R + E402N + S434P + A475L + Y491F + K495N + G628W + Y715P | | ++ | + |

TABLE 4-continued

| Variant Number | Amino Acid Changes[1] | Silent Nucleotide Changes[2] | Activity Fold improvement over Var. 269[3] | Stability Fold improvement over Var. 269[3] |
|---|---|---|---|---|
| 487 | Q258N + Q291W + Q313M + D369R + Q381V + E402N + S434P + A475L + K495N + S501R + G628W + Y715P | | ++ | + |
| 488 | Q258N + Q291W + Q313M + D369R + E402N + S434P + A475L + K495N + G628W + S764F | | ++ | + |
| 489 | Q258N + Q291W + Q313M + D369R + E385L + E402N + S434P + A475L + K495N + G628W | | ++ | + |
| 490 | Q258N + Q291W + Q313M + D369R + E402N + S434P + A475L + K495N + N627H + G628W + A732G | | ++ | + |
| 491 | Q258N + Q291W + Q313M + D369R + E402N + S434P + A475L + K495N + G628W + A689I | c852t | ++ | + |
| 492 | Q258N + Q291W + Q313M + D369R + E402N + S434P + A475L + K495N + G628W + T685V + Y715P + T777N | | ++ | + |
| 493 | Q258N + Q291W + Q313M + D369R + E402N + S434P + A475L + K495N + G628W + D650Y + Q716R + L757K | | ++ | + |
| 494 | Q258N + Q291W + Q313M + D369R + E402N + S434P + A475L + K495N + G628W + Y715P | | ++ | + |
| 495 | Q258N + Q291W + Q313M + D369R + E402N + S434P + A475L + K495N + V562L + G628W | c729t | ++ | ** |
| 496 | Q258N + Q291W + Q313M + D369R + E402N + S434P + A475L + K495N + A505C + G628W + S764F | | ++ | + |
| 497 | Q258N + V260G + Q291W + Q313M + D369R + E402N + S434P + A475L + K495N + G628W | | ++ | ++ |
| 498 | Q258N + Q291W + Q313M + D369R + E402N + S434P + A475L + K495N + G628W + Y715P + E819V | | ++ | + |
| 499 | A109T + Q258N + Q291W + Q313M + D369R + E402N + S434P + A475L + K495N + G628W | | ++ | + |
| 500 | Q258N + Q291W + Q313M + D369R + E402N + S434P + A475L + K495N + G628W + S652D + V846F | c27t | ++ | + |
| 501 | Q258N + Q291W + Q313M + D369R + E402N + S434P + A475L + K495N + G628W + Q690K | | + | + |
| 502 | D47I + Q258N + Q291W + Q313M + D369R + E402N + S434P + A475L + K495N + G628W | | + | ++ |
| 503 | Q258N + Q291W + Q313M + A343C + D369R + E402N + S434P + A475L + K495N + G628W | | + | + |
| 504 | E21Q + V175A + Q258N + Q291W + Q313M + D369R + E402N + S434P + A475L + K495N + G628W | c249t | + | ** |
| 505 | Q258N + Q291W + Q313M + E360D + D369R + E402N + S434P + A475L + K495N + G628W + L757K | | + | ** |
| 506 | Q258N + Q291W + Q313M + F314L + D369R + E402N + S434P + A475L + K495N + S604I + N627H + G628W + A732G | | + | + |
| 507 | A109T + Q258N + Q291W + Q313M + D369R + E402N + S434P + A475L + K495N + G628W + V775C | | + | + |
| 508 | Q258N + Q291W + Q313M + D369R + E402N + S434P + A475L + K495N + G628W + S764F | | + | + |
| 509 | P29Q + Q258N + Q291W + Q313M + D369R + E402N + S434P + A475L + K495N + G628W | | + | ** |
| 510 | A136L + Q258N + Q291W + Q313M + D369R + E402N + S434P + A475L + K495N + G628W + S764F + P870S | | + | + |
| 511 | Q258N + Q291W + Q313M + D369R + E385L + E402N + S434P + K495N + G628W | c1425g | + | + |
| 512 | Q258N + Q291W + Q313M + D369R + E402N + S434P + A475L + K495N + G628W + T687M | g2160a | + | + |
| 513 | Q258N + Q291W + Q313M + D369R + E402N + S434P + A475L + K495N + N588F + G628W | | + | ** |
| 514 | Q258N + Q291W + Q313M + D358K + D369R + E402N + S434P + A475L + K495N + G628W | c951a | + | + |
| 515 | Y135M + Q258N + Q291W + Q313M + D369R + E402N + S434P + A475L + K495N + G628W + Y715P | t1341c | + | + |
| 516 | Q258N + Q291W + Q313M + D369R + E402N + S434P + A475L + K495N + G628W + T785L | | + | ** |
| 517 | A79G + Q258N + Q291W + Q313M + D369R + E402N + S434P + A475L + K495N + G628W | | + | + |
| 518 | A109T + Q258N + Q291W + Q313M + D369R + E402N + S434P + A475L + K495N + G628W + S848N | | + | + |
| 519 | I106V + Q258N + Q291W + Q313M + F314V + D369R + E402N + S434P + A475L + K495N + G628W | | + | + |
| 520 | Q258N + Q291W + Q313M + D369R + E402N + S434P + A475L + K495N + G628W + A732G | | + | + |
| 521 | Q258N + Q291W + Q313M + D369R + E402N + S434P + A475L + K495N + G628W + L757K | | + | + |
| 522 | Q258N + Q291W + Q313M + D369R + E402N + S434P + A475L + K495N + N627H + G628W + T687M + E822K | | + | + |
| 523 | Q258N + Q291W + Q313M + D369R + E402N + S434P + A475L + K495N + G616D + G628W | | + | + |
| 524 | A79M + Q258N + Q291W + Q313M + D369R + E402N + S434P + A475L + K495N + G628W | | + | + |

TABLE 4-continued

| Variant Number | Amino Acid Changes[1] | Silent Nucleotide Changes[2] | Activity Fold improvement over Var. 269[3] | Stability Fold improvement over Var. 269[3] |
|---|---|---|---|---|
| 525 | I106V + Q258N + Q291W + Q313M + D369R + E402N + S434P + A475L + K495N + G628W | | + | + |
| 526 | Q258N + Q291W + Q313M + F314V + D369R + E402N + S434P + A475L + K495N + A617V + G628W | | + | ** |
| 527 | Q258N + Q291W + Q313M + F314V + D369R + E402N + S434P + A475L + K495N + G628W | | + | + |
| 528 | Q258N + Q291W + Q313M + D369R + E402N + S434P + P436Q + A475L + K495N + G626D + G628W | | + | + |
| 529 | Q258N + Q291W + Q313M + D369R + E402N + S434P + A475L + K495N + G628W + T687C | | + | + |
| 530 | Q85N + Q258N + Q291W + Q313M + D369R + E402N + S434P + A475L + K495N + G628W | | + | + |
| 531 | A109S + Q258N + Q291W + Q313M + D369R + E402N + S434P + A475L + K495N + N536K + G628W | | + | + |
| 532 | S58G + Q258N + Q291W + Q313M + D369R + E402N + S434P + A475L + K495N + G628W | | + | + |
| 533 | E21Q + Q258N + Q291W + Q313M + D369R + Q381V + E402N + S434P + A475L + K495N + G628W | | + | ** |
| 534 | Q258N + L275Y + Q291W + Q313M + D369R + E402N + S434P + A475L + K495N + G628W | | + | + |
| 535 | Q258N + Q291W + Q313M + D369R + E402N + S434P + A475L + K495N + A505C + G628W | | + | ** |
| 536 | E21R + Q258N + Q291W + Q313M + D369R + E402N + S434P + A475L + K495N + G628W | | + | ** |
| 537 | V25A + Q258N + Q291W + Q313M + D369R + E402N + S434P + A475L + K495N + G628W | | + | + |
| 538 | H26R + Q258N + Q291W + Q313M + D369R + E402N + S434P + A475L + K495N + G628W | t282c | + | ** |
| 539 | L30K + Q258N + Q291W + Q313M + D369R + E402N + S434P + A475L + K495N + G628W | | + | * |
| 540 | N45H + Q258N + Q291W + Q313M + D369R + E402N + S434P + A475L + K495N + G628W | | + | ** |
| 541 | Q258N + Q291W + Q313M + D369R + E402N + S434P + A475L + E493V + K495N + G628W | | + | ** |
| 542 | P29R + Q258N + Q291W + Q313M + D369R + E402N + S434P + A475L + K495N + G628W | | + | * |
| 543 | P29M + Q258N + Q291W + Q313M + D369R + E402N + S434P + A475L + K495N + G628W + A732S + A748T + V840I | c21t + c1911t | + | ** |
| 544 | Q55R + Q258N + Q291W + Q313M + D369R + E402N + S434P + A475L + K495N + G628W | | + | ** |
| 545 | K24G + Q258N + Q291W + Q313M + D369R + E402N + S434P + A475L + K495N + G628W | | + | + |
| 546 | G180E + Q258N + Q291W + Q313M + D369R + E402N + S434P + A475L + K495N + G628W | | + | ** |
| 547 | Q258N + Q291W + Q313M + D369R + E402N + S434P + K495N + G628W | c1425g | + | ** |
| 548 | Q258N + Q291W + Q313M + D369R + E402N + S434P + A475L + Q479R + K495N + S501R + G628W + Y715P + E819L | | + | + |
| 549 | A79E + Q258N + Q291W + Q313M + D369R + E402N + S434P + A475L + K495N + G628W | | + | + |
| 550 | Q258N + Q291W + Q313M + D369R + E402N + S434P + A475L + K495N + G628W + R672G | | + | ** |
| 551 | Q258N + Q291W + Q313M + F314V + D369R + E402N + S434P + A475L + K495N + A505C + G628W | g2493a | + | + |
| 552 | Q258N + Q291W + Q313M + D369R + E402N + S434P + A475L + K495N + G628W + T687K | | + | + |
| 553 | Q27R + Q258N + Q291W + Q313M + D369R + E402N + S434P + A475L + K495N + G628W | c1689g | + | ** |
| 554 | V253F + Q258N + Q291W + Q313M + D369R + E402N + S434P + A475L + K495N + G628W | | + | + |
| 555 | S22L + Q258N + Q291W + Q313M + D369R + E402N + S434P + A475L + K495N + G628W | | + | ** |
| 556 | Q258N + Q291W + Q313M + D369R + E402N + S434P + A475L + K495N + G628W + Q690H | a321t | + | + |
| 557 | Q258N + Q291W + Q313M + D369R + E402N + S434P + A475L + K495N + G628W + S799N | | + | ** |
| 558 | Q258N + Q291W + Q313M + F314V + E360D + D369R + E402N + S434P + A475L + K495N + G628W | | + | + |
| 559 | Q258N + Q291W + Q313M + D369R + E402N + S434P + A475L + K495N + G628W + E822M | | + | + |
| 560 | K24T + Q258N + Q291W + Q313M + D369R + E402N + S434P + A475L + K495N + G628W | | + | + |
| 563 | S22L + Q258N + Q291W + Q313M + D369R + E402N + S434P + A475L + Q479R + K495N + G628W | | + | + |
| 561 | Q258N + Q291W + Q313M + D369R + E402N + S434P + A475L + K495N + G628W + S787G | | + | + |

TABLE 4-continued

| Variant Number | Amino Acid Changes[1] | Silent Nucleotide Changes[2] | Activity Fold improvement over Var. 269[3] | Stability Fold improvement over Var. 269[3] |
|---|---|---|---|---|
| 562 | Q258N + Q291W + Q313M + D369R + E402N + S434P + A475L + K495N + R612H + G628W + L757K + S787G | | + | * |
| 564 | Q258N + Q291W + Q313M + D369R + E402N + S434P + A475L + K495N + G628W + T687K + E822M | | + | ** |
| 565 | Q258N + Q291W + Q313M + D369R + E402N + S434P + M454E + A475L + K495N + G628W | | + | ** |
| 566 | Q258N + Q291W + Q313M + D369R + E402N + S434P + A475L + K495N + V562C + G628W | | + | ** |
| 567 | S22R + Q258N + Q291W + Q313M + D369R + E402N + S434P + A475L + K495N + G628W | | + | ** |
| 568 | V25G + Q258N + Q291W + Q313M + D369R + E402N + S434P + A475L + K495N + G628W | c2478t | + | ** |
| 569 | Q258N + Q291W + Q313M + D369R + E402N + S434P + A475L + K495N + G628W + T685V | c1842t | + | ** |
| 570 | Q258N + Q291W + Q313M + D369R + E402N + A404S + S434P + A475L + K495N + G628W | | + | ** |
| 571 | G216L + Q258N + Q291W + Q313M + D369R + E402N + S434P + A475L + K495N + G628W | | + | ** |
| 572 | V25R + Q258N + Q291W + Q313M + D369R + E402N + S434P + A475L + K495N + G628W | | + | ** |
| 573 | V25G + Q258N + Q291W + Q313M + D369R + E402N + S434P + A475L + K495N + G628W | | + | ** |
| 574 | Q27H + Q258N + Q291W + Q313M + D369R + E402N + S434P + A475L + K495N + G628W | | + | ** |
| 575 | K24L + Q258N + Q291W + Q313M + D369R + E402N + S434P + A475L + K495N + G628W | | + | ** |
| 576 | Q258N + Q291W + Q313M + D369R + E402N + S434P + A475L + K495N + G628W + D650F + L757K | | + | ** |
| 577 | Q258N + Q291W + Q313M + D369R + E402N + S434P + A475L + T482A + K495N + G628W | | + | ** |
| 578 | Q258N + Q291W + Q313M + D369R + E402N + S434P + A475L + K495N + A617V + G628W | | + | ** |
| 579 | Q258N + Q291W + Q313M + D369R + E402N + S434P + A475L + K495N + S501C + G628W | | + | ** |
| 580 | Q258N + Q291W + Q313M + D369R + E402N + S434P + K495N + N536K + G628W + R817P | c1425g | + | + |
| 582 | Q258N + Q291W + Q313M + D369R + E402N + S434P + A475L + K495N + G628W + T777N | | + | ** |
| 581 | G180E + Q258N + Q291W + Q313M + D369R + E402N + S434P + A475L + R476Q + K495N + G628W | | + | ** |
| 583 | Q119E + Q258N + Q291W + Q313M + D369R + E402N + S434P + A475L + K495N + G628W | | + | + |
| 584 | A109S + Q258N + Q291W + Q313M + D369R + E402N + S434P + K495N + G628W + S848N | g558a + t1296c + c1425g | + | + |
| 585 | Q258N + Q291W + Q313M + D369R + E402N + S434P + A475L + K495N + G628W + Y850H | | + | ** |
| 586 | Q258N + Q291W + Q313M + D369R + E402N + S434P + P436E + A475L + K495N + G628W | | + | ** |
| 587 | Q258N + Q291W + Q313M + D369R + E402N + S434P + A475L + K495N + G628W + R769H + E819A | | + | ** |
| 588 | Q258N + Q291W + Q313M + D369R + E402N + S434P + A475L + T496A + G628W | | + | ** |
| 589 | Q258N + V260L + Q291W + Q313M + D369R + E402N + S434P + A475L + K495N + G628W | | + | ** |
| 590 | D244H + Q258N + Q291W + Q313M + D369R + E402N + S434P + A475L + K495N + G628W | c814t | + | ** |
| 591 | Q258N + Q291W + Q313M + D369R + E402N + S434P + A475L + K495N + G628W + E819V | c1197a | + | ** |
| 592 | Q258N + Q291W + Q313M + D369R + E402N + S434P + A475L + K495N + G628W + S652D | | + | ** |
| 593 | Q258N + Q291W + D311N + Q313M + D369R + E402N + S434P + A475L + K495N + R612H + G628W + A689I + K866I | g1479a | + | * |
| 594 | Q258N + Q291W + Q313M + D369R + E402N + S434P + A475L + K495N + G628W + T783H | c1917t | + | + |
| 595 | Q258N + Q291W + Q313M + D369R + E402N + S434P + A475L + K495N + G628W + T823K | | + | ** |
| 596 | Q258N + Q291W + Q313M + D369R + E402N + S434P + A475L + K495N + G628W + D650N + S787G | | + | ** |
| 597 | Q258N + Q291W + Q313M + D369R + E402N + S434P + A475L + K495N + G628W + K708F | g1869a | + | + |
| 598 | Q258N + Q291W + Q313M + D369R + E360D + D369R + E402N + S434P + A475L + K495N + G628W + S652D | | + | ** |
| 599 | Q258N + Q291W + Q313M + D369R + E402N + S434P + A475L + K495N + G628W + E822G | a321g | + | ** |
| 600 | L237Y + Q258N + Q291W + Q313M + D369R + E402N + S434P + A475L + K495N + G628W | | + | + |

TABLE 4-continued

| Variant Number | Amino Acid Changes[1] | Silent Nucleotide Changes[2] | Activity Fold improvement over Var. 269[3] | Stability Fold improvement over Var. 269[3] |
|---|---|---|---|---|
| 601 | Q258N + Q291W + Q313M + D369R + E402N + S434P + A475L + E494K + K495N + G628W | | + | ** |
| 602 | Q258N + Q291W + Q313M + E360D + D369R + E402N + S434P + D470N + A475L + K495N + G628W + L757K | c312t | + | * |
| 603 | Q258N + Q291W + Q313M + D369R + E402N + S434P + A475L + K495N + G628W + S764F | | ** | + |
| 604 | Q258N + Q291W + Q313M + D369R + E402N + S434P + A475L + K495N + G628W + D650F | | ** | ** |
| 605 | Q258N + Q291W + Q313M + D369R + E402N + S434P + A475L + K495N + G628W + S848N | | ** | ** |
| 606 | Q258N + Q291W + Q313M + D369R + E402N + S434P + A475L + K495N + T496A + N536K + G628W | | ** | ** |
| 607 | Q258N + Q291W + Q313M + D369R + E402N + K421R + S434P + A475L + K495N + G628W + T777N | | ** | ** |
| 608 | Q258N + Q291W + Q313M + D369R + E402N + S434P + A475L + K495N + N627H + G628W + E822M | | ** | ** |
| 609 | Q258N + Q291W + Q313M + D369R + E402N + S434P + A475L + K495N + G628W + F634A | t1944g + c1962t | ** | ** |
| 610 | A4V + Q258N + Q291W + Q313M + D369R + E402N + S434P + A475L + K495N + G628W | c1635t | ** | ** |
| 611 | Q258N + Q291W + Q313M + D369R + E402N + S434P + N437W + A475L + K495N + G628W | | ** | ** |
| 612 | Y135Q + Q258N + Q291W + Q313M + D369R + E402N + S434P + A475L + K495N + G628W | | ** | + |
| 613 | Y135Q + Q258N + Q291W + Q313M + D369R + E402N + S434P + A475L + K495N + G628W + V673A + T685V | t99c | ** | ** |
| 614 | Q258N + Q291W + Q313M + D369R + E402N + S434P + A475L + K495N + G628W + L757K + P806L | | ** | ** |
| 615 | Q258N + Q291W + Q313M + D369R + E402N + S434P + A475L + K495N + V559T + G628W | c1476t | ** | ** |
| 616 | Y135M + Q258N + Q291W + Q313M + D369R + E402N + S434P + A475L + K495N + G628W | | ** | ** |
| 617 | Q258N + Q291W + Q313M + D369R + E402N + S434P + A475L + K495N + G628W + V775C | | ** | + |
| 618 | Q258N + Q291W + Q313M + D369R + E402N + S434P + A475L + K495N + N627H + G628W | | ** | ** |
| 619 | Q258N + Q291W + Q313M + D369R + E402N + A405T + S434P + A475L + K495N + G628W | | ** | ** |
| 620 | I221V + Q258N + Q291W + Q313M + D369R + E402N + S434P + A475L + K495N + G628W | | ** | ** |
| 621 | Q258N + Q291W + Q313M + D369R + E402N + S434P + A475L + K495N + S501R + G628W + T685V | | ** | ** |
| 622 | Q258N + Q291W + Q313M + D369R + A394G + E402N + S434P + A475L + K495N + G628W + L757K | | ** | + |
| 624 | Q258N + Q291W + Q313M + D369R + E402N + S434P + A475L + K495N + G616D + G628W | | ** | + |
| 623 | P161S + Q258N + Q291W + Q313M + D358K + D369R + E402N + S434P + A475L + K495N + G628W | | ** | * |
| 625 | Q258N + Q291W + Q313M + D369R + E402N + S434P + A475L + K495N + G628W + K807R | | ** | + |
| 626 | Q258N + Q291W + Q313M + D369R + E402N + S434P + A475L + K495N + G628W + A732M | | ** | + |
| 627 | Q258N + Q291W + Q313M + D369R + E402N + S434P + A475L + K495N + A505C + G628W + E822G | | ** | ** |
| 628 | Q258N + Q291W + Q313M + D369R + E402N + S434P + A475L + E493V + K495N + G628W + S652D | | ** | + |
| 629 | A15V + Q258N + Q291W + Q313M + D369R + E402N + S434P + A475L + K495N + G628W | | ** | + |
| 630 | Q258N + Q291W + Q313M + D369R + E402N + S434P + A475L + K495N + G628W + K866Q | | ** | ** |
| 631 | Q258N + Q291W + Q313M + D369R + E402N + S434P + A475L + E493A + K495N + G628W + S652D + Q690A | | ** | + |
| 632 | Q258N + Q291W + Q313M + D369R + E402N + S434P + A475L + K495N + G628W + E819L | | ** | ** |
| 633 | Q258N + Q291W + Q313M + D369R + E402N + S434P + A475L + K495N + G628W + E819V | | ** | + |
| 634 | G180E + Q258N + Q291W + Q313M + D369R + E385L + E402N + S434P + A475L + K495N + G628W | | ** | ** |
| 635 | Q258N + Q291W + Q313M + D369R + E402N + S434P + A475L + K495N + G628W + D751N | g2430a | ** | ** |
| 636 | G202M + Q258N + Q291W + Q313M + D369R + E402N + S434P + A475L + K495N + N627H + G628W + T687K + E822A | | ** | ** |
| 637 | Q258N + Q291W + Q313M + D369R + E402N + S434P + A475L + K495N + G628W + K866I | | ** | ** |
| 638 | Q258N + Q291W + Q313M + D369R + E402N + S434P + A475L + K495N + G628W + T783Q | | ** | ** |

TABLE 4-continued

| Variant Number | Amino Acid Changes[1] | Silent Nucleotide Changes[2] | Activity Fold improvement over Var. 269[3] | Stability Fold improvement over Var. 269[3] |
|---|---|---|---|---|
| 639 | Q258N + Q291W + Q313M + D369L + E402N + S434P + A475L + K495N + G628W | | ** | ** |
| 640 | Q258N + Q291W + Q313M + D369R + E402N + S434P + A475L + E493Y + K495N + A505C + G628W | | ** | ** |
| 641 | Q258N + Q291W + Q313M + D369R + E402N + S434P + A475L + T482A + K495N + G628W + D646N | | ** | + |
| 642 | Q258N + Q291W + Q313M + D369R + E402N + S434P + A475L + A477G + K495N + G628W + S764F + S848N | | ** | + |
| 643 | Q258N + Q291W + Q313M + D369R + E402N + S434P + A475L + K495N + G628W + I847T | c1434t | ** | + |
| 644 | Q258N + Q291W + Q313M + D369R + E402N + S434P + A475L + K495N + G628W + T685V + Y850Q | g2472a | ** | + |
| 645 | Y135M + Q258N + Q291W + Q313M + D369R + E402N + S434P + A475L + K495N + S501R + G628W + T685V + T777N | | ** | + |
| 646 | Q258N + Q291W + Q313M + D369R + E402N + S434P + A475L + K495N + G628W + Y850Q | | ** | + |

Table 4: Thermoactivity conditions: pH 4.5, 70° C. for 21 hrs. Thermostability conditions: enzyme residual activity was determined after incubated at pH 4.5, 70° C. for 2 hrs.
[1]Amino acid changes are indicated with respect to SEQ ID NO: 2; the backbone sequence contains substitutions Q258N + Q291W + Q313M + D369R + E402N + S434P + A475L + K495N + G628W
[2]Nucleotide changes are indicated relative to SEQ ID NO: 1.
[3]Fold improvement is with respect to Variant 269 (SEQ ID NO: 7)
* = 0.2 to 0.5 fold improvement
** = 0.6 to 1.0 fold improvement
+ = 1.1 to 1.9 fold improvement
++ = 2.0 to 2.9 fold improvement
+++ = 3.0 to 3.9 fold improvement
++++ = 4.0 to 4.9 fold improvement

TABLE 5

| Variant Number | Amino Acid Changes[1] | Silent Nucleotide Changes[2] | Activity Fold improvement over Var. 481[3] | Stability Fold improvement over Var. 481[3] |
|---|---|---|---|---|
| 481 | Q258N + Q291W + Q313M + D369R + E402N + S434P + A475L + K495N + G628W + A689I + Y715P | | | |
| 647 | D47I + Q258N + Q291W + Q313M + A343C + D369R + E402N + S434P + A475L + K495N + G628W + T687K + A689I + Y715P | | ++++ | ++++ |
| 648 | A109S + Q258N + V260G + Q291W + Q313M + A343C + D369R + E402N + S434P + A475L + K495N + G628W + A689I + Y715P | | ++++ | ++ |
| 649 | A109T + Q258N + V260G + Q291W + Q313M + A343C + D369R + E402N + S434P + A475L + K495N + G628W + T687W + A689I + Y715P + S764F | | ++++ | ++ |
| 650 | D47I + Q258N + V260G + Q291W + Q313M + A343C + D369R + E402N + S434P + A475L + K495N + G628W + T687C + A689I + Y715P + S764F | | +++ | + |
| 651 | Q258N + V260G + Q291W + Q313M + A343C + D369R + E402N + S434P + A475L + K495N + G628W + A689I + Y715P | c2292t | +++ | + |
| 652 | D47I + Q258N + V260G + Q291W + Q313M + D369R + E402N + S434P + A475L + K495N + G628W + T687C + A689I + Y715P | | +++ | + |
| 653 | D47I + A109T + Q258N + V260G + Q291W + Q313M + A343C + D369R + E402N + S434P + A475L + K495N + G628W + A689I + Y715P | | +++ | ++ |
| 654 | Q258N + V260G + Q291W + Q313M + D369R + E402N + S434P + A475L + K495N + G628W + T687W + A689I + Y715P | | +++ | ++ |
| 655 | Q258N + V260G + Q291W + Q313M + A343C + D369R + E402N + S434P + A475L + K495N + G628W + A689I + Y715P + S764F | | +++ | + |
| 656 | Q258N + V260G + Q291W + Q313M + D369R + E402N + S434P + A475L + K495N + G628W + A689I + Y715P + A732G | | +++ | + |
| 657 | D47I + A109T + Q258N + V260G + Q291W + Q313M + A343C + D369R + E402N + S434P + A475L + K495N + G628W + A689I + Y715P + S764F | | +++ | + |
| 658 | Q258N + V260G + Q291W + Q313M + A343C + D369R + E402N + S434P + A475L + K495N + G628W + A689I + Y715P + S764F | | +++ | + |
| 659 | D47I + A109T + Q258N + V260G + Q291W + Q313M + A343C + D369R + E402N + S434P + A475L + K495N + G628W + A689I + Y715P + S764F | | +++ | + |
| 660 | D47I + A109T + Q258N + V260G + Q291W + Q313M + A343C + D369R + E402N + S434P + A475L + K495N + G628W + A689I + Y715P | | ++ | + |
| 661 | A109T + Q258N + V260G + Q291W + Q313M + A343C + D369R + E402N + S434P + A475L + K495N + G628W + T687C + A689I + Y715P | | ++ | ++ |
| 662 | D47I + I106V + Q258N + V260G + Q291W + Q313M + F314L + D369R + E402N + S434P + A475L + K495N + G628W + A689I + Y715P + A732G | | ++ | ++ |
| 663 | Q258N + Q291W + Q313M + A343C + D369R + E402N + S434P + A475L + K495N + G628W + T687W + A689I + Y715P | | ++ | + |
| 664 | I106V + Q258N + V260G + Q291W + Q313M + F314L + D369R + E402N + S434P + K495N + G628W + A689I + Y715P + A732G | c1425g | ++ | + |

TABLE 5-continued

| Variant Number | Amino Acid Changes[1] | Silent Nucleotide Changes[2] | Activity Fold improvement over Var. 481[3] | Stability Fold improvement over Var. 481[3] |
|---|---|---|---|---|
| 665 | Q258N + V260G + Q291W + Q313M + F314L + D369R + E402N + S434P + A475L + K495N + G628W + A689I + Y715P | | ++ | + |
| 666 | D47I + A109S + Q258N + V260G + Q291W + Q313M + A343C + D369R + E402N + S434P + A475L + K495N + G628W + T687W + A689I + Y715P | | ++ | + |
| 667 | Q258N + V260G + Q291W + Q313M + F314V + D369R + E402N + S434P + A475L + K495N + G628W + S652D + A689I + Y715P + A732G | c747t | ++ | + |
| 668 | Q258N + V260G + Q291W + Q313M + A343C + D369R + E402N + S434P + A475L + K495N + G628W + A689I + Y715P | | ++ | + |
| 669 | I106V + Q258N + V260G + Q291W + Q313M + F314V + D369R + E402N + S434P + A475L + K495N + G628W + S652D + A689I + Y715P + A732G | | ++ | ++ |
| 670 | Q258N + V260G + Q291W + Q313M + A343C + D369R + E402N + S434P + A475L + K495N + G628W + A689I + Y715P + S764F | | ++ | + |
| 671 | D47I + Q258N + V260G + Q291W + Q313M + A343C + D369R + E402N + S434P + A475L + K495N + G628W + A689I + Y715P | | ++ | + |
| 672 | I106V + Q258N + V260G + Q291W + Q313M + F314L + D369R + E402N + S434P + A475L + K495N + G628W + S652D + A689I + Y715P + A732M | | ++ | + |
| 673 | A109T + Q258N + V260G + Q291W + Q313M + A343C + D369R + E402N + S434P + A475L + K495N + G628W + A689I + Y715P + S764F | | ++ | + |
| 674 | Q258N + V260G + Q291W + Q313M + A343C + D369R + E402N + S434P + A475L + K495N + G628W + A689I + Y715P | | ++ | + |
| 675 | Q258N + V260G + Q291W + Q313M + A343G + D369R + E402N + S434P + Q474L + A475L + K495N + G628W + A689I + Y715P | | ++ | + |
| 676 | D47I + Q258N + V260G + Q291W + Q313M + A343C + D369R + E402N + S434P + A475L + K495N + G628W + A689I + Y715P + S764F | | ++ | + |
| 677 | D47I + A109T + Q258N + V260G + Q291W + Q313M + D369R + E402N + S434P + A475L + K495N + G628W + A689I + Y715P + S764F | t300c | ++ | + |
| 678 | Q258N + V260G + Q291W + Q313M + A343C + D369R + E402N + S434P + A475L + K495N + G628W + A689I + Y715P + S764F | | ++ | + |
| 679 | D47I + A109T + Q258N + V260G + Q291W + Q313M + A343C + D369R + E402N + S434P + A475L + K495N + G628W + A689I + Y715P | | ++ | + |
| 680 | Q258N + V260G + Q291W + Q313M + A343C + D369R + E402N + S434P + A475L + K495N + G628W + A689I + Y715P + S764F | | ++ | + |
| 681 | Q258N + V260G + Q291W + Q313M + D369R + E402N + S434P + A475L + K495N + G628W + A689I + Y715P | | ++ | + |
| 682 | D47I + Q258N + V260G + Q291W + Q313M + A343C + D369R + E402N + S434P + A475L + K495N + G628W + A689I + Y715P | | ++ | + |
| 683 | Q258N + V260G + Q291W + Q313M + D369R + E402N + S434P + A475L + K495N + G628W + A689I + Y715P | | ++ | + |
| 684 | A109T + Q258N + V260G + Q291W + Q313M + A343C + D369R + E402N + S434P + A475L + K495N + G628W + A689I + Y715P | | ++ | + |
| 685 | I106V + Q258N + V260G + Q291W + Q313M + D369R + E402N + S434P + A475L + K495N + G628W + A689I + Y715P + A732G + P870S | | ++ | ++ |
| 686 | Q258N + V260G + Q291W + Q313M + D369R + E402N + S434P + A475L + K495N + G628W + A689I + Y715P | | ++ | + |
| 687 | I106V + Q258N + V260G + Q291W + Q313M + F314V + D369R + E402N + S434P + A475L + K495N + G628W + A689I + Y715P + A732M | | ++ | ++ |
| 688 | Q258N + Q291W + Q313M + F314V + D369R + E402N + S434P + A475L + K495N + G628W + A689I + Y715P + A732G | | ++ | + |
| 689 | I106V + Q258N + V260G + Q291W + Q313M + D369R + E402N + S434P + A475L + K495N + G628W + A689I + Y715P + A732V | | ++ | + |
| 690 | Q258N + V260G + Q291W + Q313M + A343C + D369R + E402N + S434P + A475L + K495N + G628W + A689I + Y715P | | ++ | + |
| 691 | Q258N + V260G + Q291W + Q313M + A343C + D369R + E402N + S434P + A475L + K495N + G628W + A689I + Y715P | | ++ | + |
| 692 | D47I + I106V + Q258N + Q291W + Q313M + F314L + D369R + E402N + S434P + A475L + K495N + G628W + A689I + Y715P + A732G | | ++ | + |
| 693 | Q258N + V260G + Q291W + Q313M + D369R + E402N + S434P + A475L + K495N + G628W + A689I + Y715P | c306t | ++ | + |
| 694 | Q258N + V260G + Q291W + Q313M + D369R + E402N + S434P + A475L + K495N + G628W + A689I + Y715P | | ++ | + |
| 695 | Q258N + V260G + Q291W + Q313M + D369R + E402N + S434P + K495N + G628W + S652D + A689I + Y715P + A732G | c1425g | ++ | + |
| 696 | D47I + I106V + Q258N + V260G + Q291W + Q313M + D369R + E402N + S434P + K495N + G628W + S652D + A689I + Y715P + A732G | c1425g | ++ | ++ |
| 697 | D47I + I106V + Q258N + V260G + Q291W + Q313M + D369R + E402N + S434P + K495N + G628W + S652D + A689I + Y715P | c1425g | ++ | + |
| 698 | Q258N + V260G + Q291W + Q313M + A343C + D369R + E402N + S434P + A475L + K495N + G628W + A689I + Y715P | | ++ | + |
| 699 | C8A + L9F + D47I + Q258N + V260G + Q291W + Q313M + D369R + E402N + S434P + K495N + G628W + A689I + Y715P + A732G | c1425g | ++ | + |
| 700 | D47I + Q258N + V260G + Q291W + Q313M + F314V + D369R + E402N + S434P + A475L + K495N + G628W + A689I + Y715P + A732G + D844G | | ++ | + |
| 701 | Q258N + V260G + Q291W + Q313M + D369R + E402N + S434P + A475L + K495N + G628W + A689I + Y715P | | ++ | + |
| 702 | I106V + Q258N + V260G + Q291W + Q313M + D369R + E402N + S434P + A475L + K495N + G628W + A689I + Y715P + A732G | | ++ | ++ |

TABLE 5-continued

| Variant Number | Amino Acid Changes[1] | Silent Nucleotide Changes[2] | Activity Fold improvement over Var. 481[3] | Stability Fold improvement over Var. 481[3] |
|---|---|---|---|---|
| 703 | D47N + Q258N + V260G + Q291W + Q313M + F314V + D369R + E402N + S434P + A475L + K495N + G628W + A689I + Y715P + A732G | | ++ | ++ |
| 704 | Q258N + V260G + Q291W + Q313M + D369R + E402N + S434P + A475L + K495N + G628W + A689I + Y715P | | ++ | + |
| 705 | D47I + I106V + Q258N + Q291W + Q313M + D369R + E402N + S434P + A475L + K495N + G628W + S652D + A689I + Y715P + A732M | | ++ | + |
| 706 | A109T + Q258N + Q291W + Q313M + D369R + E402N + S434P + A475L + K495N + G628W + T687W + A689I + Y715P | | ++ | + |
| 707 | Q258N + V260G + Q291W + Q313M + A343C + D369R + E402N + S434P + A475L + K495N + G628W + A689I + Y715P | | ++ | + |
| 708 | V25A + Q258N + Q291W + Q313M + D369R + E402N + S434P + A475L + K495N + G628W + A689I + Y715P | | ++ | + |
| 709 | D47I + Q258N + V260G + Q291W + Q313M + D369R + E402N + S434P + A475L + K495N + G628W + A689I + Y715P + A732M | | ++ | + |
| 710 | Q258N + Q291W + Q313M + D369R + E402N + S434P + A475L + K495N + G628W + T687W + A689I + Y715P | | ++ | + |
| 711 | D47I + I106V + Q258N + V260G + Q291W + Q313M + F314V + D369R + E402N + S434P + A475L + K495N + G628W + S652D + A689I + Y715P | | ++ | ++ |
| 712 | D47I + A109T + Q258N + Q291W + Q313M + A343C + D369R + E402N + S434P + A475L + K495N + G628W + A689I + Y715P | | ++ | + |
| 713 | D47I + Q258N + Q291W + Q313M + A343C + D369R + E402N + S434P + A475L + K495N + G628W + A689I + Y715P + S764F | | ++ | + |
| 714 | Q258N + V260G + Q291W + Q313M + D369R + E402N + S434P + A475L + K495N + G628W + T687K + A689I + Y715P | c1173t | + | + |
| 715 | A109T + Q258N + Q291W + Q313M + A343C + D369R + E402N + S434P + A475L + K495N + G628W + A689I + Y715P + S764F | | + | + |
| 716 | Q258N + V260G + Q291W + Q313M + D369R + E402N + S434P + A475L + K495N + G628W + A689I + Y715P | | + | + |
| 717 | D47I + I106V + Q258N + Q291W + Q313M + D369R + E402N + S434P + A475L + K495N + G628W + A689I + Y715P | | + | + |
| 718 | Q258N + V260G + Q291W + Q313M + D369R + E402N + S434P + A475L + K495N + G628W + A689I + Y715P + S764F | | + | + |
| 719 | Q258N + V260G + Q291W + Q313M + F314L + D369R + E402N + S434P + K495N + G628W + S652D + A689I + Y715P | c1425g | + | + |
| 720 | Q258N + V260G + Q291W + Q313M + D369R + E402N + S434P + A475L + K495N + G628W + A689I + Y715P | | + | + |
| 721 | Q258N + V260G + Q291W + Q313M + A343C + D369R + E402N + S434P + A475L + K495N + G628W + A689I + Y715P | | + | + |
| 722 | Q258N + Q291W + Q313M + D369R + E402N + S434P + A475L + K495N + G628W + A689I + Y715P + S764F | | + | + |
| 723 | Q258N + V260G + Q291W + Q313M + F314V + D369R + E402N + S434P + K495N + G628W + A689I + Y715P | c1425g | + | + |
| 724 | L237Y + Q258N + V260G + Q291W + Q313M + A343C + D369R + E402N + S434P + A475L + K495N + G628W + A689I + Y715P | | + | ** |
| 725 | Q258N + V260G + Q291W + Q313M + D369R + E402N + S434P + A475L + K495N + G628W + A689I + Y715P | | + | + |
| 726 | Q258N + V260G + Q291W + Q313M + D369R + E402N + S434P + A475L + K495N + G628W + A689I + Y715P | | + | + |
| 727 | Q258N + V260G + Q291W + Q313M + D369R + E402N + S434P + A475L + K495N + G628W + A689I + Y715P | | + | + |
| 728 | Q85N + Q258N + Q291W + Q313M + D369R + E402N + S434P + A475L + K495N + G628W + A689I + Y715P + L757K | | + | + |
| 729 | Q258N + V260G + Q291W + Q313M + D369R + E402N + S434P + A475L + K495N + G628W + A689I + Y715P | | + | + |
| 730 | Q258N + V260G + Q291W + Q313M + D369R + E402N + S434P + A475L + K495N + G628W + A689I + Y715P | g2235a | + | + |
| 731 | Q258N + V260G + Q291W + Q313M + D369R + E402N + S434P + A475L + K495N + S604C + G628W + A689I + Y715P | | + | + |
| 732 | D47I + Q258N + V260G + Q291W + Q313M + D369R + E402N + S434P + A475L + R476G + K495N + N588F + G628W + D651E + A689I + Y715P | | + | + |
| 733 | Q85N + Q258N + Q291W + Q313M + D369R + E402N + S434P + P436Q + A475L + K495N + G628W + A689I + Y715P + L757K | | + | + |
| 734 | I106V + Q258N + Q291W + Q313M + D369R + E402N + S434P + A475L + K495N + G628W + A689I + Y715P + A732M | | + | + |
| 735 | Q258N + V260G + Q291W + Q313M + D369R + E402N + S434P + A475L + K495N + G628W + A689I + Y715P | | + | + |
| 736 | Q258N + V260G + Q291W + Q313M + F314L + D369R + E402N + S434P + A475L + K495N + G628W + A689I + Y715P | | + | + |
| 737 | Q258N + Q291W + Q313M + D369R + E402N + S434P + K495N + G628W + S652D + A689I + Y715P + A732G | c1425g | + | + |
| 738 | A109T + Q258N + Q291W + Q313M + A343C + D369R + E402N + S434P + A475L + K495N + G628W + A689I + Y715P | | + | + |
| 739 | D47I + Q258N + Q291W + Q313M + F314L + D369R + E402N + S434P + A475L + K495N + G628W + A689I + Y715P + Y736N | c2277a | + | + |
| 740 | Q258N + Q291W + Q313M + F314L + D369R + E402N + S434P + A475L + K495N + G628W + S652D + A689I + Y715P + A732G | | + | + |

TABLE 5-continued

| Variant Number | Amino Acid Changes[1] | Silent Nucleotide Changes[2] | Activity Fold improvement over Var. 481[3] | Stability Fold improvement over Var. 481[3] |
|---|---|---|---|---|
| 741 | V25A + Q85N + Q258N + Q291W + Q313M + D369R + E402N + S434P + P436Q + A475L + K495N + G616D + G628W + D650Y + A689I + Y715P + L757K | | + | + |
| 742 | Q258N + Q291W + Q313M + D369R + E402N + S434P + A475L + K495N + G628W + A689I + Y715P + S764F | | + | + |
| 743 | V253F + Q258N + Q291W + Q313M + D369R + E402N + S434P + A475L + K495N + G628W + A689I + Q690K + D709E + E710G + Y715P | | + | + |
| 744 | Q85N + V175A + Q258N + L275Y + Q291W + Q313M + D369R + E402N + S434P + A475L + K495N + G628W + A689I + Y715P | | + | + |
| 745 | Q258N + Q291W + Q313M + D369R + E402N + S434P + A475L + K495N + G628W + A689I + Q690K + Y715P | | + | ** |
| 746 | V25A + Q85N + Q258N + Q291W + Q313M + D369R + E402N + S434P + A475L + K495N + G616D + G628W + A689I + Y715P + L757K | | + | + |
| 747 | Q85N + Q258N + Q291W + Q313M + D369R + E402N + S434P + A475L + K495N + G628W + A689I + Y715P | | + | + |
| 748 | V25A + Q85N + Q258N + Q291W + Q313M + D369R + E402N + S434P + A475L + K495N + G628W + A689I + Y715P | c57a | + | + |
| 749 | Q258N + Q291W + Q313M + D369R + E402N + S434P + A475L + K495N + G628W + T687C + A689I + Y715P | | + | ** |
| 750 | Q258N + Q291W + Q313M + D369R + E402N + S434P + A475L + K495N + G628W + A689I + Q690H + Y715P + M816L | | + | + |
| 751 | V25A + Q85N + Q258N + L275Y + Q291W + Q313M + D369R + E402N + S434P + A475L + K495N + G616D + G628W + A689I + Y715P + V846F | | + | + |
| 752 | Q258N + Q291W + Q313M + D369R + E402N + S434P + A475L + K495N + G628W + A689I + Y715P + V846Q | | + | + |
| 753 | A79E + Q258N + Q291W + Q313M + D369R + E402N + S434P + A475L + K495N + G626D + G628W + A689I + Y715P | | + | ** |
| 754 | Q258N + Q291W + Q313M + A343C + D369R + E402N + S434P + A475L + K495N + G628W + A689I + Y715P | | + | ** |
| 755 | A79E + Q258N + Q291W + Q313M + D369R + E402N + S434P + A475L + K495N + A505C + G628W + A689I + Y715P | | + | + |
| 756 | Q258N + Q291W + Q313M + F314L + D369R + Q381V + E402N + S434P + A475L + K495N + G628W + A689I + Y715P | | + | + |
| 757 | D47I + I106V + Q258N + V260G + Q291W + Q313M + D369R + E402N + S434P + A475L + K495N + G628W + A689I + Y715P | c1704t | + | + |
| 758 | Q85N + Q258N + Q291W + Q313M + D369R + E402N + S434P + A475L + K495N + G628W + A689I + Y715P | | + | + |
| 759 | V25A + Q85N + Q258N + Q291W + Q313M + D369R + E402N + S434P + P436Q + A475L + K495N + G628W + A689I + Y715P + L757K + V846Q | | + | + |
| 760 | V25A + Q85N + Q258N + Q291W + Q313M + D369R + E402N + S434P + P436Q + A475L + K495N + G628W + D650N + A689I + Y715P | g2274t | + | + |
| 761 | D47I + I106V + Q258N + V260G + Q291W + Q313M + D369R + E402N + S434P + A475L + K495N + S550C + G628W + S652D + A689I + Y715P + A732G | | + | + |
| 762 | A109S + Q258N + V260G + Q291W + Q313M + D369R + E402N + S434P + A475L + K495N + S604A + G628W + A689I + Y715P | | + | + |
| 763 | V25A + Q85N + Q258N + Q291W + Q313M + D369R + E402N + S434P + A475L + K495N + G628W + A689I + Y715P + V846Q | | + | + |
| 764 | D47I + Q258N + V260G + Q291W + Q313M + D369R + E402N + S434P + A475L + K495N + G628W + A689I + Y715P | | + | + |
| 765 | A109T + Q258N + Q291W + Q313M + D369R + E402N + S434P + A475L + K495N + G628W + A689I + Y715P | | + | + |
| 766 | Q258N + V260G + Q291W + Q313M + F314L + D369R + E402N + S434P + K495N + N588F + G628W + A689I + Y715P + A732M | c1425g | + | + |
| 767 | Q85N + Q258N + Q291W + Q313M + D369R + E402N + S434P + A475L + K495N + G616D + G628W + A689I + Y715P | | + | + |
| 768 | V25A + Q85N + Q258N + Q291W + Q313M + D369R + E402N + S434P + P436Q + A475L + K495N + G616D + G628W + D650N + A689I + Y715P | | + | + |
| 769 | A79E + Q258N + Q291W + Q313M + D369R + E402N + S434P + A475L + K495N + A505C + G628W + V674I + A689I + Y715P | | + | + |
| 770 | V25A + Q258N + Q291W + Q313M + D369R + E402N + S434P + A475L + K495N + G628W + A689I + Y715P + L757K | c483t | + | + |
| 771 | V25A + Q85H + Q258N + L275F + Q291W + Q313M + D369R + E402N + S434P + A475L + K495N + G628W + D650N + A689I + Y715P + L757I | | + | + |
| 772 | K24T + A79E + A136L + Q258N + D274Y + Q291W + Q313M + D369R + E402N + S434P + A475L + K495N + A505C + G628W + A689I + Y715P | | + | + |
| 773 | V25A + Q85N + Q258N + Q291W + Q313M + D369R + E402N + S434P + A475L + K495N + G628W + A689I + Y715P | | + | + |
| 774 | Q258N + Q291W + Q313M + D369R + E402N + S434P + A475L + K495N + G628W + A689I + Y715P | | + | ** |
| 775 | Q258N + Q291W + Q313M + D369R + E402N + S434P + A475L + K495N + G628W + A689I + Y715P | g633a | + | ** |
| 776 | K24G + A79E + Q258N + D274Y + Q291W + Q313M + D369R + E402N + S434P + A475L + K495N + A505C + G628W + A689I + Y715P | | + | ** |
| 777 | Q85N + V175A + Q258N + Q291W + Q313M + D369R + E402N + S434P + A475L + K495N + G628W + A689I + Y715P | | + | + |
| 778 | V25A + Q85N + Q258N + Q291W + Q313M + D369R + E402N + S434P + A475L + K495N + G628W + D650N + A689I + Y715P | | + | + |

TABLE 5-continued

| Variant Number | Amino Acid Changes[1] | Silent Nucleotide Changes[2] | Activity Fold improvement over Var. 481[3] | Stability Fold improvement over Var. 481[3] |
|---|---|---|---|---|
| 779 | V25A + Q85N + Q258N + L275Y + Q291W + Q313M + D369R + E402N + S434P + A475L + K495N + G628W + A689I + Y715P + L757K | | + | + |
| 780 | A79M + Q258N + Q291W + Q313M + D369R + E402N + S434P + A475L + K495N + A505C + G628W + A689I + Y715P | | + | + |
| 781 | Q85N + Q258N + Q291W + Q313M + D369R + E402N + S434P + P436Q + A475L + K495N + G628W + A689I + Y715P+ | | + | + |
| 782 | Q85N + Q258N + Q291W + Q313M + D369R + E402N + S434P + A475L + K495N + G628W + A689I + Y715P | | + | + |
| 783 | Q85N + Q258N + Q291W + Q313M + D369R + E402N + S434P + A475L + K495N + G628W + A689I + Y715P | | + | + |
| 784 | Q258N + Q291W + Q313M + D369R + E402N + S434P + A475L + K495N + G628W + A689I + Y715P | | + | + |
| 785 | Q258N + Q291W + Q313M + A343C + D369R + E402N + S434P + A475L + K495N + G628W + A689I + Y715P | | + | ** |
| 786 | Q258N + Q291W + Q313M + D369R + E402N + S434P + A475L + K495N + G628W + A689I + Y715P | | + | ** |
| 787 | Q258N + Q291W + Q313M + D369R + E402N + S434P + A475L + K495N + G628W + A689I + Y715P | | + | ** |
| 788 | Q258N + Q291W + Q313M + D369R + E402N + S434P + A475L + K495N + G628W + A689I + Y715P | | + | + |
| 789 | Q85N + Q258N + Q291W + Q313M + D369R + E402N + S434P + A475L + K495N + G628W + A689I + Y715P | g927a | + | + |
| 790 | I106V + Q258N + Q291W + Q313M + D369R + E402N + S434P + A475L + K495N + G628W + A689I + Y715P | | ** | + |
| 791 | D47I + Q258N + V260G + Q291W + Q313M + D369R + E402N + S434P + A475L + K495N + S604A + G628W + A689I + Y715P | | ** | + |
| 792 | Q258N + Q291W + Q313M + D369R + E402N + S434P + A475L + K495N + G628W + A689I + Y715P | | ** | + |
| 793 | Q258N + Q291W + Q313M + D369R + E402N + S434P + A475L + K495N + G628W + A689I + Y715P | | ** | ** |
| 794 | V25A + Q258N + Q291W + Q313M + D369R + E402N + S434P + A475L + K495N + G628W + A689I + Y715P | | ** | ** |
| 795 | Q258N + V260G + Q291W + Q313M + A343C + D369R + E402N + S434P + Q474I + A475L + K495N + G628W + A689I + Y715P + S764F | | ** | + |
| 796 | Q258N + Q291W + Q313M + A343C + D369R + E402N + S434P + A475L + K495N + G628W + A689I + Y715P | | ** | + |
| 797 | D47I + Q258N + Q291W + Q313M + D369R + E402N + S434P + A475L + K495N + N588F + G628W + A689I + Y715P | | ** | + |
| 798 | S58G + Q258N + Q291W + Q313M + D369R + Q381V + E402N + S434P + A475L + K495N + G628W + A689I + Y715P | | ** | + |
| 799 | V253F + Q258N + Q291W + Q313M + D369R + E402N + S434P + A475L + K495N + G628W + A689I + Y715P + T785L + M816L | | ** | + |
| 800 | A243G + Q258N + V260G + Q291W + Q313M + D369R + E402N + S434P + A475L + K495N + G628W + A689I + Y715P + S764F | | ** | + |
| 801 | I106V + Q258N + V260G + Q291W + Q313M + D369R + E402N + S434P + A475L + K495N + N588F + S652D + G628W + A689I + Y715P + D733G | c597t | ** | ++ |
| 802 | Q258N + Q291W + Q313M + D369R + E402N + S434P + A475L + K495N + G628W + A689I + Y715P + V846L | | ** | ** |
| 803 | Q258N + Q291W + Q313M + D369R + E402N + S434P + A475L + K495N + S604A + G628W + A689I + Y715P | | ** | + |
| 804 | A79G + Q258N + Q291W + Q313M + D369R + E402N + S434P + A475L + K495N + G628W + A689I + Y715P + T777N | | ** | + |
| 805 | Q258N + Q291W + Q313M + D369R + E402N + S434P + A475L + K495N + G628W + A689I + Y715P | | ** | ** |
| 806 | V25A + Q258N + Q291W + Q313M + D369R + E402N + S434P + A475L + K495N + G628W + A689I + Y715P | | ** | ** |
| 807 | K24T + A79E + Q258N + D274Y + Q291W + Q313M + D369R + E402N + S434P + A475L + K495N + A505C + G628W + A689I + Y715P + T777N | | ** | + |
| 808 | D47I + Q258N + Q291W + Q313M + A343C + D369R + E402N + S434P + A475L + K495N + S604V + G628W + T687C + A689I + Y715P + S764F + L869R | | ** | + |
| 809 | Q258N + D274Y + Q291W + Q313M + D369R + E385L + E402N + S434P + A475L + K495N + G626D + G628W + A689I + Y715P + T777N | | ** | ** |
| 810 | S58G + Q258N + Q291W + Q313M + D369R + Q381V + E402N + S434P + N437D + A475L + K495N + G628W + A689I + Q690H + D709E + E710G + Y715P | c489t | ** | ** |
| 811 | D47I + Q258N + V260G + Q291W + Q313M + A343C + D369R + E402N + S434P + Q474I + A475L + K495N + G628W + A689I + Y715P | | ** | + |
| 812 | Q258N + Q291W + Q313M + D369R + E402N + S434P + N437K + A475L + K495N + G628W + A689I + Y715P + T785L | | ** | + |
| 813 | A109S + Q258N + Q291W + Q313M + D369R + E402N + S434P + A475L + K495N + S604I + G628W + A689I + Y715P | | ** | + |
| 814 | Q258N + V260G + Q291W + Q313M + D369R + E402N + S434P + A475L + K495N + S604V + G628W + A689I + Y715P + K807R | c624t | ** | + |
| 815 | Q258N + Q291W + Q313M + A343C + D369R + E402N + S434P + A475L + K495N + S604V + G628W + A689I + Y715P | | ** | + |
| 816 | Q258N + Q291W + Q313M + D369R + E402N + S434P + A475L + K495N + G628W + A689I + Y715P + L757K | | ** | ** |

TABLE 5-continued

| Variant Number | Amino Acid Changes[1] | Silent Nucleotide Changes[2] | Activity Fold improvement over Var. 481[3] | Stability Fold improvement over Var. 481[3] |
|---|---|---|---|---|
| 817 | D47I + Q258N + Q291W + Q313M + D369R + E402N + S434P + K495N + N588F + G628W + S652D + A689I + Y715P | c1425g | ** | + |
| 818 | A79M + A136L + Q258N + D274Y + Q291W + Q313M + D369R + E402N + S434P + A475L + K495N + A505C + G628W + A689I + Y715P + T783A | | ** | + |
| 819 | D47I + A109T + Q258N + V260G + Q291W + Q313M + D369R + E402N + S434P + A475L + K495N + S604V + G628W + A689I + Y715P + S764F | | ** | + |
| 820 | S58G + Q258N + Q291W + Q313M + D369R + E402N + S434P + A475L + K495N + G628W + A689I + Y715P + T785L | | * | ** |
| 821 | K24G + A136L + Q258N + D274Y + Q291W + Q313M + D369R + E402N + S434P + A475L + K495N + A505C + G628W + A689I + Y715P + T777N | g240a | * | ** |
| 822 | S58G + Q258N + Q291W + Q313M + D369R + Q381V + E402N + S434P + A475L + K495N + G628W + A689I + Y715P + T785L | c2007t | * | + |
| 823 | S58G + Q258N + Q291W + Q313M + D369R + E402N + S434P + A475L + K495N + G628W + A689I + Y715P + T785L + M816L | | * | ** |

Table 5: Thermoactivity conditions: pH 4.2, 70° C. for 21 hrs. Thermostability conditions: enzyme residual activity was determined after incubated at pH 4.5, 70° C. for 3 hrs.
[1] Amino acid changes are indicated with respect to SEQ ID NO: 2; the backbone sequence contains substitutions Q258N + Q291W + Q313M + D369R + E402N + S434P + A475L + K495N + G628W + A689I + Y715P.
[2] Nucleotide changes are indicated relative to SEQ ID NO: 1.
[3] Fold improvement is with respect to Variant 481 (SEQ ID NO: 9):
* = 0.2 to 0.5 fold improvement
** = 0.6 to 1.0 fold improvement
+ = 1.1 to 1.9 fold improvement
++ = 2.0 to 2.9 fold improvement
+++ = 3.0 to 3.9 fold improvement
++++ = 4.0 to 4.9 fold improvement

TABLE 6

| Variant Number | Amino Acid Changes[1] | Silent Nucleotide Changes[2] | Activity Fold improvement over Var. 647[3] | Stability Fold improvement over Var. 647[3] |
|---|---|---|---|---|
| 647 | D47I + Q258N + Q291W + Q313M + A343C + D369R + E402N + S434P + A475L + K495N + G628W + T687K + A689I + Y715P | | | |
| 824 | D47I + A79G + Q85N + Q258N + V260G + Q291W + Q313M + A343C + D369R + E402N + S434P + A475L + K495N + G628W + T687K + A689I + Y715P + A732M | | ++++ | + |
| 825 | D47I + Q258N + V260G + Q291W + Q313M + F314L + A343C + D369R + E402N + S434P + A475L + K495N + G628W + T687C + A689I + Y715P + A732G | | ++++ | + |
| 826 | D47I + A79E + Q85N + Q258N + Q291W + Q313M + A343C + D369R + E402N + S434P + A475L + K495N + A505C + G628W + T687W + A689I + Y715P | c1947t | +++ | ++ |
| 827 | D47I + A79E + Q85N + Q258N + V260G + Q291W + Q313M + F314L + A343C + D369R + E402N + S434P + A475L + K495N + G628W + T687K + A689I + Y715P | | +++ | ** |
| 828 | D47I + A79G + Q85N + Q258N + V260G + L275Y + Q291W + Q313M + F314V + A343C + D369R + E402N + S434P + A475L + K495N + A505C + G628W + T687C + A689I + Y715P + S764Y + R769H | c1677t | +++ | ++ |
| 829 | D47I + A79G + Q85N + Q258N + V260G + Q291W + Q313M + F314V + A343C + D369R + E402N + S434P + A475L + K495N + G628W + T687K + A689I + Y715P | | +++ | ++ |
| 830 | D47I + A79M + Q85N + Q258N + V260G + L275Y + Q291W + Q313M + F314L + A343C + D369R + E402N + S434P + A475L + K495N + A505C + G628W + T687K + A689I + Y715P | | +++ | ++ |
| 831 | D47I + A79M + Q85N + Q258N + Q291W + Q313M + A343C + D369R + E402N + S434P + A475L + K495N + A505C + G628W + T687C + A689I + Y715P + A732G | t756c | +++ | ++ |
| 832 | D47I + Q258N + V260G + Q291W + Q313M + F314V + A343C + D369R + E402N + S434P + K495N + A505C + G628W + T687C + A689I + Y715P + A732G | | +++ | + |
| 833 | D47I + A79M + Q258N + V260G + Q291W + Q313M + F314V + A343C + D369R + E402N + S434P + K495N + G628W + T687K + A689I + Y715P + A732G | | +++ | ** |
| 834 | D47I + Q258N + L275Y + Q291W + Q313M + F314V + A343C + D369R + E402N + S434P + K495N + G628W + T687K + A689I + Y715P + A732G | | +++ | + |
| 835 | D47I + A79E + Q85N + Q258N + V260G + Q291W + Q313M + F314V + A343C + D369R + E402N + S434P + K495N + A505C + G628W + T687W + A689I + Y715P + A732V | | +++ | ++ |

TABLE 6-continued

| Variant Number | Amino Acid Changes[1] | Silent Nucleotide Changes[2] | Activity Fold improvement over Var. 647[3] | Stability Fold improvement over Var. 647[3] |
|---|---|---|---|---|
| 836 | D47I + A79M + Q258N + V260G + Q291W + Q313M + A343C + D369R + E402N + S434P + K495N + A505C + G628W + T687K + A689I + Y715P + A732M | | +++ | * |
| 837 | D47I + Q85N + Q258N + V260G + Q291W + Q313M + F314V + A343C + D369R + E402N + S434P + A475L + K495N + G628W + T687C + A689I + Y715P | | +++ | ** |
| 838 | D47I + A79G + Q258N + V260G + L275Y + Q291W + Q313M + A343C + D369R + E402N + S434P + A475L + K495N + G628W + T687C + A689I + Y715P + A732G | | +++ | + |
| 839 | D47I + Q258N + V260G + Q291W + Q313M + F314V + A343C + D369R + E402N + S434P + A475L + K495N + G628W + T687W + A689I + Y715P + A732G | | +++ | ++ |
| 840 | D47I + Q258N + V260G + Q291W + Q313M + F314V + A343C + D369R + E402N + S434P + A475L + K495N + G628W + T687K + A689I + Y715P + A732M | | +++ | ** |
| 841 | D47I + A79G + Q85N + Q258N + V260G + Q291W + Q313M + A343C + D369R + E402N + S434P + A475L + K495N + G628W + T687K + A689I + Y715P | | +++ | ** |
| 842 | D47I + A79G + Q85N + Q258N + V260G + L275Y + Q291W + Q313M + F314V + A343C + D369R + E402N + S434P + A475L + K495N + G628W + T687C + A689I + Y715P + A732G | | +++ | ** |
| 843 | D47I + A79G + Q258N + V260G + Q291W + Q313M + A343C + D369R + E402N + S434P + A475L + K495N + G628W + T687K + A689I + Y715P + A732M | | +++ | ** |
| 844 | D47I + Q85N + Q258N + V260G + Q291W + Q313M + A343C + D369R + E402N + S434P + K495N + G628W + T687K + A689I + Y715P | | +++ | + |
| 845 | D47I + Q85N + Q258N + V260G + L275Y + Q291W + Q313M + A343C + D369R + E402N + S434P + K495N + G628W + T687K + A689I + Y715P + A732G | | +++ | + |
| 846 | D47I + A79M + Q85N + Q258N + V260G + L275Y + Q291W + Q313M + A343C + D369R + E402N + S434P + K495N + G628W + T687W + A689I + Y715P | | +++ | * |
| 847 | D47I + A79G + Q85N + Q258N + V260G + Q291W + Q313M + A343C + D369R + E402N + S434P + A475L + K495N + A505C + G628W + T687K + A689I + Y715P | | +++ | ** |
| 848 | D47I + Q258N + V260G + Q291W + Q313M + F314V + A343C + D369R + E402N + S434P + A475L + K495N + G628W + T687C + A689I + Y715P + A732G | c498t | +++ | + |
| 849 | D47I + A79G + Q85N + Q258N + V260G + L275Y + Q291W + Q313M + F314V + A343C + D369R + E402N + S434P + A475L + K495N + G628W + T687K + A689I + Y715P | | +++ | ++ |
| 850 | D47I + Q85N + Q258N + Q291W + Q313M + A343C + D369R + E402N + S434P + A475L + K495N + G628W + T687W + A689I + Y715P + A732G | | +++ | ++ |
| 851 | D47I + A79G + Q85N + Q258N + V260G + L275Y + Q291W + Q313M + F314V + A343C + D369R + E402N + S434P + A475L + K495N + A505C + G628W + T687C + A689I + Y715P | c1335t | +++ | ** |
| 852 | D47I + Q258N + V260G + Q291W + Q313M + A343C + D369R + E402N + S434P + A475L + K495N + A505C + G628W + T687K + A689I + Y715P + A732G | | +++ | + |
| 853 | D47I + Q258N + Q291W + Q313M + F314V + A343C + D369R + E402N + S434P + A475L + K495N + G628W + T687W + A689I + Y715P + A732G | | +++ | ++ |
| 854 | D47I + A79G + Q85N + Q258N + Q291W + Q313M + F314V + A343C + D369R + E402N + S434P + K495N + G628W + T687K + A689I + Y715P | | +++ | ** |
| 855 | D47I + A79M + Q85N + Q258N + Q291W + Q313M + A343C + D369R + E402N + S434P + A475L + K495N + G628W + T687K + A689I + Y715P + A732G | | +++ | * |
| 856 | D47I + Q85N + Q258N + V260G + Q291W + Q313M + F314V + A343C + D369R + E402N + S434P + A475L + K495N + G628W + T687K + A689I + Y715P | | +++ | * |
| 857 | D47I + Q85N + Q258N + L275Y + Q291W + Q313M + F314V + A343C + D369R + E402N + S434P + K495N + G628W + T687C + A689I + Y715P | | +++ | ++ |
| 858 | D47I + A79G + Q85N + Q258N + V260G + L275Y + Q291W + Q313M + F314V + A343C + D369R + E402N + S434P + A475L + K495N + G628W + T687K + A689I + Y715P + A732G | | +++ | ** |
| 859 | D47I + Q258N + V260G + Q291W + Q313M + A343C + D369R + E402N + S434P + A475L + K495N + G628W + T687K + A689I + Y715P | c1377t | ++ | + |
| 860 | D47I + Q85N + Q258N + V260G + L275Y + Q291W + Q313M + A343C + D369R + E402N + S434P + A475L + K495N + G628W + T687K + A689I + Y715P | | ++ | + |

TABLE 6-continued

| Variant Number | Amino Acid Changes[1] | Silent Nucleotide Changes[2] | Activity Fold improvement over Var. 647[3] | Stability Fold improvement over Var. 647[3] |
|---|---|---|---|---|
| 861 | D47I + A79G + Q258N + Q291W + Q313M + F314L + A343C + D369R + E402N + S434P + A475L + K495N + G628W + T687K + A689I + Y715P | | + | ++ |
| 862 | D47I + Q258N + Q291W + Q313M + F314V + A343C + D369R + E402N + S434P + K495N + G628W + T687K + A689I + Y715P | | + | + |
| 863 | D47I + Q258N + V260G + L275Y + Q291W + Q313M + A343C + D369R + E402N + S434P + A475L + K495N + A505C + G628W + D646N + T687K + A689I + Y715P + A732G | | + | + |
| 864 | D47I + Q258N + V260G + Q291W + Q313M + A343C + D369R + E402N + S434P + A475L + K495N + G628W + T687K + A689I + Y715P | | + | + |
| 865 | D47I + Q258N + V260G + Q291W + Q313M + F314V + A343C + D369R + E402N + S434P + K495N + G628W + T687K + A689I + Y715P + A732V | | + | + |
| 866 | D47I + A79G + Q85N + Q258N + Q291W + Q313M + A343C + D369R + E402N + S434P + P439S + A475L + K495N + G628W + T687K + A689I + Y715P | | + | * |
| 867 | D47I + Q85N + Q258N + Q291W + Q313M + F314V + A343C + D369R + D395N + E402N + S434P + A475L + K495N + G628W + T687K + A689I + Y715P + A732V | | + | + |
| 868 | D47I + A79G + Q258N + Q291W + Q313M + A343C + D369R + E402N + S434P + A475L + K495N + A505C + G628W + T687C + A689I + T693A + Y715P + T827I | | ** | + |
| 869 | D47I + Q85N + Q258N + V260G + Q291W + Q313M + A343C + D369R + E402N + S434P + A475L + K495N + A505C + G628W + T687K + A689I + Y715P + A732V | t237g | ** | + |
| 870 | D47I + A79G + Q258N + L275Y + Q291W + Q313M + A343C + D369R + E402N + S434P + A475L + K495N + A505C + G628W + T687K + A689I + T693E + N723G + A730S + Y855* | a2185c | ** | + |

Table 6: Thermoactivity conditions: pH 4, 70° C. for 21 hrs. Thermostablity conditions: enzyme residual activity was determined after incubated at pH 4.5, 70° C. for 24 hrs. Amino acid and silent nucleotide changes are indicated with respect to wild type sequence.
[1]Amino acid changes are indicated with respect to SEQ ID NO: 2; the backbone sequence contains substitutions D47I + Q258N + Q291W + Q313M + A343C + D369R + E402N + S434P + A475L + K495N + G628W + T687K + A689I + Y715P.
[2]Nucleotide changes are indicated relative to SEQ ID NO: 1.
[3]Fold improvement is with respect to Variant 647 (SEQ ID NO: 15):
* = 0.2 to 0.5 fold improvement
** = 0.6 to 1.0 fold improvement
+ = 1.1 to 1.9 fold improvement
++ = 2.0 to 2.9 fold improvement
+++ = 3.0 to 3.9 fold improvement
++++ = 4.0 to 4.9 fold improvement

TABLE 7

| Variant Number | Amino Acid Changes[1] | Silent Nucleotide Changes[2] | Activity Fold improvement over Var. 664[3] | Stability Fold improvement over Var. 664[3] |
|---|---|---|---|---|
| 664 | I106V + Q258N + V260G + Q291W + Q313M + F314L + D369R + E402N + S434P + K495N + G628W + A689I + Y715P + A732G | c1425g | | |
| 871 | D47I + A79E + Q85N + I106V + A109T + Q258N + V260G + Q291W + Q313M + F314V + A343C + D369R + E402N + S434P + K495N + G628W + A689I + Y715P + A732G | c1425g | ++ | + |
| 872 | D47I + A79E + Q85N + I106V + Q258N + V260G + Q291W + Q313M + F314V + A343C + D369R + E402N + S434P + K495N + A505C + G628W + A689I + Y715P + A732G | c1425g | +++ | + |
| 873 | A79M + Q85N + I106V + A109T + Q258N + V260G + Q291W + Q313M + F314V + A343C + D369R + E402N + S434P + K495N + G628W + A689I + Y715P + A732G | c246t + c1425g + c2346t | +++ | + |
| 874 | D47I + A79E + I106V + A109T + Q258N + V260G + Q291W + Q313M + F314L + A343C + D369R + E402N + S434P + K495N + G628W + A689I + Y715P + A732G | c1425g | +++ | + |
| 875 | D47I + A79G + Q85N + I106V + A109T + Q258N + V260G + L275Y + Q291W + Q313M + F314L + A343C + D369R + E402N + S434P + K495N + G628W + A689I + Y715P + A732G | c1425g | +++ | + |
| 876 | A79E + Q85N + I106V + A109T + Q258N + V260G + Q291W + Q313M + F314L + A343C + D369R + E402N + S434P + K495N + G628W + A689I + Y715P + A732G | c1425g | +++ | + |
| 877 | A79G + Q85N + I106V + A109T + Q258N + V260G + L275F + Q291W + Q313M + F314V + A343C + D369R + E402N + S434P + K495N + A505C + G628W + T687C + A689I + Y715P + A732G | c1425g | +++ | + |

TABLE 7-continued

| Variant Number | Amino Acid Changes[1] | Silent Nucleotide Changes[2] | Activity Fold improvement over Var. 664[3] | Stability Fold improvement over Var. 664[3] |
|---|---|---|---|---|
| 878 | D47I + I106V + Q258N + V260G + Q291W + Q313M + F314L + A343C + D369R + E402N + S434P + K495N + G628W + A689I + Y715P + A732G | c1425g | ++ | + |
| 879 | D47I + A79E + Q85N + I106V + A109S + Q258N + V260G + Q291W + Q313M + F314V + A343C + D369R + E402N + S434P + K495N + G628W + A689I + Y715P + A732G | c1425g | ++ | + |
| 880 | D47I + A79E + Q85N + I106V + Q258N + V260G + L275Y + Q291W + Q313M + F314L + N315D + D369R + E402N + S434P + K495N + A505C + G628W + T687W + A689I + Y715P + A732G | c1425g | ++ | ** |
| 881 | D47I + Q85N + I106V + Q258N + V260G + L275Y + Q291W + Q313M + F314L + D369R + E402N + S434P + K495N + G628W + A689I + Y715P + A732G | c1425g | ++ | + |
| 882 | A79E + Q85N + I106V + A109S + Q258N + V260G + Q291W + Q313M + F314V + D369R + E402N + S434P + K495N + G628W + A689I + Y715P + A732G | c1425g | ++ | + |
| 883 | A79G + I106V + Q258N + V260G + Q291W + Q313M + F314V + A343C + D369R + E402N + S434P + K495N + G628W + T687W + A689I + Y715P + A732G | c1425g | ++ | + |
| 884 | D47I + A79G + Q85N + I106V + Q258N + V260G + L275Y + Q291W + Q313M + F314L + A343C + D369R + E402N + S434P + K495N + A505C + G628W + A689I + Y715P + A732G | c1425g + g2235a | ++ | + |
| 885 | D47I + Q85N + I106V + A109S + Q258N + V260G + Q291W + Q313M + F314V + A343C + D369R + E402N + S434P + K495N + G628W + A689I + Y715P + A732G | c1425g+ | ++ | + |
| 886 | D47I + A79E + Q85N + I106V + Q258N + V260G + Q291W + Q313M + F314L + A343C + D369R + E402N + S434P + K495N + G628W + A689I + Y715P + A732G | c811t + c1425g | ++ | + |
| 887 | D47I + A79M + Q85N + I106V + Q258N + V260G + Q291W + Q313M + F314V + A343C + D369R + E402N + S434P + K495N + G628W + A689I + Y715P + A732G | c1425g | ++ | + |
| 888 | D47I + I106V + A109T + Q258N + V260G + Q291W + Q313M + F314V + A343C + D369R + E402N + S434P + K495N + G628W + A689I + Y715P + A732G | c1425g + c1806t | ++ | + |
| 889 | D47I + A79G + Q85N + I106V + Q258N + V260G + Q291W + Q313M + F314V + D369R + E402N + S434P + K495N + A505C + G628W + A689I + Y715P + A732G | c1425g | ++ | + |
| 890 | A79M + I106V + Q258N + V260G + Q291W + Q313M + F314L + D369R + E402N + S434P + K495N + G628W + A689I + Y715P + A732G | c1425g | ++ | + |
| 891 | A79M + Q85N + I106V + Q258N + V260G + Q291W + Q313M + F314L + A343C + D369R + E402N + S434P + K495N + A505C + G628W + A689I + Y715P + A732G | c1425g | ++ | + |
| 892 | A79M + Q85N + I106V + Q258N + V260G + Q291W + Q313M + F314V + A343C + D369R + E402N + S434P + K495N + G628W + A689I + Y715P + A732G | c1425g | ++ | + |
| 893 | D47I + A79G + Q85N + I106V + A109S + Q258N + V260G + Q291W + Q313M + F314L + D369R + E402N + S434P + K495N + G628W + A689I + Y715P + A732G | c1425g + c2541t | ++ | + |
| 894 | A79E + Q85H + I106V + Q258N + V260G + Q291W + Q313M + F314L + D369R + E402N + S434P + K495N + G628W + A689I + Y715P + A732G | c540t + c1425g | ++ | + |
| 895 | D47I + A79G + Q85N + I106V + Q258N + V260G + Q291W + Q313M + F314L + D369R + E402N + S434P + K495N + G628W + A689I + Y715P + A732G | c1425g | ++ | + |
| 896 | A79G + Q85N + I106V + Q258N + V260G + Q291W + Q313M + F314L + A343C + D369R + E402N + S434P + K495N + G628W + A689I + Y715P + A732G | c1425 | ++ | + |
| 897 | D47I + A79E + Q85N + I106V + Q258N + V260G + L275Y + Q291W + Q313M + F314L + A343C + D369R + E402N + S434P + K495N + G628W + A689I + Y715P + A732G | c1425g | ++ | + |
| 898 | D47I + I106V + A109T + Q258N + V260G + Q291W + Q313M + F314V + D369R + E402N + S434P + K495N + G628W + A689I + Y715P + A732G | c468t + c1425g | ++ | + |
| 899 | C8G + D47I + Q85N + I106V + Q258N + V260G + Q291W + Q313M + F314L + D369R + E402N + S434P + K495N + G628W + A689I + Y715P + A732G | c1425g | ++ | + |
| 900 | A79E + Q85N + I106V + Q258N + V260G + Q291W + Q313M + F314L + D369R + E402N + S434P + K495N + G628W + A689I + Y715P + A732G | c1425g | ++ | + |
| 901 | A79G + Q85N + I106V + Q258N + V260G + Q291W + Q313M + F314L + A343C + D369R + E402N + S434P + K495N + G628W + A689I + Y715P + A732G | c1425g | ++ | + |

TABLE 7-continued

| Variant Number | Amino Acid Changes[1] | Silent Nucleotide Changes[2] | Activity Fold improvement over Var. 664[3] | Stability Fold improvement over Var. 664[3] |
|---|---|---|---|---|
| 902 | D47I + A79G + Q85N + I106V + Q258N + V260G + Q291W + Q313M + F314V + A343C + D369R + E402N + S434P + K495N + T591I + G628W + A689I + Y715P + A732G | c1425g | ++ | + |
| 903 | Q85N + I106V + A109T + Q258N + V260G + Q291W + Q313M + F314V + A343C + D369R + E402N + S434P + K495N + G628W + A689I + Y715P + A732G | g150a + c1425g | ++ | + |
| 904 | A79M + I106V + Q258N + V260G + Q291W + Q313M + F314V + A343C + D369R + E402N + S434P + K495N + G628W + A689I + Y715P + A732G | c1425g | ++ | + |
| 905 | Q85N + I106V + Q258N + V260G + Q291W + Q313M + F314V + A343C + D369R + E402N + S434P + K495N + G628W + A689I + Y715P + A732G | c1425g | ++ | + |
| 906 | Q85N + I106V + A109S + Q258N + V260G + Q291W + Q313M + F314L + D369R + E402N + S434P + K495N + A505C + G628W + A689I + Y715P + A732G | c1425g | ++ | + |
| 907 | I106V + Q258N + V260G + Q291W + Q313M + F314L + D369R + E402N + S434P + K495N + A505C + G628W + T687K + A689I + Y715P + A732G | c1425g | ++ | ** |
| 908 | Q85N + I106V + A109T + Q258N + V260G + Q291W + Q313M + F314V + D369R + E402N + S434P + K495N + G628W + A689I + Y715P + A732G | c1425g | ++ | + |
| 909 | D47I + Q85N + I106V + A109T + Q258N + V260G + Q291W + Q313M + F314V + A343G + D369R + E402N + S434P + K495N + G628W + A689I + Y715P + A732G | t237g + c1425g | ++ | + |
| 910 | D47I + Q85N + I106V + A109T + Q258N + V260G + Q291W + Q313M + F314L + A343C + D369R + E402N + S434P + K495N + G628W + A689I + Y715P + A732G | c1425g | ++ | + |
| 911 | D47I + Q85N + I106V + A109S + Q258N + V260G + L275Y + Q291W + Q313M + F314L + A343C + D369R + E402N + S434P + K495N + G628W + A689I + Y715P + A732G | c1425g | ++ | + |
| 912 | D47I + I106V + Q258N + V260G + Q291W + Q313M + F314V + A343C + D369R + E402N + S434P + K495N + G628W + A689I + Y715P + A732G | c933t + c1425g | ++ | + |
| 913 | I106V + Q258N + V260G + Q291W + Q313M + F314V + D369R + E402N + S434P + K495N + G628W + A689I + Y715P + A732G | c1425g | ++ | ** |
| 914 | D47I + I106V + Q258N + V260G + Q291W + Q313M + F314L + A343C + D369R + E402N + S434P + K495N + G628W + A689I + Y715P + A732G | c1425g | ++ | ** |
| 915 | D47I + Q85N + I106V + A109S + Q258N + V260G + L275Y + Q291W + Q313M + F314V + A343C + D369R + E402N + S434P + A475L + K495N + G628W + T687C + A689I + Y715P + A732G | | ++ | + |
| 916 | D47I + A79M + I106V + Q258N + V260G + Q291W + Q313M + F314L + D369R + E402N + S434P + K495N + G628W + A689I + Y715P + A732G | c1425g | ++ | + |
| 917 | A79G + Q85N + I106V + A109S + Q258N + V260G + Q291W + Q313M + F314V + D369R + E402N + S434P + K495N + A505C + G628W + A689I + Y715P + A732G | c1425g | ++ | + |
| 918 | D47I + A79E + Q85N + I106V + Q258N + V260G + Q291W + Q313M + F314L + D369R + E402N + S434P + K495N + G628W + A689I + Y715P + A732G | c1425g | ++ | + |
| 919 | Q85N + I106V + Q258N + V260G + L275Y + Q291W + Q313M + F314V + A343C + D369R + E402N + S434P + K495N + G628W + T687W + A689I + Y715P + A732G | c1425g | ++ | ** |
| 920 | I106V + Q258N + V260G + L275Y + Q291W + Q313M + F314L + A343C + D369R + E402N + S434P + K495N + G628W + A689I + Y715P + A732G | c1425g | ++ | ** |
| 921 | D47I + Q85N + I106V + A109T + Q258N + V260G + Q291W + Q313M + F314V + D369R + E402N + S434P + K495N + G628W + A689I + Y715P + A732G | c1425g | ++ | + |
| 922 | Q85N + I106V + A109S + Q258N + V260G + L275Y + Q291W + Q313M + F314V + A343C + D369R + E402N + S434P + K495N + G628W + A689I + Y715P + A732G | c1425g | ++ | + |
| 923 | D47I + A79M + I106V + A109S + Q258N + V260G + Q291W + Q313M + F314L + A343C + D369R + E402N + S434P + K495N + G628W + A689I + Y715P + A732G | c1425g | ++ | + |
| 924 | A79M + Q85N + I106V + Q258N + V260G + Q291W + Q313M + F314L + A343C + D369R + E402N + S434P + K495N + G628W + A689I + Y715P + A732G | c1425g | ++ | + |

TABLE 7-continued

| Variant Number | Amino Acid Changes[1] | Silent Nucleotide Changes[2] | Activity Fold improvement over Var. 664[3] | Stability Fold improvement over Var. 664[3] |
|---|---|---|---|---|
| 925 | A79M + Q85N + I106V + Q258N + V260G + L275Y + Q291W + Q313M + F314L + A343C + D369R + E402N + S434P + K495N + A505C + G628W + A689I + Y715P + A732G | c699t + c1425g | ++ | ** |

Table 7: Thermoactivity conditions: pH 4, 70° C. for 21 hrs. Thermostability conditions: enzyme residual activity was determined after incubated at pH 4.5, 70° C. for 24 hrs.
[1]Amino acid changes are indicated with respect to SEQ ID NO: 2; the backbone sequence contains substitutions I106V + Q258N + V260G + Q291W + Q313M + F314L + D369R + E402N + S434P + K495N + G628W + A689I + Y715P + A732G.
[2]Nucleotide changes are indicated relative to SEQ ID NO: 1.
[3]Fold improvement is with respect to Variant 664 (SEQ ID NO: 13)
* = 0.2 to 0.5 fold improvement
** = 0.6 to 1.0 fold improvement
+ = 1.1 to 1.9 fold improvement
++ = 2.0 to 2.9 fold improvement
+++ = 3.0 to 3.9 fold improvement Table 8 illustrates exemplary properties of C1 Bgl variants with increased thermoactivity and/or thermostability compared to the wild-type enzyme.

TABLE 8

| | at least x fold greater x = | activity | than variant No.: | under conditions: | Exemplary Variant(s) | See Table |
|---|---|---|---|---|---|---|
| An exemplary embodiment has | 5 | Thermoactivity | wildtype | pH 5, 65° C., 21 h | 3 | 2 |
| | 2 | Thermostability* | wildtype | pH 5, 65° C., 6 h | 3 | 2 |
| | 2, 3, 4, 5 or 6 | Thermoactivity | 3 | pH 5, 70° C., 21 h | 269 | 3 |
| | 1.1, 2, or 3 | Thermostability | 3 | pH 5, 65° C., 16 h | 269 | 3 |
| | 2, 3, or 4 | Thermoactivity | 269 | pH 4.5, 70° C., 21 h | 481 | 4 |
| | 1.1 or 2 | Thermostability | 269 | pH 4.5, 70° C., 2 h | 481 | 4 |
| | 2, 3, or 4 | Thermoactivity | 481 | pH 4.2, 70° C., 21 h | 647 | 5 |
| | 1.1, 2, or 4 | Thermostability | 481 | pH 4.5, 70° C., 3 h | 647 | 5 |
| | 3 or 4 | Thermoactivity | 647 | pH 4, 70° C., 21 h | 824, 825 | 6 |
| | 1.1 or 2 | Thermostability | 647 | pH 4.5, 70° C., 24 h | 824, 825 | 6 |
| | 2 or 3 | Thermoactivity | 664 | pH 4, 70° C., 21 h | 871, 885, 916 | 7 |
| | 1.1 | Thermostability | 664 | pH 4.5, 70° C., 24 h | 871, 885, 916 | 7 |

For example, in some embodiments, a variant has at least 5-fold greater thermoactivity and/or at least 2-fold greater thermostability than wildtype Bgl1. For example and not limitation, Variant 3 has these properties. For example, in another embodiment, a variant has at least 4-fold greater thermoactivity and/or at least 4-fold greater thermostability than Variant 481 Bgl1. For example and not limitation, Variant 647 has these properties.

The amino acid sequences of β-glucosidase variants not specifically described herein can be readily generated and identified using methods that are well known to those having ordinary skill in the art. Some β-glucosidase variants of the invention having at least 70% sequence identity to residues 20-870 of SEQ ID NO:2 and one or more substitutions disclosed herein, also have one or more substitutions, deletions or insertions in addition to those specifically disclosed herein. The effect, if any, of such substitutions, deletions or insertions on β-glucosidase activity and thermostability can be determined using assays known in the art and described herein (see e.g., Examples 3 and 5, infra). For illustration, variant number 1 in Table 2 has the following substitutions relative to residues 20-870 of SEQ ID NO:2: M181Y+Q291W+E402N+S434P. To determine the effect of a further substitution (e.g., replacement of isoleucine at position 20 with leucine) the variant in this case, I20L+M181Y+Q291W+E402N+S434P) is expressed and its properties compared to the parent (in this case, M181Y+Q291W+E402N+S434P).

Further, libraries of β-glucosidase polypeptide variants (and polynucleotides encoding the variants) may be generated from a parental sequence (e.g., such as one or more variants exemplified herein) and screened using the high throughput screen for presence of β-glucosidase activity described in, for example, Example 5. Mutagenesis and directed evolution methods known in the art can be readily applied to polynucleotides encoding β-glucosidase variants exemplified herein to generate variant libraries that can be expressed, screened, and assayed using the methods described herein. Mutagenesis and directed evolution methods are well known in the art. See, e.g., Ling, et al., 1999, "Approaches to DNA mutagenesis: an overview," *Anal. Biochem.*, 254(2):157-78; Dale, et al., 1996, "Oligonucleotide-directed random mutagenesis using the phosphorothioate method," *Methods Mol. Biol.*, 57:369-74; Smith, 1985, "In vitro mutagenesis," *Ann. Rev. Genet.*, 19:423-462; Botstein, et al., 1985, "Strategies and applications of in vitro mutagenesis," *Science*, 229:1193-1201; Carter, 1986, "Site-directed mutagenesis," *Biochem. J.*, 237:1-7; Kramer, et al., 1984, "Point Mismatch Repair," *Cell*, 38:879-887; Wells, et al., 1985, "Cassette mutagenesis: an efficient method for generation of multiple mutations at defined sites," *Gene*, 34:315-323; Minshull, et al., 1999, "Protein evolution by molecular breeding," *Current Opinion in Chemical Biology*, 3:284-290;

Christians, et al., 1999, "Directed evolution of thymidine kinase for AZT phosphorylation using DNA family shuffling," *Nature Biotechnology*, 17:259-264; Crameri, et al., 1998, "DNA shuffling of a family of genes from diverse species accelerates directed evolution," *Nature*, 391:288-291; Crameri, et al., 1997, "Molecular evolution of an arsenate detoxification pathway by DNA shuffling," *Nature Biotechnology*, 15:436-438; Zhang, et al., 1997 "Directed evolution of an effective fucosidase from a galactosidase by DNA shuffling and screening," *Proceedings of the National Academy of Sciences, U.S.A.*, 94:45-4-4509; Crameri, et al., 1996, "Improved green fluorescent protein by molecular evolution using DNA shuffling," *Nature Biotechnology*, 14:315-319; Stemmer, 1994, "Rapid evolution of a protein in vitro by DNA shuffling," *Nature*, 370:389-391; Stemmer, 1994, "DNA shuffling by random fragmentation and reassembly: In vitro recombination for molecular evolution," *Proceedings of the National Academy of Sciences, U.S.A.*, 91:10747-10751; WO 95/22625; WO 97/0078; WO 97/35966; WO 98/27230; WO 00/42651; and WO 01/75767, all of which are incorporated herein by reference.

In generating variants that comprise substitutions, insertions or deletions at positions in addition to those described supra, the ordinarily skilled practitioner will be aware that certain regions of the β-glucosidase protein are less tolerant than others to substitutions (especially non-conservative substitutions). Thus, in some embodiments, variant Bgl1 proteins retain conserved residues and functional domains from the parent.

β-Glucosidase Activity and Thermostability Assays

β-glucosidase activity can be determined by methods described in Examples 3 and 5, as well as any other methods known in the art. β-glucosidase activity may be determined, for example, using a para-nitrophenyl-β-D-glucopyranoside (pNPG) assay or using a cellobiose assay.

For example, a colorimetric pNPG (p-nitrophenyl-β-D-glucopyranoside)-based assay may be used to measure β-glucosidase activity. One such assay is described in Example 3, infra. In another exemplary pNPG assay, in a total volume of 100 μL, 20 μL clear media supernatant containing β-glucosidase enzyme is added to 4 mM pNPG (Sigma-Aldrich, Inc. St. Louis, Mo.) solution in 50 mM sodium phosphate buffer at pH 5. The reactions are incubated at pH 5, 50° C. for 1.5 hours. The reaction mixture is quenched with 100 μL of 1M sodium carbonate pH 11 solution. The absorbance of the solution is measured at 405 nm to determine the conversion of pNPG to p-nitrophenol. The release of p-nitrophenol ($\epsilon=17,700$ M-1 cm-1) is measured at 405 nm to calculate β-glucosidase activity. Detectable β-glucosidase activity is observed under high throughput screening conditions (pH 7, 50° C.). See Breves et al., 1997, *Appl. Environmental Microbiol.* 63:3902, incorporated herein by reference.

Alternatively, β-glucosidase activity may be determined using an assay in which cellobiose is the substrate. One suitable assay is described in Example 3, infra. Another suitable assay is carried out as follows: In a total volume of 100 μL, 25 μL clear media supernatant containing β-glucosidase enzyme is added to 10 g/L cellobiose (Fluka Cat. No. 22150, Sigma-Aldrich, Inc., St. Louis, Mo.) in 100 mM sodium phosphate buffer (pH 6-7) or sodium acetate buffer (pH 5-5.5). The reaction is incubated at 45-70° C. for an appropriate time (25 minutes to overnight depending on the enzyme concentration) while shaking. Glucose production may be determined using any number of art-known methods for measuring glucose. In one approach, glucose production is determined using an enzymatic glucose assay (K-GLUC, Megazyme, Ireland). 10 μl of each reaction is added to 190 μl GOPOD reagent (supplied as part of the K-GLUC assay kit). The reaction is incubated at 45° C. for 20 minutes and the absorbance of the solution was measured at 510 nm. The GOPOD reagent contains 50 mM Potassium phosphate buffer pH7.4, 0.011M p-hydroxybenzoic acid, 0.008% w/v sodium azide, glucose oxidase (>12,000 U/L), peroxidase (>650 U/L) and 80 mg/L 4-aminoantipyrine. The glucose oxidase enzyme in the reagent reacts with any glucose present in the sample and produces hydrogen peroxide which then reacts with the 4-aminoantipyrine to produce a quinoneimine dye in quantities proportionate with the amount of glucose present and can be measured spectrophotometrically at 510 nm.

Signal Peptide

In general, the β-glucosidase polypeptides are secreted from the host cell in which they are expressed (e.g., a yeast or fungal cell) and are expressed as a pre-protein including a signal peptide, i.e., an amino acid sequence linked to the amino terminus of a polypeptide and which directs the encoded polypeptide into the cell secretory pathway. In one embodiment, the signal peptide is the endogenous C1 β-glucosidase signal peptide having the sequence set forth as residues 1-19 of SEQ ID NO:2. In other embodiments, signal peptides from other C1 secreted proteins are used.

Still other signal peptides may be used, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, and *T. reesei* cellobiohydrolase II (TrCBH2).

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137 (incorporated herein by reference).

Useful signal peptides for yeast host cells also include those from the genes for *Saccharomyces cerevisiae* alpha-factor, *Saccharomyces cerevisiae* SUC2 invertase (see Taussig and Carlson, 1983, *Nucleic Acids Res* 11:1943-54; SwissProt Accession No. P00724), and others. See, e.g., Romanos et al., 1992, *Yeast* 8:423-488. Variants of these signal peptides and other signal peptides are suitable.

Fusion Polypeptides and Additional Sequence Elements

In some embodiments, a β-glucosidase polypeptide variant of the invention includes additional sequences which do not alter the encoded activity of a β-glucosidase. For example, the β-glucosidase may be linked to an epitope tag or to other sequence useful in β-glucosidase purification.

The present invention also provides β-glucosidase variant fusion polypeptides, wherein the fusion polypeptide comprises an amino acid sequence encoding a β-glucosidase variant polypeptide of the present invention or fragment thereof, linked either directly or indirectly through the N- or C-terminus of the β-glucosidase variant polypeptide to an amino acid sequence encoding at least a second (additional) polypeptide. The β-glucosidase variant fusion polypeptide may further include amino acid sequence encoding a third, fourth, fifth, or additional polypeptides. Typically, each additional polypeptide has a biological activity, or alternatively, is a portion of a polypeptide that has a biological activity, where the portion has the effect of improving expression and/or secretion of the fusion polypeptide from the desired expression host. These sequences may be fused, either directly or indirectly, to the N- or C-terminus of the β-glucosidase variant polypeptide or fragment thereof, or alternatively, to the N- or C-terminus of the additional polypeptides having biological activity.

Typically, the additional polypeptide(s) encode an enzyme or active fragment thereof, and/or a polypeptide that improves expression and/or secretion of the fusion polypeptide from the desired expression host cell. More typically, the additional polypeptide(s) encode(s) a cellulase (for example, a β-glucosidase having a different amino acid sequence from the β-glucosidase variant polypeptide in the fusion polypeptide (e.g., a wildtype β-glucosidase or a variant thereof, including a different *T. aurentiacus* β-glucosidase variant polypeptide), or a polypeptide exhibiting CBH or EG activity) and/or a polypeptide that improves expression and secretion from the desired host cell, such as, for example, a polypeptide that is normally expressed and secreted from the desired expression host, such as a secreted polypeptide normally expressed from filamentous fungi. These include glucoamylase, α-amylase and aspartyl proteases from *Aspergillus niger, Aspergillus niger* var. *awamori*, and *Aspergillus oryzae*, cellobiohydrolase I, cellobiohydrolase II, endoglucanase I and endoglucase III from *Trichoderma* and glucoamylase from *Neurospora* and *Humicola* species. See WO 98/31821, which is incorporated herein by reference.

The polypeptide components of the fusion polypeptide may be linked to each other indirectly via a linker. Linkers suitable for use in the practice of the present invention are described in WO 2007/075899, which is incorporated herein by reference. Exemplary linkers include peptide linkers of from 1 to about 40 amino acid residues in length, including those from about 1 to about 20 amino acid residues in length, and those from about 1 to about 10 amino acid residues in length. In some embodiments, the linkers may be made up of a single amino acid residue, such as, for example, a Gly, Ser, Ala, or Thr residue or combinations thereof, particularly Gly and Ser. Linkers employed in the practice of the present invention may be cleavable. Suitable cleavable linkers may contain a cleavage site, such as a protease recognition site. Exemplary protease recognition sites are well known in the art and include, for example, Lys-Arg (the KEX2 protease recognition site, which can be cleaved by a native *Aspergillus* KEX2-like protease), Lys and Arg (the trypsin protease recognition sites). See, for example, WO 2007/075899, which is incorporated herein by reference.

IV. β-Glucosidase Polynucleotides and Expression Systems

The present invention provides polynucleotide sequences that encode C1 β-glucosidase variants of the invention. The C1 genomic and cDNA sequences are described in Section II, supra.

In one embodiment, for expression of a β-glucosidase variant described herein, the wild-type C1 β-glucosidase cDNA sequence (SEQ ID NO:1), or the portion thereof comprising the open reading frame, can be used (with changes as required at codons corresponding to substitutions (residues mutated relative to the wild-type sequence). In addition, one or more of the "silent" nucleotide changes shown in Table 2, Table 3, Table, 4, Table 5, Table 6, or Table 7 can be incorporated.

Those having ordinary skill in the art will understand that due to the degeneracy of the genetic code, a multitude of nucleotide sequences encoding β-glucosidase polypeptides of the present invention exist. Table 9 provides the standard triplet genetic code for each amino acid. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available See e.g., Henaut and Danchin in "*Escherichia Salmonella*," Neidhardt, et al. Eds., ASM Pres, Washington D.C. (1996), pp. 2047-2066, which is incorporated herein by reference. For illustration, and not for limitation, SEQ ID NO:3 shows a C1 Bgl1-encoding polynucleotide sequence designed with codon biasing for expression in *Saccharomyces cerevisiae*.

TABLE 9

GENETIC CODE

| Amino acid | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |

TABLE 9-continued

GENETIC CODE

| Amino acid | | | Codon | |
|---|---|---|---|---|
| Tryptophan | Trp | W | UGG | |
| Tyrosine | Tyr | Y | UAC | UAU |

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, *Bioinformatics* 14:372-73; Stenico et al., 1994, *Nucleic Acids Res.* 222437-46; Wright, F., 1990, *Gene* 87:23-29; Wada et al., 1992, *Nucleic Acids Res.* 20:2111-2118; Nakamura et al., 2000, *Nucl. Acids Res.* 28:292; Henaut and Danchin, "*Escherichia coli* and *Salmonella*," 1996, Neidhardt, et al. Eds., ASM Press, Washington D.C., p. 2047-2066, all of which are incorporated herein be reference). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266: 259-281; Tiwari et al., 1997, *Comput. Appl. Biosci.* 13:263-270, all of which are incorporated herein by reference).

For expression of a β-glucosidase variant in a C1 or *M. thermophilia* host, the wild-type C1 β-glucosidase cDNA sequence (SEQ ID NO:1), or the portion thereof comprising the open reading frame, can be used (with changes as required at codons corresponding to substitutions (residues mutated relative to the wild-type sequence). In addition, one or more of the "silent" nucleotide changes shown in Table 2 can be incorporated. These changes may affect β-glucosidase activity in a variety of ways. For example, without intending to be bound by a particular mechanism, silent mutations may increase the stability of mRNAs encoding the variant protein.

Expression Vectors

The present invention makes use of recombinant constructs comprising a sequence encoding a β-glucosidase as described above. In a particular aspect the present invention provides an expression vector comprising a β-glucosidase polynucleotide operably linked to a heterologous promoter. Expression vectors of the present invention may be used to transform an appropriate host cell to permit the host to express β-glucosidase protein. Methods for recombinant expression of proteins in fungi and other organisms are well known in the art, and a number expression vectors are available or can be constructed using routine methods. See, e.g., Tkacz and Lange, 2004, ADVANCES IN FUNGAL BIOTECHNOLOGY FOR INDUSTRY, AGRICULTURE, AND MEDICINE, KLUWER ACADEMIC/PLENUM PUBLISHERS. New York; Zhu et al., 2009, Construction of two Gateway vectors for gene expression in fungi *Plasmid* 6:128-33; Kavanagh, K. 2005, FUNGI: BIOLOGY AND APPLICATIONS Wiley, all of which are incorporated herein by reference.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In one aspect of this embodiment, the construct further comprises regulatory sequences, including, for example, a promoter, operably linked to the protein encoding sequence. Large numbers of suitable vectors and promoters are known to those of skill in the art.

Promoter/Gene Constructs

As discussed above, to obtain high levels of expression in a particular host it is often useful to express C1 β-glucosidase under control of a heterologous promoter. Typically a promoter sequence may be operably linked to the 5′ region of the C1 β-glucosidase coding sequence using routine methods.

Examples of useful promoters for expression of β-glucosidase polynucleotides include promoters from fungi. For example, promoter sequences that drive expression of genes other than the β-glucosidase 1 gene in C1 may be used. For example, a fungal promoter from a gene encoding cellobiohydrolase may be used.

Examples of other suitable promoters useful for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., 1984, *Mol. Cell Biol.*, 4:2306-2315, Boel et al., 1984, *EMBO J.* 3:1581-85 and EPA 137280, all of which are incorporated herein by reference), and mutant, truncated, and hybrid promoters thereof. In a yeast host, useful promoters can be from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488, incorporated herein by reference. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet,* 28:478-83 (*Trichoderma harzianum*), both of which are incorporated herein by reference.

Promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyl), *Bacillus stearothermophilus* maltogenic amylase gene (amyM), *Bacillus amyloliquefaciens* alpha-amylase gene (amyQ), *Bacillus subtilis* xylA and xylB genes and prokaryotic β-lactamase gene.

Any other promoter sequence that drives expression in a suitable host cell may be used. Suitable promoter sequences can be identified using well known methods. In one approach, a putative promoter sequence is linked 5' to a sequence encoding a reporter protein, the construct is transfected into the host cell (e.g., a C1 cell) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (Henriksen et al, 1999, *Microbiology* 145:729-34, incorporated herein by reference) or a lacZ reporter gene (Punt et al, 1997, *Gene,* 197:189-93, incorporated herein by reference). Functional promoters may be derived from naturally occurring promoter sequences by directed evolution methods. See, e.g. Wright et al., 2005, *Human Gene Therapy,* 16:881-892, incorporated herein by reference.

An expression vector optionally contains a ribosome binding site for translation initiation, and a transcription terminator, such as PinII. The vector also optionally includes appropriate sequences for amplifying expression, e.g., an enhancer.

In addition, expression vectors of the present invention optionally contain one or more selectable marker genes to provide a phenotypic trait for selection of transformed host cells. Suitable marker genes include those coding for antimicrobial resistance such as, ampicillin (ampR), kanamycin, chloramphenicol, or tetracycline resistance. Further examples include the antimicrobial streptomycin or spectinomycin (e.g., the aada gene), the streptomycin phosphotransferase (spt) gene coding for streptomycin resistance, the neomycin phosphotransferase (nptII) gene encoding kanamycin or geneticin resistance, the hygromycin phosphotransferase (hpt) gene coding for hygromycin resistance. Additional selectable marker genes include dihydrofolate reductase or neomycin resistance for eukaryotic cell culture, and tetracycline or ampicillin resistance in *E. coli*.

Synthesis and Manipulation of β-Glucosidase Polynucleotides

Polynucleotides encoding β-glucosidase can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters,* 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, et al., 1982, *Cold Spring Harbor Symp. Quant. Biol.,* 47:411-18 and Adams et al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel"), all of which are incorporated herein by reference. Reference is made to Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomeli et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

Expression Hosts

The present invention also provides engineered (recombinant) host cells that are transformed with an expression vector or DNA construct encoding β-glucosidase. Optionally, β-glucosidase expression in the cell is under the control of a heterologous promoter. Host cells of the invention may be used to produce β-glucosidase polypeptides. Thus, the present invention is directed to a host cell comprising any β-glucosidase polynucleotide of the present invention that is described hereinabove. As used herein, a genetically modified or recombinant host cell includes the progeny of said host cell that comprises a β-glucosidase polynucleotide which encodes a recombinant polypeptide of the invention. Often, the genetically modified or recombinant host cell is a microorganism. In some embodiments, the genetically modified or recombinant host cell is a prokaryote. In some embodiments, the genetically modified or recombinant host cell is a eukaryotic cell. Generally the eukaryotic host cell is a non-human cell. Suitable eukaryotic host cells include, but are not limited to, fungal cells, algal cells, insect cells, and plant cells. In some cases host cells may be modified to increase protein expression, secretion or stability, or to confer other desired characteristics. Cells (e.g., fungi) that have been mutated or selected to have low protease activity are particularly useful for expression. For example, protease deficient strains of *C. lucknowense* (e.g., in which the alkaline protease locus has been deleted or disrupted) may be used. In some embodiments, the host cells, e.g., fungi, may modified to express a recombinant cellulase.

Suitable fungal host cells include, but are not limited to, Ascomycota, Basidiomycota, Deuteromycota, Zygomycota, and Fungi imperfecti. In some embodiments the fungal host cells are yeast cells and filamentous fungal cells. The filamentous fungal host cells of the present invention include all filamentous forms of the subdivision Eumycotina and Oomycota. (see, for example, Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungal host cells of the present invention are morphologically distinct from yeast.

In some embodiments the filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella,* or teleomorphs, or anamorphs, and synonyms or taxonomic equivalents thereof.

In some embodiments of the invention, the filamentous fungal host cell is of the *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species.

In some embodiments of the invention, the filamentous fungal host cell is of the *Chrysosporium* species, e.g., *C. lucknowense, C. keratinophilum, C. tropicum, C. merdarium, C. inops, C. pannicola,* and *C. zonatum.*

In some embodiments of the invention, the filamentous fungal host cell is of the *Trichoderma* species, e.g., *T. longibrachiatum, T. viride* (e.g., ATCC 32098 and 32086), or *T. reesei,* an anamorph of *Hypocrea jecorina,* (NRRL 15709, ATTC 13631, 56764, 56765, 56466, 56767 and RL-P37 and derivatives thereof—See Sheir-Neiss et al., 1984, *Appl. Microbiol. Biotechnology,* 20:46-53, which is incorporated herein by reference), *T. koningii,* and *T. harzianum.* In addition, the term "*Trichoderma*" refers to any fungal strain that was previously classified as *Trichoderma* or currently classified as *Trichoderma.*

In some embodiments of the invention, the filamentous fungal host cell is of the *Aspergillus* species, e.g., *A. awamori, A. fumigatus, A. japonicus, A. nidulans, A. niger, A. aculeatus, A. foetidus, A. oryzae, A. sojae,* and *A. kawachi.* (Reference is made to Kelly and Hynes, 1985, *EMBO J.* 4, 475479; NRRL 3112, ATCC 11490, 22342, 44733, and 14331; Yelton et al., 1984, *Proc. Natl. Acad. Sci. USA,* 81, 1470-1474; Tilburn et al., 1982, *Gene* 26, 205-221; and Johnston et al., 1985, *EMBO J.* 4, 1307-1311, all of which are incorporated herein by reference).

In some embodiments of the invention, the filamentous fungal host cell is of the *Fusarium* species, e.g., *F. bactridioides, F. cerealis, F. crookwellense, F. culmorum, F. graminearum, F. graminum. F. oxysporum, F. roseum,* and *F. venenatum.*

In some embodiments of the invention, the filamentous fungal host cell is of the *Myceliophthora* species, e.g., *M. thermophilia.*

In some embodiments of the invention, the filamentous fungal host cell is of the *Neurospora* species, e.g., *N. crassa.* Reference is made to Case, M. E. et al., 1979, *Proc. Natl. Acad. Sci. USA,* 76, 5259-5263; U.S. Pat. No. 4,486,553; and Kinsey, J. A. and J. A. Rambosek, 1984, *Molecular and Cellular Biology* 4, 117-122, all of which are incorporated herein by reference. In some embodiments of the invention, the filamentous fungal host cell is of the *Humicola* species, e.g., *H. insolens, H. grisea,* and *H. lanuginosa.* In some embodiments of the invention, the filamentous fungal host cell is of the *Mucor* species, e.g., *M. miehei* and *M. circinelloides.* In some embodiments of the invention, the filamentous fungal host cell is of the *Rhizopus* species, e.g., *R. oryzae* and *R. niveus.* In some embodiments of the invention, the filamentous fungal host cell is of the *Penicillium* species, e.g., *P. purpurogenum, P. chrysogenum,* and *P. verruculosum.* In some embodiments of the invention, the filamentous fungal host cell is of the *Thielavia* species, e.g., *T. terrestris.* In some embodiments of the invention, the filamentous fungal host cell is of the *Tolypocladium* species, e.g., *T. inflatum* and *T. geodes.* In some embodiments of the invention, the filamentous fungal host cell is of the *Trametes* species, e.g., *T. villosa* and *T. versicolor.*

In the present invention a yeast host cell may be a cell of a species of, but not limited to *Candida, Hansenula, Saccharomyces, Schizosaccharomyces, Pichia, Kluyveromyces,* and *Yarrowia.* In some embodiments of the invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans,* and *Yarrowia lipolytica.*

In some embodiments on the invention, the host cell is an algae such as, *Chlamydomonas* (e.g., *C. reinhardtii*) and *Phormidium* (P. sp. ATCC29409).

In other embodiments, the host cell is a prokaryotic cell. Suitable prokaryotic cells include gram positive, gram negative and gram-variable bacterial cells. The host cell may be a species of, but not limited to *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Mycobacterium, Neisseria, Pantoea, Pseudomonas, Prochlorococcus, Rhodobacter, Rhodopseudornonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium,*

*Tropheryma, Francisella, Temecula, Thermosynechococcus, Thermococcus, Ureaplasma, Xanthomomas, Xylella, Yersinia* and *Zymomonas*.

In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces,* and *Zymomonas*.

In yet other embodiments, the bacterial host strain is non-pathogenic to humans. In some embodiments the bacterial host strain is an industrial strain. Numerous bacterial industrial strains are known and suitable in the present invention.

In some embodiments of the invention the bacterial host cell is of the *Agrobacterium* species, e.g., *A. radiobacter, A. rhizogenes,* and *A. rubi*. In some embodiments of the invention, the bacterial host cell is of the *Arthrobacter* species, e.g., *A. aurescens, A. citreus, A. globformis, A. hydrocarboglutamicus, A. mysorens, A. nicotianae, A. paraffineus, A. protophonniae, A. roseoparqffinus, A. sulfureus,* and *A. ureafaciens*. In some embodiments of the invention the bacterial host cell is of the *Bacillus* species, e.g., *B. thuringiensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. Some embodiments of a *Bacillus* host cell include *B. subtilis, B. licheniformis, B. megaterium, B. stearothermophilus* and *B. amyloliquefaciens*. In some embodiments the bacterial host cell is of the *Clostridium* species, e.g., *C. acetobutylicum, C. tetani* E88, *C. lituseburense, C. saccharobutylicum, C. perfringens, C. thermocellum,* and *C. beijerinckii*. In some embodiments the bacterial host cell is of the *Corynebacterium* species e.g., *C. glutamicum* and *C. acetoacidophilum*. In some embodiments the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata,* and *E. terreus*. In some embodiments the bacterial host cell is of the *Pantoea* species, e.g., *P. citrea,* and *P. agglomerans*. In some embodiments the bacterial host cell is of the *Pseudomonas* species, e.g., *P. putida, P. fluorescens, P. aeruginosa, P. mevalonii,* and P. sp. D-0I 10. In some embodiments the bacterial host cell is of the *Streptococcus* species, e.g., *S. equisimiles, S. pyogenes,* and *S. uberis*. In some embodiments the bacterial host cell is of the *Streptomyces* species, e.g., *S. ambofaciens, S. achromogenes, S. avermitilis, S. coelicolor, S. aureofaciens, S. aureus, S. fungicidicus, S. griseus,* and *S. lividans*. In some embodiments the bacterial host cell is of the *Zymomonas* species, e.g., *Z. mobilis,* and *Z. lipolytica*.

Strains that may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Host cells may be genetically modified to have characteristics that improve protein secretion, protein stability or other properties desirable for expression and/or secretion of a protein. For example, knock out of Alp1 function results in a cell that is protease deficient. Knock out of pyr5 function results in a cell with a pyrimidine deficient phenotype. In particular embodiments host cells are modified to delete endogenous cellulase protein-encoding sequences or otherwise eliminate expression of one or more endogenous cellulases. In one embodiment expression of one or more endogenous cellulases is inhibited to increase production of cellulases of interest. Genetic modification can be achieved by genetic engineering techniques or using classical microbiological techniques, such as chemical or UV mutagenesis and subsequent selection. A combination of recombinant modification and classical selection techniques may be used to produce the organism of interest. Using recombinant technology, nucleic acid molecules can be introduced, deleted, inhibited or modified, in a manner that results in increased yields of β-glucosidase within the organism or in the culture. For example, knock out of Alp1 function results in a cell that is protease deficient. Knock out of pyr5 function results in a cell with a pyrimidine deficient phenotype. In one genetic engineering approach, homologous recombination can be used to induce targeted gene modifications by specifically targeting a gene in vivo to suppress expression of the encoded protein. In an alternative approach, siRNA, antisense, or ribozyme technology can be used to inhibit gene expression Transformation and Culture Introduction of a vector or DNA construct into a host cell can be effected by calcium phosphate transfection, DEAE-Dextran mediated transfection, electroporation, or other common techniques (See Davis et al., 1986, *Basic Methods in Molecular Biology*, which is incorporated herein by reference).

The engineered host cells can be cultured in conventional nutrient media modified as appropriate for activating promoters, selecting transformants, or amplifying the β-glucosidase polynucleotide. Culture conditions, such as temperature, pH and the like, are those previously used with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture*

*Catalogue* and supplement (1997) also from Sigma-Aldrich, Inc (St Louis, Mo.) ("Sigma-PCCS"), all of which are incorporated herein by reference.

In some embodiments, cells expressing the β-glucosidase polypeptides of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Cell-free transcription/translation systems can also be employed to produce β-glucosidase polypeptides using the polynucleotides of the present invention. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

V. Production and Recovery of β-Glucosidase Polypeptides

The present invention is also directed to a method of making a polypeptide having β-glucosidase activity, the method comprising providing a host cell transformed with any one of the described β-glucosidase polynucleotides of the present invention; culturing the transformed host cell in a culture medium under conditions in which the host cell expresses the encoded β-glucosidase polypeptide; and optionally recovering or isolating the expressed β-glucosidase polypeptide, or recovering or isolating the culture medium containing the expressed β-glucosidase polypeptide. The method further provides optionally lysing the transformed host cells after expressing the encoded β-glucosidase polypeptide and optionally recovering or isolating the expressed β-glucosidase polypeptide from the cell lysate. The present invention further provides a method of making a β-glucosidase polypeptide, said method comprising cultivating a host cell transformed with a β-glucosidase polynucleotide under conditions suitable for the production of the β-glucosidase polypeptide and recovering the β-glucosidase polypeptide.

Typically, recovery or isolation of the β-glucosidase polypeptide is from the host cell culture medium, the host cell or both, using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. Purification of BGL1 is described in Parry et al., 2001, *Biochem. J.* 353:117, and Hong et al., 2007, *Appl. Microbiol. Biotechnol.* 73:1331, both incorporated herein by reference. In addition to the references noted supra, a variety of purification methods are well known in the art, including, for example, those set forth in Sandana (1997) *Bioseparation of Proteins*, Academic Press, Inc.; Bollag et al. (1996) *Protein Methods*, 2$^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* 3$^{rd}$ *Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference.

Immunological methods may be used to purify β-glucosidase polypeptides. In one approach, antibody raised against the β-glucosidase polypeptides (e.g., against a polypeptide comprising SEQ ID NO:2 or an immunogenic fragment thereof) using conventional methods is immobilized on beads, mixed with cell culture media under conditions in which the β-glucosidase is bound, and precipitated. In a related approach immunochromatography is used.

As noted, in some embodiments the β-glucosidase is expressed as a fusion protein including a non-enzyme portion. In some embodiments the β-glucosidase sequence is fused to a purification facilitating domain. As used herein, the term "purification facilitating domain" refers to a domain that mediates purification of the polypeptide to which it is fused. Suitable purification domains include metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al., 1984, *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the HHDH polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al., 1992, *Protein Expression and Purification* 3:263-281) while the enterokinase cleavage site provides a means for separating the HHDH polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

VI. Methods of Using β-Glucosidase Polypeptides and Cells Expressing β-Glucosidase Polypeptides As described supra, β-glucosidase polypeptides of the present invention can be used to catalyze the hydrolysis of a sugar dimer with the release of the corresponding sugar monomer, for example, the conversion of cellobiose with the release of glucose. Thus, the present invention provides a method for producing glucose, by (a) providing a cellobiose; and (b) contacting the cellobiose with a β-glucosidase polypeptide of the invention under conditions sufficient to form a reaction mixture for converting the cellobiose to glucose. The β-glucosidase polypeptide may be utilized in such methods in either isolated form or as part of a composition, such as any of those described herein. The β-glucosidase polypeptide may also be provided in cell culturing media or in a cell lysate. For example, after producing the β-glucosidase polypeptide by culturing a host cell transformed with a β-glucosidase polynucleotide or vector of the present invention, the β-glucosidase need not be isolated from the culture medium (i.e., if the β-glucosidase is secreted into the culture medium) or cell lysate (i.e., if the β-glucosidase is not secreted into the culture medium) or used in purified form to be useful in further methods of using the β-glucosidase polypeptide. Any composition, cell culture medium, or cell lysate containing a β-glucosidase polypeptide of the present invention may be suitable for using in methods that utilize a β-glucosidase. Therefore, the present invention further provides a method for producing glucose, by: (a) providing a cellobiose; and (b) contacting the cellobiose with a culture medium or cell lysate or composition comprising a β-glucosidase polypeptide of the present invention under conditions sufficient to form a reaction mixture for converting the cellobiose to glucose.

The present invention further provides compositions that are useful for the enzymatic conversion of cellobiose to glucose. For example, one or more β-glucosidase polypeptides of the present invention may be combined with another enzyme and/or an agent that alters the bulk material handling properties or further processability of the β-glucosidase(s) (e.g., a flow-aid agent, water, buffer, a surfactant, and the like) or that improves the efficiency of the conversion of cellobiose to glucose, as described in more detail hereinbelow. The other enzyme may be a different β-glucosidase or another cellulase enzyme.

Enzyme Mixtures

In another aspect, the invention provides an enzyme mixture that comprises a C1 Bgl1 variant polypeptide as described herein. The enzyme mixture may be cell-free, or in alternative embodiments, may not be separated from host cells that secrete an enzyme mixture component. A cell-free enzyme mixture typically comprises enzymes that have been separated from any cells. Cell-free enzyme mixtures can be prepared by any of a variety of methodologies that are known in the art, such as filtration or centrifugation methodologies. In certain embodiments, the enzyme mixture can be, for example, partially cell-free, substantially cell-free, or entirely cell-free.

The C1 Bgl1 variant and any additional enzymes present in the enzyme mixture may be secreted from a single genetically modified fungal cell or by different microbes in combined or separate fermentations. Similarly, the C1 Bgl1 variant and any additional enzymes present in the enzyme mixture may be expressed individually or in sub-groups from different strains of different organisms and the enzymes combined in vitro to make the enzyme mixture. It is also contemplated that the C1 Bgl1 variant and any additional enzymes in the enzyme mixture may be expressed individually or in sub-groups from different strains of a single organism, and the enzymes combined to make the enzyme mixture. In some embodiments, all of the enzymes are expressed from a single host organism, such the genetically modified fungal cell.

In some embodiments, the enzyme mixture comprises other types of cellulases, selected from CBH, EG, and BG cellulase. In some embodiments, the cellobiohydrolase is *T. reesei* cellobiohydrolase II. In some embodiments, the endoglucanase comprises a catalytic domain derived from the catalytic domain of a *Streptomyces avermitilis* endoglucanase. See, copending application Ser. No. 12/751,985, incorporated herein by reference. In some embodiments, the at least one cellulase is *Acidothermus cellulolyticus, Thermobifida fusca, Humicola grisea* or a *Chrysosporium* sp. Cellulase enzymes of the cellulase mixture work together resulting in decrystallization and hydrolysis of the cellulose from a biomass substrate to yield soluble sugars, such as but not limited to glucose (See Brigham et al., 1995, in Handbook on Bioethanol (C. Wyman ed.) pp 119-141, Taylor and Francis, Washington D.C., which is incorporated herein by reference).

Cellulase mixtures for efficient enzymatic hydrolysis of cellulose are known (see, e.g., Viikari et al., 2007, "Thermostable enzymes in lignocellulose hydrolysis" *Adv Biochem Eng Biotechnol* 108:121-45, and US Pat. publications US 2009/0061484; US 2008/0057541; and US 2009/0209009 to Iogen Energy Corp.), each of which is incorporated herein by reference for all purposes. In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, may be combined with cellulosic feedstock or a product of cellulose hydrolysis.

A variant β-glucosidase polypeptide of the invention may also be present in mixtures with enzymes other than cellulases that degrade cellulose, hemicellulose, pectin, and/or lignocellulose.

A "hemicellulase" as used herein, refers to a polypeptide that can catalyze hydrolysis of hemicellulose into small polysaccharides such as oligosaccharides, or monomeric saccharides. Hemicellulloses include xylan, glucuonoxylan, arabinoxylan, glucomannan and xyloglucan. Hemicellulases include, for example, the following: endoxylanases, β-xylosidases, α-L-arabinofuranosidases, a-D-glucuronidases, feruloyl esterases, coumaroyl esterases, α-galactosidases, β-galactosidases, β-mannanases, and β-mannosidases. An enzyme mixture may therefore comprise a β-glucosidase variant of the invention and one or more hemicellulases.

An endoxylanase (EC 3.2.1.8) catalyzes the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

A β-xylosidase (EC 3.2.1.37) catalyzes the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase or xylobiase.

An α-L-arabinofuranosidase (EC 3.2.1.55) catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

An alpha-glucuronidase (EC 3.2.1.139) catalyzes the hydrolysis of an alpha-D-glucuronoside to D-glucuronate and an alcohol.

An acetylxylanesterase (EC 3.1.1.72) catalyzes the hydrolysis of acetyl groups from polymeric xylan, acetylated xylose, acetylated glucose, alpha-napthyl acetate, and p-nitrophenyl acetate.

A feruloyl esterase (EC 3.1.1.73) has 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

A coumaroyl esterase (EC 3.1.1.73) catalyzes a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

An α-galactosidase (EC 3.2.1.22) catalyzes the hydrolysis of terminal, non-reducing α-D-galactose residues in α-D-galactosides, including galactose oligosaccharides, galactomannans, galactans and arabinogalactans. This enzyme may also be referred to as melibiose.

A β-galactosidase (EC 3.2.1.23) catalyzes the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

A β-mannanase (EC 3.2.1.78) catalyzes the random hydrolysis of 1,4-β-D-mannosidic linkages in mannans, galactomannans and glucomannans. This enzyme may also be referred to as mannan endo-1,4-β-mannosidase or endo-1,4-mannanase.

A β-mannosidase (EC 3.2.1.25) catalyzes the hydrolysis of terminal, non-reducing β-D-mannose residues in β-D-mannosides. This enzyme may also be referred to as mannanase or mannase.

One or more enzymes that derade pectin may also be included in an enzyme mixture that comprises a β-glucosidase variant of the invention. A pectinase catalyzes the hydrolysis of pectin into smaller units such as oligosaccharide or monomeric saccharides. An enzyme mixture may comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

An endo-polygalacturonase (EC 3.2.1.15) catalyzes the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glucanohydrolase, endogalacturonase; endo-D-galacturonase or poly(1,4-α-D-galacturonide) glucanohydrolase.

A pectin methyl esterase (EC 3.1.1.11) catalyzes the reaction: pectin+n H2O=n Methanol+pectate. The enzyme may also been known as pectinesterase, pectin demethoxylase, pectin methoxylase, pectin methylesterase, pectase, pectinoesterase or pectin pectylhydrolase.

A endo-galactanase (EC 3.2.1.89) catalyzes the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 413-D-galactanohydrolase.

A pectin acetyl esterase catalyzes the deacetylation of the acetyl groups at the hydroxyl groups of GalUA residues of pectin.

An endo-pectin lyase (EC 4.2.2.10) catalyzes the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

A pectate lyase (EC 4.2.2.2) catalyzes the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

An alpha rhamnosidase (EC 3.2.1.40) catalyzes the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

An exo-galacturonase (EC 3.2.1.82) hydrolyzes pectic acid from the non-reducing end, releasing digalacturonate. The enzyme may also be known as exo-poly-α-galacturonosidase, exopolygalacturonosidase or exopolygalacturanosidase.

An exo-galacturonase (EC 3.2.1.67) catalyzes a reaction of the following type: (1,4-α-D-galacturonide)n+H2O=(1,4-α-D-galacturonide)n−i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

An exopolygalacturonate lyase (EC 4.2.2.9) catalyzes eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-transeliminase, PATE, exo-PATE, exo-PGL or (1→4)-α-D-galacturonan reducing-end-disaccharide-lyase.

A rhamnogalacturonan hydrolyzes the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

A rhamnogalacturonan lyase cleaves α-L-Rhap-(1→4)-α-D-GalpA linkages in an endo-fashion in rhamnogalacturonan by beta-elimination.

A rhamnogalacturonan acetyl esterase catalyzes the deacetylation of the backbone of alternating rhamnose and galacturonic acid residues in rhamnogalacturonan.

A rhamnogalacturonan galacturonohydrolase hydrolyzes galacturonic acid from the non-reducing end of strictly alternating rhamnogalacturonan structures in an exo-fashion. This enzyme may also be known as xylogalacturonan hydrolase.

An endo-arabinanase (EC 3.2.1.99) catalyzes endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

One or more enzymes that participate in lignin degradation may also be included in an enzyme mixture that comprises a β-glucosidase variant of the invention. Enzymatic lignin depolymerization can be accomplished by lignin peroxidases, manganese peroxidases, laccases and cellobiose dehydrogenases (CDH), often working in synergy. These extracellular enzymes are often referred to as lignin-modifying enzymes or LMEs. Three of these enzymes comprise two glycosylated heme-containing peroxidases: lignin peroxidase (LIP); Mn-dependent peroxidase (MNP); and, a copper-containing phenoloxidase laccase (LCC).

Laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

Mn-dependent peroxidase. The enzymatic activity of Mn-dependent peroxidase (MnP) in is dependent on Mn2+. Without being bound by theory, it has been suggested that the main role of this enzyme is to oxidize Mn2+ to Mn3+ (Glenn et al. (1986) Arch. Biochem. Biophys. 251:688-696). Subsequently, phenolic substrates are oxidized by the Mn3+ generated.

Lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalysed oxidation of lignin in vivo (Harvey, et al. (1986) FEBS Lett. 195, 242-246).

An enzymatic mixture comprising a β-glucosidase variant of the invention may further comprise at least one of the following; a protease or a lipase that participates in cellulose degradation.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

An enzyme mixture that comprises a β-glucosidase variant of the invention may also comprise at least one expansin or expansin-like protein, such as a swollenin (see Salheimo et al., *Eur. J. Biohem.* 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

An enzyme mixture that comprises a β-glucosidase variant of the invention may also comprise at least one of the following: a polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module that mediates attachment of the cellulosome to its substrate. A scaffoldin or cellulose integrating protein for the purposes of this invention may comprise one or both of such domains.

An enzyme mixture that comprises a β-glucosidase variant of the invention may also comprise at least one cellulose induced protein or modulating protein, for example as encoded by cip1 or cip2 gene or similar genes from *Trichoderma reesei* (see Foreman et al., *J. Biol. Chem.* 278(34), 31988-31997, 2003).

An enzyme mixture that comprises a β-glucosidase variant of the invention may comprise a member of each of the classes of the polypeptides described above, several members of one polypeptide class, or any combination of these polypeptide classes.

Other Components of β-Glucosidase Compositions

β-glucosidase polypeptides of the present invention may be used in combination with other optional ingredients such as a buffer, a surfactant, and/or a scouring agent. A buffer may be used with a β-glucosidase polypeptide of the present invention (optionally combined with other cellulases, including another β-glucosidase) to maintain a desired pH within the solution in which the β-glucosidase is employed. The exact concentration of buffer employed will depend on several factors which the skilled artisan can determine. Suitable buffers are well known in the art. A surfactant may further be used in combination with the cellulases of the present invention. Suitable surfactants include any surfactant compatible with the β-glucosidase and, optionally, with any other cellulases being used. Exemplary surfactants include an anionic, a non-ionic, and ampholytic surfactants.

Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxyalkylene ethers, as well as higher fatty acid alkanolamides or alkylene oxide adduct thereof, fatty acid glycerine monoesters, and the like. Mixtures of surfactants can also be employed as is known in the art.

Production of Soluble Sugars from Cellulosic Biomass

β-glucosidase polypeptides of the present invention, as well as any composition, culture medium, or cell lysate comprising such β-glucosidase polypeptides, may be used in the production of monosaccharides, disaccharides, or oligomers of a mono- or di-saccharide as chemical or fermentation feedstock from biomass. As used herein, the term "biomass" refers to living or dead biological material that contains a polysaccharide substrate, such as, for example, cellulose, starch, and the like. Therefore, the present invention provides a method of converting a biomass substrate to a fermentable sugar, the method comprising contacting a culture medium or cell lysate containing a β-glucosidase polypeptide according to the invention, with the biomass substrate under conditions suitable for the production of the fermentable sugar. The present invention further provides a method of converting a biomass substrate to a soluble (or "fermentable") sugar by (a) pretreating a cellulose substrate to increase its susceptibility to hydrolysis; (b) contacting the pretreated cellulose substrate of step (a) with a composition, culture medium or cell lysate containing a β-glucosidase polypeptide of the present invention (and optionally other cellulases) under conditions suitable for the production of the fermentable sugar.

In some embodiments, the biomass includes cellulosic substrates that contain cellulose, hemicellulose, lignocellulose. Cellulosic substrates include, but are not limited to including but not limited to, wood, wood pulp, paper pulp, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof. The biomass may optionally be pretreated to increase the susceptibility of cellulose to hydrolysis using methods known in the art such as chemical, physical and biological pretreatments (e.g., steam explosion, pulping, grinding, acid hydrolysis, solvent exposure, and the like, as well as combinations thereof). In some embodiments, the biomass comprises transgenic plants that express ligninase and/or cellulase enzymes which degrade lignin and cellulose. See, e.g., US 20080104724, which is incorporated herein by reference.

In some embodiments, the β-glucosidase polypeptide and β-glucosidase polypeptide-containing compositions, cell culture media, and cell lysates may be reacted with the biomass or pretreated biomass at a temperature in the range of about 25° C. to about 100° C., about 30° C. to about 90° C., about 30° C. to about 80° C., about 40° C. to about 80° C. and about 35° C. to about 75° C. Also, the biomass may be reacted with the β-glucosidase polypeptides and β-glucosidase polypeptide-containing compositions, cell culture media, and cell lysates at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. In addition to the temperatures described above, conditions suitable for converting a biomass substrate to a fermentable sugar that employ a β-glucosidase polypeptide of the present invention (optionally in a composition, cell culture medium, or cell lysate) include carrying out the process at a pH in a range from about pH 3.0 to about 8.5, about pH 3.5 to about 8.5, about pH 4.0 to about 7.5, about pH 4.0 to about 7.0 and about pH 4.0 to about 6.5. Those having ordinary skill in the art will appreciate that the reaction times for converting a particular biomass substrate to a fermentable sugar may vary but the optimal reaction time can be readily determined. Exemplary reaction times may be in the range of from about 1 to about 240 hours, from about 5 to about 180 hrs and from about 10 to about 150 hrs. For example, the incubation time may be at least 1 hr, at least 5 hrs, at least 10 hrs, at least 15 hrs, at least 25 hrs, at least 50 hr, at least 100 hrs, at least 180 and the like.

Reaction of the β-glucosidase with biomass substrate or pretreated biomass substrate under these conditions may result in the release of substantial amounts of the soluble sugars from the substrate. For example at least 20%, at least 30%, at least 40%, at least 50%, at least 60%, at least 70%, at least 80%, at least 90% or more soluble sugar may be available as compared to the release of sugar by the wildtype C1. In some embodiments, the amount of soluble sugar made available may be at least 2-fold, at least 3-fold, at least 4-fold, or at least 5-fold greater than that made available by the wildtype C1 under the same conditions. In some embodiments, the soluble sugars will comprise glucose.

The soluble sugars produced by the methods of the present invention may be used to produce an alcohol (such as, for example, ethanol, butanol, and the like). The present invention therefore provides a method of producing an alcohol, where the method comprises (a) providing a fermentable sugar produced using a β-glucosidase polypeptide of the present invention in the methods described supra; (b) contacting the fermentable sugar with a fermenting microorganism to produce the alcohol or other metabolic product; and (c) recovering the alcohol or other metabolic product.

In some embodiments, the β-glucosidase polypeptide of the present invention, or composition, cell culture medium, or cell lysate containing the β-glucosidase polypeptide may be used to catalyze the hydrolysis of a biomass substrate to a fermentable sugar in the presence of a fermenting microorganism such as a yeast (e.g., *Saccharomyces* sp., such as, for example, *S. cerevisiae, Pichia* sp., and the like) or other C5 or C6 fermenting microorganisms that are well known in the art (e.g., *Zymomonas* sp., *E. coli*,), to produce an end-product such as ethanol. In one example, a simultaneous saccharification and fermentation (SSF) process is used in which the fermentable sugars (e.g., glucose and/or xylose) are removed from the system by the fermentation process.

The soluble sugars produced by the use of a β-glucosidase polypeptide of the present invention may also be used in the production of other end-products. such as, for example, acetone, an amino acid (e.g., glycine, lysine, and the like), an organic acid (e.g., lactic acid, and the like), glycerol, a diol (e.g., 1,3 propanediol, butanediol, and the like) and animal feeds.

One of skill in the art will readily appreciate that the β-glucosidase polypeptide compositions of the present invention may be used in the form of an aqueous solution or a solid concentrate. When aqueous solutions are employed, the β-glucosidase solution can easily be diluted to allow accurate concentrations. A concentrate can be in any form recognized in the art including, for example, liquids, emulsions, suspensions, gel, pastes, granules, powders, an agglomerate, a solid disk, as well as other forms that are well known in the art. Other materials can also be used with or included in the β-glucosidase composition of the present invention as desired, including stones, pumice, fillers, solvents, enzyme activators, and anti-redeposition agents depending on the intended use of the composition.

In addition to use for conversion of cellulosic biomass, β-glucosidase polypeptides and compositions thereof may also be used in the food and beverage industry for example in the process of wine making for the efficient release of monoterpenols (see, for example, Yanai and Sato (1999) *Am. J. Enol. Eltic.*, 50:231-235, which is incorporated herein by reference) and for the preparation of glycon isoflavone-enriched tofu (see, for example, Mase et al., (2004) *J. Appl. Glycosci.*, 51:211-216, which is incorporated herein by reference). β-glucosidase polypeptides of the present invention may also be employed in detergent compositions for improved cleaning performance (see, for example, U.S. Pat. No. 7,244,605; U.S. Pat. No. 5,648,263 and WO 2004/048592, which are incorporated herein by reference).

The foregoing and other aspects of the invention may be better understood in connection with the following non-limiting examples.

VII. Examples

Example 1

Wild-type C1 β-Glucosidase 1 (C1 Bgl1) Gene Acquisition and Construction of Expression Vectors The wild-type C1 bgl1 cDNA was synthesized and the DNA sequence verified. The gene was cloned into a *Saccharomyces cerevisiae*/C1 shuttle vector pYTDX20 using Pml1 cloning sites. The signal peptide and gene were under the control of a chitinase promoter (Pchi). The vector contained the REP2, rep1 and protein D (partial) origin of replication for *S. cerevisiae* and a URA3 resistance marker. The resulting plasmid (pYTDX20-C1 bgl1) was transformed into *S. cerevisiae* INVSC1 strain, and the transformed host cells were grown in HTP for C1 Bgl1 protein production. The C1 bgl1 sequence from the transformants was verified. The protein-encoding portion of the wild-type C1 bgl1 cDNA sequence is provided as SEQ ID NO: 1 and the encoded polypeptide is provided as SEQ ID NO: 2. The first 19 residues of SEQ ID NO:2 are shown in bold and comprise the signal peptide.

Example 2

Shake Flask Procedure

A single colony of *S. cerevisiae* containing a plasmid with the C1 bgl1 cDNA gene was inoculated into 1 mL Synthetic Defined-uracil (SD-ura) Broth (2 g/L synthetic prop-out minus uracil w/o yeast nitrogen base (from United States Biological, Swampscott, Mass.), 5 g/L Ammonium Sulphate, 0.1 g/L Calcium Chloride, 2 mg/L Inositol, 0.5 g/L Magnesium Sulphate, 1 g/L Potassium Phosphate monobasic ($KH_2PO_4$), 0.1 g/L Sodium Chloride) containing 6% glucose. Cells were grown for 24 hrs in an incubator at 30° C. with shaking at 250 rpm. 500 µL of the overnight culture was then diluted into 50 mL SD-ura media containing 2% glucose in a 250 mL baffled sterile shake flask and incubated at 37° C. for 48 hrs. Cells were pelleted by centrifugation (4000 rpm, 15 min, 4° C.). The clear media supernatant containing the secreted C1 Bgl1 enzyme was collected and stored at −20° C. until used.

Example 3

Assays to Determine β-Glucosidase Activity

β-glucosidase activity may be determined either by a para-nitrophenyl-β-D-glucoside (pNPG) assay, or a cellobiose assay.

A colorimetric pNPG (p-nitrophenyl-β-D-glucoside)-based assay was used for measuring β-glucosidase activity. In a total volume of 150 µL, 75 µL of clear media supernatant containing C1 Bgl1 enzyme was added to 75 µL of 3 mM pNPG (Sigma-Aldrich, Inc., St. Louis, Mo.) solution in 300 mM sodium acetate buffer, pH 5. The reactions were incubated at pH 5, 50° C. for 1.5 hrs. After reaction, 75 µL of the reaction mixture was quenched with 75 µL of 1M sodium carbonate pH 11 solution. The absorbance of the solution was measured at 405 nm to determine the conversion of pNPG to p-nitrophenyl. The amount of p-nitrophenol product was measured spectrophotometrically at 405 nm to calculate β-glucosidase activity as described by Breves, et al (1997), *Appl. Environmental Microbiol.* 63:3902-3910. Detectable β-glucosidase activity was observed under high throughput screening conditions (pH 5, 65° C.).

β-glucosidase activity was also determined using a cellobiose assay, which used cellobiose (Sigma-Aldrich, Inc., St. Louis, Mo.) as substrate. In a total volume of 150 µL, 75 µL of clear media supernatant containing C1 Bgl1 enzyme was added to 75 µL of 6.6 g/L cellobiose in 300 mM sodium acetate buffer (pH 5). The reaction was incubated at 65° C. for 21 hours with shaking. Glucose production was determined using an enzymatic glucose assay kit (K-GLUC, Megazyme, Bray, Co. Wicklow, Ireland). In a total volume of 200 µL, 15 µL of C1 Bgl1 reaction mixture was added to 185 µL of Glucose Determination Reagent (GOPOD Reagent, supplied as part of the K-GLUC assay kit). The reaction was incubated at 50° C. for 30 minutes and the absorbance of the solution was measured at 510 nm. The glucose oxidase enzyme in the GOPOD reagent reacts with glucose and produces hydrogen peroxide which then reacts with the 4-aminoantipyrine in the reagent to produce a quinoneimine dye. The amount of quinoneimine dye was measured spectrophotometrically at 510 nm to calculate β-glucosidase activity. Conversion of cellobiose to glucose was also measured using an Agilent HPLC 1200 equipped with HPX-87H ion exclusion column (300 mm×7.8 mm) with water as eluent at a flow rate of 1.0 mL/min at 80° C. The retention times of the cellobiose and glucose were 4.7 and 5.8 minute respectively. Detectable β-glucosidase activity was observed under high throughput screening conditions (pH 5, 65° C.).

Example 4

Evaluation of Optimal C1 Bql1 Activity

The native C1 Bgl1 activity profile was investigated at different temperatures (50° C., 60° C. and 65° C.) and pH (3.5-7.5) using cellobiose (3.3 g/L) as a substrate. The experimental and analytical procedures are described in Example 3. C1 Bgl1 exhibited optimum activity at pH 5 and 50° C., and detectable β-glucosidase activity (20% of optimal activity) was observed under high throughput screening conditions (pH 5 and 65° C.).

Example 5

High Throughput Assays to Identify Improved C1 Bgl1 Variants

Plasmid libraries containing variant C1 bgl1 genes were transformed into *S. cerevisiae* INVSC1 strain and plated on SD-ura agar plate containing 2% glucose. After incubation for at least 48 hours at 30° C., colonies were picked using a Q-bot® robotic colony picker (Genetix USA, Inc., Beaverton, Oreg.) into shallow, 96-well well microtiter plates containing 200 μL SD-ura media and 6% glucose. Cells were grown for 24 hours at 30° C. with shaking at 250 rpm and 85% humidity. 20 μL of this overnight culture was then transferred into 96-well microtiter plates (deep well) containing 380 μL SD-ura medium and 2% glucose as described in Example 2. The plates were incubated at 37° C. with shaking at 250 rpm and 85% humidity for 48 hours. The deep plates were centrifuged at 4000 rpm for 15 minutes and the clear media supernatant containing the secreted C1 Bgl1 enzyme was used for the high throughput pNPG or cellobiose assay.

The C1 Bgl1 libraries were screened in high throughput using both thermoactivity and thermostability assays. In the thermoactivity assay, C1 Bgl1 variants were screened with a cellobiose-based high throughput assay (Substrate: cellbiose; pH: 5.0; temperature: 65° C.; time: 21 hrs). Active C1 Bgl1 variants identified from the thermoactivity assay were subsequently subjected to the thermostability assay. In the thermostability assay, the HTP media supernatant samples containing C1 Bgl1 variant enzymes were pre-incubated at pH 5, 65° C. for 0 or 6 hours. The residual enzyme activity after the thermal challenge was measured using pNPG as substrate at pH 5, 50° C. for 1.5 hrs as described in Example 3.

Thermoactivity Assay

Thermoactivity screening was a cellobiose-based high throughput assay (HTA). In shallow, 96-well microtiter plates 75 μL of media supernatant containing C1 Bgl1 variant enzyme was added to 75 μL of 6.6 g/L cellobiose in 300 mM sodium acetate buffer pH 5.0. After sealing with aluminum/polypropylene laminate heat seal tape (Velocity 11 (Menlo Park, Calif.), Cat#06643-001), the plates were shaken at 65° C. for up to 21 hrs. The plates were centrifuged for 5 minutes at 4000 rpm. In shallow well clear microtiter plates, 15 μL of the reaction mixture was quenched with 185 μL of GOPOD Reagent solution per well. The solutions were gently mixed for 3 times and absorbance was measured at 510 nm for the identification of thermoactivity improved C1 Bgl1 variants.

Thermostability Assay

Thermostability screening was a pNPG-based high throughput assay. In shallow, 96-well microtiter plates, 180 μL of media supernatant containing active C1 Bgl1 variant enzyme was mixed with 30 μL of 1 M sodium acetate buffer pH 5.0. From a total 210 μL of the enzyme solution, 120 μL of enzyme solution was transferred into 96-well PCR plates for thermal challenge treatment, and 90 μL of enzyme solution left in the shallow 96-well plates was used as unchallenged C1 Bgl1 enzyme sample. After sealing with aluminum/polypropylene laminate heat seal tape (Velocity 11 (Menlo Park, Calif.), Cat#06643-001), the PCR plates were heated in the thermocycler (MJ Research, Waltham, Mass.) at 65° C. for 6 hrs. After thermal challenge, 90 μL of challenged enzyme solution was transferred into 96-well shallow plates. To initiate the pNPG reaction, in shallow 96-well plates, 90 μL of unchallenged or challenged enzyme solutions were mixed with 10 μL of 15 mM pNPG (Sigma-Aldrich, Inc., St. Louis, Mo.) solution in 150 mM sodium acetate buffer, pH 5. The reactions were incubated at pH 5, 50° C. for 1.5 hrs. After reaction, 100 μL of 1M sodium carbonate pH 11 solution was added to the reaction mixture to quench the reaction. The absorbance of the solution was measured at 405 nm to determine the conversion of pNPG to p-nitrophenyl. The residual activity was calculated using the formula:

% residual activity=100×(Absorbance of challenged samples/Absorbance of unchallenged samples).

Residual activities of C1 Bgl1 variants were compared with that of the native enzyme to identify the thermostability improved variants.

Example 6

Improved β-Glucosidase Activities and Stabilities of Engineered C1 Bgl1 Variants Improved C1 Bgl1 variants were identified from the high throughput screening of various C1 Bgl1 variant libraries as described in Example 5. A variant reference sequence exhibiting improved activity and stability compared to wildtype C1 Bgl1 was selected as a reference protein (Variant 3, as shown in Tables 2 and 3) and additional C1 Bgl1 variants were generated and evaluated as indicated in the legend to Table 3 to identify variants that had improved stability and activity relative to the Variant 3 reference sequence. One of the improved variants from this round was then selected as a reference protein (Variant 269, as shown in Tables 3 and 4) and additional C1 Bgl1 variants were generated and evaluated as described in the legend to Table 4 to identify variants that had improved stability and activity relative to Variant 269. A variant (Variant 481, as shown in Tables 4 and 5) was selected from this round as a reference protein and additional C1 Bgl1 variants were generated and evaluated as described in the legend to table 5 to identify variants that had improved stability and activity relative to Variant 481. Two variants (Variant 647, as shown in Tables 5 and 6; and Variant 664 as shown in Tables 5 and 7) were then selected. Each variant served as a reference protein for separate rounds of screening. Additional C1 Bgl1 variants were generated and evaluated as described in the legend to Table 6 to identify variants that had improved stability and activity relative to variant 647. C1 Bgl1 variants were also generated and evaluated as described in the legend to Table 7 to identify variants that had improved stability and activity relative to Variant 664.

Tables 2, 3, 4, 5, 6, and 7 summarize the improvement in thermoactivities and thermostabilities of certain C1 Bgl1 variants encompassed by the invention.

Example 7

Production of Improved β-Glucosidase Variants in the C1 Host

A two-step fermentation process (inoculation and main fermentations starting from spores) was used to express C1 bgl1 variant genes in C1. Six plasmids containing C1 bgl1 variant genes were transformed into C1 strain and plated on agar plates containing M3-01 medium with 22.93% sucrose (ingredients of M3-01 Medium: 6.0 g/L Sodium Nitrate, 0.52 g/L Potassium Chloride, 1.52 g/L Potassium Phosphate monobasic ($KH_2PO_4$), 0.24 g/L Magnesium Sulfate, 1.6 mg/L Copper(II) Sulfate pentahydrate ($CuSO_4 5H_2O$), 5 mg/L Ferrous Sulfate heptahydrate (FeSO$_4$7H$_2$O), 22 mg/L Zinc Sulfate heptahydrate (ZnSO$_4$7H$_2$O), 5 mg/L Manganese (II) Chloride tetrahydrate (MnCl$_2$4H$_2$O), 1.8 mg/L Cobalt(II) Sulfate heptahydrate (CoSO$_4$7H$_2$O), 1.5 mg/L Sodium Molybdate dihydrate (Na$_2$MoO$_4$2H$_2$O), 11 mg/L Boric Acid, 50 mg/L EDTA, 10.0 g/L Glucose, 1.0 g/L CAS amino acids (Tritium Microbiologie B. V., The Netherlands), 16 g/L agar, 1 ml/L 1000× Pen/Strep after sterilization (1000× Pen/Strep: 2 g Penicillin G and 5 g Streptomycin dissolved in 100 ml H$_2$O, sterilized by filtration). The pH of the medium was adjusted to 6.5 with 10 M KOH and autoclaved for 25 minutes at 121° C. The plates were incubated at 35° C. for 5 days. Spores harvested from the agar plates were used to inoculate a 100 mL F1-01 inoculum medium sterilized in a 500 mL Erlenmeyer flask to reach 5*10$^4$–10$^5$ spores/mL initial spore number. (Ingredients of F1-01 Inoculum Medium: 0.50 g/L Potassium Phosphate dibasic (K$_2$HPO$_4$), 0.05 g/L Potassium Chloride, 0.007 g/L Ferrous Sulfate heptahydrate (FeSO$_4$7H$_2$O), 1.00 g/L Yeast Extract (only KAT), 10 g/L Pharmamedia (Traders Protein, Lubbock, Tex., USA), 10 g/L D(+)Lactose monohydrate, 10 g/L Glucose after sterilization, 1 ml/L 1000× Pen/Strep after sterilization (1000× Pen/Strep: 2 g Penicillin G and 5 g Streptomycin dissolved in 100 ml H$_2$O, sterilized by filtration). The pH of the medium was adjusted to 7.0 with 10 M NaOH and autoclaved for 25 minutes at 121° C. (The pH of the medium after sterilization was 6.5). To prepare inoculum culture, the flask was incubated at 35° C., 85% humidity for 3 days with shaking at 250 rpm and 25 mm displacement. 15 mL F1-01 Main Fermentation Medium sterilized in a 100 mL Erlenmeyer flask was inoculated with 750 μL of the obtained inoculum culture (ingredients of F1-01 Main Fermentation Medium: 0.66 g/L Potassium Phosphate dibasic (K$_2$HPO$_4$), 0.24 g/L Potassium Phosphate monobasic (KH$_2$PO$_4$), 8.00 g/L Ammonium Sulphate, 12.00 g/L Sodium Citrate tribasic dehydrate, 0.15 g/L Yeast Extract (only KAT), 0.09 g/L Magnesium Sulfate heptahydrate, 0.80 g/L Calcium Chloride dihydrate, 24.80 g/L Pharmamedia (Traders Protein, Lubbock, Tex., USA), 26.40 g/L D(+)Lactose monohydrate, 64.80 g/L Cellulose (AlphaCel BH200A)). The medium was autoclaved for 25 minutes at 121° C. The main fermentation was carried out by incubation at 35° C., 85% humidity for 6 days with shaking at 300 rpm and 25 mm displacement. After finishing the main fermentation the cells were pelleted by centrifugation (4500 rpm, 15 min, 4° C.). The clear medium supernatant containing the secreted C1 Bgl1 enzyme was collected and stored at −20° C. until used.

Example 8

Improved Thermostabilities of β-Glucosidase Variants Produced in the C1 Host

Figure 1B:
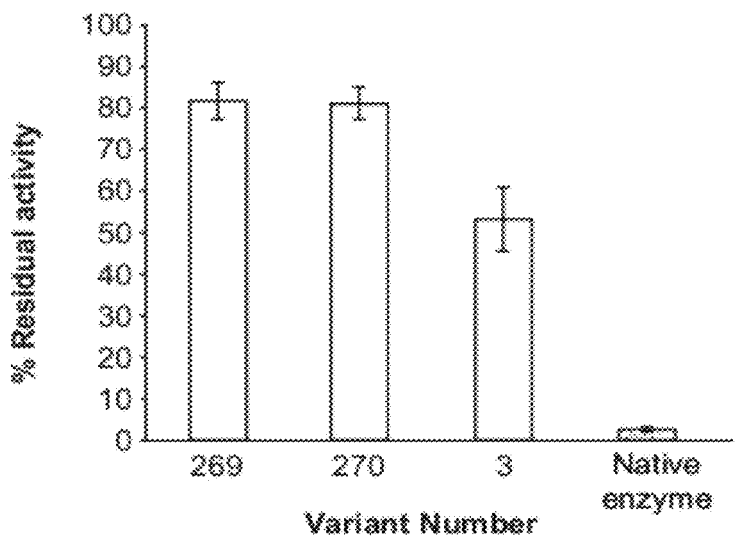
Figure 1C:
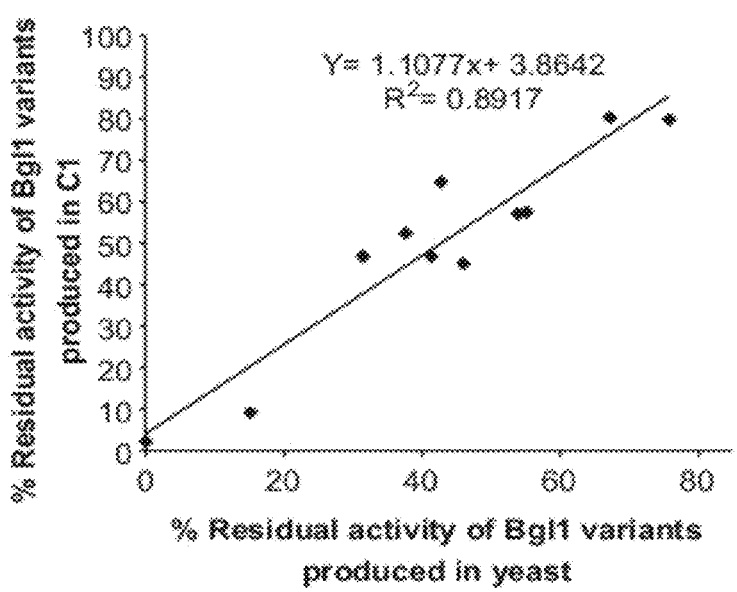

Eight C1 Bgl1 variants (3, 8, 70, 109, 143, 194, 269 and 270) and native enzyme, produced in the C1 host, were characterized to determine their stabilities at high temperature (65° C.). The samples containing various C1 Bgl1 variant enzymes were pre-incubated at pH 5, 65° C. for 0, 6 or 24 hrs. The residual enzyme activity after the thermal challenge was measured using pNPG as substrate at pH 5, 50° C. for 20 mins. The best variant of the eight exhibited up to 34-fold improvement in stability over the native enzyme (FIG. 1A and FIG. 1B). Comparison of stability profiles of the native enzyme and eight C1 Bgl1 variants, produced from yeast and from C1, showed good correlation between the two hosts. (FIG. 1C).

Example 9

Thermostabilities of C1 Bgl1 Variants

Figure 2A:
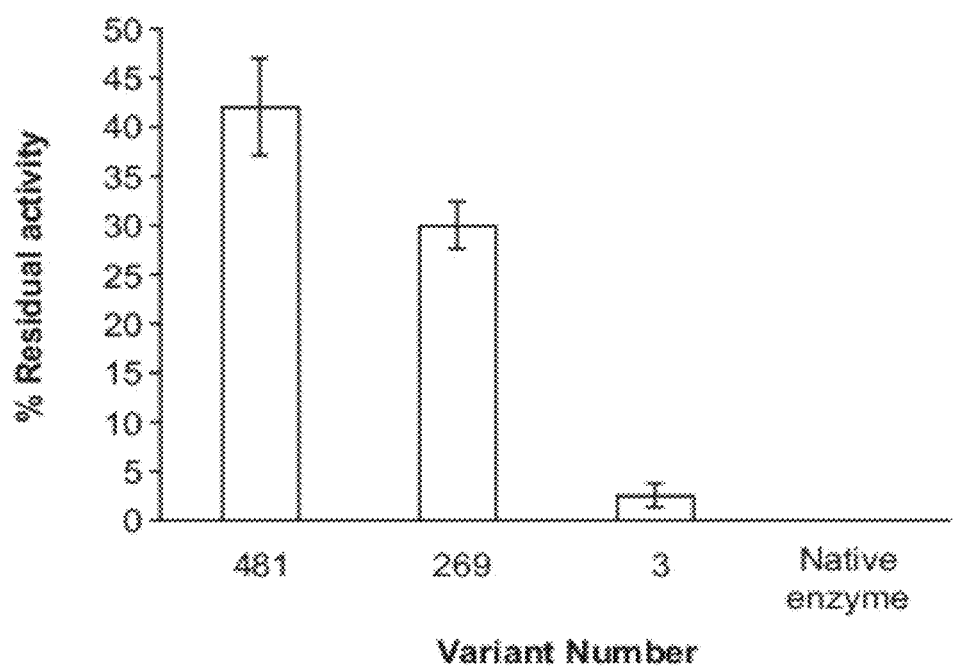
FIG. 2. (A) The thermostabilities of improved C1 Bgl1 variants 481, 269, and 3 were compared to that of the native C1 Bgl1 enzyme. The residual enzyme activity after 24 hr incubation at pH 4.5, 65° C. was measured using pNPG as substrate at pH 5, 50° C. for 20 mins. N=6-16; Error bars represent ±1 standard deviation. (B) The thermostability of improved C1 Bgl1 Variant 664 was compared to that of Variant 481. The residual enzyme activity after 4 hr incubation at pH 4, 65° C. was measured using pNPG as substrate at pH 5, 50° C. for 20 mins. N=6-24; Error bars represent ±1 standard deviation.

The thermostabilities of improved C1 Bgl1 variants 3, 269, and 481 were compared to that of the native C1 Bgl1 enzyme. The residual enzyme activity after 24 hr incubation at pH 4.5, 65° C. was measured using pNPG as substrate at pH 5, 50° C. for 20 mins. FIG. 2A shows that Variant 481 had the greatest increase in activity following thermal challenge.

Figure 2B:
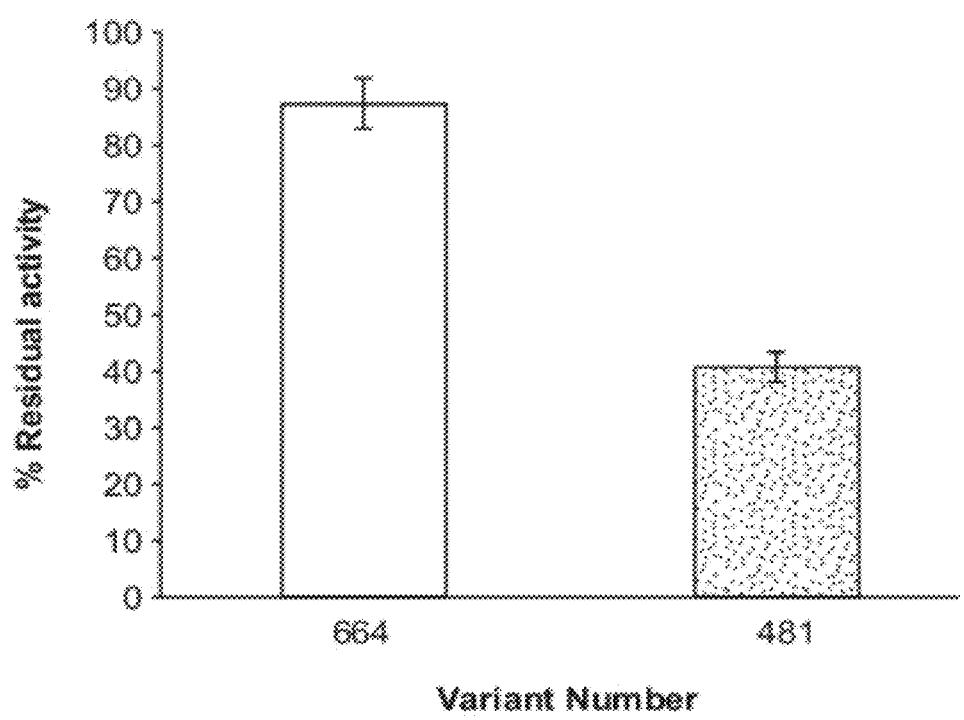

The thermostability of improved C1 Bgl1 Variant 664 was compared to that of Variant 481. The residual enzyme activity after 4 hr incubation at pH 4, 65° C. was measured using pNPG as substrate at pH 5, 50° C. for 20 mins. FIG. 2B shows that Variant 664 had improved enzyme activity after thermal challenge relative to Variant 481.

Figure 3:
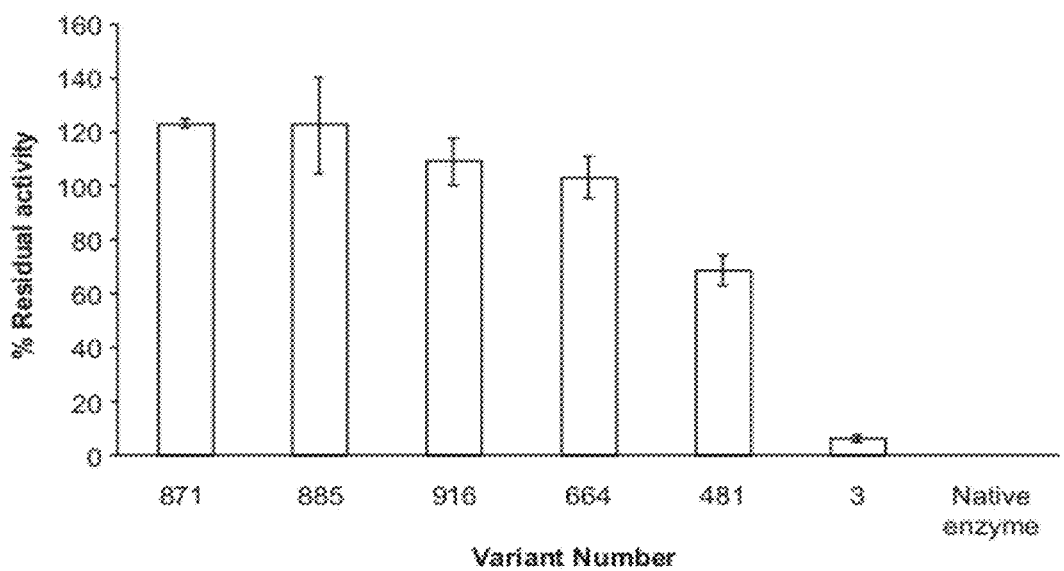
FIG. 3. The thermostabilities of improved C1 Bgl1 variants 3, 481, 664, 916, 885, and 871 were compared to that of the native C1 Bgl1 enzyme. The residual enzyme activity after 72 hr incubation at pH 4.5, 65° C. was measured using pNPG as substrate at pH 5, 50° C. for 20 mins. N=6-10; Error bars represent ±1 standard deviation.

The thermostability of improved C1 Bgl1 variants 3, 481, 664, 916, 885, and 871 was compared to the native enzyme (FIG. 3). Residual enzyme activity was measured after 72 hr incubation at pH 4.5, 65° C. using a pNPG assay at pH 5, 50° C. for 20 mins. The results showed that variants 664, 916, 885, and 871 retained substantial activity.

Figure 4:
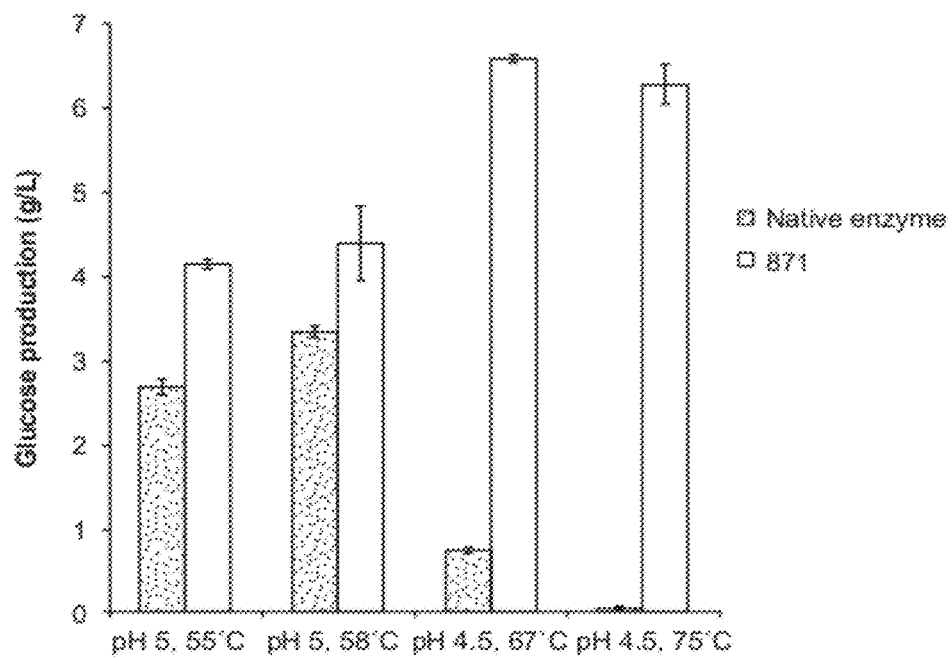
FIG. 4. The specific activity of native C1 Bgl1 was compared to that of variant 871 in a cellbiose assay. Assay conditions: pH 4.5-5, temperatures 55° C.-75° C.; 8 g/L cellobiose, 18 hr reaction. Protein concentration was normalized in reactions. N+2; Error bars represent ±1 standard deviation.

The specific activity of variant 871 was compared to the native, i.e., wildtype enzyme using a cellobiose assay (pH 4.5 or pH 5, 55° C.-75° C.; 8 g/L cellobiose, 18 hr reaction). FIG. 4 shows that variant 871 produced more glucose in the assay than the native enzyme.

Figure 5:
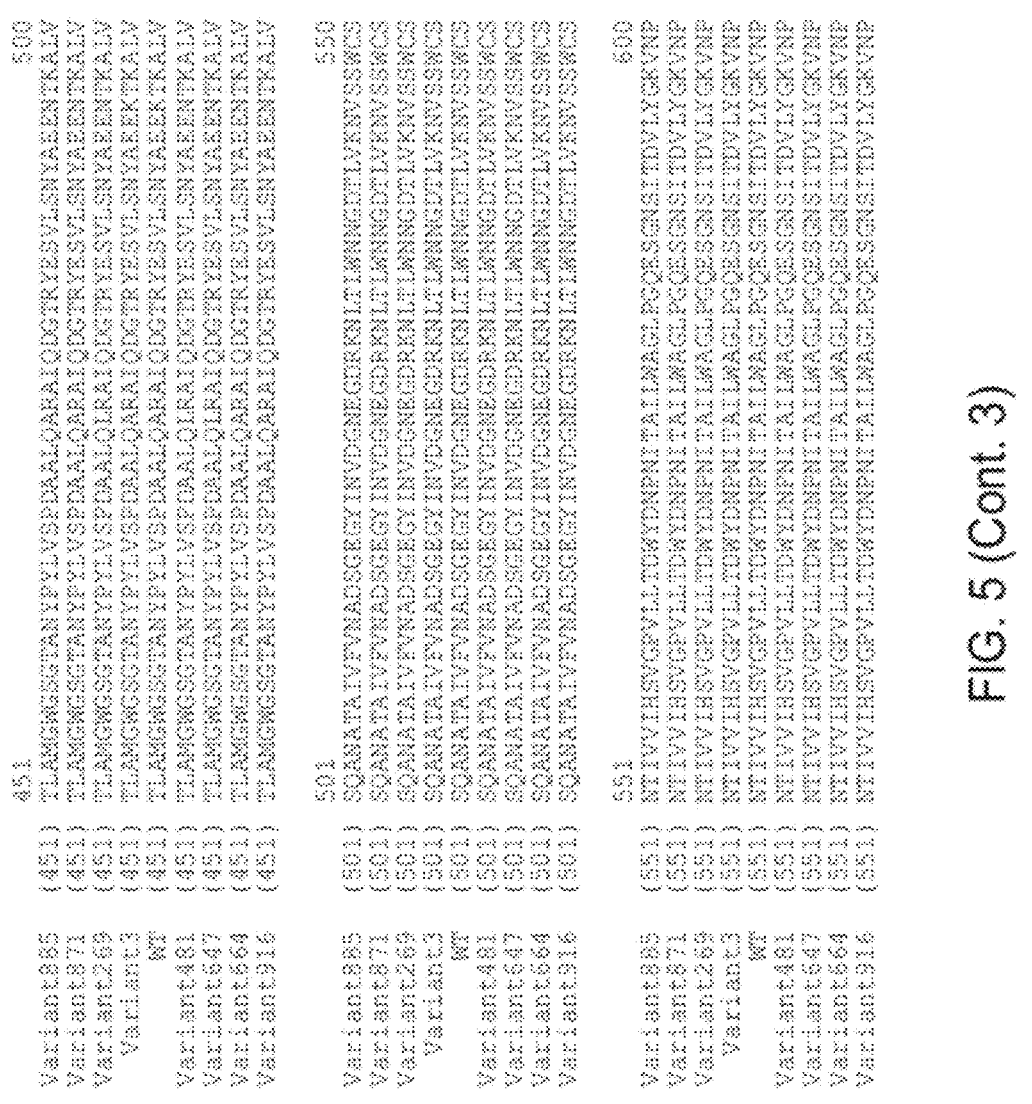
Figure 5:
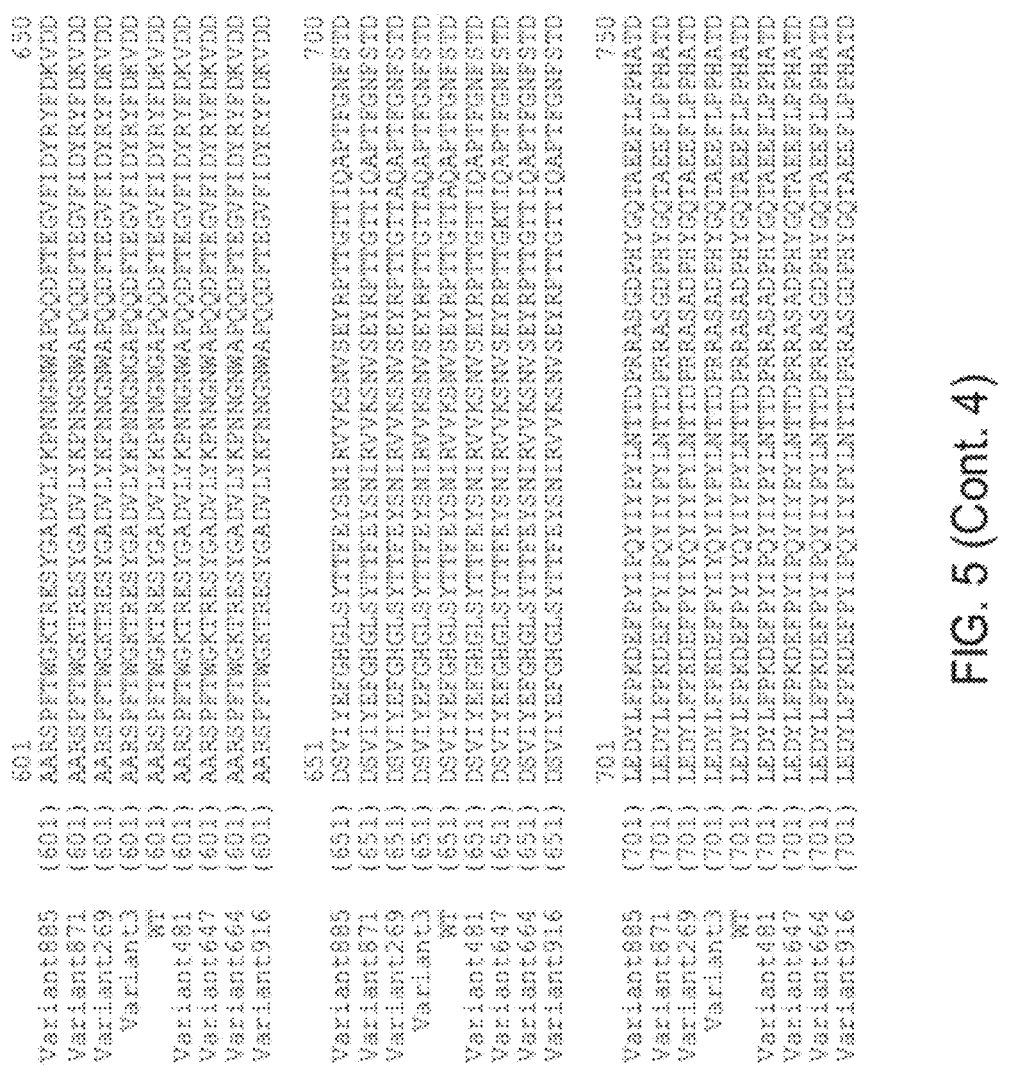
Figure 5:
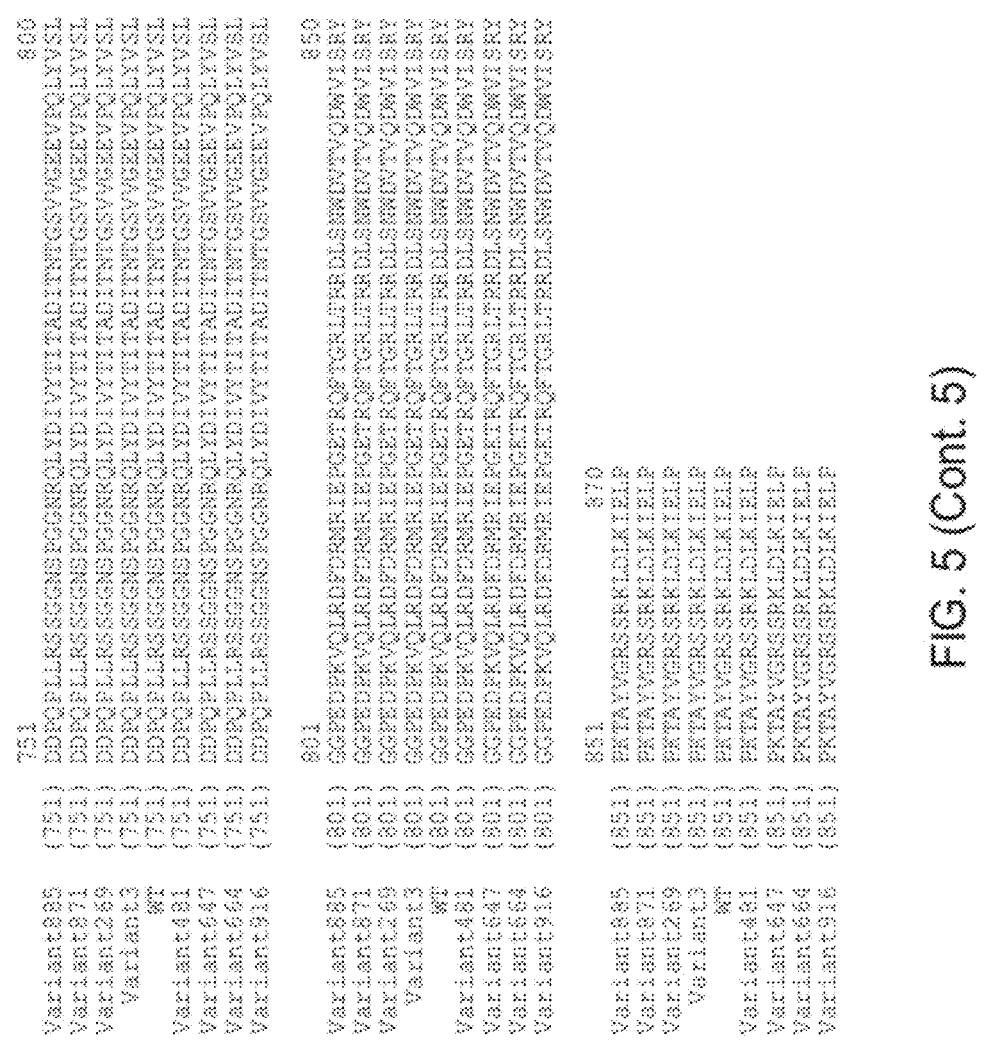

FIG. 5 shows an alignment of Variants 871, 916, 885, 664, 647, 481, 269, and 3 with the native C1 Bgl1 amino acid sequence.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

```
SEQ ID NO: 1 Wild-type C1 bgl1 cDNA Sequence
        atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccga cggctgggcg gaggcctatg cccaggccaa gtcctttgtc     180
tcccaaatga ctctgctaga gaaggtcaac ttgaccacgg gagtcggctg ggggctgag      240
```

```
cagtgcgtcg gccaagtggg cgcgatccct cgccttggac ttcgcagtct gtgcatgcat        300
gactcccctc tcggcatccg aggagccgac tacaactcag cgttccctc tggccagacc         360 gttgctgcta cctgggatcg cggtctgatg taccgtcgcg gctacgcaat gggccaggag        420
gccaaaggca agggcatcaa tgtccttctc ggaccagtcg ccggccccct tggccgcatg        480
cccgagggcg gtcgtaactg ggaaggcttc gctccggatc ccgtccttac cggcatcggc        540
atgtccgaga cgatcaaggg cattcaggat gctggcgtca tcgcttgtgc gaagcacttt        600
attggaaacg agcaggagca cttcagacag gtgccagaag cccagggata cggttacaac        660
atcagcgaaa ccctctcctc caacattgac gacaagacca tgcacgagct ctacctttgg       720
ccgtttgccg atgccgtccg ggccggcgtc ggctctgtca tgtgctcgta ccagcaggtc       780
aacaactcgt acgcctgcca gaactcgaag ctgctgaacg acctcctcaa gaacgagctt       840
gggtttcagg gcttcgtcat gagcgactgg caggcacagc acactggcgc agcaagcgcc       900
gtggctggtc tcgatatgtc catgccgggc gacacccagt tcaacactgg cgtcagtttc       960
tggggcgcca atctcaccct cgccgtcctc aacggcacag tccctgccta ccgtctcgac      1020
gacatggcca tgcgcatcat ggccgccctc ttcaaggtca ccaagaccac cgacctggaa      1080
ccgatcaact tctccttctg gaccgacgac acttatggcc cgatccactg ggccgccaag      1140
cagggctacc aggagattaa ttcccacgtt gacgtccgcg ccgaccacgg caacctcatc      1200
cgggagattg ccgccaaggg tacggtgctg ctgaagaata ccggctctct accctgaac        1260 aagccaaagt tcgtggccgt catcggcgag gatgctgggt cgagccccaa cgggcccaac      1320
ggctgcagcg accgcggctg taacgaaggc acgtcgcca tgggctgggg atccggcaca       1380
gccaactatc cgtacctcgt ttcccccgac gccgcgctcc aggcccggggc catccaggac     1440 ggcacgaggt acgagagcgt cctgtccaac tacgccgagg aaaagacaaa ggctctggtc      1500
tcgcaggcca atgcaaccgc catcgtcttc gtcaatgccg actcaggcga gggctacatc     1560
aacgtggacg gtaacgaggg cgaccgtaag aacctgactc tctggaacaa cggtgatact     1620
ctggtcaaga acgtctcgag ctggtgcagc aacaccatcg tcgtcatcca ctcggtcggc     1680
ccggtcctcc tgaccgattg gtacgacaac cccaacatca cggccattct ctgggctggt    1740
cttccgggcc aggagtcggg caactccatc accgacgtgc tttacggcaa ggtcaacccc    1800
gccgcccgct cgcccttcac ttggggcaag acccgcgaaa gctatggcgc ggacgtcctg    1860
tacaagccga ataatggcaa tggtgcgccc caacaggact tcaccgaggg cgtcttcatc    1920
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
taccggccca cgacgggcac cacggcccag gccccgacgt ttggcaactt ctccaccgac    2100
ctcgaggact atctcttccc caaggacgag ttcccctaca tctaccagta catctaccccg  2160 tacctcaaca cgaccgaccc ccggagggcc tcggccgatc cccactacgg ccagaccgcc    2220
gaggagttcc tcccgcccca cgccaccgat gacgaccccc agccgctcct ccggtcctcg    2280
ggcggaaact cccccggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                  2613
```

SEQ ID NO: 2: Wild-type C1 Bgl1 Polypeptide Sequence; signal peptide indicated in bold

```
     MKAAALSCLF GSTLAVAGAI ESRKVHQKPL ARSEPFYPSP WMNPNADGWA EAYAQAKSFV      60

SQMTLLEKVN LTTGVGWGAE QCVGQVGAIP RLGLRSLCMH DSPLGIRGAD YNSAFPSGQT     120

VAATWDRGLM YRRGYAMGQE AKGKGINVLL GPVAGPLGRM PEGGRNWEGF APDPVLTGIG     180

MSETIKGIQD AGVIACAKHF IGNEQEHFRQ VPEAQGYGYN ISETLSSNID DKTMHELYLW     240

PFADAVRAGV GSVMCSYQQV NNSYACQNSK LLNDLLKNEL GFQGFVMSDW QAQHTGAASA     300

VAGLDMSMPG DTQFNTGVSF WGANLTLAVL NGTVPAYRLD DMAMRIMAAL FKVTKTTDLE     360

PINFSFWTDD TYGPIHWAAK QGYQEINSHV DVRADHGNLI REIAAKGTVL LKNTGSLPLN     420

KPKFVAVIGE DAGSSPNGPN GCSDRGCNEG TLAMGWGSGT ANYPYLVSPD AALQARAIQD     480

GTRYESVLSN YAEEKTKALV SQANATAIVF VNADSGEGYI NVDGNEGDRK NLTLWNNGDT     540

LVKNVSSWCS NTIVVIHSVG PVLLTDWYDN PNITAILWAG LPGQESGNSI TDVLYGKVNP     600

AARSPFTWGK TRESYGADVL YKPNNGNGAP QQDFTEGVFI DYRYFDKVDD DSVIYEFGHG     660

LSYTTFEYSN IRVVKSNVSE YRPTTGTTAQ APTFGNFSTD LEDYLFPKDE FPYIYQYIYP     720

YLNTTDPRRA SADPHYGQTA EEFLPPHATD DDPQPLLRSS GGNSPGGNRQ LYDIVYTITA     780

DITNTGSVVG EEVPQLYVSL GGPEDPKVQL RDFDRMRIEP GETRQFTGRL TRRDLSNWDV     840

TVQDWVISRY PKTAYVGRSS RKLDLKIELP                                      870
```

SEQ ID NO: 3: Polynucleotide Sequence Encoding Wild-Type *Chrysosporium lucknowense*
β-glucosidase 1 protein using Codons Biased For Expression in *Saccharomyces cerevisiae*.
The protein encoded by SEQ ID NO: 3 is SEQ ID NO: 22.

```
                                                            ATAGAAAGTAGAAAGGTA
                                                             I  E  S  R  K  V

CATCAAAAACCATTAGCTAGATCAGAACCATTCTACCCTTCTCCATGGATGAACCCTAATGCAGATGGATGGGCAGAAGCATATGCTCAG
 H  Q  K  P  L  A  R  S  E  P  F  Y  P  S  P  W  M  N  P  N  A  D  G  W  A  E  A  Y  A  Q

GCCAAGAGTTTTGTCTCCCAGATGACTCTGTTGGAAAAGGTTAATCTGACAACAGGAGTAGGATGGGGTGCAGAACAGTGTGTCGGCCAA
 A  K  S  F  V  S  Q  M  T  L  L  E  K  V  N  L  T  T  G  V  G  W  G  A  E  Q  C  V  G  Q

GTTGGTGCTATCCCTAGATTGGGTCTTAGAAGTTTGTGTATGCACGATTCTCCCTTAGGTATAAGAGGCGCTGACTATAACTCAGCATTC
 V  G  A  I  P  R  L  G  L  R  S  L  C  M  H  D  S  P  L  G  I  R  G  A  D  Y  N  S  A  F

CCATCCGGGCAAACTGTTGCTGCGACATGGGACAGGGGTTTGATGTATAGAAGGGGTTATGCGATGGGTCAAGAGGCAAAGGGTAAAGGA
 P  S  G  Q  T  V  A  A  T  W  D  R  G  L  M  Y  R  R  G  Y  A  M  G  Q  E  A  K  G  K  G

ATTAATGTATTGTTGGGGCCGGTGGCGGGGCCACTGGGAAGAATGCCAGAAGGTGGAAGGAACTGGGAAGGATTCGCCCCCGACCCAGTG
 I  N  V  L  L  G  P  V  A  G  P  L  G  R  M  P  E  G  G  R  N  W  E  G  F  A  P  D  P  V

CTAACAGGTATAGGTATGTCCGAAACGATCAAAGGCATACAAGATGCAGGTGTTATCGCCTGTGCGAAGCATTTTATTGGTAATGAACAA
 L  T  G  I  G  M  S  E  T  I  K  G  I  Q  D  A  G  V  I  A  C  A  K  H  F  I  G  N  E  Q

GAGCATTTTCGTCAAGTGCCAGAGGCTCAAGGTTATGGTTATAATATTTCTGAAACTTTAAGTTCCAACATCGATGACAAAACCATGCAC
 E  H  F  R  Q  V  P  E  A  Q  G  Y  G  Y  N  I  S  E  T  L  S  S  N  I  D  D  K  T  M  H

GAGTTATACTTATGGCCTTTTGCAGACGCTGTGAGAGCTGGCGTTGGCTCTGTTATGTGCTCTTATCAGCAAGTTAATAACTCTTACGCC
 E  L  Y  L  W  P  F  A  D  A  V  R  A  G  V  G  S  V  M  C  S  Y  Q  Q  V  N  N  S  Y  A

TGTCAAAATTCCAAGTTACTAAATGACTTATTGAAGAACGAACTAGGATTCCAAGGATTCGTCATGAGCGATTGGCAAGCACAGCATACT
 C  Q  N  S  K  L  L  N  D  L  L  K  N  E  L  G  F  Q  G  F  V  M  S  D  W  Q  A  Q  H  T

GGTGCTGCATCCGCTGTGGCAGGATTAGATATGTCAATGCCAGGAGATACACAATTTAATACTGGCGTTAGTTTTTGGGGTGCAAACCTA
 G  A  A  S  A  V  A  G  L  D  M  S  M  P  G  D  T  Q  F  N  T  G  V  S  F  W  G  A  N  L

ACTTTAGCTGTTCTAAACGGTACGGTACCTGCATATCGTTTAGACGACATGGCCATGCGTATAATGGCTGCTTTATTCAAAGTTACAAAA
 T  L  A  V  L  N  G  T  V  P  A  Y  R  L  D  D  M  A  M  R  I  M  A  A  L  F  K  V  T  K

ACCACCGATTTAGAACCAATTAATTTTAGTTTTTGGACAGATGACACATATGGTCCTATACACTGGGCTGCTAAGCAAGGGTACCAAGAA
 T  T  D  L  E  P  I  N  F  S  F  W  T  D  D  T  Y  G  P  I  H  W  A  A  K  Q  G  Y  Q  E

ATAAATAGTCACGTTGACGTAAGAGCGGATCACGGCAATCTTATCAGAGAGATAGCAGCAAAGGGAACTGTATTGTTGAAGAATACTGGT
 I  N  S  H  V  D  V  R  A  D  H  G  N  L  I  R  E  I  A  A  K  G  T  V  L  L  K  N  T  G

TCATTACCACTAAACAAACCAAAGTTTGTCGCAGTCATTGGTGAAGATGCTGGTTCATCCCCTAATGGACCAAATGGTTGTAGTGACAGA
 S  L  P  L  N  K  P  K  F  V  A  V  I  G  E  D  A  G  S  S  P  N  G  P  N  G  C  S  D  R

GGCTGCAATGAAGGCACGTTGGCAATGGGCTGGGGCTCAGGGACTGCCAATTACCCCTATTTGGTCTCTCCGGATGCGGCTTTACAGGCT
```

```
               G  C  N  E  G  T  L  A  M  G  W  G  S  G  T  A  N  Y  P  Y  L  V  S  P  D  A  A  L  Q  A
AGAGCAATCCAGGATGGTACTAGATACGAGAGCGTCCTAAGTAACTATGCCGAAGAAAGACTAAGGCCTTAGTCAGTCAAGCCAATGCC
 R  A  I  Q  D  G  T  R  Y  E  S  V  L  S  N  Y  A  E  E  K  T  K  A  L  V  S  Q  A  N  A

ACTGCTATCGTTTTCGTAAACGCGGATTCTGGCGAAGGTTATATCAATGTTGATGGTAATGAAGGTGACAGAAAGAATTTAACTTTATGG
 T  A  I  V  F  V  N  A  D  S  G  E  G  Y  I  N  V  D  G  N  E  G  D  R  K  N  L  T  L  W

AATAACGGCGACACATTAGTTAAAAATGTATCAAGTTGGTGTTCCAATACTATCGTCGTGATACATTCTGTTGGTCCAGTTTTACTGACA
 N  N  G  D  T  L  V  K  N  V  S  S  W  C  S  N  T  I  V  V  I  H  S  V  G  P  V  L  L  T

GACTGGTACGATAACCCAAACATTACCGCCATTTTATGGGCAGGTCTGCCAGGGCAGGAATCAGGAAATTCCATTACGGACGTACTATAC
 D  W  Y  D  N  P  N  I  T  A  I  L  W  A  G  L  P  G  Q  E  S  G  N  S  I  T  D  V  L  Y

GGAAAGGTTAACCCAGCCGCCAGGAGCCCTTTCACATGGGGTAAGACAAGAGAGAGCTACGGAGCTGATGTTCTTTATAAACCGAACAAC
 G  K  V  N  P  A  A  R  S  P  F  T  W  G  K  T  R  E  S  Y  G  A  D  V  L  Y  K  P  N  N

GGGAATGGAGCGCCACAGCAAGATTTTACTGAAGGTGTGTTCATTGACTATAGATACTTCGACAAAGTTGACGATGACTCAGTTATATAT
 G  N  G  A  P  Q  Q  D  F  T  E  G  V  F  I  D  Y  R  Y  F  D  K  V  D  D  D  S  V  I  Y

GAATTCGGTCACGGTCTATCTTATACTACTTTTGAATATTCAAATATAAGAGTAGTCAAAAGTAATGTTTCTGAATATAGGCCGACCACC
 E  F  G  H  G  L  S  Y  T  T  F  E  Y  S  N  I  R  V  V  K  S  N  V  S  E  Y  R  P  T  T

GGAACGACGGCTCAAGCGCCTACCTTCGGTAATTTTTCAACGGATTTAGAAGATTATTTATTTCCCAAAGACGAATTTCCATACATCTAC
 G  T  T  A  Q  A  P  T  F  G  N  F  S  T  D  L  E  D  Y  L  F  P  K  D  E  F  P  Y  I  Y

CAATACATATACCCCTATCTGAATACTACCGATCCAAGAAGAGCTTCTGCCGATCCACATTACGGGCAGACTGCCGAAGAGTTCTTGCCA
 Q  Y  I  Y  P  Y  L  N  T  T  D  P  R  R  A  S  A  D  P  H  Y  G  Q  T  A  E  E  F  L  P

CCACACGCTACTGACGACGATCCTCAACCTCTTCTGAGGTCCAGTGGCGGAAATTCACCTGGTGGTAATAGGCAGCTGTATGATATTGTG
 P  H  A  T  D  D  D  P  Q  P  L  L  R  S  S  G  G  N  S  P  G  G  N  R  Q  L  Y  D  I  V

TATACTATAACGGCTGATATTACTAATACTGGTAGCGTTGTTGGTGAAGAAGTGCCGCAATTATATGTGTCTTTAGGTGGTCCGGAAGAT
 Y  T  I  T  A  D  I  T  N  T  G  S  V  V  G  E  E  V  P  Q  L  Y  V  S  L  G  G  P  E  D

CCTAAGGTTCAGTTAAGAGACTTTGATAGGATGAGAATAGAACCTGGAGAAACTAGGCAATTTACAGGTAGATTGACCCGTAGGGATCTG
 P  K  V  Q  L  R  D  F  D  R  M  R  I  E  P  G  E  T  R  Q  F  T  G  R  L  T  R  R  D  L

TCAAACTGGGATGTAACAGTGCAAGATTGGGTAATCAGCAGGTACCCGAAAACTGCATACGTGGGTAGATCTTCCCGTAAGTTAGATTTG
 S  N  W  D  V  T  V  Q  D  W  V  I  S  R  Y  P  K  T  A  Y  V  G  R  S  S  R  K  L  D  L

AAAATTGAATTGCCATAA
 K  I  E  L  P  *

SEQ ID NO: 4 C1 Variant 3 cDNA sequence
         atgaaggctg ctgcgctttc ctgcctcttc ggcagtaccc ttgccgttgc aggcgccatt            60
         gaatcgagaa aggttcacca gaagcccctc gcgagatctg aaccttttta cccgtcgcca           120
         tggatgaatc ccaacgccga cggctgggcg gaggcctatg cccaggccaa gtcctttgtc           180
         tcccaaatga ctctgctaga aaggtcaac ttgaccacgg gagtcggctg gggggctgag           240
         cagtgcgtcg gccaagtggg cgcgatccct cgccttggac ttcgcagtct gtgcatgcat           300
         gactcccctc tcggcatccg aggagccgac tacaactcag cgttccctc tggccagacc           360
         gttgctgcta cctgggatcg cggtctgatg taccgtcgcg gctacgcaat gggccaggag           420
         gccaaaggca agggcatcaa tgtccttctc ggaccagtcg ccggcccct tggccgcatg           480
         cccgagggcg gtcgtaactg ggaaggcttc gctccggatc ccgtccttac cggcatcggc           540
         atgtccgaga cgatcaaggg cattcaggat gctggcgtca tcgcttgtgc gaagcacttt           600
         attggaaacg agcaggagca cttcagacag gtgccagaag cccagggata cggttacaac           660
         atcagcgaaa ccctctcctc caacattgac gacaagacca tgcacgagct ctacctttgg           720
         ccgtttgccg atgccgtccg ggccggcgtc ggctctgtca tgtgctcgta ccagcaggtc           780
         aacaactcgt acgcctgcca gaactcgaag ctgctgaacg acctcctcaa gaacgagctt           840
         gggtttcagg gcttcgtcat gagcgactgg tgggcacagc acactggcgc agcaagcgcc           900
         gtggctggtc tcgatatgtc catgccgggc gacacccagt tcaacactgg cgtcagtttc           960
         tggggcgcca atctcacccct cgccgtcctc aacggcacag tccctgccta ccgtctcgac          1020
         gacatggcca tgcgcatcat ggccgccctc ttcaaggtca ccaagaccac cgacctggaa          1080
```

-continued

```
      ccgatcaact tctccttctg gaccctggac acttatggcc cgatccactg ggccgccaag      1140
      cagggctacc aggagattaa ttcccacgtt gacgtccgcg ccgaccacgg caacctcatc      1200
      cggaacattg ccgccaaggg tacggtgctg ctgaagaata ccggctctct acccctgaac      1260
      aagccaaagt tcgtggccgt catcggcgag gatgctgggt cgagccccaa cgggcccaac      1320
      ggctgcagcg accgcggctg taacgaaggc acgctcgcca tgggctgggg atccggcaca      1380
      gccaactatc cgtacctcgt ttcccccgac gccgcgctcc aggcccgggc catccaggac      1440
      ggcacgaggt acgagagcgt cctgtccaac tacgccgagg aaaagacaaa ggctctggtc      1500
      tcgcaggcca atgcaaccgc catcgtcttc gtcaatgccg actcaggcga gggctacatc      1560
      aacgtggacg gtaacgaggg cgaccgtaag aacctgactc tctggaacaa cggtgatact      1620
      ctggtcaaga acgtctcgag ctggtgcagc aacaccatcg tcgtcatcca ctcggtcggc      1680
      ccggtcctcc tgaccgattg gtacgacaac cccaacatca cggccattct ctgggctggt      1740
      cttccgggcc aggagtcggg caactccatc accgacgtgc tttacggcaa ggtcaacccc      1800
      gccgcccgct cgcccttcac ttggggcaag acccgcgaaa gctatggcgc ggacgtcctg      1860
      tacaagccga ataatggcaa tggtgcgccc aacaggact tcaccgaggg cgtcttcatc       1920
      gactaccgct acttcgacaa ggttgacgat gactcggtca tctacgagtt cggccacggc      1980
      ctgagctaca ccaccttcga gtacagcaac atccgcgtcg tcaagtccaa cgtcagcgag      2040
      taccggccca cgacgggcac cacggcccag cccccgacgt tggcaacttt ctccaccgac      2100
      ctcgaggact atctcttccc caaggacgag ttcccctaca tctaccagta catctacccg      2160
      tacctcaaca cgaccgaccc ccggagggcc tcggccgatc cccactacgg ccagaccgcc      2220
      gaggagttcc tcccgcccca cgccaccgat gacgaccccc agccgctcct ccggtcctcg      2280
      ggcggaaact cccccggcgg caaccgccag ctgtacgaca ttgtctacac aatcacggcc      2340
      gacatcacga atacgggctc cgttgtaggc gaggaggtac cgcagctcta cgtctcgctg      2400
      ggcggtcccg aggatcccaa ggtgcagctg cgcgactttg acaggatgcg gatcgaaccc      2460
      ggcgagacga ggcagttcac cggccgcctg acgcgcagag atctgagcaa ctgggacgtc      2520
      acggtgcagg actgggtcat cagcaggtat cccaagacgg catatgttgg gaggagcagc      2580
      cggaagttgg atctcaagat tgagcttcct tga                                   2613
SEQ ID NO: 5 C1 Variant 3 Polypeptide Sequence
      MKAAALSCLF GSTLAVAGAI ESRKVHQKPL ARSEPFYPSP WMNPNADGWA EAYAQAKSFV        60
      SQMTLLEKVN LTTGVGWGAE QCVGQVGAIP RLGLRSLCMH DSPLGIRGAD YNSAFPSGQT       120
      VAATWDRGLM YRRGYAMGQE AKGKGINVLL GPVAGPLGRM PEGGRNWEGF APDPVLTGIG       180
      MSETIKGIQD AGVIACAKHF IGNEQEHFRQ VPEAQGYGYN ISETLSSNID DKTMHELYLW       240
      PFADAVRAGV GSVMCSYQQV NNSYACQNSK LLNDLLKNEL GFQGFVMSDW WAQHTGAASA       300
      VAGLDMSMPG DTQFNTGVSF WGANLTLAVL NGTVPAYRLD DMAMRIMAAL FKVTKTTDLE       360
      PINFSFWTLD TYGPIHWAAK QGYQEINSHV DVRADHGNLI RNIAAKGTVL LKNTGSLPLN       420
      KPKFVAVIGE DAGSSPNGPN GCSDRGCNEG TLAMGWGSGT ANYPYLVSPD AALQARAIQD       480
      GTRYESVLSN YAEEKTKALV SQANATAIVF VNADSGEGYI NVDGNEGDRK NLTLWNNGDT       540
      LVKNVSSWCS NTIVVIHSVG PVLLTDWYDN PNITAILWAG LPGQESGNSI TDVLYGKVNP       600
      AARSPFTWGK TRESYGADVL YKPNNGNGAP QQDFTEGVFI DYRYFDKVDD DSVIYEFGHG       660
      LSYTTFEYSN IRVVKSNVSE YRPTTGTTAQ APTFGNFSTD LEDYLFPKDE FPYIYQYIYP       720
      YLNTTDPRRA SADPHYGQTA EEFLPPHATD DDPQPLLRSS GGNSPGGNRQ LYDIVYTITA       780
```

```
         DITNTGSVVG EEVPQLYVSL GGPEDPKVQL RDFDRMRIEP GETRQFTGRL TRRDLSNWDV       840

TVQDWVISRY PKTAYVGRSS RKLDLKIELP                                       870

SEQ ID NO: 6 C1 Variant 269 cDNA Sequence
         atgaaggctg ctgcgctttc ctgcctcttc ggcagtaccc ttgccgttgc aggcgccatt        60
gaatcgagaa aggttcacca gaagcccctc gcgagatctg aacctttta cccgtcgcca       120 tggatgaatc ccaacgccga cggctgggcg gaggcctatg cccaggccaa gtcctttgtc       180
tcccaaatga ctctgctaga aaggtcaac ttgaccacgg agtcggctg ggggctgag         240 cagtgcgtcg gccaagtggg cgcgatccct cgccttggac ttcgcagtct gtgcatgcat       300
gactcccctc tcggcatccg aggagccgac tacaactcag cgttcccctc tggccagacc       360
gttgctgcta cctgggatcg cggtctgatg taccgtcgcg gctacgcaat gggccaggag       420
gccaaaggca agggcatcaa tgtccttctc ggaccagtcg ccggccccct tggccgcatg       480
cccgagggcg tcgtaactg ggaaggcttc gctccggatc ccgtccttac cggcatcggc        540
atgtccgaga cgatcaaggg cattcaggat gctggcgtca tcgcttgtgc gaagcacttt       600
attggaaacg agcaggagca cttcagacag gtgccagaag cccagggata cggttacaac       660
atcagcgaaa ccctctcctc caacattgac gacaagacca tgcacgagct ctacctttgg       720
ccgtttgccg atgccgtccg ggccggcgtc ggctctgtca tgtgctcgta caaccaggtc       780
aacaactcgt acgcctgcca gaactcgaag ctgctgaacg acctcctcaa gaacgagctt       840
gggtttcagg gcttcgtcat gagcgactgg tgggcacagc acactggcgc agcaagcgcc       900
gtggctggtc tcgatatgtc catgccgggc gacaccatgt tcaacactgg cgtcagtttc       960
tggggcgcca atctcaccct cgccgtcctc aacggcacag tccctgccta ccgtctcgac      1020
gacatggcca tgcgcatcat ggccgccctc ttcaaggtca ccaagaccac cgacctggaa      1080
ccgatcaact tctccttctg gacccgcgac acttatggcc cgatccactg ggccgccaag      1140
cagggctacc aggagattaa ttcccacgtt gacgtccgcg ccgaccacgg caacctcatc      1200
cggaacattg ccgccaaggg tacggtgctg ctgaagaata ccggctctct accccctgaac      1260 aagccaaagt cgtggccgt catcggcgag gatgctgggc gagccccaa cgggcccaac       1320 ggctgcagcg accgcggctg taacgaaggc acgctcgcca tgggctgggg atccggcaca      1380
gccaactatc cgtacctcgt tttcccccgac gccgcgctcc agttgcgggc catccaggac     1440
ggcacgaggt acgagagcgt cctgtccaac tacgccgagg aaaatacaaa ggctctggtc      1500
tcgcaggcca atgcaaccgc catcgtcttc gtcaatgccg actcaggcga gggctacatc     1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaacccc      1800
gccgcccgct cgcccttcac ttggggcaag accgcgaaa gctatggcgc ggacgtcctg       1860
tacaagccga ataatggcaa ttgggcgccc caacaggact tcaccgaggg cgtcttcatc      1920
gactaccgct acttcgacaa ggttgacgat gactcggtca tctacgagtt cggccacggc      1980
ctgagctaca ccaccttcga gtacagcaac atccgcgtcg tcaagtccaa cgtcagcgag      2040
taccggccca cgacgggcac cacggcccag ccccgacgt ttggcaactt ctccaccgac       2100
ctcgaggact atctcttccc caaggacgag ttccctaca tctaccagta catctacccg        2160
tacctcaaca cgaccgaccc ccgagggcc tcggccgatc cccactacgg ccagaccgcc       2220
gaggagttcc tcccgccca cgccaccgat gacgacccccc agccgctcct ccggtcctcg      2280
```

```
                ggcggaaact ccccoggcgg caaccgccag ctgtacgaca ttgtctacac aatcacggcc    2340
                gacatcacga atacgggctc cgttgtaggc gaggaggtac cgcagctcta cgtctcgctg    2400
                ggcggtcccg aggatcccaa ggtgcagctg cgcgactttg acaggatgcg gatcgaaccc    2460
                ggcgagacga ggcagttcac cggccgcctg acgcgcgaga tctgagcaa  ctgggacgtc    2520
                acggtgcagg actgggtcat cagcaggtat cccaagacgg catatgttgg gaggagcagc    2580
                cggaagttgg atctcaagat tgagcttcct tga                                  2613
SEQ ID NO: 7 C1 Variant 269 Polypeptide Sequence
        MKAAALSCLF GSTLAVAGAI ESRKVHQKPL ARSEPFYPSP WMNPNADGWA EAYAQAKSFV              60
        SQMTLLEKVN LTTGVGWGAE QCVGQVGAIP RLGLRSLCMH DSPLGIRGAD YNSAFPSGQT             120
        VAATWDRGLM YRRGYAMGQE AKGKGINVLL GPVAGPLGRM PEGGRNWEGF APDPVLTGIG             180
        MSETIKGIQD AGVIACAKHF IGNEQEHFRQ VPEAQGYGYN ISETLSSNID DKTMHELYLW             240
        PFADAVRAGV GSVMCSYNQV NNSYACQNSK LLNDLLKNEL GFQGFVMSDW WAQHTGAASA             300
        VAGLDMSMPG DTMFNTGVSF WGANLTLAVL NGTVPAYRLD DMAMRIMAAL FKVTKTTDLE             360
        PINFSFWTRD TYGPIHWAAK QGYQEINSHV DVRADHGNLI RNIAAKGTVL LKNTGSLPLN             420
        KPKFVAVIGE DAGPSPNGPN GCSDRGCNEG TLAMGWGSGT ANYPYLVSPD AALQLRAIQD             480
        GTRYESVLSN YAEENTKALV SQANATAIVF VNADSGEGYI NVDGNEGDRK NLTLWNNGDT             540
        LVKNVSSWCS NTIVVIHSVG PVLLTDWYDN PNITAILWAG LPGQESGNSI TDVLYGKVNP             600
        AARSPFTWGK TRESYGADVL YKPNNGNWAP QQDFTEGVFI DYRYFDKVDD DSVIYEFGHG             660
        LSYTTFEYSN IRVVKSNVSE YRPTTGTTAQ APTFGNFSTD LEDYLFPKDE FPYIYQYIYP             720
        YLNTTDPRRA SADPHYGQTA EEFLPPHATD DDPQPLLRSS GGNSPGGNRQ LYDIVYTITA             780
        DITNTGSVVG EEVPQLYVSL GGPEDPKVQL RDFDRMRIEP GETRQFTGRL TRRDLSNWDV             840
        TVQDWVISRY PKTAYVGRSS RKLDLKIELP                                              870
SEQ ID NO: 8 C1 Variant 481 cDNA Sequence
                atgaaggctg ctgcgctttc tgcctcttc  ggcagtaccc ttgccgttgc aggcgccatt      60
                gaatcgagaa aggttcacca gaagcccctc gcgagatctg aacctttta  cccgtcgcca     120
                tggatgaatc ccaacgccga cggctgggcg gaggcctatg cccaggccaa gtcctttgtc     180
                tcccaaatga ctctgctaga gaaggtcaac ttgaccacgg gagtcggctg ggggggctgag    240
                cagtgcgtcg gccaagtggg cgcgatccct cgccttggac ttcgcagtct gtgcatgcat    300
                gactcccctc tcggcatccg aggagccgac tacaactcag cgttcccctc tggccagacc    360
                gttgctgcta cctgggatcg cggtctgatg taccgtcgcg gctacgcaat gggccaggag    420
                gccaaaggca agggcatcaa tgtccttctc ggaccagtcg ccggccccct tggccgcatg    480
                cccgagggcg gtcgtaactg ggaaggcttc gctccggatc ccgtccttac cggcatcggc    540
                atgtccgaga cgatcaaggg cattcaggat gctggcgtca tcgcttgtgc gaagcacttt    600
                attggaaacg agcaggagca cttcagacag gtgccagaag cccagggata cggttacaac    660
                atcagcgaaa ccctctcctc caacattgac gacaagacca tgcacgagct ctacctttgg    720
                ccgtttgccg atgccgtccg ggccggcgtc ggctctgtca tgtgctcgta caaccaggtc    780
                aacaactcgt acgcctgcca gaactcgaag ctgctgaacg acctcctcaa gaacgagctt    840
                gggtttcagg gcttcgtcat gagcgactgg tgggcacagc acactggcgc agcaagcgcc    900
                gtggctggtc tcgatatgtc catgccgggc gacaccatgt tcaacactgg cgtcagtttc    960
                tggggcgcca atctcaccct cgccgtcctc aacggcacag tccctgccta ccgtctcgac   1020
                gacatggcca tgcgcatcat ggccgccctc ttcaaggtca ccaagaccac cgacctggaa   1080
```

```
ccgatcaact tctccttctg gacccgcgac acttatggcc cgatccactg ggccgccaag      1140
cagggctacc aggagattaa ttcccacgtt gacgtccgcg ccgaccacgg caacctcatc      1200
cggaacattg ccgccaaggg tacggtgctg ctgaagaata ccggctctct acccctgaac      1260
aagccaaagt tcgtggccgt catcgcgag gatgctgggc gagccccaa cgggcccaac       1320 ggctgcagcg accgcggctg taacgaaggc acgctcgcca tgggctgggg atccggcaca      1380
gccaactatc cgtacctcgt tttccccgac gccgcgctcc agttgcgggc catccaggac      1440
ggcacgaggt acgagagcgt cctgtccaac tacgccgagg aaaatacaaa ggctctggtc      1500
tcgcaggcca atgcaaccgc catcgtcttc gtcaatgccg actcaggcga gggctacatc      1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaacccc      1800
gccgcccgct cgcccttcac ttggggcaag acccgcgaaa gctatggcgc ggacgtcctg      1860
tacaagccga taatggcaa ttgggcgccc aacaggact tcaccgaggg cgtcttcatc        1920
gactaccgct acttcgacaa ggttgacgat gactcggtca tctacgagtt cggccacggc      1980
ctgagctaca ccaccttcga gtacagcaac atccgcgtcg tcaagtccaa cgtcagcgag      2040
taccggccca cgacgggcac cacgattcag gccccgacgt ttggcaactt ctccaccgac      2100
ctcgaggact atctcttccc caaggacgag ttcccctaca tcccgcagta catctacccg      2160
tacctcaaca cgaccgaccc ccggagggcc tcggccgatc ccactacgg ccagaccgcc       2220 gaggagttcc tcccgcccca cgccaccgat gacgaccccc agccgctcct ccggtcctcg      2280
ggcggaaact cccccggcgg caaccgccag ctgtacgaca ttgtctacac aatcacggcc      2340
gacatcacga atacgggctc cgttgtaggc gaggaggtac cgcagctcta cgtctcgctg      2400
ggcggtcccg aggatcccaa ggtgcagctg cgcgactttg acaggatgcg gatcgaaccc      2460
ggcgagacga ggcagttcac cggccgcctg acgcgcagag atctgagcaa ctgggacgtc      2520
acggtgcagg actgggtcat cagcaggtat cccaagacgg catatgttgg gaggagcagc      2580
cggaagttgg atctcaagat tgagcttcct tga                                   2613
```

SEQ ID NO: 9 C1 Variant 481 Polypeptide Sequence
```
MKAAALSCLF GSTLAVAGAI ESRKVHQKPL ARSEPFYPSP WMNPNADGWA EAYAQAKSFV       60
SQMTLLEKVN LTTGVGWGAE QCVGQVGAIP RLGLRSLCMH DSPLGIRGAD YNSAFPSGQT      120
VAATWDRGLM YRRGYAMGQE AKGKGINVLL GPVAGPLGRM PEGGRNWEGF APDPVLTGIG      180
MSETIKGIQD AGVIACAKHF IGNEQEHFRQ VPEAQGYGYN ISETLSSNID DKTMHELYLW      240
PFADAVRAGV GSVMCSYNQV NNSYACQNSK LLNDLLKNEL GFQGFVMSDW WAQHTGAASA      300
VAGLDMSMPG DTMFNTGVSF WGANLTLAVL NGTVPAYRLD DMAMRIMAAL FKVTKTTDLE      360
PINFSFWTRD TYGPIHWAAK QGYQEINSHV DVRADHGNLI RNIAAKGTVL LKNTGSLPLN      420
KPKFVAVIGE DAGPSPNGPN GCSDRGCNEG TLAMGWGSGT ANYPYLVSPD AALQLRAIQD      480
GTRYESVLSN YAEENTKALV SQANATAIVF VNADSGEGYI NVDGNEGDRK NLTLWNNGDT      540
LVKNVSSWCS NTIVVIHSVG PVLLTDWYDN PNITAILWAG LPGQESGNSI TDVLYGKVNP      600
AARSPFTWGK TRESYGADVL YKPNNGNWAP QQDFTEGVFI DYRYFDKVDD DSVIYEFGHG      660
LSYTTFEYSN IRVVKSNVSE YRPTTGTTIQ APTFGNFSTD LEDYLFPKDE FPYIPQYIYP      720
YLNTTDPRRA SADPHYGQTA EEFLPPHATD DDPQPLLRSS GGNSPGGNRQ LYDIVYTITA      780
```

DITNTGSVVG EEVPQLYVSL GGPEDPKVQL RDFDRMRIEP GETRQFTGRL TRRDLSNWDV       840

TVQDWVISRY PKTAYVGRSS RKLDLKIELP                                       870

SEQ ID NO: 10 C1 Variant 482 cDNA Sequence
       atgaaggctg ctgcgctttc ctgcctcttc ggcagtaccc ttgccgttgc aggcgccatt             60
gaatcgagaa aggttcacca gaagcccctc gcgagatctg aaccttttta cccgtcgcca            120
tggatgaatc caacgccga cggctgggcg gaggcctatg cccaggccaa gtcctttgtc            180
tcccaaatga ctctgctaga aaggtcaac ttgaccacgg agtcggctg gggggctgag             240 cagtgcgtcg gccaagtggg cgcgatccct cgccttggac ttcgcagtct gtgcatgcat            300
gactcccctc tcggcatccg aggagccgac tacaactcag cgttcccctc tggccagacc            360
gttgctgcta cctgggatcg cggtctgatg taccgtcgcg gctacgcaat gggccaggag            420
gccaaaggca agggcatcaa tgtccttctc ggaccagtcg ccggccccct tggccgcatg            480
cccgagggcg tcgtaactg gaaggcttc gctccggatc ccgtccttac cggcatcggc             540
atgtccgaga cgatcaaggg cattcaggat gctggcgtca tcgcttgtgc gaagcacttt            600
attggaaacg agcaggagca cttcagacag gtgccagaag cccagggata cggttacaac            660
atcagcgaaa ccctctcctc aacattgac gacaagacca tgcacgagct ctacctttgg             720
ccgtttgccg atgccgtccg ggccggcgtc ggctctgtca tgtgctcgta caaccaggtc            780
aacaactcgt acgcctgcca gaactcgaag ctgctgaacg acctcctcaa gaacgagctt            840
gggtttcagg gcttcgtcat gagcgactgg tgggcacagc acactggcgc agcaagcgcc            900
gtggctggtc tcgatatgtc catgccgggc gacaccatgt caacactgg cgtcagtttc             960 tggggcgcca atctcaccct cgccgtcctc aacggcacag tccctgccta ccgtctcgac           1020
gacatggcca tgcgcatcat ggccgccctc ttcaaggtca ccaagaccac cgacctggaa           1080
ccgatcaact tctccttctg gacccgcgac acttatggcc cgatccactg ggccgccaag           1140
cagggctacc aggagattaa ttcccacgtt gacgtccgcg ccgaccacgg caacctcatc           1200
cggaacattg ccgccaaggg tacggtgctg ctgaagaata ccggctctct acccctgaac           1260
aagccaaagt cgtggccgt catcggcgaa gatgctgggc gagccccaa cgggcccaac             1320 ggctgcagcg accgcggctg taacgaaggc acgctcgcca tgggctgggg atccggcaca           1380
gccaactatc cgtacctcgt tttccccgac gccgcgctcc agttgcgggc catccaggac           1440
ggcacgaggt acgagagcgt cctgtccaac tacgccgagg aaaatacaaa ggctctggtc           1500
tcgcaggcca atgcaaccgc catcgtcttc gtcaatgccg actcaggcga gggctacatc           1560
aacgtggacg gtaacgaggg cgaccgtaag aacctgactc tctggaacaa cggtgatact           1620
ctggtcaaga acgtctcgag ctggtgcagc aacaccatcg tcgtcatcca ctcggtcggc           1680
ccggtcctcc tgaccgattg gtacgacaac cccaacatca cggccattct ctgggctggt           1740
cttccgggcc aggagtcggg caactccatc accgacgtgc tttacggcaa ggtcaacccc           1800
gccgcccgct cgcccttcac ttggggcaag accgcgaaa gctatggcgc ggacgtcctg           1860
tacaagccga ataatggcaa ttgggcgccc caacaggact tcaccgaggg cgtcttcatc           1920
gactaccgct acttcgacaa ggttgacgat gactcggtca tctacgagtt cggccacggc           1980
ctgagctaca ccaccttcga gtacagcaac atccgcgtcg tcaagtccaa cgtcagcgag           2040
taccggccca cgacgggcac cacggcccag gccccgacgt tggcaacatt ctccaccgac           2100
ctcgaggact atctcttccc caaggacgag ttccctaca tcccgcagta catctaccca            2160
tacctcaaca cgaccgaccc ccgagggcc tcggccgatc cccactacgg ccagaccgcc             2220
gaggagttcc tcccgcccca cgccaccgat gacgaccccc agccgctcct ccggtcctcg           2280

```
          ggcggaaact cccccggcgg caaccgccag ctgtacgaca ttgtctacac aatcacggcc    2340
          gacatcacga atacgggctc cgttgtaggc gaggaggtac cgcagctcta cgtctcgctg    2400
          ggcggtcccg aggatcccaa ggtgcagctg cgcgactttg acaggatgcg gatcgaaccc    2460
          ggcgagaaaa ggcagttcac cggccgcctg acgcgcgaga tctgagcaa  ctgggacgtc    2520
          acggtgcagg actgggtcat cagcaggtat cccaagacgg catatgttgg gaggagcagc    2580
          cggaagttgg atctcaagat tgagcttcct tga                                 2613
SEQ ID NO: 11 C1 Variant 482 polypeptide sequence
          MKAAALSCLF GSTLAVAGAI ESRKVHQKPL ARSEPFYPSP WMNPNADGWA EAYAQAKSFV     60
          SQMTLLEKVN LTTGVGWGAE QCVGQVGAIP RLGLRSLCMH DSPLGIRGAD YNSAFPSGQT    120
          VAATWDRGLM YRRGYAMGQE AKGKGINVLL GPVAGPLGRM PEGGRNWEGF APDPVLTGIG    180
          MSETIKGIQD AGVIACAKHF IGNEQEHFRQ VPEAQGYGYN ISETLSSNID DKTMHELYLW    240
          PFADAVRAGV GSVMCSYNQV NNSYACQNSK LLNDLLKNEL GFQGFVMSDW WAQHTGAASA    300
          VAGLDMSMPG DTMFNTGVSF WGANLTLAVL NGTVPAYRLD DMAMRIMAAL FKVTKTTDLE    360
          PINFSFWTRD TYGPIHWAAK QGYQEINSHV DVRADHGNLI RNIAAKGTVL LKNTGSLPLN    420
          KPKFVAVIGE DAGPSPNGPN GCSDRGCNEG TLAMGWGSGT ANYPYLVSPD AALQLRAIQD    480
          GTRYESVLSN YAEENTKALV SQANATAIVF VNADSGEGYI NVDGNEGDRK NLTLWNNGDT    540
          LVKNVSSWCS NTIVVIHSVG PVLLTDWYDN PNITAILWAG LPGQESGNSI TDVLYGKVNP    600
          AARSPFTWGK TRESYGADVL YKPNNGNWAP QQDFTEGVFI DYRYFDKVDD DSVIYEFGHG    660
          LSYTTFEYSN IRVVKSNVSE YRPTTGTTAQ APTFGNFSTD LEDYLFPKDE FPYIPQYIYP    720
          YLNTTDPRRA SADPHYGQTA EEFLPPHATD DDPQPLLRSS GGNSPGGNRQ LYDIVYTITA    780
          DITNTGSVVG EEVPQLYVSL GGPEDPKVQL RDFDRMRIEP GEKRQFTGRL TRRDLSNWDV    840
          TVQDWVISRY PKTAYVGRSS RKLDLKIELP                                     870
SEQ ID NO: 12 C1 Variant 664 cDNA Sequence
          atgaaggctg ctgcgctttc ctgcctcttc ggcagtaccc ttgccgttgc aggcgccatt     60
          gaatcgagaa aggttcacca gaagcccctc gcgagatctg aacctttta cccgtcgcca    120
          tggatgaatc ccaacgccga cggctgggcg gaggcctatg cccaggccaa gtcctttgtc    180
          tcccaaatga ctctgctaga gaaggtcaac ttgaccacgg gagtcggctg ggggctgag    240
          cagtgcgtcg gccaagtggg cgcgatccct cgccttggac ttcgcagtct gtgcatgcat    300
          gactcccctc tcggcgtgcg aggagccgac tacaactcag cgttcccctc tggccagacc    360
          gttgctgcta cctgggatcg cggtctgatg taccgtcgcg gctacgcaat gggccaggag    420
          gccaaaggca agggcatcaa tgtccttctc ggaccagtcg ccggcccct  tggccgcatg    480
          cccgagggcg gtcgtaactg ggaaggcttc gctccggatc ccgtccttac cggcatcggc    540
          atgtccgaga cgatcaaggg cattcaggat gctggcgtca tcgcttgtgc aagcactt     600
          attggaaacg agcaggagca cttcagacag gtgccagaag cccagggata cggttacaac    660
          atcagcgaaa ccctctcctc caacattgac gacaagacca tgcacgagct ctacctttgg    720
          ccgtttgccg atgccgtccg gccggcgtc  ggctctgtca tgtgctcgta caaccagggc    780
          aacaactcgt acgcctgcca gaactcgaag ctgctgaacg acctcctcaa gaacgagctt    840
          gggtttcagg gcttcgtcat gagcgactgg tgggcacagc acactggcgc agcaagcgcc    900
          gtggctggtc tcgatatgtc catgccgggc gacaccatgc tgaacactgg cgtcagtttc    960
          tggggcgcca atctcaccct cgccgtcctc aacggcacag tccctgccta ccgtctcgac   1020
          gacatggcca tgcgcatcat ggccgccctc ttcaaggtca ccaagaccac cgacctggaa   1080
```

```
ccgatcaact tctccttctg gacccgcgac acttatggcc cgatccactg ggccgccaag      1140
cagggctacc aggagattaa ttcccacgtt gacgtccgcg ccgaccacgg caacctcatc      1200
aagccaaagt tcgtggccgt catcggcgag gatgctgggc cgagccccaa cgggcccaac      1320
ggctgcagcg accgcggctg taacgaaggc acgctcgcca tgggctgggg atccggcaca      1380
gccaactatc cgtacctcgt ttcccccgac gccgcgctcc aggcgcgggc catccaggac      1440
ggcacgaggt acgagagcgt cctgtccaac tacgccgagg aaaatacaaa ggctctggtc      1500
tcgcaggcca atgcaaccgc catcgtcttc gtcaatgccg actcaggcga gggctacatc      1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaacccc      1800
gccgcccgct cgcccttcac ttggggcaag acccgcgaaa gctatggcgc ggacgtcctg      1860
tacaagccga ataatggcaa ttgggcgccc caacaggact tcaccgaggg cgtcttcatc      1920
gactaccgct acttcgacaa ggttgacgat gactcggtca tctacgagtt cggccacggc      1980
ctgagctaca ccaccttcga gtacagcaac atccgcgtcg tcaagtccaa cgtcagcgag      2040
taccggccca cgacgggcac cacgattcag gccccgacgt ttggcaactt ctcaaccgac      2100
ctcgaggact atctcttccc caaggacgag ttcccctaca tcccgcagta catctacccg      2160
tacctcaaca cgaccgaccc ccggagggcc tcgggcgatc cccactacgg ccagaccgcc      2220
gaggagttcc tcccgcccca cgccaccgat gacgaccccc agccgctcct ccggtcctcg      2280
ggcggaaact cccccggcgg caaccgccag ctgtacgaca ttgtctacac aatcacggcc      2340
gacatcacga atacgggctc cgttgtaggc gaggaggtac cgcagctcta cgtctcgctg      2400
ggcggtcccg aggatcccaa ggtgcagctg cgcgactttg acaggatgcg gatcgaaccc      2460
ggcgagacga ggcagttcac cggccgcctg acgcgcgaga tctgagcaa ctgggacgtc       2520
acggtgcagg actgggtcat cagcaggtat cccaagacgg catatgttgg gaggagcagc      2580
cggaagttgg atctcaagat tgagcttcct tga                                   2613
```

SEQ ID NO: 13 C1 Variant 664 polypeptide sequence

```
MKAAALSCLF GSTLAVAGAI ESRKVHQKPL ARSEPFYPSP WMNPNADGWA EAYAQAKSFV       60
SQMTLLEKVN LTTGVGWGAE QCVGQVGAIP RLGLRSLCMH DSPLGVRGAD YNSAFPSGQT      120
VAATWDRGLM YRRGYAMGQE AKGKGINVLL GPVAGPLGRM PEGGRNWEGF APDPVLTGIG      180
MSETIKGIQD AGVIACAKHF IGNEQEHFRQ VPEAQGYGYN ISETLSSNID DKTMHELYLW      240
PFADAVRAGV GSVMCSYNQG NNSYACQNSK LLNDLLKNEL GFQGFVMSDW WAQHTGAASA      300
VAGLDMSMPG DTMLNTGVSF WGANLTLAVL NGTVPAYRLD DMAMRIMAAL FKVTKTTDLE      360
PINFSFWTRD TYGPIHWAAK QGYQEINSHV DVRADHGNLI RNIAAKGTVL LKNTGSLPLN      420
KPKFVAVIGE DAGPSPNGPN GCSDRGCNEG TLAMGWGSGT ANYPYLVSPD AALQARAIQD      480
GTRYESVLSN YAEENTKALV SQANATAIVF VNADSGEGYI NVDGNEGDRK NLTLWNNGDT      540
LVKNVSSWCS NTIVVIHSVG PVLLTDWYDN PNITAILWAG LPGQESGNSI TDVLYGKVNP      600
AARSPFTWGK TRESYGADVL YKPNNGNWAP QQDFTEGVFI DYRYFDKVDD DSVIYEFGHG      660
LSYTTFEYSN IRVVKSNVSE YRPTTGTTIQ APTFGNFSTD LEDYLFPKDE FPYIPQYIYP      720
YLNTTDPRRA SGDPHYGQTA EEFLPPHATD DDPQPLLRSS GGNSPGGNRQ LYDIVYTITA      780
DITNTGSVVG EEVPQLYVSL GGPEDPKVQL RDFDRMRIEP GETRQFTGRL TRRDLSNWDV      840
TVQDWVISRY PKTAYVGRSS RKLDLKIELP                                       870
```

SEQ ID NO: 14 C1 Variant 647 cDNA Sequence

```
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccat tggctgggcg gaggcctatg cccaggccaa gtcctttgtc     180
tcccaaatga ctctgctaga aaggtcaac ttgaccacgg agtcggctg ggggctgag      240
cagtgcgtcg gccaagtggg cgcgatccct cgccttggac ttcgcagtct gtgcatgcat     300
gactcccctc tcggcatccg aggagccgac tacaactcag cgttcccctc tggccagacc     360
gttgctgcta cctgggatcg cggtctgatg taccgtcgcg gctacgcaat gggccaggag     420
gccaaaggca agggcatcaa tgtccttctc ggaccagtcg ccggccccct tggccgcatg     480
cccgagggcg gtcgtaactg ggaaggcttc gctccggatc ccgtccttac cggcatcggc     540
atgtccgaga cgatcaaggg cattcaggat gctggcgtca tcgcttgtgc gaagcacttt     600
attggaaacg agcaggagca cttcagacag gtgccagaag cccagggata cggttacaac     660
atcagcgaaa ccctctcctc caacattgac gacaagacca tgcacgagct ctacctttgg     720
ccgtttgccg atgccgtccg ggccggcgtc ggctctgtca tgtgctcgta caaccaggtc     780
aacaactcgt acgcctgcca gaactcgaag ctgctgaaca acctcctcaa gaacgagctt     840
gggtttcagg gcttcgtcat gagcgactgg tgggcacagc acactggcgc agcaagcgcc     900
gtggctggtc tcgatatgtc catgccgggc gacaccatgt caacactgg cgtcagtttc     960
tggggcgcca atctcaccct cgccgtcctc aacggcacag tccctgccta ccgtctcgac    1020
gacatgtgca tgcgcatcat ggccgccctc ttcaaggtca ccaagaccac cgacctggaa    1080
ccgatcaact tctccttctg gacccgcgac acttatggcc cgatccactg ggccgccaag    1140
cagggctacc aggagattaa ttcccacgtt gacgtccgcg ccgaccacgg caacctcatc    1200
cggaacattg ccgccaaggg tacggtgctg ctgaagaata ccggctctct acccctgaac    1260
aagccaaagt tcgtggccgt catcggcgag gatgctgggc cgagccccaa cgggcccaac    1320
ggctgcagcg accgcggctg taacgaaggc acgctcgcca tgggctgggg atccggcaca    1380
gccaactatc cgtacctcgt tttccccgac gccgcgctcc agttgcgggc catccaggac    1440
ggcacgaggt acgagagcgt cctgtccaac tacgccgagg aaaatacaaa ggctctggtc    1500
tcgcaggcca atgcaaccgc catcgtcttc gtcaatgccg actcaggcga gggctacatc    1560
aacgtggacg gtaacgaggc cgaccgtaag aacctgactc tctggaacaa cggtgatact    1620
ctggtcaaga acgtctcgag ctggtgcagc aacaccatcg tcgtcatcca ctcggtcggc    1680
ccggtcctcc tgaccgattg gtacgacaac cccaacatca cggccattct ctgggctggt    1740
cttccggggcc aggagtcggg caactccatc accgacgtgc tttacggcaa ggtcaaccc    1800
gccgcccgct cgccccttcac ttgggcaag acccgcgaaa gctatggcgc ggacgtcctg    1860
tacaagccga ataatggcaa ttgggcgccc caacaggact tcaccgaggg cgtcttcatc    1920
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
taccggccca cgacgggcaa aacgattcag gccccgacgt tggcaacttt ctccaccgac    2100
ctcgaggact atctcttccc caaggacgag ttcccctaca tcccgcagta catctacccg    2160
tacctcaaca cgaccgaccc ccggagggcc tcggccgatc cccactacgg ccagaccgcc    2220
gaggagttcc tcccgccca cgccaccgat gacgaccccc agccgctcct ccggtcctcg    2280
ggcggaaact cccccggcgg caaccgccag ctgtacgaca ttgtctacac aatcacggcc    2340
gacatcacga atacgggctc cgttgtaggc gaggaggtac cgcagctcta cgtctcgctg    2400
```

```
                ggcggtcccg aggatcccaa ggtgcagctg cgcgactttg acaggatgcg gatcgaaccc           2460
ggcgagacga ggcagttcac cggccgcctg acgcgcgaga tctgagcaa ctgggacgtc            2520 acggtgcagg actgggtcat cagcaggtat cccaagacgg catatgttgg gaggagcagc           2580
cggaagttgg atctcaagat tgagcttcct tga                                        2613

SEQ ID NO: 15 C1 Variant 647 polypeptide sequence
                MKAAALSCLF GSTLAVAGAI ESRKVHQKPL ARSEPFYPSP WMNPNAIGWA EAYAQAKSFV             60

SQMTLLEKVN LTTGVGWGAE QCVGQVGAIP RLGLRSLCMH DSPLGIRGAD YNSAFPSGQT            120

VAATWDRGLM YRRGYAMGQE AKGKGINVLL GPVAGPLGRM PEGGRNWEGF APDPVLTGIG            180

MSETIKGIQD AGVIACAKHF IGNEQEHFRQ VPEAQGYGYN ISETLSSNID DKTMHELYLW            240

PFADAVRAGV GSVMCSYNQV NNSYACQNSK LLNDLLKNEL GFQGFVMSDW WAQHTGAASA            300

VAGLDMSMPG DTMFNTGVSF WGANLTLAVL NGTVPAYRLD DMCMRIMAAL FKVTKTTDLE            360

PINFSFWTRD TYGPIHWAAK QGYQEINSHV DVRADHGNLI RNIAAKGTVL LKNTGSLPLN            420

KPKFVAVIGE DAGPSPNGPN GCSDRGCNEG TLAMGWGSGT ANYPYLVSPD AALQLRAIQD            480

GTRYESVLSN YAEENTKALV SQANATAIVF VNADSGEGYI NVDGNEGDRK NLTLWNNGDT            540

LVKNVSSWCS NTIVVIHSVG PVLLTDWYDN PNITAILWAG LPGQESGNSI TDVLYGKVNP            600

AARSPFTWGK TRESYGADVL YKPNNGNWAP QQDFTEGVFI DYRYFDKVDD DSVIYEFGHG            660

LSYTTFEYSN IRVVKSNVSE YRPTTGKTIQ APTFGNFSTD LEDYLFPKDE FPYIPQYIYP            720

YLNTTDPRRA SADPHYGQTA EEFLPPHATD DDPQPLLRSS GGNSPGGNRQ LYDIVYTITA            780

DITNTGSVVG EEVPQLYVSL GGPEDPKVQL RDFDRMRIEP GETRQFTGRL TRRDLSNWDV            840

TVQDWVISRY PKTAYVGRSS RKLDLKIELP                                            870

SEQ ID NO: 16 C1 Variant 871 cDNA Sequence
                atgaaggctg ctgcgctttc ctgcctcttc ggcagtaccc ttgccgttgc aggcgccatt             60
gaatcgagaa aggttcacca gaagcccctc gcgagatctg aaccttttta cccgtcgcca            120
tggatgaatc ccaacgccat cggctgggcg gaggcctatg cccaggccaa gtcctttgtc            180
tcccaaatga ctctgctaga aaaggtcaac ttgaccacgg gagtcggctg ggggagggag            240
cagtgcgtcg gcaacgtggg cgcgatccct cgccttggac ttcgcagtct gtgcatgcat            300
gactcccctc tcggcgtgcg aggaaccgac tacaactcag cgttcccctc tggccagacc            360
gttgctgcta cctgggatcg cggtctgatg taccgtcgcg gctacgcaat gggccaggag            420
gccaaaggca agggcatcaa tgtccttctc ggaccagtcg ccggccccct tggccgcatg            480
cccgagggcg gtcgtaactg gaaggcttc gctccggatc ccgtccttac cggcatcggc            540
atgtccgaga cgatcaaggg cattcaggat gctggcgtca tcgcttgtgc gaagcacttt            600
attggaaacg agcaggagca cttcagacag gtgccagaag cccagggata cggttacaac            660
atcagcgaaa ccctctcctc aacattgac gacaagacca tgcacgagct ctacctttgg            720
ccgtttgccg atgccgtccg ggccggcgtc ggctctgtca tgtgctcgta caaccagggc            780
aacaactcgt acgcctgcca gaactcgaag ctgctgaacg acctcctcaa gaacgagctt            840
gggtttcagg gcttcgtcat gagcgactgg tgggcacagc acactggcgc agcaagcgcc            900 gtgctggtc tcgatatgtc catgccgggc gacaccatgt tcaacactgg cgtcagtttc            960
tggggcgcca atctcaccct cgccgtcctc aacggcacag tccctgccta ccgtctcgac           1020
gacatgtgca tgcgcatcat ggccgccctc ttcaaggtca ccaagaccac cgacctggaa           1080
ccgatcaact tctccttctg gacccgcgac acttatggcc cgatccactg ggccgccaag           1140
cagggctacc aggagattaa ttcccacgtt gacgtccgcg ccgaccacgg caacctcatc           1200
cggaacattg ccgccaaggg tacggtgctg ctgaagaata ccggctctct acccctgaac           1260
```

```
aagccaaagt tcgtggccgt catcggcgag gatgctgggc cgagccccaa cgggcccaac        1320
ggctgcagcg accgcggctg taacgaaggc acgctcgcca tgggctgggg atccggcaca        1380
gccaactatc cgtacctcgt ttcccccgac gccgcgctcc aggcgcgggc catccaggac        1440
ggcacgaggt acgagagcgt cctgtccaac tacgccgagg aaaatacaaa ggctctggtc        1500
tcgcaggcca atgcaaccgc catcgtcttc gtcaatgccg actcaggcga gggctacatc        1560
aacgtggacg gtaacgaggg cgaccgtaag aacctgactc tctggaacaa cggtgatact        1620
ctggtcaaga acgtctcgag ctggtgcagc aacaccatcg tcgtcatcca ctcggtcggc        1680
ccggtcctcc tgaccgattg gtacgacaac cccaacatca cggccattct ctgggctggt        1740
cttccgggcc aggagtcggg caactccatc accgacgtgc tttacggcaa ggtcaacccc        1800
gccgcccgct cgcccttcac ttggggcaag acccgcgaaa gctatggcgc ggacgtcctg        1860
tacaagccga ataatggcaa ttgggcgccc caacaggact tcaccgaggg cgtcttcatc        1920
gactaccgct acttcgacaa ggttgacgat gactcggtca tctacgagtt cggccacggc        1980
ctgagctaca ccaccttcga gtacagcaac atcgcgtcg tcaagtccaa cgtcagcgag         2040
taccggccca cgacgggcac cacgattcag gccccgacgt ttggcaactt ctccaccgac        2100
ctcgaggact atctcttccc caaggacgag ttcccctaca tcccgcagta catctacccg        2160
tacctcaaca cgaccgaccc ccgagggccc tcgggcgatc ccactacgg ccagaccgcc         2220 gaggagttcc tcccgcccca cgccaccgat gacgacccc agccgctcct ccggtcctcg         2280
ggcggaaact cccccggcgg caaccgccag ctgtacgaca ttgtctacac aatcacggcc        2340
gacatcacga atacgggctc cgttgtaggc gaggaggtac cgcagctcta cgtctcgctg        2400
ggcggtcccg aggatcccaa ggtgcagctg cgcgactttg acaggatgcg gatcgaaccc        2460
ggcgagacga ggcagttcac cggccgcctg acgcgcgagg atctgagcaa ctgggacgtc        2520
acggtgcagg actgggtcat cagcaggtat cccaagacgg catatgttgg gaggagcagc        2580
cggaagttgg atctcaagat tgagcttcct tga                                     2613
```

SEQ ID NO: 17 C1 Variant 871 polypeptide sequence
```
MKAAALSCLF GSTLAVAGAI ESRKVHQKPL ARSEPFYPSP WMNPNAIGWA EAYAQAKSFV         60

SQMTLLEKVN LTTGVGWGEE QCVGNVGAIP RLGLRSLCMH DSPLGVRGTD YNSAFPSGQT        120

VAATWDRGLM YRRGYAMGQE AKGKGINVLL GPVAGPLGRM PEGGRNWEGF APDPVLTGIG        180

MSETIKGIQD AGVIACAKHF IGNEQEHFRQ VPEAQGYGYN ISETLSSNID DKTMHELYLW        240

PFADAVRAGV GSVMCSYNQG NNSYACQNSK LLNDLLKNEL GFQGFVMSDW WAQHTGAASA        300

VAGLDMSMPG DTMVNTGVSF WGANLTLAVL NGTVPAYRLD DMCMRIMAAL FKVTKTTDLE        360

PINFSFWTRD TYGPIHWAAK QGYQEINSHV DVRADHGNLI RNIAAKGTVL LKNTGSLPLN        420

KPKFVAVIGE DAGPSPNGPN GCSDRGCNEG TLAMGWGSGT ANYPYLVSPD AALQARAIQD        480

GTRYESVLSN YAEENTKALV SQANATAIVF VNADSGEGYI NVDGNEGDRK NLTLWNNGDT        540

LVKNVSSWCS NTIVVIHSVG PVLLTDWYDN PNITAILWAG LPGQESGNSI TDVLYGKVNP        600

AARSPFTWGK TRESYGADVL YKPNNGNWAP QQDFTEGVFI DYRYFDKVDD DSVIYEFGHG        660

LSYTTFEYSN IRVVKSNVSE YRPTTGTTIQ APTFGNFSTD LEDYLFPKDE FPYIPQYIYP        720

YLNTTDPRRA SGDPHYGQTA EEFLPPHATD DDPQPLLRSS GGNSPGGNRQ LYDIVYTITA        780

DITNTGSVVG EEVPQLYVSL GGPEDPKVQL RDFDRMRIEP GETRQFTGRL TRRDLSNWDV        840

TVQDWVISRY PKTAYVGRSS RKLDLKIELP                                         870
```

SEQ ID NO: 18 C1 Variant 885 cDNA sequence

```
    atgaaggctg ctgcgctttc ctgcctcttc ggcagtaccc ttgccgttgc aggcgccatt      60
    gaatcgagaa aggttcacca gaagcccctc gcgagatctg aaccttttta cccgtcgcca     120
    tggatgaatc caacgccat cggctgggcg gaggcctatg cccaggccaa gtcctttgtc     180
    tcccaaatga ctctgctaga aaggtcaac ttgaccacgg gagtcggctg gggggctgag     240
    cagtgcgtcg gcaacgtggg cgcgatccct cgccttggac ttcgcagtct gtgcatgcat     300
    gactcccctc tcggcgtgcg aggaagcgac tacaactcag cgttcccctc tggccagacc     360
    gttgctgcta cctgggatcg cggtctgatg taccgtcgcg gctacgcaat gggccaggag     420
    gccaaaggca agggcatcaa tgtccttctc ggaccagtcg ccggccccct tggccgcatg     480
    cccgaggcg gtcgtaactg ggaaggcttc gctccggatc ccgtccttac cggcatcggc     540
    atgtccgaga cgatcaaggg cattcaggat gctggcgtca tcgcttgtgc gaagcacttt     600
    attggaaacg agcaggagca cttcagacag gtgccagaag cccagggata cggttacaac     660
    atcagcgaaa ccctctcctc caacattgac gacaagacca tgcacgagct ctacctttgg     720
    ccgtttgccg atgccgtccg ggccggcgtc ggctctgtca tgtgctcgta caaccagggc     780
    aacaactcgt acgcctgcca gaactcgaag ctgctgaacg acctcctcaa gaacgagctt     840
    gggtttcagg gcttcgtcat gagcgactgg tgggcacagc acactggcgc agcaagcgcc     900
    gtggctggtc tcgatatgtc catgccgggc gacaccatgt caacactgg cgtcagtttc     960
    tggggcgcca atctcaccct cgccgtcctc aacggcacag tccctgccta ccgtctcgac    1020
    gacatgtgca tgcgcatcat ggccgccctc ttcaaggtca ccaagaccac cgacctggaa    1080
    ccgatcaact tctccttctg gacccgcgac acttatggcc cgatccactg ggccgccaag    1140
    cagggctacc aggagattaa ttcccacgtt gacgtccgcg ccgaccacgg caacctcatc    1200
    cggaacattg ccgccaaggg tacggtgctg ctgaagaata ccggctctct accctgaac    1260
    aagccaaagt tcgtggccgt catcggcgag gatgctgggc gagccccaa cgggcccaac    1320
    ggctgcagcg accgcggctg taacgaaggc acgctcgcca tgggctgggg atccggcaca    1380
    gccaactatc cgtacctcgt tccccccgac gccgcgctcc aggcgcgggc catccaggac    1440
    ggcacgaggt acgagagcgt cctgtccaac tacgccgagg aaaatacaaa ggctctggtc    1500
    tcgcaggcca atgcaaccgc catcgtcttc gtcaatgccg actcaggcga gggctacatc    1560
    aacgtggacg gtaacgaggg cgaccgtaag aacctgactc tctggaacaa cggtgatact    1620
    ctggtcaaga acgtctcgag ctggtgcagc aacaccatcg tcgtcatcca ctcggtcggc    1680
    ccggtcctcc tgaccgattg gtacgacaac cccaacatca cggccattct ctgggctggt    1740
    cttccgggcc aggagtcggg caactccatc accgacgtgc tttacggcaa ggtcaacccc    1800
    gccgcccgct cgcccttcac ttggggcaag accgcgaaa gctatggcgc ggacgtcctg    1860
    tacaagccga ataatggcaa ttgggcgccc caacaggact tcaccgaggg cgtcttcatc    1920
    gactaccgct acttcgacaa ggttgacgat gactcggtca tctacgagtt cggccacggc    1980
    ctgagctaca ccaccttcga gtacagcaac atccgcgtcg tcaagtccaa cgtcagcgag    2040
    taccggccca cgacgggcac cacgattcag gccccgacgt ttggcaactt ctccaccgac    2100
    ctcgaggact atctcttccc caaggacgag ttccctaca tcccgcagta catctacccg    2160
    tacctcaaca cgaccgaccc ccgagggcc tcgggcgatc ccactacgg ccagaccgcc    2220
    gaggagttcc tcccgcccca cgccaccgat gacgaccccc agccgctcct ccgtcctcg    2280
    ggcggaaact cccccggcg caaccgccag ctgtacgaca ttgtctacac aatcacggcc    2340
    gacatcacga atacgggctc cgttgtaggc gaggaggtac cgcagctcta cgtctcgctg    2400
```

```
                  ggcggtcccg aggatcccaa ggtgcagctg cgcgactttg acaggatgcg gatcgaaccc    2460
ggcgagacga ggcagttcac cggccgcctg acgcgcgaga atctgagcaa ctgggacgtc    2520
acggtgcagg actgggtcat cagcaggtat cccaagacgg catatgttgg gaggagcagc    2580
cggaagttgg atctcaagat tgagcttcct tga                                  2613

SEQ ID NO: 19 C1 Variant 885 polypeptide sequence
                  MKAAALSCLF GSTLAVAGAI ESRKVHQKPL ARSEPFYPSP WMNPNAIGWA EAYAQAKSFV      60

SQMTLLEKVN LTTGVGWGAE QCVGNVGAIP RLGLRSLCMH DSPLGVRGSD YNSAFPSGQT     120

VAATWDRGLM YRRGYAMGQE AKGKGINVLL GPVAGPLGRM PEGGRNWEGF APDPVLTGIG     180

MSETIKGIQD AGVIACAKHF IGNEQEHFRQ VPEAQGYGYN ISETLSSNID DKTMHELYLW     240

PFADAVRAGV GSVMCSYNQG NNSYACQNSK LLNDLLKNEL GFQGFVMSDW WAQHTGAASA     300

VAGLDMSMPG DTMVNTGVSF WGANLTLAVL NGTVPAYRLD DMCMRIMAAL FKVTKTTDLE     360

PINFSFWTRD TYGPIHWAAK QGYQEINSHV DVRADHGNLI RNIAAKGTVL LKNTGSLPLN     420

KPKFVAVIGE DAGPSPNGPN GCSDRGCNEG TLAMGWGSGT ANYPYLVSPD AALQARAIQD     480

GTRYESVLSN YAEENTKALV SQANATAIVF VNADSGEGYI NVDGNEGDRK NLTLWNNGDT     540

LVKNVSSWCS NTIVVIHSVG PVLLTDWYDN PNITAILWAG LPGQESGNSI TDVLYGKVNP     600

AARSPFTWGK TRESYGADVL YKPNNGNWAP QQDFTEGVFI DYRYFDKVDD DSVIYEFGHG     660

LSYTTFEYSN IRVVKSNVSE YRPTTGTTIQ APTFGNFSTD LEDYLFPKDE FPYIPQYIYP     720

YLNTTDPRRA SGDPHYGQTA EEFLPPHATD DDPQPLLRSS GGNSPGGNRQ LYDIVYTITA     780

DITNTGSVVG EEVPQLYVSL GGPEDPKVQL RDFDRMRIEP GETRQFTGRL TRRDLSNWDV     840

TVQDWVISRY PKTAYVGRSS RKLDLKIELP                                       870

SEQ ID NO: 20 C1 Variant 916 cDNA sequence
                  atgaaggctg ctgcgctttc ctgcctcttc ggcagtaccc ttgccgttgc aggcgccatt      60
gaatcgagaa aggttcacca gaagcccctc gcgagatctg aacttttta cccgtcgcca     120 tggatgaatc ccaacgccat cggctgggcg gaggcctatg cccaggccaa gtccttgtc     180 tcccaaatga ctctgctaga aaggtcaac ttgaccacgg gagtcggctg ggggatggag     240
cagtgcgtcg gccaagtggg cgcgatccct cgccttggac ttcgcagtct gtgcatgcat     300
gactcccctc tcggcgtgcg aggagccgac tacaactcag cgttccctc tggccagacc     360 gttgctgcta cctgggatcg cggtctgatg taccgtcgcg gctacgcaat gggccaggag     420
gccaaaggca agggcatcaa tgtccttctc ggaccagtcg ccggcccct ggccgcatg     480 cccgagggcg gtcgtaactg gaaggcttc gctccggatc ccgtccttac cggcatcggc     540
atgtccgaga cgatcaaggg cattcaggat gctggcgtca tcgcttgtgc aagcactt     600 attggaaacg agcaggagca cttcagacag gtgccagaag cccagggata cggttacaac     660
atcagcgaaa ccctctcctc caacattgac gacaagacca tgcacgagct ctacctttgg     720
ccgtttgccg atgccgtccg gccggcgtc ggctctgtca tgtgctcgta caaccagggc     780
aacaactcgt acgcctgcca gaactcgaag ctgctgaacg acctcctcaa gaacgagctt     840 gggttttcagg gcttcgtcat gagcgactgg tgggcacagc acactggcgc agcaagcgcc     900
gtggctggtc tcgatatgtc catgccgggc gacaccatgc tgaacactgg cgtcagtttc     960
tggggcgcca atctcaccct cgccgtcctc aacggacag tccctgccta ccgtctcgac    1020
gacatggcca tgcgcatcat ggccgccctc ttcaaggtca ccaagaccac cgacctggaa    1080
ccgatcaact tctccttctg gacccgcgac acttatggcc cgatccactg gccgccaag    1140 cagggctacc aggagattaa tcccacgtt gacgtccgcg ccgaccacgg caacctcatc    1200
```

```
          cggaacattg ccgccaaggg tacggtgctg ctgaagaata ccggctctct acccctgaac      1260
aagccaaagt tcgtggccgt catcggcgag gatgctgggc cgagccccaa cgggcccaac      1320
ggctgcagcg accgcggctg taacgaaggc acgctcgcca tgggctgggg atccggcaca      1380
gccaactatc cgtacctcgt tccccccgac gccgcgctcc aggcgcgggc catccaggac      1440
ggcacgaggt acgagagcgt cctgtccaac tacgccgagg aaaatacaaa ggctctggtc      1500
tcgcaggcca atgcaaccgc catcgtcttc gtcaatgccg actcaggcga gggctacatc      1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaacccc      1800
gccgcccgct cgcccttcac ttggggcaag acccgcgaaa gctatggcgc ggacgtcctg      1860
tacaagccga taatggcaa ttgggcgccc caacaggact tcaccgaggg cgtcttcatc       1920
gactaccgct acttcgacaa ggttgacgat gactcggtca tctacgagtt cggccacggc      1980
ctgagctaca ccaccttcga agacagcaac atccgcgtcg tcaagtccaa cgtcagcgag      2040
taccggccca cgacgggcac cacgattcag gccccgacgt tggcaacttt ctccaccgac      2100
ctcgaggact atctcttccc caaggacgag ttcccctaca tcccgcagta catctacccg      2160
tacctcaaca cgaccgaccc ccgagggccc tcgggcgatc ccactacgg ccagaccgcc        2220 gaggagttcc tcccgcccca cgccaccgat gacgaccccc agccgctcct ccggtcctcg      2280
ggcggaaact cccccggcgg caaccgccag ctgtacgaca ttgtctacac aatcacggcc      2340
ggcatcacga atacgggctc cgttgtaggc gaggaggtac cgcagctcta cgtctcgctg      2400
ggcggtcccg aggatcccaa ggtgcagctg cgcgactttg acaggatgcg gatcgaaccc      2460
ggcgagacga ggcagttcac cggccgcctg acgcgcgaga tctgagcaa ctgggacgtc       2520 acggtgcagg actgggtcat cagcaggtat cccaagacg catatgttgg gaggagcagc       2580
cggaagttgg atctcaagat tgagcttcct tga                                    2613
SEQ ID NO: 21 C1 Variant 916 polypeptide sequence
          MKAAALSCLF GSTLAVAGAI ESRKVHQKPL ARSEPFYPSP WMNPNAIGWA EAYAQAKSFV       60

SQMTLLEKVN LTTGVGWGME QCVGQVGAIP RLGLRSLCMH DSPLGVRGAD YNSAFPSGQT       120

VAATWDRGLM YRRGYAMGQE AKGKGINVLL GPVAGPLGRM PEGGRNWEGF APDPVLTGIG       180

MSETIKGIQD AGVIACAKHF IGNEQEHFRQ VPEAQGYGYN ISETLSSNID DKTMHELYLW       240

PFADAVRAGV GSVMCSYNQG NNSYACQNSK LLNDLLKNEL GFQGFVMSDW WAQHTGAASA       300

VAGLDMSMPG DTMLNTGVSF WGANLTLAVL NGTVPAYRLD DMAMRIMAAL FKVTKTTDLE       360

PINFSFWTRD TYGPIHWAAK QGYQEINSHV DVRADHGNLI RNIAAKGTVL LKNTGSLPLN       420

KPKFVAVIGE DAGPSPNGPN GCSDRGCNEG TLAMGWGSGT ANYPYLVSPD AALQARAIQD       480

GTRYESVLSN YAEENTKALV SQANATAIVF VNADSGEGYI NVDGNEGDRK NLTLWNNGDT       540

LVKNVSSWCS NTIVVIHSVG PVLLTDWYDN PNITAILWAG LPGQESGNSI TDVLYGKVNP       600

AARSPFTWGK TRESYGADVL YKPNNGNWAP QQDFTEGVFI DYRYFDKVDD DSVIYEFGHG       660

LSYTTFEYSN IRVVKSNVSE YRPTTGTTIQ APTFGNFSTD LEDYLFPKDE FPYIPQYIYP       720

YLNTTDPRRA SGDPHYGQTA EEFLPPHATD DDPQPLLRSS GGNSPGGNRQ LYDIVYTITA       780

DITNTGSVVG EEVPQLYVSL GGPEDPKVQL RDFDRMRIEP GETRQFTGRL TRRDLSNWDV       840

TVQDWVISRY PKTAYVGRSS RKLDLKIELP                                        870
```

What is claimed is:

1. A recombinant β-glucosidase (Bgl1) variant comprising an amino acid sequence that has at least 95% identity to amino acid residues 20-870 of SEQ ID NO:2 and comprises amino acid substitutions at positions Q291, D369, and E402, wherein the positions are numbered with reference to SEQ ID NO:2.

2. The recombinant Bgl1 variant of claim 1, comprising amino acid substitutions Q291W, D369R, and E402N.

3. The recombinant Bgl1 variant of claim 1, further comprising amino acid substitutions Q258N, Q313M, S434P, K495N, and G628W.

4. The recombinant Bgl1 variant of claim 3, further comprising amino acid substitutions A689I and Y715P.

5. The recombinant Bgl1 variant of claim 4, further comprising amino acid substitutions D47I, A343C, and T687K.

6. The recombinant Bgl1 variant of claim 4, further comprising amino acid substitutions I106V, V260G, F314V/L, and A732G.

7. The recombinant Bgl1 variant of claim 6, further comprising amino acid substitutions D47I, A79E, Q85N, A109T, and A343C.

8. The recombinant Bgl1 variant of claim 6, further comprising amino acid substitutions D47I, Q85N, A109S, and A343C.

9. The recombinant Bgl1 variant of claim 6, further comprising amino acid substitutions D47I and A79M.

10. The recombinant Bgl1 variant of claim 6, which comprises amino acids 20-870 of SEQ ID NO:17.

11. The recombinant Bgl1 variant of claim 6, which comprises amino acids 20-870 of SEQ ID NO:13, amino acids 20-870 of SEQ ID NO:19, or amino acids 20-870 of SEQ ID NO:21.

12. The recombinant Bgl1 variant of claim 4, further comprising an amino acid substitution A475L.

13. The recombinant Bgl1 variant of claim 1, wherein the variant has increased thermostability after incubation at pH 5 at 65° C. for six hours relative to wild-type Bgl1 having amino acid residues 20-870 of SEQ ID NO:2.

14. The recombinant Bgl1 variant of claim 13, wherein the variant has increased thermoactivity after incubation at pH 5 at 65° C. for twenty one hours relative to wild-type Bgl1 having amino acid residues 20-870 of SEQ ID NO:2.

15. The recombinant Bgl1 variant of claim 1, wherein the variant has at least 97% sequence identity to amino acid residues 20-870 of SEQ ID NO:2.

16. An enzyme composition comprising the recombinant Bgl1 variant of claim 1.

17. The enzyme composition of claim 16, wherein the enzyme composition comprises
 a) a recombinant endoglucanase (EG) polypeptide;
 b) a recombinant cellobiohydrolase polypeptide (CBH); or
 c) a recombinant EG polypeptide and a recombinant CBH polypeptide.

18. The enzyme composition of claim 17, further comprising at least one polypeptide selected from a hemicellulase, a pectinase, a lignin peroxidase, a manganese peroxidase, a laccase, or a cellobiose dehydrogenase.

19. A method of producing glucose, the method comprising incubating cellobiose with the recombinant Bgl1 variant of claim 1 under conditions in which glucose is produced.

20. A method of producing ethanol, the method comprising incubating cellobiose with the recombinant Bgl1 variant of claim 1 under conditions in which glucose is produced; and incubating said glucose with at least one fermenting microorganism in a fermentation reaction under conditions in which ethanol is produced.

* * * * *

UNITED STATES PATENT AND TRADEMARK OFFICE
CERTIFICATE OF CORRECTION

PATENT NO. : 8,143,050 B2
APPLICATION NO. : 12/954447
DATED : March 27, 2012
INVENTOR(S) : Jie Yang et al.

It is certified that error appears in the above-identified patent and that said Letters Patent is hereby corrected as shown below:

In column 227, claim 3, please delete "claim 1" and insert --claim 2--.

In column 227, claim 6, please delete "1106V" and insert --I106V--.

Signed and Sealed this
Twenty-ninth Day of January, 2013

David J. Kappos
*Director of the United States Patent and Trademark Office*

SEQUENCE LISTING

<160> NUMBER OF SEQ ID NOS: 22

<210> SEQ ID NO 1
<211> LENGTH: 2613
<212> TYPE: DNA
<213> ORGANISM: Myceliophthora thermophila

<400> SEQUENCE: 1

```
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccga cggctgggcg gaggcctatg cccaggccaa gtcctttgtc     180
tcccaaatga ctctgctaga gaaggtcaac ttgaccacgg gagtcggctg ggggctgag      240
cagtgcgtcg gccaagtggg cgcgatccct cgccttggac ttcgcagtct gtgcatgcat     300
gactcccctc tcggcatccg aggagccgac tacaactcag cgttcccctc tggccagacc     360
gttgctgcta cctgggatcg cggtctgatg taccgtcgcg gctacgcaat gggccaggag     420
gccaaaggca agggcatcaa tgtccttctc ggaccagtcg ccggccccct tggccgcatg     480
cccgagggcg gtcgtaactg ggaaggcttc gctccggatc ccgtccttac cggcatcggc     540
atgtccgaga cgatcaaggg cattcaggat gctggcgtca tcgcttgtgc gaagcacttt     600
attggaaacg agcaggagca cttcagacag gtgccagaag cccagggata cggttacaac     660
atcagcgaaa ccctctcctc caacattgac gacaagacca tgcacgagct ctacctttgg     720
ccgtttgccg atgccgtccg ggccggcgtc ggctctgtca tgtgctcgta ccagcaggtc     780
aacaactcgt acgcctgcca gaactcgaag ctgctgaacg acctcctcaa gaacgagctt     840
gggtttcagg gcttcgtcat gagcgactgg caggcacagc acactggcgc agcaagcgcc     900
gtggctggtc tcgatatgtc catgccgggc gacacccagt tcaacactgg cgtcagtttc     960
tggggcgcca atctcaccct cgccgtcctc aacggcacag tccctgccta ccgtctcgac    1020
gacatggcca tgcgcatcat ggccgccctc ttcaaggtca ccaagaccac cgacctggaa    1080
ccgatcaact tctccttctg gaccgacgac acttatggcc cgatccactg ggccgccaag    1140
cagggctacc aggagattaa ttcccacgtt gacgtccgcg ccgaccacgg caacctcatc    1200
cgggagattg ccgccaaggg tacggtgctg ctgaagaata ccggctctct accccctgaac    1260
aagccaaagt tcgtggccgt catcggcgag gatgctgggt cgagccccaa cgggcccaac    1320
ggctgcagcg accgcggctg taacgaaggc acgctcgcca tgggctgggg atccggcaca    1380
gccaactatc cgtacctcgt tccccccgac gccgcgctcc aggcccgggc catccaggac    1440
ggcacgaggt acgagagcgt cctgtccaac tacgccgagg aaaagacaaa ggctctggtc    1500
tcgcaggcca atgcaaccgc catcgtcttc gtcaatgccg actcaggcga gggctacatc    1560
aacgtggacg gtaacgaggg cgaccgtaag aacctgactc tctggaacaa cggtgatact    1620
ctggtcaaga cgtctcgag ctggtgcagc aacaccatcg tcgtcatcca ctcggtcggc    1680
ccggtcctcc tgaccgattg gtacgacaac cccaacatca cggccattct ctgggctggt    1740
cttccgggcc aggagtcggg caactccatc accgacgtgc tttacggcaa ggtcaacccc    1800
gccgccgct cgcccttcac ttggggcaag acccgcgaaa gctatggcgc ggacgtcctg    1860
tacaagccga ataatggcaa tggtgcgccc aacaggact tcaccgaggg cgtcttcatc    1920
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
```

-continued

```
taccggccca cgacgggcac cacggcccag gccccgacgt ttggcaactt ctccaccgac    2100
ctcgaggact atctcttccc caaggacgag ttccccctaca tctaccagta catctacccg   2160
tacctcaaca cgaccgaccc ccggagggcc tcggccgatc cccactacgg ccagaccgcc    2220
gaggagttcc tcccgcccca cgccaccgat gacgaccccc agccgctcct ccggtcctcg    2280
ggcggaaact cccccggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                 2613
```

<210> SEQ ID NO 2
<211> LENGTH: 870
<212> TYPE: PRT
<213> ORGANISM: Myceliophthora thermophila

<400> SEQUENCE: 2

```
Met Lys Ala Ala Ala Leu Ser Cys Leu Phe Gly Ser Thr Leu Ala Val
  1               5                  10                  15

Ala Gly Ala Ile Glu Ser Arg Lys Val His Gln Lys Pro Leu Ala Arg
             20                  25                  30

Ser Glu Pro Phe Tyr Pro Ser Pro Trp Met Asn Pro Asn Ala Asp Gly
         35                  40                  45

Trp Ala Glu Ala Tyr Ala Gln Ala Lys Ser Phe Val Ser Gln Met Thr
     50                  55                  60

Leu Leu Glu Lys Val Asn Leu Thr Thr Gly Val Gly Trp Gly Ala Glu
 65                  70                  75                  80

Gln Cys Val Gly Gln Val Gly Ala Ile Pro Arg Leu Gly Leu Arg Ser
                 85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
```

```
                    275                 280                 285
Asp Trp Gln Ala Gln His Thr Gly Ala Ala Ser Ala Val Ala Gly Leu
290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
                340                 345                 350

Val Thr Lys Thr Thr Asp Leu Glu Pro Ile Asn Phe Ser Phe Trp Thr
            355                 360                 365

Asp Asp Thr Tyr Gly Pro Ile His Trp Ala Ala Lys Gln Gly Tyr Gln
370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
                420                 425                 430

Gly Ser Ser Pro Asn Gly Pro Asn Gly Cys Ser Asp Arg Gly Cys Asn
            435                 440                 445

Glu Gly Thr Leu Ala Met Gly Trp Gly Ser Gly Thr Ala Asn Tyr Pro
            450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Lys Thr
                485                 490                 495

Lys Ala Leu Val Ser Gln Ala Asn Ala Thr Ala Ile Val Phe Val Asn
                500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
                580                 585                 590

Val Leu Tyr Gly Lys Val Asn Pro Ala Ala Arg Ser Pro Phe Thr Trp
            595                 600                 605

Gly Lys Thr Arg Glu Ser Tyr Gly Ala Asp Val Leu Tyr Lys Pro Asn
            610                 615                 620

Asn Gly Asn Gly Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
                660                 665                 670

Val Val Lys Ser Asn Val Ser Glu Tyr Arg Pro Thr Thr Gly Thr Thr
            675                 680                 685

Ala Gln Ala Pro Thr Phe Gly Asn Phe Ser Thr Asp Leu Glu Asp Tyr
690                 695                 700
```

```
Leu Phe Pro Lys Asp Glu Phe Pro Tyr Ile Tyr Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
        755                 760                 765

Arg Gln Leu Tyr Asp Ile Val Tyr Thr Ile Thr Ala Asp Ile Thr Asn
    770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
                820                 825                 830

Arg Asp Leu Ser Asn Trp Asp Val Thr Val Gln Asp Trp Val Ile Ser
            835                 840                 845

Arg Tyr Pro Lys Thr Ala Tyr Val Gly Arg Ser Ser Arg Lys Leu Asp
    850                 855                 860

Leu Lys Ile Glu Leu Pro
865                 870

<210> SEQ ID NO 3
<211> LENGTH: 2556
<212> TYPE: DNA
<213> ORGANISM: Artificial
<220> FEATURE:
<223> OTHER INFORMATION: Synthetic DNA

<400> SEQUENCE: 3
atagaaagta gaaaggtaca tcaaaaacca ttagctagat cagaaccatt ctacccttct      60
ccatggatga accctaatgc agatggatgg gcagaagcat atgctcaggc caagagtttt    120
gtctcccaga tgactctgtt ggaaaaggtt aatctgacaa caggagtagg atggggtgca    180
gaacagtgtg tcggccaagt tggtgctatc cctagattgg gtcttagaag tttgtgtatg    240
cacgattctc ccttaggtat aagaggcgct gactataact cagcattccc atccgggcaa    300
actgttgctg cgacatggga caggggtttg atgtatagaa ggggttatgc gatgggtcaa    360
gaggcaaagg gtaaaggaat taatgtattg ttggggccgg tggcggggcc actgggaaga    420
atgccagaag gtggaaggaa ctgggaagga ttcgcccccg acccagtgct aacaggtata    480
ggtatgtccg aaacgatcaa aggcatacaa gatgcaggtg ttatcgcctg tgcgaagcat    540
tttattggta atgaacaaga gcattttcgt caagtgccag aggctcaagg ttatggttat    600
aatatttctg aaactttaag ttccaacatc gatgacaaaa ccatgcacga gttatactta    660 tggcctttg cagacgctgt gagagctggc gttggctctg ttatgtgctc ttatcagcaa    720
gttaataact cttacgcctg tcaaaattcc aagttactaa atgacttatt gaagaacgaa    780
ctaggattcc aaggattcgt catgagcgat tggcaagcac agcatactgg tgctgcatcc    840
gctgtggcag gattagatat gtcaatgcca ggagatacac aatttaatac tggcgttagt    900
tttgggggtg caaacctaac tttagctgtt ctaaacggta cggtacctgc atatcgttta    960
gacgacatgg ccatgcgtat aatggctgct ttattcaaag ttacaaaaac caccgattta   1020
gaaccaatta attttagttt ttggacagat gacacatatg gtcctataca ctgggctgct   1080
aagcaagggt accaagaaat aaatagtcac gttgacgtaa gagcggatca cggcaatctt   1140
```

| | |
|---|---:|
| atcagagaga tagcagcaaa gggaactgta ttgttgaaga atactggttc attaccacta | 1200 |
| aacaaaccaa agtttgtcgc agtcattggt gaagatgctg gttcatcccc taatggacca | 1260 |
| aatggttgta gtgacagagg ctgcaatgaa ggcacgttgg caatgggctg gggctcaggg | 1320 |
| actgccaatt acccctattt ggtctctccg gatgcggctt tacaggctag agcaatccag | 1380 |
| gatggtacta gatacgagag cgtcctaagt aactatgccg aagaaaagac taaggcctta | 1440 |
| gtcagtcaag ccaatgccac tgctatcgtt ttcgtaaacg cggattctgg cgaaggttat | 1500 |
| atcaatgttg atggtaatga aggtgacaga aagaatttaa ctttatggaa taacggcgac | 1560 |
| acattagtta aaaatgtatc aagttggtgt tccaatacta tcgtcgtgat acattctgtt | 1620 |
| ggtccagttt tactgacaga ctggtacgat aacccaaaca ttaccgccat tttatgggca | 1680 |
| ggtctgccag ggcaggaatc aggaaaattcc attacggacg tactatacgg aaaggttaac | 1740 |
| ccagccgcca ggagcccttt cacatggggt aagacaagag agagctacgg agctgatgtt | 1800 |
| ctttataaac cgaacaacgg gaatggagcg ccacagcaag attttactga aggtgtgttc | 1860 |
| attgactata gatacttcga caaagttgac gatgactcag ttatatatga attcggtcac | 1920 |
| ggtctatctt atactacttt tgaatattca aatataagag tagtcaaaag taatgtttct | 1980 |
| gaatataggc cgaccaccgg aacgacggct caagcgccta ccttcggtaa tttttcaacg | 2040 |
| gatttagaag attatttatt tcccaaagac gaatttccat acatctacca atacatatac | 2100 |
| ccctatctga atactaccga tccaagaaga gcttctgccg atccacatta cgggcagact | 2160 |
| gccgaagagt tcttgccacc acacgctact gacgacgatc ctcaacctct tctgaggtcc | 2220 |
| agtggcggaa attcacctgg tggtaatagg cagctgtatg atattgtgta tactataacg | 2280 |
| gctgatatta ctaatactgg tagcgttgtt ggtgaagaag tgccgcaatt atatgtgtct | 2340 |
| ttaggtggtc cggaagatcc taaggttcag ttaagagact ttgataggat gagaatagaa | 2400 |
| cctggagaaa ctaggcaatt tacaggtaga ttgacccgta gggatctgtc aaactgggat | 2460 |
| gtaacagtgc aagattgggt aatcagcagg tacccgaaaa ctgcatacgt gggtagatct | 2520 |
| tcccgtaagt tagatttgaa aattgaattg ccataa | 2556 |

<210> SEQ ID NO 4
<211> LENGTH: 2613
<212> TYPE: DNA
<213> ORGANISM: Artificial
<220> FEATURE:
<223> OTHER INFORMATION: Synthetic DNA

<400> SEQUENCE: 4

| | |
|---|---:|
| atgaaggctg ctgcgctttc ctgcctcttc ggcagtaccc ttgccgttgc aggcgccatt | 60 |
| gaatcgagaa aggttcacca gaagcccctc gcgagatctg aaccttttta cccgtcgcca | 120 |
| tggatgaatc ccaacgccga cggctgggcg gaggcctatg cccaggccaa gtcctttgtc | 180 |
| tcccaaatga ctctgctaga aaggtcaac ttgaccacgg gagtcggctg gggggctgag | 240 |
| cagtgcgtcg gccaagtggg cgcgatccct cgccttggac ttcgcagtct gtgcatgcat | 300 |
| gactcccctc tcggcatccg aggagccgac tacaactcag cgttcccctc tggccagacc | 360 |
| gttgctgcta cctgggatcg cggtctgatg taccgtcgcg gctacgcaat gggccaggag | 420 |
| gccaaaggca agggcatcaa tgtccttctc ggaccagtcg ccggcccct tggccgcatg | 480 |
| cccgagggcg gtcgtaactg ggaaggcttc gctccggatc ccgtccttac cggcatcggc | 540 |
| atgtccgaga cgatcaaggg cattcaggat gctggcgtca tcgcttgtgc gaagcacttt | 600 |
| attggaaacg agcaggagca cttcagacag gtgccagaag cccagggata cggttacaac | 660 |

```
atcagcgaaa ccctctcctc caacattgac gacaagacca tgcacgagct ctacctttgg    720
ccgtttgccg atgccgtccg ggccggcgtc ggctctgtca tgtgctcgta ccagcaggtc    780
aacaactcgt acgcctgcca gaactcgaag ctgctgaacg acctcctcaa gaacgagctt    840
gggtttcagg gcttcgtcat gagcgactgg tgggcacagc acactggcgc agcaagcgcc    900
gtggctggtc tcgatatgtc catgccgggc gacacccagt tcaacactgg cgtcagtttc    960
tggggcgcca atctcaccct cgccgtcctc aacggcacag tccctgccta ccgtctcgac   1020
gacatggcca tgcgcatcat ggccgccctc ttcaaggtca ccaagaccac cgacctggaa   1080
ccgatcaact tctccttctg gaccctggac acttatggcc cgatccactg ggccgccaag   1140
cagggctacc aggagattaa ttcccacgtt gacgtccgcg ccgaccacgg caacctcatc   1200
cggaacattg ccgccaaggg tacggtgctg ctgaagaata ccggctctct accccctgaac   1260 aagccaaagt tcgtggccgt catcggcgag gatgctgggt cgagcccaa cgggcccaac   1320 ggctgcagcg accgcggctg taacgaaggc acgctcgcca tgggctgggg atccggcaca   1380
gccaactatc cgtacctcgt tccccccgac gccgcgctcc aggcccgggc catccaggac   1440
ggcacgaggt acgagagcgt cctgtccaac tacgccgagg aaaagacaaa ggctctggtc   1500
tcgcaggcca atgcaaccgc catcgtcttc gtcaatgccg actcaggcga gggctacatc   1560
aacgtggacg gtaacgaggg cgaccgtaag aacctgactc tctggaacaa cggtgatact   1620
ctggtcaaga acgtctcgag ctggtgcagc aacaccatcg tcgtcatcca ctcggtcggc   1680
ccggtcctcc tgaccgattg gtacgacaac cccaacatca cggccattct ctgggctggt   1740
cttccgggcc aggagtcggg caactccatc accgacgtgc tttacggcaa ggtcaacccc   1800
gccgcccgct cgcccttcac ttggggcaag acccgcgaaa gctatggcgc ggacgtcctg   1860
tacaagccga ataatggcaa tggtgcgccc caacaggact tcaccgaggg cgtcttcatc   1920
gactaccgct acttcgacaa ggttgacgat gactcggtca tctacgagtt cggccacggc   1980
ctgagctaca ccaccttcga gtacagcaac atccgcgtcg tcaagtccaa cgtcagcgag   2040
taccggccca cgacgggcac cacggcccag gccccgacgt ttggcaactt ctccaccgac   2100
ctcgaggact atctcttccc caaggacgag ttcccctaca tctaccagta catctacccg   2160
tacctcaaca cgaccgaccc ccggagggcc tcggccgatc cccactacgg ccagaccgcc   2220
gaggagttcc tcccgcccca cgccaccgat gacgaccccc agccgctcct ccggtcctcg   2280
ggcggaaact cccccggcgg caaccgccag ctgtacgaca ttgtctacac aatcacggcc   2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                2613
```

<210> SEQ ID NO 5  
<211> LENGTH: 870  
<212> TYPE: PRT  
<213> ORGANISM: Artificial  
<220> FEATURE:  
<223> OTHER INFORMATION: Synthetic polypeptide

<400> SEQUENCE: 5

```
Met Lys Ala Ala Ala Leu Ser Cys Leu Phe Gly Ser Thr Leu Ala Val
1               5                   10                  15
```

-continued

```
Ala Gly Ala Ile Glu Ser Arg Lys Val His Gln Lys Pro Leu Ala Arg
         20                  25                  30

Ser Glu Pro Phe Tyr Pro Ser Pro Trp Met Asn Pro Asn Ala Asp Gly
             35                  40                  45

Trp Ala Glu Ala Tyr Ala Gln Ala Lys Ser Phe Val Ser Gln Met Thr
 50                  55                  60

Leu Leu Glu Lys Val Asn Leu Thr Thr Gly Val Gly Trp Gly Ala Glu
 65                  70                  75                  80

Gln Cys Val Gly Gln Val Gly Ala Ile Pro Arg Leu Gly Leu Arg Ser
                 85                  90                  95

Leu Cys Met His Asp Ser Pro Leu Gly Ile Arg Gly Ala Asp Tyr Asn
             100                 105                 110

Ser Ala Phe Pro Ser Gly Gln Thr Val Ala Ala Thr Trp Asp Arg Gly
         115                 120                 125

Leu Met Tyr Arg Arg Gly Tyr Ala Met Gly Gln Glu Ala Lys Gly Lys
130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Leu Asp Thr Tyr Gly Pro Ile His Trp Ala Ala Lys Gln Gly Tyr Gln
370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Ser Ser Pro Asn Gly Pro Asn Gly Cys Ser Asp Arg Gly Cys Asn
        435                 440                 445
```

-continued

```
Glu Gly Thr Leu Ala Met Gly Trp Ser Gly Thr Ala Asn Tyr Pro
    450                 455                 460
Tyr Leu Val Ser Pro Asp Ala Ala Leu Gln Ala Arg Ala Ile Gln Asp
465                 470                 475                 480
Gly Thr Arg Tyr Glu Ser Val Leu Ser Asn Tyr Ala Glu Glu Lys Thr
                485                 490                 495
Lys Ala Leu Val Ser Gln Ala Asn Ala Thr Ala Ile Val Phe Val Asn
                500                 505                 510
Ala Asp Ser Gly Glu Gly Tyr Ile Asn Val Asp Gly Asn Glu Gly Asp
            515                 520                 525
Arg Lys Asn Leu Thr Leu Trp Asn Asn Gly Asp Thr Leu Val Lys Asn
530                 535                 540
Val Ser Ser Trp Cys Ser Asn Thr Ile Val Ile His Ser Val Gly
545                 550                 555                 560
Pro Val Leu Leu Thr Asp Trp Tyr Asp Asn Pro Asn Ile Thr Ala Ile
                565                 570                 575
Leu Trp Ala Gly Leu Pro Gly Gln Glu Ser Gly Asn Ser Ile Thr Asp
            580                 585                 590
Val Leu Tyr Gly Lys Val Asn Pro Ala Ala Arg Ser Pro Phe Thr Trp
            595                 600                 605
Gly Lys Thr Arg Glu Ser Tyr Gly Ala Asp Val Leu Tyr Lys Pro Asn
610                 615                 620
Asn Gly Asn Gly Ala Pro Gln Gln Asp Phe Thr Glu Gly Val Phe Ile
625                 630                 635                 640
Asp Tyr Arg Tyr Phe Asp Lys Val Asp Asp Ser Val Ile Tyr Glu
                645                 650                 655
Phe Gly His Gly Leu Ser Tyr Thr Thr Phe Glu Tyr Ser Asn Ile Arg
                660                 665                 670
Val Val Lys Ser Asn Val Ser Glu Tyr Arg Pro Thr Thr Gly Thr Thr
            675                 680                 685
Ala Gln Ala Pro Thr Phe Gly Asn Phe Ser Thr Asp Leu Glu Asp Tyr
        690                 695                 700
Leu Phe Pro Lys Asp Glu Phe Pro Tyr Ile Tyr Gln Tyr Ile Tyr Pro
705                 710                 715                 720
Tyr Leu Asn Thr Thr Asp Pro Arg Arg Ala Ser Ala Asp Pro His Tyr
                725                 730                 735
Gly Gln Thr Ala Glu Glu Phe Leu Pro Pro His Ala Thr Asp Asp Asp
            740                 745                 750
Pro Gln Pro Leu Leu Arg Ser Ser Gly Gly Asn Ser Pro Gly Gly Asn
        755                 760                 765
Arg Gln Leu Tyr Asp Ile Val Tyr Thr Ile Thr Ala Asp Ile Thr Asn
    770                 775                 780
Thr Gly Ser Val Val Gly Glu Glu Val Pro Gln Leu Tyr Val Ser Leu
785                 790                 795                 800
Gly Gly Pro Glu Asp Pro Lys Val Gln Leu Arg Asp Phe Asp Arg Met
                805                 810                 815
Arg Ile Glu Pro Gly Glu Thr Arg Gln Phe Thr Gly Arg Leu Thr Arg
                820                 825                 830
Arg Asp Leu Ser Asn Trp Asp Val Thr Val Gln Asp Trp Val Ile Ser
            835                 840                 845
Arg Tyr Pro Lys Thr Ala Tyr Val Gly Arg Ser Ser Arg Lys Leu Asp
    850                 855                 860
Leu Lys Ile Glu Leu Pro
```

<210> SEQ ID NO 6
<211> LENGTH: 2613
<212> TYPE: DNA
<213> ORGANISM: Artificial
<220> FEATURE:
<223> OTHER INFORMATION: Synthetic DNA

<400> SEQUENCE: 6

| | | | | | |
|---|---|---|---|---|---|
| atgaaggctg | ctgcgctttc | ctgcctcttc | ggcagtaccc | ttgccgttgc | aggcgccatt | 60 |
| gaatcgagaa | aggttcacca | gaagcccctc | gcgagatctg | aaccttttta | cccgtcgcca | 120 |
| tggatgaatc | ccaacgccga | cggctgggcg | gaggcctatg | cccaggccaa | gtcctttgtc | 180 |
| tcccaaatga | ctctgctaga | gaaggtcaac | ttgaccacgg | gagtcggctg | ggggctgag | 240 |
| cagtgcgtcg | gccaagtggg | cgcgatccct | cgccttggac | ttcgcagtct | gtgcatgcat | 300 |
| gactcccctc | tcggcatccg | aggagccgac | tacaactcag | cgttcccctc | tggccagacc | 360 |
| gttgctgcta | cctgggatcg | cggtctgatg | taccgtcgcg | gctacgcaat | gggccaggag | 420 |
| gccaaaggca | agggcatcaa | tgtccttctc | ggaccagtcg | ccggcccct | tggccgcatg | 480 |
| cccgagggcg | gtcgtaactg | ggaaggcttc | gctccggatc | ccgtccttac | cggcatcggc | 540 |
| atgtccgaga | cgatcaaggg | cattcaggat | gctggcgtca | tcgcttgtgc | gaagcacttt | 600 |
| attggaaacg | agcaggagca | cttcagacag | gtgccagaag | cccagggata | cggttacaac | 660 |
| atcagcgaaa | ccctctcctc | caacattgac | gacaagacca | tgcacgagct | ctacctttgg | 720 |
| ccgtttgccg | atgccgtccg | gccggcgtc | ggctctgtca | tgtgctcgta | caaccaggtc | 780 |
| aacaactcgt | acgcctgcca | gaactcgaag | ctgctgaacg | acctcctcaa | gaacgagctt | 840 |
| gggtttcagg | gcttcgtcat | gagcgactgg | tgggcacagc | acactggcgc | agcaagcgcc | 900 |
| gtggctggtc | tcgatatgtc | catgccgggc | gacaccatgt | tcaacactgg | cgtcagtttc | 960 |
| tggggcgcca | atctcacccct | cgccgtcctc | aacggcacag | tccctgccta | ccgtctcgac | 1020 |
| gacatggcca | tgcgcatcat | ggccgccctc | ttcaaggtca | ccaagaccac | cgacctggaa | 1080 |
| ccgatcaact | tctccttctg | gacccgcgac | acttatggcc | cgatccactg | ggccgccaag | 1140 |
| cagggctacc | aggagattaa | ttcccacgtt | gacgtccgcg | ccgaccacgg | caacctcatc | 1200 |
| cggaacattg | ccgccaaggg | tacggtgctg | ctgaagaata | ccggctctct | acccctgaac | 1260 |
| aagccaaagt | tcgtggccgt | catcggcgag | gatgctgggc | cgagcccaa | cgggcccaac | 1320 |
| ggctgcagcg | accgcggctg | taacgaaggc | acgctcgcca | tgggctgggg | atccggcaca | 1380 |
| gccaactatc | cgtacctcgt | ttcccccgac | gccgcgctcc | agttgcgggc | catccaggac | 1440 |
| ggcacgaggt | acgagagcgt | cctgtccaac | tacgccgagg | aaaatacaaa | ggctctggtc | 1500 |
| tcgcaggcca | atgcaaccgc | catcgtcttc | gtcaatgccg | actcaggcga | gggctacatc | 1560 |
| aacgtggacg | gtaacgaggg | cgaccgtaag | aacctgactc | tctggaacaa | cggtgatact | 1620 |
| ctggtcaaga | acgtctcgag | ctggtgcagc | aacaccatcg | tcgtcatcca | ctcggtcggc | 1680 |
| ccggtcctcc | tgaccgattg | gtacgacaac | cccaacatca | cggccattct | ctgggctggt | 1740 |
| cttccggggcc | aggagtcggg | caactccatc | accgacgtgc | tttacggcaa | ggtcaacccc | 1800 |
| gccgccgct | cgcccttcac | ttggggcaag | acccgcgaaa | gctatggcgc | ggacgtcctg | 1860 |
| tacaagccga | taatggcaa | ttgggcgccc | caacaggact | tcaccgaggg | cgtcttcatc | 1920 |
| gactaccgct | acttcgacaa | ggttgacgat | gactcggtca | tctacgagtt | cggccacggc | 1980 |
| ctgagctaca | ccaccttcga | gtacagcaac | atccgcgtcg | tcaagtccaa | cgtcagcgag | 2040 |

-continued

```
taccggccca cgacgggcac cacggcccag ccccgacgt ttggcaactt ctccaccgac    2100
ctcgaggact atctcttccc caaggacgag ttccctaca tctaccagta catctacccg    2160
tacctcaaca cgaccgaccc ccggagggcc tcggccgatc cccactacgg ccagaccgcc    2220
gaggagttcc tcccgcccca cgccaccgat gacgaccccc agccgctcct ccggtcctcg    2280
ggcggaaact cccccggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                2613
```

<210> SEQ ID NO 7
<211> LENGTH: 870
<212> TYPE: PRT
<213> ORGANISM: Artificial
<220> FEATURE:
<223> OTHER INFORMATION: Synthetic polypeptide

<400> SEQUENCE: 7

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Val Asn Asn Ser Tyr Ala Cys Gln Asn Ser Lys Leu Leu
            260                 265                 270
```

-continued

```
Asn Asp Leu Leu Lys Asn Glu Leu Gly Phe Gln Gly Phe Val Met Ser
    275                 280                 285
Asp Trp Trp Ala Gln His Thr Gly Ala Ala Ser Ala Val Ala Gly Leu
290                 295                 300
Asp Met Ser Met Pro Gly Asp Thr Met Phe Asn Thr Gly Val Ser Phe
305                 310                 315                 320
Trp Gly Ala Asn Leu Thr Leu Ala Val Leu Asn Gly Thr Val Pro Ala
                325                 330                 335
Tyr Arg Leu Asp Asp Met Ala Met Arg Ile Met Ala Ala Leu Phe Lys
            340                 345                 350
Val Thr Lys Thr Thr Asp Leu Glu Pro Ile Asn Phe Ser Phe Trp Thr
        355                 360                 365
Arg Asp Thr Tyr Gly Pro Ile His Trp Ala Ala Lys Gln Gly Tyr Gln
    370                 375                 380
Glu Ile Asn Ser His Val Asp Val Arg Ala Asp His Gly Asn Leu Ile
385                 390                 395                 400
Arg Asn Ile Ala Ala Lys Gly Thr Val Leu Leu Lys Asn Thr Gly Ser
                405                 410                 415
Leu Pro Leu Asn Lys Pro Lys Phe Val Ala Val Ile Gly Glu Asp Ala
            420                 425                 430
Gly Pro Ser Pro Asn Gly Pro Asn Gly Cys Ser Asp Arg Gly Cys Asn
        435                 440                 445
Glu Gly Thr Leu Ala Met Gly Trp Gly Ser Gly Thr Ala Asn Tyr Pro
    450                 455                 460
Tyr Leu Val Ser Pro Asp Ala Ala Leu Gln Leu Arg Ala Ile Gln Asp
465                 470                 475                 480
Gly Thr Arg Tyr Glu Ser Val Leu Ser Asn Tyr Ala Glu Glu Asn Thr
                485                 490                 495
Lys Ala Leu Val Ser Gln Ala Asn Ala Thr Ala Ile Val Phe Val Asn
            500                 505                 510
Ala Asp Ser Gly Glu Gly Tyr Ile Asn Val Asp Gly Asn Glu Gly Asp
        515                 520                 525
Arg Lys Asn Leu Thr Leu Trp Asn Asn Gly Asp Thr Leu Val Lys Asn
    530                 535                 540
Val Ser Ser Trp Cys Ser Asn Thr Ile Val Ile His Ser Val Gly
545                 550                 555                 560
Pro Val Leu Leu Thr Asp Trp Tyr Asp Asn Pro Asn Ile Thr Ala Ile
                565                 570                 575
Leu Trp Ala Gly Leu Pro Gly Gln Glu Ser Gly Asn Ser Ile Thr Asp
            580                 585                 590
Val Leu Tyr Gly Lys Val Asn Pro Ala Ala Arg Ser Pro Phe Thr Trp
        595                 600                 605
Gly Lys Thr Arg Glu Ser Tyr Gly Ala Asp Val Leu Tyr Lys Pro Asn
    610                 615                 620
Asn Gly Asn Trp Ala Pro Gln Gln Asp Phe Thr Glu Gly Val Phe Ile
625                 630                 635                 640
Asp Tyr Arg Tyr Phe Asp Lys Val Asp Asp Ser Val Ile Tyr Glu
                645                 650                 655
Phe Gly His Gly Leu Ser Tyr Thr Thr Phe Glu Tyr Ser Asn Ile Arg
            660                 665                 670
Val Val Lys Ser Asn Val Ser Glu Tyr Arg Pro Thr Thr Gly Thr Thr
        675                 680                 685
Ala Gln Ala Pro Thr Phe Gly Asn Phe Ser Thr Asp Leu Glu Asp Tyr
```

|  |  |  |  |  |  |
|---|---|---|---|---|---|
| | 690 | | 695 | | 700 |

Leu Phe Pro Lys Asp Glu Phe Pro Tyr Ile Tyr Gln Tyr Ile Tyr Pro
705                     710                     715                     720

Tyr Leu Asn Thr Thr Asp Pro Arg Arg Ala Ser Ala Asp Pro His Tyr
                725                     730                     735

Gly Gln Thr Ala Glu Glu Phe Leu Pro Pro His Ala Thr Asp Asp Asp
                740                     745                     750

Pro Gln Pro Leu Leu Arg Ser Ser Gly Gly Asn Ser Pro Gly Gly Asn
                755                     760                     765

Arg Gln Leu Tyr Asp Ile Val Tyr Thr Ile Thr Ala Asp Ile Thr Asn
770                     775                     780

Thr Gly Ser Val Val Gly Glu Glu Val Pro Gln Leu Tyr Val Ser Leu
785                     790                     795                     800

Gly Gly Pro Glu Asp Pro Lys Val Gln Leu Arg Asp Phe Asp Arg Met
                805                     810                     815

Arg Ile Glu Pro Gly Thr Arg Gln Phe Thr Gly Arg Leu Thr Arg
                820                     825                     830

Arg Asp Leu Ser Asn Trp Asp Val Thr Val Gln Asp Trp Val Ile Ser
                835                     840                     845

Arg Tyr Pro Lys Thr Ala Tyr Val Gly Arg Ser Ser Arg Lys Leu Asp
850                     855                     860

Leu Lys Ile Glu Leu Pro
865                     870

<210> SEQ ID NO 8
<211> LENGTH: 2613
<212> TYPE: DNA
<213> ORGANISM: Artificial
<220> FEATURE:
<223> OTHER INFORMATION: Synthetic DNA

<400> SEQUENCE: 8

```
atgaaggctg ctgcgctttc ctgcctcttc ggcagtaccc ttgccgttgc aggcgccatt      60
gaatcgagaa aggttcacca gaagcccctc gcgagatctg aacctttta  cccgtcgcca     120
tggatgaatc ccaacgccga cggctgggcg gaggcctatg cccaggccaa gtcctttgtc     180
tcccaaatga ctctgctaga aaggtcaac ttgaccacgg gagtcggctg gggggctgag      240
cagtgcgtcg gccaagtggg cgcgatccct cgccttggac ttcgcagtct gtgcatgcat     300
gactcccctc tcggcatccg aggagccgac tacaactcag cgttccctc  tggccagacc    360
gttgctgcta cctgggatcg cggtctgatg taccgtcgcg gctacgcaat gggccaggag    420
gccaaaggca agggcatcaa tgtccttctc ggaccagtcg ccggccccct tggccgcatg    480
cccgagggcg gtcgtaactg ggaaggcttc gctccggatc ccgtccttac cggcatcggc    540
atgtccgaga cgatcaaggg cattcaggat gctggcgtca tcgcttgtgc gaagcacttt    600
attggaaacg agcaggagca cttcagacag gtgccagaag cccagggata cggttacaac    660
atcagcgaaa ccctctcctc caacattgac gacaagacca tgcacgagct ctacctttgg    720
ccgtttgccg atgccgtccg ggccggcgtc ggctctgtca tgtgctcgta caaccaggtc    780
aacaactcgt acgcctgcca gaactcgaag ctgctgaacg acctcctcaa gaacgagctt    840
gggtttcagg gcttcgtcat gagcgactgg tgggcacagc acactggcgc agcaagcgcc    900
gtggctggtc tcgatatgtc catgccgggc gacaccatgt caacactgg  cgtcagtttc    960
tggggcgcca atctcacccc tcgccgtcct caacggcacag tccctgccta ccgtctcgac   1020
gacatggcca tgcgcatcat ggccgccctc ttcaaggtca ccaagaccac cgacctggaa   1080
```

```
ccgatcaact tctccttctg acccgcgac acttatggcc cgatccactg ggccgccaag    1140
cagggctacc aggagattaa ttcccacgtt gacgtccgcg ccgaccacgg caacctcatc    1200
cggaacattg ccgccaaggg tacggtgctg ctgaagaata ccggctctct accccctgaac   1260 aagccaaagt tcgtggccgt catcggcgag gatgctgggc cgagcccaa cgggcccaac    1320 ggctgcagcg accgcggctg taacgaaggc acgctcgcca tgggctgggg atccggcaca    1380
gccaactatc cgtacctcgt ttcccccgac gccgcgctcc agttgcgggc catccaggac    1440
ggcacgaggt acgagagcgt cctgtccaac tacgccgagg aaaatacaaa ggctctggtc    1500
tcgcaggcca atgcaaccgc catcgtcttc gtcaatgccg actcaggcga gggctacatc    1560
aacgtggacg gtaacgaggg cgaccgtaag aacctgactc tctggaacaa cggtgatact    1620
ctggtcaaga acgtctcgag ctggtgcagc aacaccatcg tcgtcatcca ctcggtcggc    1680
ccggtcctcc tgaccgattg gtacgacaac cccaacatca cggccattct ctgggctggt    1740
cttccgggcc aggagtcggg caactccatc accgacgtgc tttacggcaa ggtcaacccc    1800
gccgcccgct cgcccttcac ttggggcaag acccgcgaaa gctatggcgc ggacgtcctg    1860
tacaagccga ataatggcaa ttgggcgccc caacaggact tcaccgaggg cgtcttcatc    1920
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
taccggccca cgacgggcac cacgattcag gccccgacgt ttggcaactt ctccaccgac    2100
ctcgaggact atctcttccc caaggacgag ttccctaca tccgcagta catctacccg      2160 tacctcaaca cgaccgaccc ccggagggcc tcggccgatc cccactacgg ccagaccgcc    2220
gaggagttcc tcccgcccca cgccaccgat gacgacccc agccgctcct ccggtcctcg     2280
ggcggaaact cccccggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                 2613
```

<210> SEQ ID NO 9  
<211> LENGTH: 870  
<212> TYPE: PRT  
<213> ORGANISM: Artificial  
<220> FEATURE:  
<223> OTHER INFORMATION: Synthetic polypeptide

<400> SEQUENCE: 9

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95
```

```
Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
    290                 295                 300

Asp Met Ser Met Pro Gly Asp Thr Met Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Leu Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
```

```
                  515                 520                 525
Arg Lys Asn Leu Thr Leu Trp Asn Asn Gly Asp Thr Leu Val Lys Asn
530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
                580                 585                 590

Val Leu Tyr Gly Lys Val Asn Pro Ala Ala Arg Ser Pro Phe Thr Trp
                595                 600                 605

Gly Lys Thr Arg Glu Ser Tyr Gly Ala Asp Val Leu Tyr Lys Pro Asn
                610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
                660                 665                 670

Val Val Lys Ser Asn Val Ser Glu Tyr Arg Pro Thr Thr Gly Thr Thr
                675                 680                 685

Ile Gln Ala Pro Thr Phe Gly Asn Phe Ser Thr Asp Leu Glu Asp Tyr
                690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
                740                 745                 750

Pro Gln Pro Leu Leu Arg Ser Ser Gly Gly Asn Ser Pro Gly Gly Asn
                755                 760                 765

Arg Gln Leu Tyr Asp Ile Val Tyr Thr Ile Thr Ala Asp Ile Thr Asn
                770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
                820                 825                 830

Arg Asp Leu Ser Asn Trp Asp Val Thr Val Gln Asp Trp Val Ile Ser
                835                 840                 845

Arg Tyr Pro Lys Thr Ala Tyr Val Gly Arg Ser Ser Arg Lys Leu Asp
                850                 855                 860

Leu Lys Ile Glu Leu Pro
865                 870

<210> SEQ ID NO 10
<211> LENGTH: 2613
<212> TYPE: DNA
<213> ORGANISM: Artificial
<220> FEATURE:
<223> OTHER INFORMATION: Synthetic DNA

<400> SEQUENCE: 10
atgaaggctg ctgcgctttc ctgcctcttc ggcagtaccc ttgccgttgc aggcgccatt    60
```

```
gaatcgagaa aggttcacca gaagcccctc gcgagatctg aacctttta cccgtcgcca      120 tggatgaatc ccaacgccga cggctgggcg gaggcctatg cccaggccaa gtcctttgtc      180
tcccaaatga ctctgctaga aaggtcaac ttgaccacgg agtcggctg ggggctgag        240 cagtgcgtcg gccaagtggg cgcgatccct cgccttggac ttcgcagtct gtgcatgcat      300
gactcccctc tcggcatccg aggagccgac tacaactcag cgttcccctc tggccagacc      360
gttgctgcta cctgggatcg cggtctgatg taccgtcgcg gctacgcaat gggccaggag      420
gccaaaggca agggcatcaa tgtccttctc ggaccagtcg ccggcccct tggccgcatg       480 cccgagggcg tcgtaactg ggaaggcttc gctccggatc ccgtccttac cggcatcggc       540
atgtccgaga cgatcaaggg cattcaggat gctggcgtca tcgcttgtgc gaagcacttt      600
attggaaacg agcaggagca cttcagacag gtgccgaag cccagggata cggttacaac       660
atcagcgaaa ccctctcctc caacattgac gacaagacca tgcacgagct ctacctttgg     720
ccgtttgccg atgccgtccg ggccggcgtc ggctctgtca tgtgctcgta caaccaggtc     780
aacaactcgt acgcctgcca gaactcgaag ctgctgaacg acctcctcaa gaacgagctt     840
gggtttcagg gcttcgtcat gagcgactgg tgggcacagc acactggcgc agcaagcgcc     900
gtggctggtc tcgatatgtc catgccgggc gacaccatgt tcaacactgg cgtcagtttc     960
tggggcgcca atctcaccct cgccgtcctc aacggcacag tccctgccta ccgtctcgac    1020
gacatggcca tgcgcatcat ggccgccctc ttcaaggtca ccaagaccac cgacctggaa    1080
ccgatcaact tctccttctg gacccgcgac acttatggcc cgatccactg ggccgccaag    1140
cagggctacc aggagattaa ttcccacgtt gacgtccgcg ccgaccacgg caacctcatc    1200
cggaacattg ccgccaaggg tacggtgctg ctgaagaata ccggctctct acccctgaac    1260
aagccaaagt tcgtggccgt catcggcgaa gatgctgggc cgagccccaa cgggcccaac    1320
ggctgcagcg accgcggctg taacgaaggc acgctcgcca tgggctgggg atccggcaca    1380
gccaactatc cgtacctcgt ttcccccgac gccgcgctcc agttgcgggc catccaggac    1440
ggcacgaggt acgagagcgt cctgtccaac tacgccgagg aaaatacaaa ggctctggtc    1500
tcgcaggcca atgcaaccgc catcgtcttc gtcaatgccg actcaggcga gggctacatc    1560
aacgtggacg gtaacgaggg cgaccgtaag aacctgactc tctggaacaa cggtgatact    1620
ctggtcaaga acgtctcgag ctggtgcagc aacaccatcg tcgtcatcca ctcggtcggc    1680
ccggtcctcc tgaccgattg gtacgacaac cccaacatca cggccattct ctgggctggt    1740
cttccgggcc aggagtcggg caactccatc accgacgtgc tttacggcaa ggtcaacccc    1800
gccgcccgct cgcccttcac ttggggcaag accgcgaaa gctatggcgc ggacgtcctg    1860
tacaagccga taatggcaa ttgggcgccc aacaggact tcaccgaggg cgtcttcatc      1920
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
taccggccca cgacgggcac cacggcccag gccccgacgt ttggcaactt ctccaccgac    2100
ctcgaggact atctcttccc caaggacgag ttccctaca tccgcagta catctaccca      2160 tacctcaaca cgaccgaccc ccggagggcc tcggccgatc cccactacgg ccagaccgcc    2220
gaggagttcc tcccgcccca cgccaccgat gacgaccccc agccgctcct ccggtcctcg    2280
ggcggaaact ccccgggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
```

-continued

```
ggcgagaaaa ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                 2613
```

<210> SEQ ID NO 11
<211> LENGTH: 870
<212> TYPE: PRT
<213> ORGANISM: Artificial
<220> FEATURE:
<223> OTHER INFORMATION: Synthetic polypeptide

<400> SEQUENCE: 11

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
    290                 295                 300

Asp Met Ser Met Pro Gly Asp Thr Met Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
```

-continued

```
                340                 345                 350
Val Thr Lys Thr Thr Asp Leu Glu Pro Ile Asn Phe Ser Phe Trp Thr
            355                 360                 365

Arg Asp Thr Tyr Gly Pro Ile His Trp Ala Ala Lys Gln Gly Tyr Gln
        370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
                420                 425                 430

Gly Pro Ser Pro Asn Gly Pro Asn Gly Cys Ser Asp Arg Gly Cys Asn
            435                 440                 445

Glu Gly Thr Leu Ala Met Gly Trp Gly Ser Gly Thr Ala Asn Tyr Pro
            450                 455                 460

Tyr Leu Val Ser Pro Asp Ala Ala Leu Gln Leu Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
                500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
            530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
            595                 600                 605

Gly Lys Thr Arg Glu Ser Tyr Gly Ala Asp Val Leu Tyr Lys Pro Asn
            610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Thr Thr
            675                 680                 685

Ala Gln Ala Pro Thr Phe Gly Asn Phe Ser Thr Asp Leu Glu Asp Tyr
            690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Asn Ser Pro Gly Gly Asn
            755                 760                 765
```

```
Arg Gln Leu Tyr Asp Ile Val Tyr Thr Ile Thr Ala Asp Ile Thr Asn
            770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Lys Arg Gln Phe Thr Gly Arg Leu Thr Arg
                820                 825                 830

Arg Asp Leu Ser Asn Trp Asp Val Thr Val Gln Asp Trp Val Ile Ser
            835                 840                 845

Arg Tyr Pro Lys Thr Ala Tyr Val Gly Arg Ser Ser Arg Lys Leu Asp
            850                 855                 860

Leu Lys Ile Glu Leu Pro
865                 870

<210> SEQ ID NO 12
<211> LENGTH: 2613
<212> TYPE: DNA
<213> ORGANISM: Artificial
<220> FEATURE:
<223> OTHER INFORMATION: Synthetic DNA

<400> SEQUENCE: 12
atgaaggctg ctgcgctttc ctgcctcttc ggcagtaccc ttgccgttgc aggcgccatt       60
gaatcgagaa aggttcacca gaagcccctc gcgagatctg aaccttttta cccgtcgcca      120
tggatgaatc ccaacgccga cggctgggcg gaggcctatg cccaggccaa gtcctttgtc      180
tcccaaatga ctctgctaga gaaggtcaac ttgaccacgg agtcggctg ggggctgag        240 cagtgcgtcg ccaagtgggc gcgatcccct cgccttggac ttcgcagtct gtgcatgcat      300
gactcccctc tcggcgtgcg aggagccgac tacaactcag cgttcccctc tggccagacc      360
gttgctgcta cctgggatcg cggtctgatg taccgtcgcg gctacgcaat gggccaggag      420
gccaaaggca agggcatcaa tgtccttctc ggaccagtcg ccggccccct tggccgcatg      480
cccgagggcg tcgtaactg gaaggcttc gctccggatc ccgtccttac cggcatcggc        540
atgtccgaga cgatcaaggg cattcaggat gctggcgtca tcgcttgtgc gaagcacttt      600
attggaaacg agcaggagca cttcagacag gtgccagaag cccagggata cggttacaac      660
atcagcgaaa ccctctcctc caacattgac gacaagacca tgcacgagct ctacctttgg      720
ccgtttgccg atgccgtccg ggccggcgtc ggctctgtca tgtgctcgta caaccagggc      780
aacaactcgt acgcctgcca gaactcgaag ctgctgaacg acctcctcaa gaacgagctt      840
gggtttcagg gcttcgtcat gagcgactgg tgggcacagc acactggcgc agcaagcgcc      900
gtggctggtc tcgatatgtc catgccgggc gacaccatgc tgaacactgg cgtcagtttc      960
tggggcgcca atctcacccct cgccgtcctc aacggcacag tccctgccta ccgtctcgac     1020
gacatggcca tgcgcatcat ggccgccctc ttcaaggtca ccaagaccac cgacctggaa     1080
ccgatcaact tctccttctg gacccgcgac acttatggcc cgatccactg ggccgccaag     1140
cagggctacc aggagattaa ttcccacgtt gacgtccgcg ccgaccacgg caacctcatc     1200
cggaacattg ccgccaaggg tacggtgctg ctgaagaata ccggctctct acccctgaac     1260
aagccaaagt tcgtggccgt catcggcgag gatgctgggc cgagcccaa cgggcccaac      1320 ggctgcagcg accgcggctg taacgaaggc acgctcgcca tgggctgggg atccggcaca     1380
gccaactatc cgtacctcgt ttccccgac gccgcgctcc aggcgcgggc catccaggac      1440
ggcacgaggt acgagagcgt cctgtccaac tacgccgagg aaaatacaaa ggctctggtc     1500
```

```
tcgcaggcca atgcaaccgc catcgtcttc gtcaatgccg actcaggcga gggctacatc      1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaaccc      1800 gccgcccgct cgcccttcac ttggggcaag acccgcgaaa gctatggcgc ggacgtcctg      1860
tacaagccga ataatggcaa ttgggcgccc aacaggact tcaccgaggg cgtcttcatc      1920
gactaccgct acttcgacaa ggttgacgat gactcggtca tctacgagtt cggccacggc      1980
ctgagctaca ccaccttcga gtacagcaac atccgcgtcg tcaagtccaa cgtcagcgag      2040
taccggccca cgacgggcac cacgattcag gccccgacgt ttggcaactt ctccaccgac      2100
ctcgaggact atctcttccc caaggacgag ttccctaca tcccgcagta catctacccg      2160
tacctcaaca cgaccgaccc ccggagggcc tcgggcgatc cccactacgg ccagaccgcc      2220
gaggagttcc tcccgcccca cgccaccgat gacgaccccc agccgctcct ccggtcctcg      2280
ggcggaaact cccccggcgg caaccgccag ctgtacgaca ttgtctacac aatcacggcc      2340
gacatcacga atacgggctc cgttgtaggc gaggaggtac cgcagctcta cgtctcgctg      2400
ggcggtcccg aggatcccaa ggtgcagctg cgcgactttg acaggatgcg gatcgaaccc      2460
ggcgagacga ggcagttcac cggccgcctg acgcgcagag atctgagcaa ctgggacgtc      2520
acggtgcagg actgggtcat cagcaggtat cccaagacgg catatgttgg gaggagcagc      2580
cggaagttgg atctcaagat tgagcttcct tga                                 2613

<210> SEQ ID NO 13
<211> LENGTH: 870
<212> TYPE: PRT
<213> ORGANISM: Artificial
<220> FEATURE:
<223> OTHER INFORMATION: Synthetic polypeptide

<400> SEQUENCE: 13

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Val Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
```

```
                    165                 170                 175
Thr Gly Ile Gly Met Ser Glu Thr Ile Lys Gly Ile Gln Asp Ala Gly
                180                 185                 190

Val Ile Ala Cys Ala Lys His Phe Ile Gly Asn Glu Gln Glu His Phe
                195                 200                 205

Arg Gln Val Pro Glu Ala Gln Gly Tyr Gly Tyr Asn Ile Ser Glu Thr
            210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Gly Asn Asn Ser Tyr Ala Cys Gln Asn Ser Lys Leu Leu
                260                 265                 270

Asn Asp Leu Leu Lys Asn Glu Leu Gly Phe Gln Gly Phe Val Met Ser
            275                 280                 285

Asp Trp Trp Ala Gln His Thr Gly Ala Ala Ser Ala Val Ala Gly Leu
            290                 295                 300

Asp Met Ser Met Pro Gly Asp Thr Met Leu Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
                340                 345                 350

Val Thr Lys Thr Thr Asp Leu Glu Pro Ile Asn Phe Ser Phe Trp Thr
            355                 360                 365

Arg Asp Thr Tyr Gly Pro Ile His Trp Ala Ala Lys Gln Gly Tyr Gln
            370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
                420                 425                 430

Gly Pro Ser Pro Asn Gly Pro Asn Gly Cys Ser Asp Arg Gly Cys Asn
            435                 440                 445

Glu Gly Thr Leu Ala Met Gly Trp Gly Ser Gly Thr Ala Asn Tyr Pro
            450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
                500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590
```

```
Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
    610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
                660                 665                 670

Val Val Lys Ser Asn Val Ser Glu Tyr Arg Pro Thr Thr Gly Thr Thr
            675                 680                 685

Ile Gln Ala Pro Thr Phe Gly Asn Phe Ser Thr Asp Leu Glu Asp Tyr
        690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Gly Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
        755                 760                 765

Arg Gln Leu Tyr Asp Ile Val Tyr Thr Ile Thr Ala Asp Ile Thr Asn
    770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
        835                 840                 845

Arg Tyr Pro Lys Thr Ala Tyr Val Gly Arg Ser Ser Arg Lys Leu Asp
    850                 855                 860

Leu Lys Ile Glu Leu Pro
865                 870

<210> SEQ ID NO 14
<211> LENGTH: 2613
<212> TYPE: DNA
<213> ORGANISM: Artificial
<220> FEATURE:
<223> OTHER INFORMATION: Synthetic DNA

<400> SEQUENCE: 14
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccat ggctggggcg gaggcctatg cccaggccaa gtcctttgtc     180
tcccaaatga ctctgctaga aaggtcaac ttgaccacgg gagtcggctg ggggctgag       240 cagtgcgtcg ccaagtgggc gcgatccct cgccttggac ttcgcagtct gtgcatgcat     300
gactcccctc tcggcatccg aggagccgac tacaactcag cgttcccctc tggccagacc     360
gttgctgcta cctgggatcg cggtctgatg taccgtcgcg ctacgcaatg ggcaggag       420 gccaaaggca agggcatcaa tgtccttctc ggaccagtcg ccggccccct tggccgcatg     480
```

-continued

```
cccgagggcg gtcgtaactg ggaaggcttc gctccggatc ccgtccttac cggcatcggc    540
atgtccgaga cgatcaaggg cattcaggat gctggcgtca tcgcttgtgc gaagcacttt    600
attggaaacg agcaggagca cttcagacag gtgccagaag cccagggata cggttacaac    660
atcagcgaaa ccctctcctc aacattgac gacaagacca tgcacgagct ctacctttgg     720
ccgtttgccg atgccgtccg ggccggcgtc ggctctgtca tgtgctcgta caaccaggtc    780
aacaactcgt acgcctgcca gaactcgaag ctgctgaacg acctcctcaa gaacgagctt    840
gggtttcagg gcttcgtcat gagcgactgg tgggcacagc acactggcgc agcaagcgcc    900
gtggctggtc tcgatatgtc catgccgggc gacaccatgt tcaacactgg cgtcagtttc    960
tggggcgcca atctcaccct cgccgtcctc aacggcacag tccctgccta ccgtctcgac   1020
gacatgtgca tgcgcatcat ggccgccctc ttcaaggtca ccaagaccac cgacctggaa   1080
ccgatcaact tctccttctg gacccgcgac acttatggcc cgatccactg gccgccaag    1140 cagggctacc aggagattaa ttcccacgtt gacgtccgcg ccgaccacgg caacctcatc   1200
cggaacattg ccgccaaggg tacggtgctg ctgaagaata ccggctctct accctgaac    1260 aagccaaagt tcgtggccgt catcggcgag atgctgggc cgagcccaa cgggcccaac     1320 ggctgcagcg accgcggctg taacgaaggc acgctcgcca tgggctgggg atccggcaca   1380
gccaactatc cgtacctcgt ttcccccgac gccgcgctcc agttgcgggc catccaggac   1440
ggcacgaggt acgagagcgt cctgtccaac tacgccgagg aaaatacaaa ggctctggtc   1500
tcgcaggcca atgcaaccgc catcgtcttc gtcaatgccg actcaggcga gggctacatc   1560
aacgtggacg gtaacgaggg cgaccgtaag aacctgactc tctggaacaa cggtgatact   1620
ctggtcaaga cgtctcgag ctggtgcagc aacaccatcg tcgtcatcca ctcggtcggc    1680
ccggtcctcc tgaccgattg gtacgacaac cccaacatca cggccattct ctgggctggt   1740
cttccgggcc aggagtcggg caactccatc accgacgtgc tttacggcaa ggtcaacccc   1800
gccgcccgct cgcccttcac ttggggcaag acccgcgaaa gctatggcgc ggacgtcctg   1860
tacaagccga ataatggcaa ttgggcgccc caacaggact tcaccgaggg cgtcttcatc   1920
gactaccgct acttcgacaa ggttgacgat gactcggtca tctacgagtt cggccacggc   1980
ctgagctaca ccaccttcga gtacagcaac atccgcgtcg tcaagtccaa cgtcagcgag   2040
taccggccca cgacgggcaa aacgattcag gccccgacgt ttggcaactt ctccaccgac   2100
ctcgaggact atctcttccc caaggacgag ttccctaca tcccgcagta catctacccg     2160
tacctcaaca cgaccgaccc ccggagggcc tcggccgatc ccactacgg ccagaccgcc    2220 gaggagttcc tcccgcccca cgccaccgat gacgaccccc agccgctcct ccggtcctcg   2280
ggcggaaact cccccggcgg caaccgccag ctgtacgaca ttgtctacac aatcacggcc   2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                 2613
```

<210> SEQ ID NO 15
<211> LENGTH: 870
<212> TYPE: PRT
<213> ORGANISM: Artificial
<220> FEATURE:
<223> OTHER INFORMATION: Synthetic polypeptide

<400> SEQUENCE: 15

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Ile Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
290                 295                 300

Asp Met Ser Met Pro Gly Asp Thr Met Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Cys Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

```
Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
            435                 440                 445

Glu Gly Thr Leu Ala Met Gly Trp Ser Gly Thr Ala Asn Tyr Pro
        450                 455                 460

Tyr Leu Val Ser Pro Asp Ala Ala Leu Gln Leu Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
            595                 600                 605

Gly Lys Thr Arg Glu Ser Tyr Gly Ala Asp Val Leu Tyr Lys Pro Asn
            610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Lys Thr
            675                 680                 685

Ile Gln Ala Pro Thr Phe Gly Asn Phe Ser Thr Asp Leu Glu Asp Tyr
            690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Ala Ser Ala Asp Pro His Tyr
                725                 730                 735

Gly Gln Thr Ala Glu Glu Phe Leu Pro Pro His Ala Thr Asp Asp
            740                 745                 750

Pro Gln Pro Leu Leu Arg Ser Ser Gly Gly Asn Ser Pro Gly Gly Asn
            755                 760                 765

Arg Gln Leu Tyr Asp Ile Val Tyr Thr Ile Thr Ala Asp Ile Thr Asn
            770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
            835                 840                 845
```

Arg Tyr Pro Lys Thr Ala Tyr Val Gly Arg Ser Ser Arg Lys Leu Asp
    850                 855                 860

Leu Lys Ile Glu Leu Pro
865                 870

<210> SEQ ID NO 16
<211> LENGTH: 2613
<212> TYPE: DNA
<213> ORGANISM: Artificial
<220> FEATURE:
<223> OTHER INFORMATION: Synthetic DNA

<400> SEQUENCE: 16

| | | | | | |
|---|---|---|---|---|---|
| atgaaggctg | ctgcgctttc | ctgcctcttc | ggcagtaccc | ttgccgttgc | aggcgccatt | 60 |
| gaatcgagaa | aggttcacca | gaagcccctc | gcgagatctg | aacctttta | cccgtcgcca | 120 |
| tggatgaatc | ccaacgccat | cggctgggcg | gaggcctatg | cccaggccaa | gtcctttgtc | 180 |
| tcccaaatga | ctctgctaga | aaggtcaac | ttgaccacgg | gagtcggctg | ggggaggag | 240 |
| cagtgcgtcg | gcaacgtggg | cgcgatccct | cgccttggac | ttcgcagtct | gtgcatgcat | 300 |
| gactcccctc | tcggcgtgcg | aggaaccgac | tacaactcag | cgttccctc | tggccagacc | 360 |
| gttgctgcta | cctgggatcg | cggtctgatg | taccgtcgcg | gctacgcaat | gggccaggag | 420 |
| gccaaaggca | agggcatcaa | tgtccttctc | ggaccagtcg | ccggccccct | ggccgcatg | 480 |
| cccgagggcg | gtcgtaactg | ggaaggcttc | gctccggatc | ccgtccttac | cggcatcggc | 540 |
| atgtccgaga | cgatcaaggg | cattcaggat | gctggcgtca | tcgcttgtgc | gaagcacttt | 600 |
| attggaaacg | agcaggagca | cttcagacag | gtgccagaag | cccagggata | cggttacaac | 660 |
| atcagcgaaa | ccctctcctc | caacattgac | gacaagacca | tgcacgagct | ctaccttgg | 720 |
| ccgtttgccg | atgccgtccg | ggccggcgtc | ggctctgtca | tgtgctcgta | caaccagggc | 780 |
| aacaactcgt | acgcctgcca | gaactcgaag | ctgctgaacg | acctcctcaa | gaacgagctt | 840 |
| gggtttcagg | gcttcgtcat | gagcgactgg | tgggcacagc | acactggcgc | agcaagcgcc | 900 |
| gtggctggtc | tcgatatgtc | catgccgggc | gacaccatgg | tcaacactgg | cgtcagttc | 960 |
| tggggcgcca | atctcaccct | cgccgtcctc | aacggcacag | tccctgccta | ccgtctcgac | 1020 |
| gacatgtgca | tgcgcatcat | ggccgccctc | ttcaaggtca | ccaagaccac | cgacctggaa | 1080 |
| ccgatcaact | tctccttctg | gacccgcgac | acttatggcc | cgatccactg | ggccgccaag | 1140 |
| cagggctacc | aggagattaa | ttcccacgtt | gacgtccgcg | ccgaccacgg | caacctcatc | 1200 |
| cggaacattg | ccgccaaggg | tacggtgctg | ctgaagaata | ccggctctct | accctgaac | 1260 |
| aagccaaagt | tcgtggccgt | catcggcgag | gatgctgggc | cgagcccaa | cgggcccaac | 1320 |
| ggctgcagcg | accgcggctg | taacgaaggc | acgctcgcca | tgggctgggg | atccggcaca | 1380 |
| gccaactatc | cgtacctcgt | ttccccgac | gccgcgctcc | aggcgcgggc | catccaggac | 1440 |
| ggcacgaggt | acgagagcgt | cctgtccaac | tacgccgagg | aaaatacaaa | ggctctggtc | 1500 |
| tcgcaggcca | atgcaaccgc | catcgtcttc | gtcaatgccg | actcaggcga | gggctacatc | 1560 |
| aacgtggacg | gtaacgaggg | cgaccgtaag | aacctgactc | tctggaacaa | cggtgatact | 1620 |
| ctggtcaaga | acgtctcgag | ctggtgcagc | aacaccatcg | tcgtcatcca | ctcggtcggc | 1680 |
| ccggtcctcc | tgaccgattg | gtacgacaac | cccaacatca | cggccattct | ctgggctggt | 1740 |
| cttccgggcc | aggagtcggg | caactccatc | accgacgtgc | tttacggcaa | ggtcaacccc | 1800 |
| gccgcccgct | cgcccttcac | ttggggcaag | acccgcgaaa | gctatggcgc | ggacgtcctg | 1860 |
| tacaagccga | taatggcaa | tgggcgcccc | caacaggact | tcaccgaggg | cgtcttcatc | 1920 |

```
gactaccgct acttcgacaa ggttgacgat gactcggtca tctacgagtt cggccacggc   1980
ctgagctaca ccaccttcga gtacagcaac atccgcgtcg tcaagtccaa cgtcagcgag   2040
taccggccca cgacgggcac cacgattcag gccccgacgt ttggcaactt ctccaccgac   2100
ctcgaggact atctcttccc caaggacgag ttccctaca tcccgcagta catctacccg    2160
tacctcaaca cgaccgaccc ccggagggcc tcgggcgatc cccactacgg ccagaccgcc   2220
gaggagttcc tcccgcccca cgccaccgat gacgaccccc agccgctcct ccggtcctcg   2280
ggcggaaact cccccggcgg caaccgccag ctgtacgaca ttgtctacac aatcacggcc   2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                 2613
```

<210> SEQ ID NO 17
<211> LENGTH: 870
<212> TYPE: PRT
<213> ORGANISM: Artificial
<220> FEATURE:
<223> OTHER INFORMATION: Synthetic polypeptide

<400> SEQUENCE: 17

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Ile Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Glu Glu Glu
65                  70                  75                  80

Gln Cys Val Gly Asn Val Gly Ala Ile Pro Arg Leu Gly Leu Arg Ser
                85                  90                  95

Leu Cys Met His Asp Ser Pro Leu Gly Val Arg Gly Thr Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

-continued

```
Pro Phe Ala Asp Ala Val Arg Ala Gly Val Gly Ser Val Met Cys Ser
            245                 250                 255

Tyr Asn Gln Gly Asn Asn Ser Tyr Ala Cys Gln Asn Ser Lys Leu Leu
        260                 265                 270

Asn Asp Leu Leu Lys Asn Glu Leu Gly Phe Gln Gly Phe Val Met Ser
    275                 280                 285

Asp Trp Trp Ala Gln His Thr Gly Ala Ala Ser Ala Val Ala Gly Leu
290                 295                 300

Asp Met Ser Met Pro Gly Asp Thr Met Val Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Cys Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
        515                 520                 525

Arg Lys Asn Leu Thr Leu Trp Asn Asn Gly Asp Thr Leu Val Lys Asn
    530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
    610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
            660                 665                 670
```

Val Val Lys Ser Asn Val Ser Glu Tyr Arg Pro Thr Thr Gly Thr Thr
            675                 680                 685

Ile Gln Ala Pro Thr Phe Gly Asn Phe Ser Thr Asp Leu Glu Asp Tyr
        690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Gly Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Gly Gly Asn Ser Pro Gly Gly Asn
        755                 760                 765

Arg Gln Leu Tyr Asp Ile Val Tyr Thr Ile Thr Ala Asp Ile Thr Asn
        770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
        835                 840                 845

Arg Tyr Pro Lys Thr Ala Tyr Val Gly Arg Ser Ser Arg Lys Leu Asp
        850                 855                 860

Leu Lys Ile Glu Leu Pro
865                 870

<210> SEQ ID NO 18
<211> LENGTH: 2613
<212> TYPE: DNA
<213> ORGANISM: Artificial
<220> FEATURE:
<223> OTHER INFORMATION: Synthetic DNA

<400> SEQUENCE: 18
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccat cggctgggcg gaggcctatg cccaggccaa gtcctttgtc     180
tcccaaatga ctctgctaga aaggtcaac ttgaccacgg gagtcggctg gggggctgag      240
cagtgcgtcg gcaacgtggg cgcgatccct cgccttggac ttcgcagtct gtgcatgcat     300
gactcccctc tcggcgtgcg aggaagcgac tacaactcag cgttcccctc tggccagacc     360
gttgctgcta cctgggatcg cggtctgatg taccgtcgcg gctacgcaat gggccaggag     420
gccaaaggca agggcatcaa tgtccttctc ggaccagtcg ccggccccct tggccgcatg     480
cccgagggcg gtcgtaactg ggaaggcttc gctccggatc ccgtccttac cggcatcggc     540
atgtccgaga cgatcaaggg cattcaggat gctggcgtca tcgcttgtgc gaagcacttt     600
attggaaacg agcaggagca cttcagacag gtgccagaag cccagggata cggttacaac     660
atcagcgaaa ccctctcctc aacattgac gacaagacca tgcacgagct ctacctttgg     720
ccgtttgccg atgccgtccg ggccggcgtc ggctctgtca tgtgctcgta caaccagggc     780
aacaactcgt acgcctgcca gaactcgaag ctgctgaacg acctcctcaa gaacgagctt     840
gggtttcagg gcttcgtcat gagcgactgg tgggcacagc acactggcgc agcaagcgcc     900

```
gtggctggtc tcgatatgtc catgccgggc gacaccatgg tcaacactgg cgtcagtttc    960
tggggcgcca atctcaccct cgccgtcctc aacggcacag tccctgccta ccgtctcgac   1020
gacatgtgca tgcgcatcat ggccgccctc ttcaaggtca ccaagaccac cgacctggaa   1080
ccgatcaact tctccttctg gacccgcgac acttatggcc cgatccactg ggccgccaag   1140
cagggctacc aggagattaa ttcccacgtt gacgtccgcg ccgaccacgg caacctcatc   1200
cggaacattg ccgccaaggg tacggtgctg ctgaagaata ccggctctct acccctgaac   1260
aagccaaagt tcgtggccgt catcggcgag gatgctgggc cgagcccaa cgggcccaac   1320
ggctgcagcg accgcggctg taacgaaggc acgctcgcca tgggctgggg atccggcaca   1380
gccaactatc cgtacctcgt tccccccgac gccgcgctcc aggcgcgggc catccaggac   1440
ggcacgaggt acgagagcgt cctgtccaac tacgccgagg aaaatacaaa ggctctggtc   1500
tcgcaggcca atgcaaccgc catcgtcttc gtcaatgccg actcaggcga gggctacatc   1560
aacgtggacg gtaacgaggg cgaccgtaag aacctgactc tctggaacaa cggtgatact   1620
ctggtcaaga acgtctcgag ctggtgcagc aacaccatcg tcgtcatcca ctcggtcggc   1680
ccggtcctcc tgaccgattg gtacgacaac cccaacatca cggccattct ctgggctggt   1740
cttccgggcc aggagtcggg caactccatc accgacgtgc tttacggcaa ggtcaacccc   1800
gccgcccgct cgcccttcac ttggggcaag accgcgaaaa gctatggcgc ggacgtcctg   1860
tacaagccga ataatggcaa ttgggcgccc caacaggact tcaccgaggg cgtcttcatc   1920
gactaccgct acttcgacaa ggttgacgat gactcggtca tctacgagtt cggccacggc   1980
ctgagctaca ccaccttcga gtacagcaac atccgcgtcg tcaagtccaa cgtcagcgag   2040
taccggccca cgacgggcac cacgattcag gccccgacgt ttggcaactt ctccaccgac   2100
ctcgaggact atctcttccc caaggacgag ttccctaca tcccgcagta catctacccg   2160
tacctcaaca cgaccgaccc ccggagggcc tcgggcgatc cccactacgg ccagaccgcc   2220
gaggagttcc tcccgcccca cgccaccgat gacgaccccc agccgctcct ccggtcctcg   2280
ggcgaaaact ccccccggcgg caaccgccag ctgtacgaca ttgtctacac aatcacggcc   2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                2613
```

<210> SEQ ID NO 19
<211> LENGTH: 870
<212> TYPE: PRT
<213> ORGANISM: Artificial
<220> FEATURE:
<223> OTHER INFORMATION: Synthetic polypeptide

<400> SEQUENCE: 19

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Ile Gly
        35                  40                  45

Trp Ala Glu Ala Tyr Ala Gln Ala Lys Ser Phe Val Ser Gln Met Thr
    50                  55                  60
```

```
Leu Leu Glu Lys Val Asn Leu Thr Thr Gly Val Gly Trp Gly Ala Glu
 65                  70                  75                  80

Gln Cys Val Gly Asn Val Gly Ala Ile Pro Arg Leu Gly Leu Arg Ser
                 85                  90                  95

Leu Cys Met His Asp Ser Pro Leu Gly Val Arg Gly Ser Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Gly Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
    290                 295                 300

Asp Met Ser Met Pro Gly Asp Thr Met Val Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Cys Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Asn Thr
                485                 490                 495
```

```
Lys Ala Leu Val Ser Gln Ala Asn Ala Thr Ala Ile Val Phe Val Asn
            500                 505                 510
Ala Asp Ser Gly Glu Gly Tyr Ile Asn Val Asp Gly Asn Glu Gly Asp
        515                 520                 525
Arg Lys Asn Leu Thr Leu Trp Asn Asn Gly Asp Thr Leu Val Lys Asn
530                 535                 540
Val Ser Ser Trp Cys Ser Asn Thr Ile Val Ile His Ser Val Gly
545                 550                 555                 560
Pro Val Leu Leu Thr Asp Trp Tyr Asp Asn Pro Asn Ile Thr Ala Ile
                565                 570                 575
Leu Trp Ala Gly Leu Pro Gly Gln Glu Ser Gly Asn Ser Ile Thr Asp
            580                 585                 590
Val Leu Tyr Gly Lys Val Asn Pro Ala Ala Arg Ser Pro Phe Thr Trp
        595                 600                 605
Gly Lys Thr Arg Glu Ser Tyr Gly Ala Asp Val Leu Tyr Lys Pro Asn
    610                 615                 620
Asn Gly Asn Trp Ala Pro Gln Gln Asp Phe Thr Glu Gly Val Phe Ile
625                 630                 635                 640
Asp Tyr Arg Tyr Phe Asp Lys Val Asp Asp Ser Val Ile Tyr Glu
                645                 650                 655
Phe Gly His Gly Leu Ser Tyr Thr Thr Phe Glu Tyr Ser Asn Ile Arg
            660                 665                 670
Val Val Lys Ser Asn Val Ser Glu Tyr Arg Pro Thr Thr Gly Thr Thr
        675                 680                 685
Ile Gln Ala Pro Thr Phe Gly Asn Phe Ser Thr Asp Leu Glu Asp Tyr
    690                 695                 700
Leu Phe Pro Lys Asp Glu Phe Pro Tyr Ile Pro Gln Tyr Ile Tyr Pro
705                 710                 715                 720
Tyr Leu Asn Thr Thr Asp Pro Arg Arg Ala Ser Gly Asp Pro His Tyr
                725                 730                 735
Gly Gln Thr Ala Glu Glu Phe Leu Pro Pro His Ala Thr Asp Asp Asp
            740                 745                 750
Pro Gln Pro Leu Leu Arg Ser Ser Gly Gly Asn Ser Pro Gly Gly Asn
        755                 760                 765
Arg Gln Leu Tyr Asp Ile Val Tyr Thr Ile Thr Ala Asp Ile Thr Asn
    770                 775                 780
Thr Gly Ser Val Val Gly Glu Glu Val Pro Gln Leu Tyr Val Ser Leu
785                 790                 795                 800
Gly Gly Pro Glu Asp Pro Lys Val Gln Leu Arg Asp Phe Asp Arg Met
                805                 810                 815
Arg Ile Glu Pro Gly Glu Thr Arg Gln Phe Thr Gly Arg Leu Thr Arg
            820                 825                 830
Arg Asp Leu Ser Asn Trp Asp Val Thr Val Gln Asp Trp Val Ile Ser
        835                 840                 845
Arg Tyr Pro Lys Thr Ala Tyr Val Gly Arg Ser Ser Arg Lys Leu Asp
    850                 855                 860
Leu Lys Ile Glu Leu Pro
865                 870

<210> SEQ ID NO 20
<211> LENGTH: 2613
<212> TYPE: DNA
<213> ORGANISM: Artificial
<220> FEATURE:
<223> OTHER INFORMATION: Synthetic DNA
```

<400> SEQUENCE: 20

```
atgaaggctg ctgcgctttc ctgcctcttc ggcagtaccc ttgccgttgc aggcgccatt        60
gaatcgagaa aggttcacca gaagcccctc gcgagatctg aaccttttta cccgtcgcca       120
tggatgaatc ccaacgccat cggctgggcg gaggcctatg cccaggccaa gtcctttgtc       180
tcccaaatga ctctgctaga aaggtcaac ttgaccacgg gagtcggctg ggggatggag        240
cagtgcgtcg gccaagtggg cgcgatccct cgccttggac ttcgcagtct gtgcatgcat       300
gactcccctc tcggcgtgcg aggagccgac tacaactcag cgttcccctc tggccagacc       360
gttgctgcta cctgggatcg cggtctgatg taccgtcgcg gctacgcaat gggccaggag       420
gccaaaggca agggcatcaa tgtccttctc ggaccagtcg ccggccccct tggccgcatg       480
cccgagggcg gtcgtaactg ggaaggcttc gctccggatc ccgtccttac cggcatcggc       540
atgtccgaga cgatcaaggg cattcaggat gctggcgtca tcgcttgtgc gaagcacttt       600
attggaaacg agcaggagca cttcagacag gtgccgaaag cccagggata cggttacaac       660
atcagcgaaa ccctctcctc caacattgac gacaagacca tgcacgagct ctaccttggg       720
ccgtttgccg atgccgtccg ggccggcgtc ggctctgtca tgtgctcgta caaccagggc       780
aacaactcgt acgcctgcca gaactcgaag ctgctgaacg acctcctcaa gaacgagctt       840
gggtttcagg gcttcgtcat gagcgactgg tgggcacagc acactggcgc agcaagcgcc       900
gtggctggtc tcgatatgtc catgccgggc gacaccatgc tgaacactgg cgtcagtttc       960
tggggcgcca atctcaccct cgccgtcctc aacggcacag tccctgccta ccgtctcgac      1020
gacatggcca tgcgcatcat ggccgccctc ttcaaggtca ccaagaccac cgacctggaa      1080
ccgatcaact tctccttctg gacccgcgac acttatggcc cgatccactg ggccgccaag      1140
cagggctacc aggagattaa ttcccacgtt gacgtccgcg ccgaccacgg caacctcatc      1200
cggaacattg ccgccaaggg tacggtgctg ctgaagaata ccggctctct acccctgaac      1260
aagccaaagt tcgtggccgt catcggcgag gatgctgggc cgagccccaa cgggcccaac      1320
ggctgcagcg accgcggctg taacgaaggc acgctcgcca tgggctgggg atccggcaca      1380
gccaactatc cgtacctcgt ttcccccgac gccgcgctcc aggcgcgggc catccaggac      1440
ggcacgaggt acgagagcgt cctgtccaac tacgccgagg aaaatacaaa ggctctggtc      1500
tcgcaggcca atgcaaccgc catcgtcttc gtcaatgccg actcaggcga gggctacatc      1560
aacgtggacg gtaacgaggg cgaccgtaag aacctgactc tctggaacaa cggtgatact      1620
ctggtcaaga acgtctcgag ctggtgcagc aacaccatcg tcgtcatcca ctcggtcggc      1680
ccggtcctcc tgaccgattg gtacgacaac cccaacatca cggccattct ctgggctggt      1740
cttccgggcc aggagtcggg caactccatc accgacgtgc tttacggcaa ggtcaacccc      1800
gccgcccgct cgcccttcac ttggggcaag accgcgaaaa gctatggcgc ggacgtcctg      1860
tacaagccga taatggcaa ttgggcgccc caacaggact tcaccgaggg cgtcttcatc       1920
gactaccgct acttcgacaa ggttgacgat gactcggtca tctacgagtt cggccacggc      1980
ctgagctaca ccaccttcga gtacagcaac atccgcgtcg tcaagtccaa cgtcagcgag      2040
taccggccca cgacgggcac cacgattcag gccccgacgt ttggcaactt ctccaccgac      2100
ctcgaggact atctcttccc caaggacgag ttccctaca tcccgcagta catctaccg        2160
tacctcaaca cgaccgaccc ccggagggcc tcgggcgatc cccactacgg ccagaccgcc      2220
gaggagttcc tcccgcccca cgccaccgat gacgaccccc agccgctcct ccggtcctcg      2280
ggcggaaaact ccccggcgg caaccgccag ctgtacgaca ttgtctacac aatcacggcc      2340
```

```
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                 2613
```

<210> SEQ ID NO 21
<211> LENGTH: 870
<212> TYPE: PRT
<213> ORGANISM: Artificial
<220> FEATURE:
<223> OTHER INFORMATION: Synthetic polypeptide

<400> SEQUENCE: 21

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Ile Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Met Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Val Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Gly Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
    290                 295                 300

Asp Met Ser Met Pro Gly Asp Thr Met Leu Asn Thr Gly Val Ser Phe
305                 310                 315                 320
```

-continued

Trp Gly Ala Asn Leu Thr Leu Ala Val Leu Asn Gly Thr Val Pro Ala
            325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
            355                 360                 365

Arg Asp Thr Tyr Gly Pro Ile His Trp Ala Ala Lys Gln Gly Tyr Gln
            370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
            435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Asn Thr
            485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
            530                 535                 540

Val Ser Ser Trp Cys Ser Asn Thr Ile Val Val Ile His Ser Val Gly
545                 550                 555                 560

Pro Val Leu Leu Thr Asp Trp Tyr Asp Asn Pro Asn Ile Thr Ala Ile
            565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
            595                 600                 605

Gly Lys Thr Arg Glu Ser Tyr Gly Ala Asp Val Leu Tyr Lys Pro Asn
            610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
            645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Thr Thr
            675                 680                 685

Ile Gln Ala Pro Thr Phe Gly Asn Phe Ser Thr Asp Leu Glu Asp Tyr
            690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Gly Asp Pro His Tyr
            725                 730                 735

Gly Gln Thr Ala Glu Glu Phe Leu Pro Pro His Ala Thr Asp Asp Asp

-continued

```
                740                 745                 750
Pro Gln Pro Leu Leu Arg Ser Ser Gly Gly Asn Ser Pro Gly Gly Asn
            755                 760                 765
Arg Gln Leu Tyr Asp Ile Val Tyr Thr Ile Thr Ala Asp Ile Thr Asn
        770                 775                 780
Thr Gly Ser Val Val Gly Glu Val Pro Gln Leu Tyr Val Ser Leu
785                 790                 795                 800
Gly Gly Pro Glu Asp Pro Lys Val Gln Leu Arg Asp Phe Asp Arg Met
                805                 810                 815
Arg Ile Glu Pro Gly Glu Thr Arg Gln Phe Thr Gly Arg Leu Thr Arg
            820                 825                 830
Arg Asp Leu Ser Asn Trp Asp Val Thr Val Gln Asp Trp Val Ile Ser
        835                 840                 845
Arg Tyr Pro Lys Thr Ala Tyr Val Gly Arg Ser Ser Arg Lys Leu Asp
    850                 855                 860
Leu Lys Ile Glu Leu Pro
865                 870

<210> SEQ ID NO 22
<211> LENGTH: 851
<212> TYPE: PRT
<213> ORGANISM: Myceliophthora thermophila

<400> SEQUENCE: 22

Ile Glu Ser Arg Lys Val His Gln Lys Pro Leu Ala Arg Ser Glu Pro
1               5                   10                  15
Phe Tyr Pro Ser Pro Trp Met Asn Pro Asn Ala Asp Gly Trp Ala Glu
            20                  25                  30
Ala Tyr Ala Gln Ala Lys Ser Phe Val Ser Gln Met Thr Leu Leu Glu
        35                  40                  45
Lys Val Asn Leu Thr Thr Gly Val Gly Trp Gly Ala Glu Gln Cys Val
    50                  55                  60
Gly Gln Val Gly Ala Ile Pro Arg Leu Gly Leu Arg Ser Leu Cys Met
65                  70                  75                  80
His Asp Ser Pro Leu Gly Ile Arg Gly Ala Asp Tyr Asn Ser Ala Phe
                85                  90                  95
Pro Ser Gly Gln Thr Val Ala Ala Thr Trp Asp Arg Gly Leu Met Tyr
            100                 105                 110
Arg Arg Gly Tyr Ala Met Gly Gln Glu Ala Lys Gly Lys Gly Ile Asn
        115                 120                 125
Val Leu Leu Gly Pro Val Ala Gly Pro Leu Gly Arg Met Pro Glu Gly
    130                 135                 140
Gly Arg Asn Trp Glu Gly Phe Ala Pro Asp Pro Val Leu Thr Gly Ile
145                 150                 155                 160
Gly Met Ser Glu Thr Ile Lys Gly Ile Gln Asp Ala Gly Val Ile Ala
                165                 170                 175
Cys Ala Lys His Phe Ile Gly Asn Glu Gln Glu His Phe Arg Gln Val
            180                 185                 190
Pro Glu Ala Gln Gly Tyr Gly Tyr Asn Ile Ser Glu Thr Leu Ser Ser
        195                 200                 205
Asn Ile Asp Asp Lys Thr Met His Glu Leu Tyr Leu Trp Pro Phe Ala
    210                 215                 220
Asp Ala Val Arg Ala Gly Val Gly Ser Val Met Cys Ser Tyr Gln Gln
225                 230                 235                 240
Val Asn Asn Ser Tyr Ala Cys Gln Asn Ser Lys Leu Leu Asn Asp Leu
```

```
                        245                 250                 255
Leu Lys Asn Glu Leu Gly Phe Gln Gly Phe Val Met Ser Asp Trp Gln
            260                 265                 270

Ala Gln His Thr Gly Ala Ala Ser Ala Val Ala Gly Leu Asp Met Ser
        275                 280                 285

Met Pro Gly Asp Thr Gln Phe Asn Thr Gly Val Ser Phe Trp Gly Ala
    290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
                325                 330                 335

Thr Thr Asp Leu Glu Pro Ile Asn Phe Ser Phe Trp Thr Asp Asp Thr
            340                 345                 350

Tyr Gly Pro Ile His Trp Ala Ala Lys Gln Gly Tyr Gln Glu Ile Asn
        355                 360                 365

Ser His Val Asp Val Arg Ala Asp His Gly Asn Leu Ile Arg Glu Ile
    370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Ser Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
        435                 440                 445

Ser Pro Asp Ala Ala Leu Gln Ala Arg Ala Ile Gln Asp Gly Thr Arg
    450                 455                 460

Tyr Glu Ser Val Leu Ser Asn Tyr Ala Glu Glu Lys Thr Lys Ala Leu
465                 470                 475                 480

Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
        515                 520                 525

Trp Cys Ser Asn Thr Ile Val Val Ile His Ser Val Gly Pro Val Leu
    530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
        595                 600                 605

Gly Ala Pro Gln Gln Asp Phe Thr Glu Gly Val Phe Ile Asp Tyr Arg
    610                 615                 620

Tyr Phe Asp Lys Val Asp Asp Ser Val Ile Tyr Glu Phe Gly His Gly
625                 630                 635                 640

Gly Leu Ser Tyr Thr Thr Phe Glu Tyr Ser Asn Ile Arg Val Val Lys
                645                 650                 655

Ser Asn Val Ser Glu Tyr Arg Pro Thr Thr Gly Thr Thr Ala Gln Ala
            660                 665                 670
```

-continued

```
Pro Thr Phe Gly Asn Phe Ser Thr Asp Leu Glu Asp Tyr Leu Phe Pro
        675                 680                 685

Lys Asp Glu Phe Pro Tyr Ile Tyr Gln Tyr Ile Tyr Pro Tyr Leu Asn
    690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Asp Pro Gln Pro
                725                 730                 735

Leu Leu Arg Ser Ser Gly Gly Asn Ser Pro Gly Gly Asn Arg Gln Leu
            740                 745                 750

Tyr Asp Ile Val Tyr Thr Ile Thr Ala Asp Ile Thr Asn Thr Gly Ser
        755                 760                 765

Val Val Gly Glu Glu Val Pro Gln Leu Tyr Val Ser Leu Gly Gly Pro
    770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
                805                 810                 815

Ser Asn Trp Asp Val Thr Val Gln Asp Trp Val Ile Ser Arg Tyr Pro
            820                 825                 830

Lys Thr Ala Tyr Val Gly Arg Ser Ser Arg Lys Leu Asp Leu Lys Ile
        835                 840                 845

Glu Leu Pro
    850
```